United States Patent

Nagase et al.

[11] Patent Number: 6,087,369
[45] Date of Patent: Jul. 11, 2000

[54] INDOLE DERIVATIVES, PROCESS FOR PRODUCING THE SAME AND MEDICINAL USES OF THE SAME

[75] Inventors: Hiroshi Nagase; Akira Mizusuna; Koji Kawai, all of Kamakura; Izumi Nakatani, Yokohama, all of Japan

[73] Assignee: Toray Industries, Ltd., Tokyo, Japan

[21] Appl. No.: 09/135,580

[22] Filed: Aug. 18, 1998

Related U.S. Application Data

[62] Division of application No. 08/709,835, Sep. 10, 1996, Pat. No. 5,852,030, which is a continuation of application No. 08/244,198, filed as application No. PCT/JP93/09188, Sep. 29, 1993, abandoned.

[30] Foreign Application Priority Data

Sep. 29, 1992 [JP] Japan ..................... 4-259841

[51] Int. Cl.[7] ............ A61K 31/44; C07D 489/10
[52] U.S. Cl. .............................. 514/279; 546/31
[58] Field of Search .............. 546/31; 514/279

[56] References Cited

U.S. PATENT DOCUMENTS

| | | | |
|---|---|---|---|
| 4,816,586 | 3/1989 | Portoghese | 546/34 |
| 5,225,417 | 7/1993 | Dappen et al. | 514/279 |
| 5,332,818 | 7/1994 | Nagase et al. | 546/37 |
| 5,352,680 | 10/1994 | Portghese et al. | 546/36 |
| 5,354,863 | 10/1994 | Dappen et al. | 546/35 |
| 5,457,208 | 10/1995 | Portghese et al. | 546/35 |
| 5,849,731 | 12/1998 | Nagase et al. | 546/31 |

FOREIGN PATENT DOCUMENTS

| | | |
|---|---|---|
| 9107966 | 11/1990 | Japan . |
| 4342529 | 11/1992 | Japan . |
| WO8900995 | 2/1989 | WIPO . |
| 94-07896 | 4/1994 | WIPO . |

OTHER PUBLICATIONS

Portoghese et al "Design of Peptidomimetic δ Opioid Receptor Antagonists Using the Message–Address Concept", J. Med. Chem. 1990, 33, 1714–1720.

Portoghese et al "Naltrindole 5'–Isothiocyanate: A Nonequilibrium, Highly Selective δ Opioid Receptor Antagonist", J. Med. Chem. 1990, 33, 1547–1548.

Portoghese "δ Opioid Antagonist Activity and Binding Studies of Regioisomeric Isothiocyanate Derivatives of Naltrindole: Evidence for δ Receptor Subtypes" J. Med. Chem. 1992, 35, 4086–4091.

Portoghese A Remarkable Change of Opioid Receptor Selectivity on the Attachment of a Peptidomimetic κ Address Element to the δ Antagonist Natrindole: 5'–[$N^2$–Alkylamidino)methyl]naltrindole Derivatives as a Novel Class of κ Opioid Receptor Antagonists, J. Med. Chem. 1993, 36, 179–180.

Nagase et al. Chem. Abstr. vol. 119, Entry 95503 (1992).
Nagase et al. Chem. Abstr. vol. 115 Entry 174658 (1990).

*Primary Examiner*—Richard L. Raymond
*Attorney, Agent, or Firm*—Birch, Stewart, Kolasch & Birch, LLP

[57] ABSTRACT

A novel compound which is a δ-opioid antagonist having high selectivity and activity, that exhibits immunosuppressive action, antiallergic action, anti-inflammatory action and brain cell-protecting action is disclosed. The compound according to the present invention is an indole derivative represented by the formula (I):

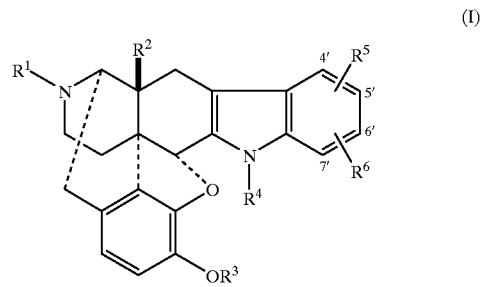

and pharmaceutically acceptable acid addition salts thereof. The present invention also provides an immunosuppressive agent, antiallergic agent, anti-inflammatory agent and brain cell-protecting agent comprising the derivative or the salt as an effective ingredient.

7 Claims, 1 Drawing Sheet

INDOLE DERIVATIVES, PROCESS FOR PRODUCING THE SAME AND MEDICINAL USES OF THE SAME

This application is a continuation divisional of application Ser. No. 08/709,835, filed on Sep. 10, 1996, now U.S. Pat. No. 5,852,030, which is a continuation of application Ser. No. 08/244,198, filed on May 27, 1994, now abandoned, which is the national phase of PCT International Application No. PCT/JP93/0188 filed on Sep. 29, 1993 under 35 U.S.C. § 371. The entire contents of each of the above identified applications are hereby incorporated by reference.

TECHNICAL FIELD

The present invention relates to compounds having affinities to δ-opioid receptor. δ-opioid receptor relates to analgetic, immune and circulatory systems (especially blood pressure) and ligands having high selectivities to this receptor can be used as analgesics, immunosuppressive agents (employed in organ transplantation (kidney, liver and heart), skin transplantation, treatment of autoimmune diseases (rheumatism, various allergies and collagen diseases) and the like], immunopotentiating agents (anti-tumor agents and anti-virus agents), blood pressure-lowering agents and the like.

PRIOR ART

Opioid receptors include three types called μ, δ and κ. Among these, δ-opioid receptor relates various pharmacological effects as mentioned above. However, the number of agonists and antagonists having high selectivities to this receptor is small and the mechanism has not yet been clarified. Recently, a non-peptidic antagonist NTI was discovered by Portoghese (Portoghese, P. S. et al., J. Med. Chem., 31, 281 (1988); 33, 1714 (1990)). Subsequently, synthesis of an antagonist (5'-NTII) which can irreversibly bind to the receptor was reported (Portoghese, P. S. et al., J. Med. Chem. 33, 1547 (1990)). Since a ligand which irreversibly binds to the receptor is very useful in studying the receptor, researchers are paying more and more attention to 5'-NTII. However, its antagonist activity and selectivity to δ-opioid receptor are low. Therefore, as a probe for studying the receptor, a ligand having higher activity and selectivity is demanded.

On the other hand, participation of endogenous opioid peptides such as enkephalin, and morphine in immune system has been pointed out and it is known that opioids may possibly be immunopotentiating agents and immunosuppressive agents. Paying attention to this, the present inventors studied the influence on the immune system by NTI. As a result, it was shown that this compound exhibits immunosuppressive action in vitro and in vivo (Japanese Laid-open Patent Application (Kokai) No. 3-223288). Since currently used immunosuppressive agents have problems in toxicities and side effects, an agent having a low toxicity or having a different mechanism of action is demanded. It is expected that δ-opioid antagonist is one of the candidates thereof.

It has recently been discovered that opioids relate to flow of calcium ion into cells, which has a relationship with ischemia in brain, and that opioids have brain cell-protecting action. Thus, use of opioids as a brain cell-protecting agent is increasingly expected.

DISCLOSURE OF THE INVENTION

An object of the present invention is to provide a δ-opioid antagonist having high antagonist activity and receptor selectivity.

Another object of the present invention is to provide a δ-opioid antagonist having high immunosuppressive action and brain cell-protecting action.

To attain the above-mentioned objects, the present inventors intensively studied to discover that the compound represented by the formula (I) below has the above-mentioned characteristics, thereby completing the present invention. That is, the present invention provides an indole derivative represented by the formula (I):

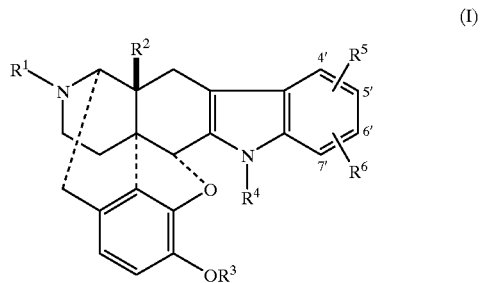

[wherein $R^1$ represents $C_1$-$C_5$ alkyl, $C_4$-$C_6$ cycloalkylalkyl, $C_5$-$C_7$ cycloalkenylalkyl, aryl, $C_1$-$C_3$ aralkyl, $C_4$-$C_5$ trans-alkenyl, allyl, $C_1$-$C_3$ furan-2-ylalkyl or $C_1$-$C_3$ thiophene-2-ylalkyl;

$R^2$ represents hydrogen, hydroxy, $C_1$-$C_5$ alkanoyloxy or $C_1$-$C_5$ alkoxy;

$R^3$ represents hydrogen, $C_1$-$C_5$ alkyl, $C_1$-$C_5$ alkanoyl or benzyl;

$R^4$ represents hydrogen, $C_1$-$C_5$ alkyl or benzyl;

$R^5$ and $R^6$, the same or different, represent hydrogen, iodine, trifluoromethyl, trifluoromethoxy, cyano, phenyl, $C_1$-$C_3$ hydroxyalkyl, $SR^7$, $SOR^7$, $SO_2R^7$, $(CH_2)_mCO_2R^7$ (wherein m represents an integer of 0–3, $R^7$ represents $C_1$-$C_5$ alkyl), $SO_2NR^8R^9$, $CONR^8R^9$, $(CH_2)_nNR^8R^9$ (wherein n represents an integer of 1–3, $R^8$ and $R^9$, the same or different, represent $C_1$-$C_5$ alkyl, or $C_4$-$C_6$ cycloalkylalkyl), isothiocyanato (NCS; bonded to one of 4'-, 6'- and 7'-positions) or nitro (bonded to one of 4'-, 6'- and 7'-positions), with the proviso that $R^5$ and $R^6$ are not simultaneously hydrogen atoms)

or $R^5$ and $R^6$ are bonded and cooperatively represent $C_3$-$C_6$ alkylene (with the proviso that one or more hydrogen atoms in the alkylene moiety may be substituted with $R^{10}$ (wherein $R^{10}$ represents $C_1$-$C_5$ alkyl, $C_1$-$C_5$ alkoxy, $C_1$-$C_5$ alkanoyl, $C_1$-$C_5$ hydroxyalkyl, $SR^7$, $SOR^7$, $SO_2R^7$ $(CH_2)_mCO_2R^7$, $SO_2NR^8R^9$, $CONR^8R^9$, $(CH_2)_nNR^8R^9$ (wherein m, n, $R^7$, $R^8$ and $R^9$ represent the same meanings as described above, respectively), and with the proviso that said alkylene is bonded to carbon atoms adjacent to each other on the benzene ring to form a ring) or $R^5$ and $R^6$ cooperatively represent —S═T—U═V— (wherein at least one of S, T, U and V represents nitrogen and the remainders represent CH (with the proviso that the hydrogen may be substituted with said $R^{10}$) which is bonded to carbon atoms adjacent to each other on the benzene ring to form a ring);

the formula (I) includes (+) isomers, (−) isomers and racemates]

and pharmaceutically acceptable acid addition salts thereof.

The present invention also provides an immunosuppressive agent, a brain cell-protecting agent, an antiallergic agent and an anti-inflammatory agent comprising as an effective ingredient the indole derivative or the pharmaceutically acceptable acid addition salt thereof according to the present invention.

The present invention further provides a process for producing the indole derivative or the pharmaceutically acceptable acid addition salt thereof according to the present invention, comprising the step of reaction of a compound of the formula (III):

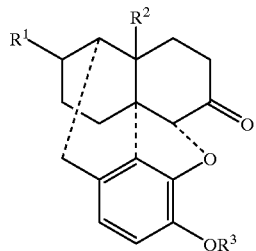

(III)

(wherein $R^1$, $R^2$ and $R^3$ represent the same meanings as described above, respectively)
with a phenylhydrazine derivative of the formula (IV):

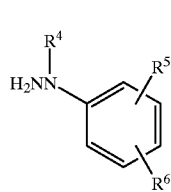

(IV)

(wherein $R^4$, $R^5$ and $R^6$ represent the same meanings as described above, respectively)
in the presence of an acid catalyst.

By the present invention, novel indole derivatives which are δ-opioid antagonists having high selectivities and activities, and phamaceutically acceptable acid addition salts thereof, as well as a process for producing the same, were provided. The indole derivatives according to the present invention have excellent immunosuppressive actions, brain cell-protecting actions, antiallergic actions and anti-inflammatory actions.

BEST MODE FOR CARRYING OUT THE INVENTION

Figure 1:
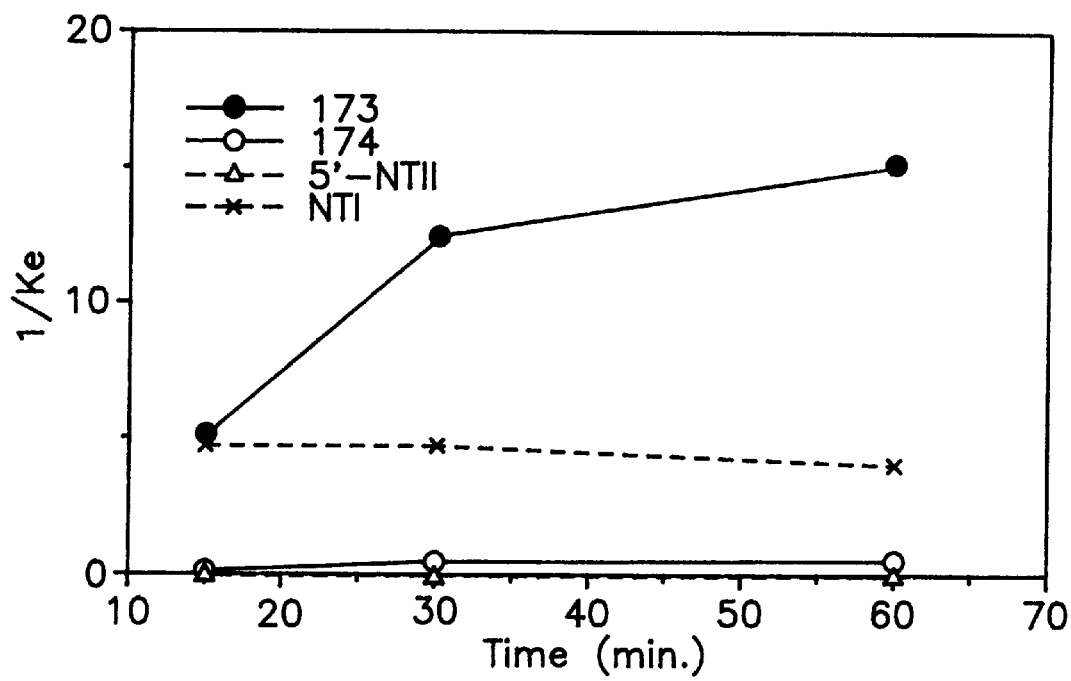
FIG. 1 shows the change in antagonist action of compounds 173 and 174 according to the present invention against DPDPE with time, which was determined by calculating Ke value at 15 minutes, 30 minutes and 1 hour from the addition of the test compounds, using MVD.

As mentioned above, the indole derivatives according to the present invention are represented by the above-described formula (I).

Among the indole derivatives represented by the above-described formula (I), those in which $R^5$ and $R^6$ are bonded each other are represented by the following formula (II):

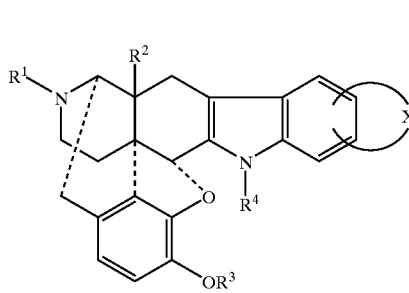

(II)

[wherein X represents $C_3$-$C_6$ alkylene (with the proviso that one or more hydrogen atoms in the alkylene moiety may be substituted with $R^{10}$ (wherein $R^{10}$ represents $C_1$-$C_5$ alkyl, $SR^7$, $SOR^7$, $SO_2R^7$, $(CH_2)_mCO_2R^7$, $SO_2NR^8R^9$, $CONR^8R^9$, $(CH_2)_nNR^8R^9$ (wherein m, n, $R^7$, $R^8$ and $R^9$ represent the same meanings as mentioned above, respectively), or —S=T—U=V— (wherein at least one of S, T, U and V represents nitrogen and the remainders represent CH (with the proviso that the hydrogen may be substituted with said $R^{10}$) which is bonded to carbon atoms adjacent to each other on the benzene ring to form a ring), the number of hydrogen atoms substituted with $R^{10}$ being appropriately selected from the range in which the substitution can be carried out].

Among the indole derivatives represented by the formula (I), those represented by the following formula (IIa) are preferred, wherein $R^1$, $R^2$, $R^3$ and $R^4$ have the same meanings as described above, respectively, $R^5$ and $R^6$ are bonded to form $C_4$ alkylene with the proviso that one or more hydrogen atoms in the alkylene moiety may be substituted with $R^{10}$ (wherein $R^{10}$ represents $C_1$-$C_5$ alkyl, $C_1$-$C_5$ alkoxy, $C_1$-$C_5$ alkanoyl, $C_1$-$C_5$ hydroxyalkyl, $SR^7$, $SOR^7$, $SO_2R^7$ $(CH_2)_mCO_2R^7$, $SO_2NR^8R^9$, $CONR^8R^9$, $(CH_2)_n NR^8R^9$ (wherein m, n, $R^7$, $R^8$ and $R^9$ represent the same meanings as described above, respectively).

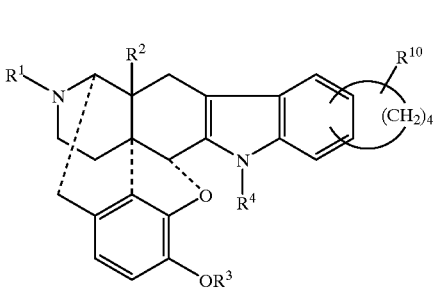

(IIa)

Preferred examples of the acid for forming pharmaceutically acceptable acid addition salts include inorganic acids such as hydrochloric acid, sulfuric acid, hydrobromic acid, hydriodic acid and phosphoric acid; organic carboxylic acids such as acetic acid, lactic acid, citric acid, oxalic acid, glutaric acid, malic acid, tartaric acid, fumaric acid, mandelic acid, maleic acid, benzoic acid and phthalic acid; and organic sulfonic acids such as methanesulfonic acid, ethanesulfonic acid, benzenesulfonic acid, p-toluenesulfonic acid and the like. Among these, hydrochloric acid, phosphoric acid, tartaric acid and methanesulfonic acid are preferred, although not limited thereto.

Compound 1 represented by the formula (I) wherein $R^1$ is cyclopropylmethyl, $R^2$ is hydroxy, $R^3$ is hydrogen, $R^4$ is hydrogen and $R^5$ is 5'-iodine, that is, the compound represented by the following formula:

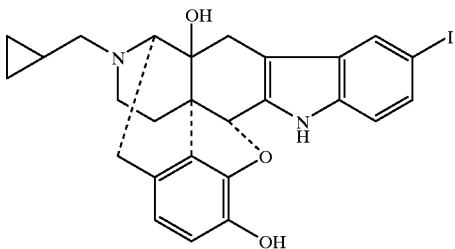

is named 17-cyclopropylmethyl-6,7-didehydro-4,5α-epoxy-3,14β-dihydroxy-5'-iodo-6,7-2',3'-indolomorphinan in accordance with the nomenclature of NTI. In accordance with this nomenclature, specific examples of the compounds according to the present invention include 17-cyclopropylmethyl-6,7-didehydro-4,5α-epoxy-3,14β-dihydroxy-4'-iodo-6,7-2',3,-indolomorphinan, 17-cyclopropylmethyl-6,7-didehydro-4,5α-epoxy-3,14β-dihydroxy-6'-iodo-6,7-2',3'-indolomorphinan, 17-cyclopropylmethyl-6,7-didehydro-4,5α-epoxy-3,14β-dihydroxy-7'-iodo-6,7-2',3'-indolomorphinan, 17-allyl-6,7-didehydro-4,5α-epoxy-3,14β-dihydroxy-4'-iodo-6,7-2',3'-indolomorphinan, 17-allyl-6,7-didehydro-4,5α-epoxy-3,14β-dihydroxy-5'-iodo-6,7-2',3'-indolomorphinan, 17-allyl-6,7-didehydro-4,5α-epoxy-3,14β-dihydroxy-6'-iodo-6,7-2',3'-indolomorphinan, 17-allyl-6,7-didehydro-4,5α-epoxy-3,14β-dihydroxy-7'-iodo-6,7-2',3'-indolomorphinan, 17-cyclopropylmethyl-6,7-didehydro-4,5α-epoxy-3,14β-dihydroxy-4'-trifluoromethyl-6,7-2',3'-indolomorphinan, 17-cyclopropylmethyl-6,7-didehydro-4,5α-epoxy-3,14β-dihydroxy-5'-trifluoromethyl-6,7-2',3'-indolomorphinan, 17-cyclopropylmethyl-6,7-didehydro-4,5α-epoxy-3,14β-dihydroxy-6'-trifluoromethyl-6,7-2',3'-indolomorphinan, 17-cyclopropylmethyl-6,7-didehydro-4,5α-epoxy-3,14β-dihydroxy-7'-trifluoromethyl-6,7-2',3'-indolomorphinan, 17-allyl-6,7-didehydro-4,5α-epoxy-3,14β-dihydroxy-4'-trifluoromethyl-6,7-2',3'-indolomorphinan, 17-allyl-6,7-didehydro-4,5α-epoxy-3,14β-dihydroxy-5'-trifluoromethyl-6,7-2',3'-indolomorphinan, 17-allyl-6,7-didehydro-4,5α-epoxy-3,14β-dihydroxy-6'-trifluoromethyl-6,7-2',3'-indolomorphinan, 17-allyl-6,7-didehydro-4,5α-epoxy-3,14β-dihydroxy-7'-trifluoromethyl-6,7-2',3'-indolomorphinan, 17-cyclopropylmethyl-6,7-didehydro-4,5α-epoxy-3,14β-dihydroxy-4'-trifluoromethoxy-6,7-2',3'-indolomorphinan, 17-cyclopropylmethyl-6,7-didehydro-4,5α-epoxy-3,14β-dihydroxy-5'-trifluoromethoxy-6,7-2',3'-indolomorphinan, 17-cyclopropylmethyl-6,7-didehydro-4,5α-epoxy-3,14β-dihydroxy-6'-trifluoromethoxy-6,7-2',3'-indolomorphinan, 17-cyclopropylmethyl-6,7-didehydro-4,5α-epoxy-3,14β-dihydroxy-7'-trifluoromethoxy-6,7-2',3'-indolomorphinan, 17-allyl-6,7-didehydro-4,5α-epoxy-3,14β-dihydroxy-4'-trifluoromethoxy-6,7-2',3'-indolomorphinan, 17-allyl-6,7-didehydro-4,5α-epoxy-3,14β-dihydroxy- 5'-trifluoromethoxy-6,7-2',3'-indolomorphinan, 17-allyl-6,7-didehydro-4,5α-epoxy-3,14β-dihydroxy-6'-trifluoromethoxy-6,7-2',3'-indolomorphinan, 17-allyl-6,7-didehydro-4,5α-epoxy-3,14β-dihydroxy-7'-trifluoromethoxy-6,7-2',3'-indolomorphinan, 17-cyclopropylmethyl-6,7-didehydro-4,5α-epoxy-3,14β-dihydroxy-4'-cyano-6,7-2',3'-indolomorphinan, 17-cyclopropylmethyl-6,7-didehydro-4,5α-epoxy-3,14β-dihydroxy-5'-cyano-6,7-2',3'-indolomorphinan, 17-cyclopropylmethyl-6,7-didehydro-4,5α-epoxy-3,14β-dihydroxy-6'-cyano-6,7-2',3'-indolomorphinan, 17-cyclopropylmethyl-6,7-didehydro-4,5α-epoxy-3,14β-dihydroxy-7'-cyano-6,7-2',3'-indolomorphinan, 17-allyl-6,7-didehydro-4,5α-epoxy-3,14β-dihydroxy-4'-cyano-6,7-2',3'-indolomorphinan, 17-allyl-6,7-didehydro-4,5α-epoxy-3,14β-dihydroxy-5'-cyano-6,7-2',3'-indolomorphinan, 17-allyl-6,7-didehydro-4,5α-epoxy-3,14β-dihydroxy-6'-cyano-6,7-2',3'-indolomorphinan, 17-allyl-6,7-didehydro-4,5α-epoxy-3,14β-dihydroxy-7'-cyano-6,7-2',3'-indolomorphinan, 17-cyclopropylmethyl-6,7-didehydro-4,5α-epoxy-3,14β-dihydroxy-4'-phenyl-6,7-2',3'-indolomorphinan, 17-cyclopropylmethyl-6,7-didehydro-4,5α-epoxy-3,14β-dihydroxy-5'-phenyl-6,7-2',3'-indolomorphinan, 17-cyclopropylmethyl-6,7-didehydro-4,5α-epoxy-3,14β-dihydroxy-6'-phenyl-6,7-2',3'-indolomorphinan, 17-cyclopropylmethyl-6,7-didehydro-4,5α-epoxy-3,14β-dihydroxy-7'-phenyl-6,7-2',3 '-indolomorphinan, 17-allyl-6,7-didehydro-4,5α-epoxy-3,14β-dihydroxy-4'-phenyl-6,7-2',3'-indolomorphinan, 17-allyl-6,7-didehydro-4,5α-epoxy-3,14β-dihydroxy-5'-phenyl-6,7-2',3'-indolomorphinan, 17-allyl-6,7-didehydro-4,5α-epoxy-3,14β-dihydroxy-6'-phenyl-6,7-2',3'-indolomorphinan, 17-allyl-6,7-didehydro-4,5α-epoxy-3,14β-dihydroxy-7'-phenyl-6,7-2',3'-indolomorphinan, 17-cyclopropylmethyl-6,7-didehydro-4,5α-epoxy-3,14β-dihydroxy-4'-hydroxymethyl-6,7-2',3'-indolomorphinan, 17-cyclopropylmethyl-6,7-didehydro-4,5α-epoxy-3,14β-dihydroxy-5'-hydroxymethyl-6,7-2',3'-indolomorphinan, 17-cyclopropylmethyl-6,7-didehydro-4,5α-epoxy-3,14β-dihydroxy-6'-hydroxymethyl-6,7-2',3'-indolomorphinan, 17-cyclopropylmethyl-6,7-didehydro-4,5α-epoxy-3,14β-dihydroxy-7'-hydroxymethyl-6,7-2',3'-indolomorphinan, 17-allyl-6,7-didehydro-4,5α-epoxy-3,14β-dihydroxy-4'-hydroxymethyl-6,7-2',3'-indolomorphinan, 17-allyl-6,7-didehydro-4,5α-epoxy-3,14β-dihydroxy-5'-hydroxymethyl-6,7-2',3'-indolomorphinan, 17-allyl-6,7-didehydro-4,5α-epoxy-3,14β-dihydroxy-6β-hydroxymethyl-6,7-2',3'-indolomorphinan, 17-allyl-6,7-didehydro-4,5α-epoxy-3,14β-dihydroxy-7'-hydroxymethyl-6,7-2',3'-indolomorphinan, 17-cyclopropylmethyl-6,7-didehydro-4,5α-epoxy-3,14β-dihydroxy-4'-(2-hydroxyethyl)-6,7-2',3'-indolomorphinan, 17-cyclopropylmethyl-6,7-didehydro-4,5α-epoxy-3,14β-dihydroxy-5'-( 2-hydroxyethyl)-6,7-2',3'-indolomorphinan, 17-cyclopropylmethyl-6,7-didehydro-4,5α-epoxy-3,14β-dihydroxy-6'-(2-hydroxyethyl)-6,7-2',3'-indolomorphinan, 17-cyclopropylmethyl-6,7-didehydro-4,5α-epoxy-3,14β-dihydroxy-7'-(2-hydroxyethyl)-6,7-2',3'-indolomorphinan, 17-allyl-6,7-didehydro-4,5α-epoxy-3,14β-dihydroxy-4'-(2-hydroxyethyl)-6,7-2',3'-indolomorphinan, 17-allyl-6,7-didehydro-4,5α-epoxy-3,14β-dihydroxy-5'-(2-hydroxyethyl)-6,7-2',3'-indolomorphinan, 17-allyl-6,7-didehydro-4,5α-epoxy-3,14β-dihydroxy-6'-(2-hydroxyethyl)-6,7-2',3'-indolomorphinan, 17-allyl-6,7-didehydro-4,5α-epoxy-3,14β-dihydroxy-7'-(2-hydroxyethyl)-6,7-2',3'-indolomorphinan, 17-cyclopropylmethyl-6,7-didehydro-4,5α-epoxy-3,14β-dihydroxy-4'-methylthio-6,7-2',3'-indolomorphinan, 17-cyclopropylmethyl-6,7-didehydro-4,5α-epoxy-3,14β-dihydroxy-5'-methylthio-6,7-2',3'-indolomorphinan, 17-cyclopropylmethyl-6,7-didehydro-4,5α-epoxy-3,14β-dihydroxy-6'-methylthio-6,7-2',3'-indolomorphinan, 17-cyclopropylmethyl-6,7-didehydro-4,5α-epoxy-3,14β-dihydroxy-7'-methylthio-6,7-2',3'-indolomorphinan, 17-allyl-6,7-didehydro-4,5α-epoxy-3,14β-dihydroxy-4'-methylthio-6,7-2',3'-indolomorphinan, 17-allyl-6,7-didehydro-4,5α-epoxy-3,14β-dihydroxy-5'-methylthio-6,7-2',3'-indolomorphinan, 17-allyl-6,7-didehydro-4,5α-epoxy-3,14β-dihydroxy-6'-methylthio-6,7-

2',3'-indolomorphinan, 17-allyl-6,7-didehydro-4,5α-epoxy-3,14β-dihydroxy-7'-methylthio-6,7-2',3'-indolomorphinan, 17-cyclopropylmethyl-6,7-didehydro-4,5α-epoxy-3,14β-dihydroxy-4'-methylsulfonyl-6,7-2',3'-indolomorphinan, 17-cyclopropylmethyl-6,7-didehydro-4,5α-epoxy-3,14β-dihydroxy-5'-methylsulfonyl-6,7-2',3'-indolomorphinan, 17-cyclopropylmethyl-6,7-didehydro-4,5α-epoxy-3,14β-dihydroxy-6'-methylsulfonyl-6,7-2',3'-indolomorphinan, 17-cyclopropylmethyl-6,7-didehydro-4,5α-epoxy-3,14β-dihydroxy-7'-methylsulfonyl-6,7-2',3'-indolomorphinan, 17-allyl-6,7-didehydro-4,5α-epoxy-3,14β-dihydroxy-4'-methylsulfonyl-6,7-2',3'-indolomorphinan, 17-allyl-6,7-didehydro-4,5α-epoxy-3,14β-dihydroxy-5'-methylsulfonyl-6,7-2',3'-indolomorphinan, 17-allyl-6,7-didehydro-4,5α-epoxy-3,14β-dihydroxy-6'-methylsulfonyl-6,7-2',3'-indolomorphinan, 17-allyl-6,7-didehydro-4,5α-epoxy-3,14β-dihydroxy-7'-methylsulfonyl-6,7-2',3'-indolomorphinan, 17-cyclopropylmethyl-6,7-didehydro-4,5α-epoxy-3,14β-dihydroxy-4'-methoxycarbonyl-6,7-2',3'-indolomorphinan, 17-cyclopropylmethyl-6,7-didehydro-4,5α-epoxy-3,14β-dihydroxy-5'-methoxycarbonyl-6,7-2',3'-indolomorphinan, 17-cyclopropylmethyl-6,7-didehydro-4,5α-epoxy-3,14β-dihydroxy-6'-methoxycarbonyl-6,7-2',3'-indolomorphinan, 17-cyclopropylmethyl-6,7-didehydro-4,5α-epoxy-3,14β-dihydroxy-7'-methoxycarbonyl-6,7-2',3'-indolomorphinan, 17-allyl-6,7-didehydro-4,5α-epoxy-3,14β-dihydroxy-4'-methoxycarbonyl-6,7-2',3'-indolomorphinan, 17-allyl-6,7-didehydro-4,5α-epoxy-3,14β-dihydroxy-5'-methoxycarbonyl-6,7-2',3'-indolomorphinan, 17-allyl-6,7-didehydro-4,5α-epoxy-3,14β-dihydroxy-6'-methoxycarbonyl-6,7-2',3'-indolomorphinan, 17-allyl-6,7-didehydro-4,5α-epoxy-3,14β-dihydroxy-7'-methoxycarbonyl-6,7-2',3'-indolomorphinan, 17-cyclopropylmethyl-6,7-didehydro-4,5α-epoxy-3,14β-dihydroxy-4'-ethoxycarbonyl-6,7-2',3'-indolomorphinan, 17-cyclopropylmethyl-6,7-didehydro-4,5α-epoxy-3,14β-dihydroxy-5'-ethoxycarbonyl-6,7-2',3'-indolomorphinan, 17-cyclopropylmethyl-6,7-didehydro-4,5α-epoxy-3,14β-dihydroxy-6'-ethoxycarbonyl-6,7-2',3'-indolomorphinan, 17-cyclopropylmethyl-6,7-didehydro-4,5α-epoxy-3,14β-dihydroxy-7'-ethoxycarbonyl-6,7-2',3'-indolomorphinan, 17-allyl-6,7-didehydro-4,5α-epoxy-3,14β-dihydroxy-4'-ethoxycarbonyl-6,7-2',3'-indolomorphinan, 17-allyl-6,7-didehydro-4,5α-epoxy-3,14β-dihydroxy-5'-ethoxycarbonyl-6,7-2',3'-indolomorphinan, 17-allyl-6,7-didehydro-4,5α-epoxy-3,14β-dihydroxy-6'-ethoxycarbonyl-6,7-2',3'-indolomorphinan, 17-allyl-6,7-didehydro-4,5α-epoxy-3,14β-dihydroxy-7'-ethoxycarbonyl-6,7-2',3'-indolomorphinan, 17-cyclopropylmethyl-6,7-didehydro-4,5α-epoxy-3,14β-dihydroxy-4'-ethoxycarbonylmethyl-6,7-2',3'-indolomorphinan, 17-cyclopropylmethyl-6,7-didehydro-4,5α-epoxy-3,14β-dihydroxy-5'-ethoxycarbonylethyl-6,7-2',3'-indolomorphinan, 17-cyclopropylmethyl-6,7-didehydro-4,5α-epoxy-3,14β-dihydroxy-6'-ethoxycarbonylmethyl-6,7-2',3'-indolomorphinan, 17-cyclopropylmethyl-6,7-didehydro-4,5α-epoxy-3,14β-dihydroxy-7'-ethoxycarbonylmethyl-6,7-2',3'-indolomorphinan, 17-allyl-6,7-didehydro-4,5α-epoxy-3,14β-dihydroxy-4'-ethoxycarbonylmethyl-6,7-2',3'-indolomorphinan, 17-allyl-6,7-didehydro-4,5α-epoxy-3,14β-dihydroxy-5'-ethoxycarbonylmethyl-6,7-2',3'-indolomorphinan, 17-allyl-6,7-didehydro-4,5α-epoxy-3,14β-dihydroxy-6'-ethoxycarbonylmethyl-6,7-2',3'-indolomorphinan, 17-allyl-6,7-didehydro-4,5α-epoxy-3,14β-dihydroxy-7'-ethoxycarbonylmethyl-6,7-2',3'-indolomorphinan, 17-cyclopropylmethyl-6,7-didehydro-4,5α-epoxy-3,14β-dihydroxy-4'-methoxycarbonylmethyl-6,7-2',3'-indolomorphinan, 17-cyclopropylmethyl-6,7-didehydro-4,5α-epoxy-3,14β-dihydroxy-5'-methoxycarbonylmethyl-6,7-2',3'-indolomorphinan, 17-cyclopropylmethyl-6,7-didehydro-4,5α-epoxy-3,14β-dihydroxy-6'-methoxycarbonylmethyl-6,7-2',3'-indolomorphinan, 17-cyclopropylmethyl-6,7-didehydro-4,5α-epoxy-3,14β-dihydroxy-7'-methoxycarbonylmethyl-6,7-2',3'-indolomorphinan, 17-allyl-6,7-didehydro-4,5α-epoxy-3,14β-dihydroxy-4'-methoxycarbonylmethyl-6,7-2',3'-indolomorphinan, 17-allyl-6,7-didehydro-4,5α-epoxy-3,14β-dihydroxy-5'-methoxycarbonylmethyl-6,7-2',3'-indolomorphinan, 17-allyl-6,7-didehydro-4,5α-epoxy-3,14β-dihydroxy-6'-methoxycarbonylmethyl-6,7-2',3'-indolomorphinan, 17-allyl-6,7-didehydro-4,5α-epoxy-3,14β-dihydroxy-7'-methoxycarbonylmethyl-6,7-2',3'-indolomorphinan, 17-cyclopropylmethyl-6,7-didehydro-4,5α-epoxy-3,14β-dihydroxy-4'-sulfamoyl-6,7-2',3'-indolomorphinan, 17-cyclopropylmethyl-6,7-didehydro-4,5α-epoxy-3,14β-dihydroxy-5'-sulfamoyl-6,7-2',3'-indolomorphinan, 17-cyclopropylmethyl-6,7-didehydro-4,5α-epoxy-3,14β-dihydroxy-6'-sulfamoyl-6,7-2',3'-indolomorphinan, 17-cyclopropylmethyl-6,7-didehydro-4,5α-epoxy-3,14β-dihydroxy-7'-sulfamoyl-6,7-2',3'-indolomorphinan, 17-allyl-6,7-didehydro-4,5α-epoxy-3,14β-dihydroxy-4'-sulfamoyl-6,7-2',3'-indolomorphinan, 17-allyl-6,7-didehydro-4,5α-epoxy-3,14β-dihydroxy-5'-sulfamoyl-6,7-2',3'-indolomorphinan, 17-allyl-6,7-didehydro-4,5α-epoxy-3,14β-dihydroxy-6'-sulfamoyl-6,7-2',3'-indolomorphinan, 17-allyl-6,7-didehydro-4,5α-epoxy-3,14β-dihydroxy-7'-sulfamoyl-6,7-2',3'-indolomorphinan, 17-cyclopropylmethyl-6,7-didehydro-4,5α-epoxy-3,14β-dihydroxy-4'-(N,N-dimethylsulfamoyl)-6,7-2',3'-indolomorphinan, 17-cyclopropylmethyl-6,7-didehydro-4,5α-epoxy-3,14β-dihydroxy-5'-(N,N-dimethylsulfamoyl)-6,7-2',3'-indolomorphinan, 17-cyclopropylmethyl-6,7-didehydro-4,5α-epoxy-3,14β-dihydroxy-6'-(N,N-dimethylsulfamoyl)-6,7-2',3'-indolomorphinan, 17-cyclopropylmethyl-6,7-didehydro-4,5α-epoxy-3,14β-dihydroxy-7'-(N,N-dimethylsulfamoyl)-6,7-2',3'-indolomorphinan, 17-allyl-6,7-didehydro-4,5α-epoxy-3,14β-dihydroxy-4'-(N,N-dimethylsulfamoyl)-6,7-2',3'-indolomorphinan, 17-allyl-6,7-didehydro-4,5α-epoxy-3,14β-dihydroxy-5'-(N,N-dimethylsulfamoyl)-6,7-2',3'-indolomorphinan, 17-allyl-6,7-didehydro-4,5α-epoxy-3,14β-dihydroxy-6'-(N,N-dimethylsulfamoyl)-6,7-2',3'-indolomorphinan, 17-allyl-6,7-didehydro-4,5α-epoxy-3,14β-dihydroxy-7'-(N,N-dimethylsulfamoyl)-6,7-2',3'-indolomorphinan, 17-cyclopropylmethyl-6,7-didehydro-4,5α-epoxy-3,14β-dihydroxy-4'-(N-cyclopropylmethylsulfamoyl)-6,7-2',3'-indolomorphinan, 17-cyclopropylmethyl-6,7-didehydro-4,5α-epoxy-3,14β-dihydroxy-5'-(N-cyclopropylmethylsulfamoyl)-6,7-2',3'-indolomorphinan, 17-cyclopropylmethyl-6,7-didehydro-4,5α-epoxy-3,14β-dihydroxy-6'-(N-cyclopropylmethylsulfamoyl)-6,7-2',3'-indolomorphinan, 17-cyclopropylmethyl-6,7-didehydro-4,5α-epoxy-3,14β-dihydroxy-7'-(N-cyclopropylmethylsulfamoyl)-6,7-2',3'-indolomorphinan, 17-allyl-6,7-didehydro-4,5α-epoxy-3,14β-dihydroxy-4'-(N-cyclopropylmethylsulfamoyl)-6,7-2',3'-indolomorphinan, 17-allyl-6,7-didehydro-4,5α-epoxy-3,14β-dihydroxy-5'-(N-cyclopropylmethylsulfamoyl)-6,7-2',3'-indolomorphinan, 17-allyl-6,7-didehydro-4,5α-epoxy-3,14β-dihydroxy-6'-(N-cyclopropylmethylsulfamoyl)-6,7-2',3'-indolomorphinan, 17-allyl-6,7-didehydro-4,5α-epoxy-3,14β-dihydroxy-7'-(N-cyclopropylmethylsulfamoyl)-6,7-2',3'-indolomorphinan, 17-cyclopropylmethyl-6,7-didehydro-4,5α-epoxy-3,14β-dihydroxy-4'-carbamoyl- 6,7-2',3'-indolomorphinan, 17-cyclopropylmethyl-6,7-didehydro-4,5α-epoxy-3,14β-dihydroxy-5'-carbamoyl-6,7-2',3'-indolomorphinan, 17-cyclopropylmethyl-6,7-didehydro-4,5α-epoxy-3,14β-dihydroxy-6'-carbamoyl-6,7-2',3'-indolomorphinan, 17-cyclopropylmethyl-6,7-didehydro-4,5α-epoxy-3,14β-dihydroxy-7'-carbamoyl-6,7-2',3'-indolomorphinan, 17-allyl-6,7-didehydro-4,5α-epoxy-3,14β-dihydroxy-4'-carbamoyl-6,7-2',3'-indolomorphinan, 17-allyl-6,7-didehydro-4,5α-epoxy-3,14β-dihydroxy-5'-carbamoyl-6,7-2',3'-indolomorphinan, 17-allyl-6,7-didehydro-4,5α-epoxy-3,14β-dihydroxy-6'-carbamoyl-6,7-2',3'-indolomorphinan, 17-allyl-6,7-didehydro-4,5α-epoxy-3,14β-dihydroxy-7'-carbamoyl-6,7-2',3'-indolomorphinan, 17-cyclopropylmethyl-6,7-didehydro-4,5α-epoxy-3,14β-dihydroxy-4'-(N,N-dimethylcarbamoyl)-6,7-2',3'-indolomorphinan, 17-cyclopropylmethyl-6,7-didehydro-4,5α-epoxy-3,14β-dihydroxy-5'-(N,N-dimethylcarbamoyl)-6,7-2',3'-indolomorphinan, 17-cyclopropylmethyl-6,7-didehydro-4,5α-epoxy-3,14β-dihydroxy-6'-(N,N-dimethylcarbamoyl)-6,7-2',3'-indolomorphinan, 17-cyclopropylmethyl-6,7-didehydro-4,5α-epoxy-3,14β-dihydroxy-7'-(N,N-dimethylcarbamoyl)-6,7-2',3'-indolomorphinan, 17-allyl-6,7-didehydro-4,5α-epoxy-3,14β-dihydroxy-4'-(N,N-dimethylcarbamoyl)-6,7-2',3'-indolomorphinan, 17-allyl-6,7-didehydro-4,5α-epoxy-3,14β-dihydroxy-5'-(N,N-dimethylcarbamoyl)-6,7-2',3'-indolomorphinan, 17-allyl-6,7-didehydro-4,5α-epoxy-3,14β-dihydroxy-6'-(N,N-dimethylcarbamoyl)-6,7-2',13'-indolomorphinan, 17-allyl-6,7-didehydro-4,5α-epoxy-3,14β-dihydroxy-7'-(N,N-dimethylcarbamoyl)-6,7-2',3'-indolomorphinan, 17-cyclopropylmethyl-6,7-didehydro-4,5α-epoxy-3,14β-dihydroxy-4'-(N-cyclopropylmethylcarbamoyl)-6,7-2',3'-indolomorphinan, 17-cyclopropylmethyl-6,7-didehydro-4,5α-epoxy-3,14β-dihydroxy-5'-(N-cyclopropylmethylcarbamoyl)-6,7-2',3'-indolomorphinan, 17-cyclopropylmethyl-6,7-didehydro-4,5α-epoxy-3,14β-dihydroxy-6'-(N-cyclopropylmethylcarbamoyl)-6,7-2',3'-indolomorphinan, 17-cyclopropylmethyl-6,7-didehydro-4,5α-epoxy-3,14β-dihydroxy-7'-(N-cyclopropylmethylcarbamoyl)-6,7-2',3'-indolomorphinan, 17-allyl-6,7-didehydro-4,5α-epoxy-3,14β-dihydroxy-4'-(N-cyclopropylmethylcarbamoyl)-6,7-2',3'-indolomorphinan, 17-allyl-6,7-didehydro-4,5α-epoxy-3,14β-dihydroxy-5'-(N-cyclopropylmethylcarbamoyl)-6,7-2',3'-indolomorphinan, 17-allyl-6,7-didehydro-4,5α-epoxy-3,14β-dihydroxy-6'-(N-cyclopropylmethylcarbamoyl)-6,7-2',3'-indolomorphinan, 17-allyl-6,7-didehydro-4,5α-epoxy-3,14β-dihydroxy-7'-(N-cyclopropylmethylcarbamoyl)-6,7-2',3'-indolomorphinan, 17-cyclopropylmethyl-6,7-didehydro-4,5α-epoxy-3,14β-dihydroxy-4'-(N,N-dimethylaminomethyl)-6,7-2',3'-indolomorphinan, 17-cyclopropylmethyl-6,7-didehydro-4,5α-epoxy-3,14β-dihydroxy-5'-(N,N-dimethylaminomethyl)-6,7-2',3'-indolomorphinan, 17-cyclopropylmethyl-6,7-didehydro-4,5α-epoxy-3,14β-dihydroxy-6'-(N,N-dimethylaminomethyl)-6,7-2',3'-indolomorphinan, 17-cyclopropylmethyl-6,7-didehydro-4,5α-epoxy-3,14β-dihydroxy-7'-(N,N-dimethylaminomethyl)-6,7-2',3'-indolomorphinan, 17-allyl-6,7-didehydro-4,5α-epoxy-3,14β-dihydroxy-4'-(N,N-dimethylaminomethyl)-6,7-2',3'-indolomorphinan, 17-allyl-6,7-didehydro-4,5α-epoxy-3,14β-dihydroxy-5'-(N,N-dimethylaminomethyl)-6,7-2',3'-indolomorphinan, 17-allyl-6,7-didehydro-4,5α-epoxy-3,14β-dihydroxy-6'-(N,N-dimethylaminomethyl)-6,7-2',3'-indolomorphinan, 17-allyl-6,7-didehydro-4,5α-epoxy-3,14β-dihydroxy-7'-(N,N-dimethylaminomethyl)-6,7-2',3'-indolomorphinan, 17-cyclopropylmethyl-6,7-didehydro-4,5α-epoxy-3,14β-dihydroxy-4'-(N-cyclopropylmethylaminomethyl)-6,7-2',3'-indolomorphinan, 17-cyclopropylmethyl-6,7-didehydro-4,5α-epoxy-3,14β-dihydroxy-5'-(N-cyclopropylmethylaminomethyl)-6,7-2',3'-indolomorphinan, 17-cyclopropylmethyl-6,7-didehydro-4,5α-epoxy-3,14β-dihydroxy-6'-(N-cyclopropylmethylaminomethyl)-6,7-2',3'-indolomorphinan, 17-cyclopropylmethyl-6,7-didehydro-4,5α-epoxy-3,14β-dihydroxy-7'-(N-cyclopropylmethylaminomethyl)-6,7-2',3'-indolomorphinan, 17-allyl-6,7-didehydro-4,5α-epoxy-3,14β-dihydroxy-4'-(N-cyclopropylmethylaminomethyl)-6,7-2',3'-indolomorphinan, 17-allyl-6,7-didehydro-4,5α-epoxy-3,14β-dihydroxy-5'-(N-cyclopropylmethylaminomethyl)-6,7-2',3'-indolomorphinan, 17-allyl-6,7-didehydro-4,5α-epoxy-3,14β-dihydroxy-6'-(N-cyclopropylmethylaminomethyl)-6,7-2',3'-indolomorphinan, 17-allyl-6,7-didehydro-4,5α-epoxy-3,14β-dihydroxy-7'-(N-cyclopropylmethylaminomethyl)-6,7-2',3'-indolomorphinan, 17-cyclopropylmethyl-6,7-didehydro-4,5α-epoxy-3,14β-dihydroxy-4'-[2-(N,N-dimethylamino)ethyl)]-6,7-2',3'-indolomorphinan, 17-cyclopropylmethyl-6,7-didehydro-4,5α-epoxy-3,14β-dihydroxy-5'-[2-(N,N-dimethylamino)ethyl)]-6,7-2',3'-indolomorphinan, 17-cyclopropylmethyl-6,7-didehydro-4,5α-epoxy-3,14β-dihydroxy-6'-[2-(N,N-dimethylamino)ethyl)]-6,7-2',3'-indolomorphinan, 17-cyclopropylmethyl-6,7-didehydro-4,5α-epoxy-3,14β-dihydroxy-7'-[2-(N,N-dimethylamino)ethyl)]-6,7-2',3'-indolomorphinan, 17-allyl-6,7-didehydro-4,5α-epoxy-3,14β-dihydroxy-4'-[2-(N,N-dimethylamino)ethyl)]-6,7-2',3'-indolomorphinan, 17-allyl-6,7-didehydro-4,5α-epoxy-3,14β-dihydroxy-5'-[2-(N,N-dimethylamino)ethyl)]-6,7-2',3'-indolomorphinan, 17-allyl-6,7-didehydro-4,5α-epoxy-3,14β-dihydroxy-6'-[2-(N,N-dimethylamino)ethyl)]-6,7-2',3'-indolomorphinan, 17-allyl-6,7-didehydro-4,5α-epoxy-3,149-dihydroxy-7'-[2-(N,N-dimethylamino)ethyl)]-6,7-2',3'-indolomorphinan, 17-cyclopropylmethyl-6,7-didehydro-4,5α-epoxy-3,14β-dihydroxy-4'-[2-(N-cyclopropylmethylamino)ethyl)]-6,7-2',3'-indolomorphinan, 17-cyclopropylmethyl-6,7-didehydro-4,5α-epoxy-3,14β-dihydroxy-5'-[2-(N-cyclopropylmethylamino)ethyl)]-6,7-2',3'-indolomorphinan, 17-cyclopropylmethyl-6,7-didehydro-4,5α-epoxy-3,14β-dihydroxy-6'-[2-(N-cyclopropylmethylamino)ethyl)]-6,7-2',3'-indolomorphinan, 17-cyclopropylmethyl-6,7-didehydro-4,5α-epoxy-3,14β-dihydroxy-7'-[2-(N-cyclopropylmethylamino)ethyl)]-6,7-2',3'-indolomorphinan, 17-allyl-6,7-didehydro-4,5α-epoxy-3,14β-dihydroxy-4'-[2-(N-cyclopropylmethylamino)ethyl)]-6,7-2',3'-indolomorphinan, 17-allyl-6,7-didehydro-4,5α-epoxy-3,14β-dihydroxy-5'-[2-(N-cyclopropylmethylamino)ethyl)]-6,7-2',3'-indolomorphinan, 17-allyl-6,7-didehydro-4,5α-epoxy-3,14β-dihydroxy-6'-[2-(N-cyclopropylmethylamino)ethyl)]-6,7-2',3'-indolomorphinan, 17-allyl-6,7-didehydro-4,5α-epoxy-3,14β-dihydroxy-7'-[2-(N-cyclopropylmethylamino)ethyl)]-6,7-2',3'-indolomorphinan, 17-cyclopropylmethyl-6,7-didehydro-4,5α-epoxy-3,14β-dihydroxy-4'-isothiocyanato-6,7-2',3'-indolomorphinan, 17-cyclopropylmethyl-6,7-didehydro-4,5α-epoxy-3,14β-dihydroxy-6'-isothiocyanato-6,7-2',3'-indolomorphinan, 17-cyclopropylmethyl-6,7-didehydro-4,5α-epoxy-3,14β-dihydroxy-7'-isothiocyanato-6,7-2',3'-indolomorphinan, 17-allyl-6,7-didehydro-4,5α-epoxy-3,14β-dihydroxy-4'-isothiocyanato-6,7-2',3'-indolomorphinan, 17-allyl-6,7-didehydro-4,5α-epoxy-3,14β-dihydroxy-6'-isothiocyanato-6,7-2',3'-indolomorphinan, 17-allyl-6,7-didehydro-4,5α-epoxy-3,14β-dihydroxy-7'-isothiocyanato-6,7-2',3'-indolomorphinan, 17-cyclopropylmethyl-6,7-didehydro-4,5α-epoxy-3,14β-dihydroxy-4'-nitro-6,7-2',3'- indolomorphinan, 17-cyclopropylmethyl-6,7-didehydro-4,5α-epoxy-3,14β-dihydroxy-6'-nitro-6,7-2',3'-indolomorphinan, 17-cyclopropylmethyl-6,7-didehydro-4,5α-epoxy-3,14β-dihydroxy-7'-nitro-6,7-2',3'-indolomorphinan, 17-allyl-6,7-didehydro-4,5α-epoxy-3,14β-dihydroxy-4'-nitro-6,7-2',3'-indolomorphinan, 17-allyl-6,7-didehydro-4,5α-epoxy-3,14β-dihydroxy-6'-nitro-6,7-2',3'-indolomorphinan, 17-allyl-6,7-didehydro-4,5α-epoxy-3,14β-dihydroxy-7'-nitro-6,7-2',3'-indolomorphinan, 17-cyclopropylmethyl-6,7-didehydro-4,5α-epoxy-3,14β-dihydroxy-1'-methyl-5'-[2-(N,N-dimethylamino)ethyl]-6,7-2',3'-indolomorphinan, 17-cyclopropylmethyl-6,7-didehydro-4,5α-epoxy-3,14β-dihydroxy-1'-methyl-5'-(N,N-dimethylamino)methyl-6,7-2',3'-indolomorphinan, 17-cyclopropylmethyl-6,7-didehydro-4,5α-epoxy-3,14β-dihydroxy-1'-methyl-5'-phenyl-6,7-2',3'-indolomorphinan, 17-cyclopropylmethyl-6,7-didehydro-4,5α-epoxy-3,14β-dihydroxy-1'-methyl-5'-methylthio-6,7-2',3'-indolomorphinan, 17-allyl-6,7-didehydro-4,5α-epoxy-3,14β-dihydroxy-1'-methyl-5'-[2-(N,N-dimethylamino)ethyl]-6,7-2',3'-indolomorphinan, 17-allyl-6,7-didehydro-4,5α-epoxy-3,14β-dihydroxy-1'-methyl-5'-(N,N-dimethylamino)methyl-6,7-2',3'-indolomorphinan, 17-allyl-6,7-didehydro-4,5α-epoxy-3,14β-dihydroxy-1'-methyl-5'-phenyl-6,7-2',3'-indolomorphinan, 17-allyl-6,7-didehydro-4,5α-epoxy-3,14β-dihydroxy-1'-methyl-5'-methylthio-6,7-2',3'-indolomorphinan, 17-cyclopropylmethyl-6,7-didehydro-4,5α-epoxy-3,14β-dihydroxy-1'-methyl-4'-methylthio-6,7-2',3'-indolomorphinan, 17-cyclopropylmethyl-6,7-didehydro-4,5α-epoxy-3,14β-dihydroxy-1'-methyl-6'-methylthio-6,7-2',3'-indolomorphinan, 17-cyclopropylmethyl-6,7-didehydro-4,5α-epoxy-3,14β-dihydroxy-1'-methyl-4'-phenyl-6,7-2',3'-indolomorphinan, 17-cyclopropylmethyl-6,7-didehydro-4,5α-epoxy-3,14β-dihydroxy-1'-methyl-6'-phenyl-6,7-2',3'-indolomorphinan, 17-cyclopropylmethyl-6,7-didehydro-4,5α-epoxy-3,14β-dihydroxy-1'-methyl-4'-[2-(N,N-dimethylamino)ethyl)]-6,7-2',3'-indolomorphinan, 17-cyclopropylmethyl-6,7-didehydro-4,5α-epoxy-3,14 β-dihydroxy-1'-methyl-6'-[2-(N,N-dimethylamino)ethyl)]-6,7-2',3'-indolomorphinan, 17-cyclopropylmethyl-6,7-didehydro-4,5α-epoxy-3,14β-dihydroxy-1'-methyl-4'-(N,N-dimethylamino)methyl-6,7-2',3'-indolomorphinan, 17-cyclopropylmethyl-6,7-didehydro-4,5α-epoxy-3,14β-dihydroxy-1'-methyl-6'-(N,N-dimethylamino)methyl-6,7-2',3'-indolomorphinan, 17-allyl-6,7-didehydro-4,5α-epoxy-3,14β-dihydroxy-1'-methyl-4'-methylthio-6,7-2',3'-indolomorphinan, 17-allyl-6,7-didehydro-4,5α-epoxy-3,14β-dihydroxy-1'-methyl-6'-methylthio-6,7-2',3'-indolomorphinan, 17-allyl-6,7-didehydro-4,5α-epoxy-3,14β-dihydroxy-1'-methyl-4'-phenyl-6,7-2',3'-indolomorphinan, 17-allyl-6,7-didehydro-4,5α-epoxy-3,14β-dihydroxy-1'-methyl-6'-phenyl-6,7-2',3'-indolomorphinan, 17-allyl-6,7-didehydro-4,5α-epoxy-3,14β-dihydroxy-1'-methyl-4'-[2-(N,N-dimethylamino)ethyl)]-6,7-2',3'-indolomorphinan, 17-allyl-6,7-didehydro-4,5α-epoxy-3,14β-dihydroxy-1'-methyl-6'-[2-(N,N-dimethylamino)ethyl)]-6,7-2',3'-indolomorphinan, 17-allyl-6,7-didehydro-4,5α-epoxy-3,14β-dihydroxy-1'-methyl-4'-(N,N-dimethylamino)methyl-6,7-2',3'-indolomorphinan, 17-allyl-6,7-didehydro-4,5α-epoxy-3,14β-dihydroxy-1'-methyl-6'-(N,N-dimethylamino)methyl-6,7-2',3'-indolomorphinan, 17-cyclopropylmethyl- 6,7-didehydro-4,5α-epoxy-3,14β-dihydroxy-1'-methyl-7'-methylthio-6,7-2',3'-indolomorphinan, 17-cyclopropylmethyl-6,7-didehydro-4,5α-epoxy-3,14β-dihydroxy-1'-methyl-7'-phenyl-6,7-2',3'-indolomorphinan, 17-cyclopropylmethyl-6,7-didehydro-4,5α-epoxy-3,14β-dihydroxy-1'-methyl-7'-[2-(N,N-dimethylamino)ethyl]-6,7-2',3'-indolomorphinan, 17-cyclopropylmethyl-6,7-didehydro-4,5α-epoxy-3,14β-dihydroxy-1'-methyl-7'-(N,N-dimethylamino)methyl-6,7-2',3'-indolomorphinan, 17-allyl-6,7-didehydro-4,5α-epoxy-3,14β-dihydroxy-1'-methyl-7'-methylthio-6,7-2',3'-indolomorphinan, 17-allyl-6,7-didehydro-4,5α-epoxy-3,14β-dihydroxy-1'-methyl-7'-phenyl-6,7-2',3'-indolomorphinan, 17-allyl-6,7-didehydro-4,5α-epoxy-3,14β-dihydroxy-1'-methyl-7'-[2-(N,N-dimethylamino)ethyl]-6,7-2',3'-indolomorphinan, 17-allyl-6,7-didehydro-4,5α-epoxy-3,14β-dihydroxy-1'-methyl-7'-(N,N-dimethylamino)methyl-6,7-2',3'-indolomorphinan, 17-cyclopropylmethyl-6,7-didehydro-4,5α-epoxy-3,14β-hydroxy-3-methoxy-4'-methoxycarbonyl-6,7-2',3'-indolomorphinan, 17-cyclopropylmethyl-6,7-didehydro-4,5α-epoxy-14β-hydroxy-3-methoxy-5'-ethoxycarbonyl-6,7-2',3'-indolomorphinan, 17-cyclopropylmethyl-6,7-didehydro-4,5α-epoxy-14β-hydroxy-3-methoxy-6'-methoxycarbonyl-6,7- 2',3'-indolomorphinan, 17-cyclopropylmethyl-6,7-didehydro-4,5α-epoxy-14β-hydroxy-3-methoxy-7'-ethoxycarbonyl-6,7-2',3'-indolomorphinan, 17-cyclopropylmethyl-6,7-didehydro-4,5α-epoxy-14β-hydroxy-3-methoxy-4'-(N-cyclopropyl-methylcarbamoyl)-6,7-2',3'-indolomorphinan, 17-cyclopropylmethyl-6,7-didehydro-4,5α-epoxy-14β-hydroxy-3-methoxy-5'-(N-cyclopropylmethylcarbamoyl)-6,7-2',3'-indolomorphinan, 17-cyclopropylmethyl-6,7-didehydro-4,5α-epoxy-14β-hydroxy-3-methoxy-6'-(N-cyclopropylmethylcarbamoyl)-6,7-2',3'-indolomorphinan, 17-cyclopropylmethyl-6,7-didehydro-4,5α-epoxy-14β-hydroxy-3-methoxy-7'-(N-cyclopropylmethylcarbamoyl)-6,7-2',3'-indolomorphinan, 17-cyclopropylmethyl-6,7-didehydro-4,5α-epoxy-14β-hydroxy-3-methoxy-4'-cyano-6,7-2',3'-indolomorphinan, 17-cyclopropylmethyl-6,7-didehydro-4,5α-epoxy-14β-hydroxy-3-methoxy-4'-cyano-6,7-2',3'-indolomorphinan, 17-cyclopropylmethyl-6,7-didehydro-4,5α-epoxy-14β-hydroxy-3-methoxy-5'-cyano-6,7-2',3'-indolomorphinan, 17-cyclopropylmethyl-6,7-didehydro-4,5α-epoxy-14β-hydroxy-3-methoxy-6'-cyano-6,7-2',3'-indolomorphinan, 17-cyclopropylmethyl-6,7-didehydro-4,5α-epoxy-14β-hydroxy-3-methoxy-4'-methylthio-6,7-2',3'-indolomorphinan, 17-cyclopropylmethyl-6,7-didehydro-4,5α-epoxy-14β-hydroxy-3-methoxy-5'-methylthio-6,7-2',3'-indolomorphinan, 17-cyclopropylmethyl-6,7-didehydro-4,5α-epoxy-14β-hydroxy-3-methoxy- 6'-methylthio-6,7-2',3'-indolomorphinan, 17-cyclopropylmethyl-6,7-didehydro-4,5α-epoxy-14β-hydroxy-3-methoxy-7'-methylthio-6,7-2',3'-indolomorphinan, 17-cyclopropylmethyl-6,7-didehydro-4,5α-epoxy-14β-hydroxy-3-methoxy-4'-methylsulfonyl-6,7-2',3'-indolomorphinan, 17-cyclopropylmethyl-6,7-didehydro-4,5α-epoxy-14β-hydroxy-3-methoxy-5'-methylsulfonyl-6,7-2',3'-indolomorphinan, 17-cyclopropylmethyl-6,7-didehydro-4,5α-epoxy-14β-hydroxy-3-methoxy-6'-methylsulfonyl-6,7-2',3'-indolomorphinan, 17-cyclopropylmethyl-6,7-didehydro-4,5α-epoxy-14β-hydroxy-3-methoxy-7'-methylsulfonyl-6,7-2',3'-indolomorphinan, 17-cyclopropylmethyl-6,7-didehydro-4,5α-epoxy-14β-hydroxy-3-methoxy-4'-[2-(N,N-dimethylamino)ethyl)]-6,7-2',3'-indolomorphinan, 17-cyclopropylmethyl-6,7-didehydro-4,5α-epoxy-14β-hydroxy-3-methoxy-5'-[2-(N,N-dimethylamino)ethyl)]-6,7-2',3'-indolomorphinan, 17-cyclopropylmethyl-6,7-didehydro-4,5α-epoxy-14β-hydroxy-3-methoxy-6'-[2-(N,N-dimethylamino)ethyl)]-6,7-2',3'-indolomorphinan, 17-cyclopropylmethyl-6,7-didehydro-4,5α-epoxy-14β-hydroxy-3-methoxy-7'-[2-(N,N-dimethylamino)ethyl)]-6,7-

2',3'-indolomorphinan, 17-cyclopropylmethyl-6,7-didehydro-4,5α-epoxy-14β-hydroxy-3-methoxy-4'-(N,N-dimethylamino)methyl- 6,7-2',3'-indolomorphinan, 17-cyclopropylmethyl-6,7-didehydro-4,5α-epoxy-14β-hydroxy-3-methoxy-5'-(N,N-dimethylamino)methyl-6,7-2',3'-indolomorphinan, 17-cyclopropylmethyl-6,7-didehydro-4,5α-epoxy-14β-hydroxy-3-methoxy-6'-(N,N-dimethylamino)methyl-6,7-2',3'-indolomorphinan, 17-cyclopropylmethyl-6,7-didehydro-4,5α-epoxy-14β-hydroxy-3-methoxy-7'-(N,N-dimethylamino)methyl-6,7-2',3'-indolomorphinan, 17-cyclopropylmethyl-6,7-didehydro-4,5α-epoxy-14β-hydroxy-3-methoxy-4'-isothiocyanato-6,7-2',3'-indolomorphinan, 17-cyclopropylmethyl-6,7-didehydro-4,5α-epoxy-14β-hydroxy-3-methoxy-6'-isothiocyanato-6,7-2',3'-indolomorphinan, 17-cyclopropylmethyl-6,7-didehydro-4,5α-epoxy-14β-hydroxy-3-methoxy-7'-isothiocyanato-6,7-2',3'-indolomorphinan, 17-cyclopropylmethyl-6,7-didehydro-4,5α-epoxy-14β-hydroxy-3-methoxy-4'-nitro-6,7-2',3'-indolomorphinan, 17-cyclopropylmethyl-6,7-didehydro-4,5α-epoxy-14β-hydroxy-3-methoxy-6'-nitro-6,7-2',3'-indolomorphinan, 17-cyclopropylmethyl-6,7-didehydro-4,5α-epoxy-14β-hydroxy-3-methoxy-7'-nitro-6,7-2',3'-indolomorphinan, 17-allyl-6,7-didehydro-4,5α-epoxy-14β-hydroxy-3-methoxy-4'-methoxycarbonyl-6,7-2',3'-indolomorphinan, 17-allyl-6,7-didehydro-4,5α-epoxy-14β-hydroxy-3-methoxy-5'-ethoxycarbonyl-6,7-2',3'-indolomorphinan, 17-allyl-6,7-didehydro-4,5α-epoxy-14β-hydroxy-3-methoxy-6'-methoxycarbonyl-6,7-2',3'-indolomorphinan, 17-allyl-6,7-didehydro-4,5α-epoxy-14β-hydroxy-3-methoxy-7'-ethoxycarbonyl-6,7-2',3'-indolomorphinan, 17-allyl-6,7-didehydro-4,5α-epoxy-14β-hydroxy-3-methoxy-4'-(N-cyclopropylmethylcarbamoyl)-6,7-2',3'-indolomorphinan, 17-allyl-6,7-didehydro-4,5α-epoxy-14β-hydroxy-3-methoxy-5'-(N-cyclopropylmethylcarbamoyl)-6,7-2',3'-indolomorphinan, 17-allyl-6,7-didehydro-4,5α-epoxy-14β-hydroxy-3-methoxy-6'-(N-cyclopropylmethylcarbamoyl)-6,7-2',3'-indolomorphinan, 17-allyl-6,7-didehydro-4,5α-epoxy-14β-hydroxy-3-methoxy-7'-(N-cyclopropylmethylcarbamoyl)-6,7-2',3'-indolomorphinan, 17-allyl-6,7-didehydro-4,5α-epoxy-14β-hydroxy-3-methoxy-4'-cyano-6,7-2',3'-indolomorphinan, 17-allyl-6,7-didehydro-4,5α-epoxy-14β-hydroxy-3-methoxy-5'-cyano-6,7-2',3'-indolomorphinan, 17-allyl-6,7-didehydro-4,5α-epoxy-14β-hydroxy-3-methoxy-6'-cyano-6,7-2',3'-indolomorphinan, 17-allyl-6,7-didehydro-4,5α-epoxy-14β-hydroxy-3-methoxy-4'-methylthio-6,7-2',3'-indolomorphinan, 17-allyl-6,7-didehydro-4,5α-epoxy-14β-hydroxy-3-methoxy-5'-methylthio-6,7-2',3'-indolomorphinan, 17-allyl-6,7-didehydro-4,5α-epoxy-14β-hydroxy-3-methoxy-6'-methylthio-6,7-2',3'-indolomorphinan, 17-allyl-6,7-didehydro-4,5α-epoxy-14β-hydroxy-3-methoxy-7'-methylthio-6,7-2',3'-indolomorphinan, 17-allyl-6,7-didehydro-4,5α-epoxy-14β-hydroxy-3-methoxy-4'-methylsulfonyl-6,7-2',3'-indolomorphinan, 17-allyl-6,7-didehydro-4,5α-epoxy-14β-hydroxy-3-methoxy-5'-methylsulfonyl-6,7-2',3'-indolomorphinan, 17-allyl-6,7-didehydro-4,5α-epoxy-14β-hydroxy-3-methoxy-6'-methylsulfonyl-6,7-2',3'-indolomorphinan, 17-allyl-6,7-didehydro-4,5α-epoxy-14β-hydroxy-3-methoxy-7'-methylsulfonyl-6,7-2',3'-indolomorphinan, 17-allyl-6,7-didehydro-4,5α-epoxy-14β-hydroxy-3-methoxy-4'-[2-(N,N-dimethylamino)ethyl]-6,7-2',3'-indolomorphinan, 17-allyl-6,7-didehydro-4,5α-epoxy-14β-hydroxy-3-methoxy-5'-[2-(N,N-dimethylamino)ethyl)]-6,7-2',3 -indolomorphinan, 17-allyl-6,7-didehydro-4,5α-epoxy-14β-hydroxy-3-methoxy-6'-[2-(N,N-dimethylamino)ethyl)]-6,7-2',3'-indolomorphinan, 17-allyl-6,7-didehydro-4,5α-epoxy-14β-hydroxy-3-methoxy-7$^1$-[2-(N,N-dimethylamino)ethyl)]-6,7-2',3'-indolomorphinan, 17-allyl-6,7-didehydro-4,5α-epoxy-14β-hydroxy-3-methoxy-4'-(N,N-dimethylamino)methyl-6,7-2',3'-indolomorphinan, 17-allyl-6,7-didehydro-4,5α-epoxy-14β-hydroxy-3-methoxy-5'-(N,N-dimethylamino)methyl-6,7-2',3'-indolomorphinan, 17-allyl-6,7-didehydro-4,5α-epoxy-14β-hydroxy-3-methoxy-6'-(N,N-dimethylamino)methyl-6,7- 2',3'-indolomorphinan, 17-allyl-6,7-didehydro-4,5α-epoxy-14β-hydroxy-3-methoxy-7'-(N,N-dimethylamino)methyl-6,7-2',3'-indolomorphinan, 17-allyl-6,7-didehydro-4,5α-epoxy-14β-hydroxy-3-methoxy-4'-isothiocyanato-6,7-2',3'-indolomorphinan, 17-allyl-6,7-didehydro-4,5α-epoxy-14β-hydroxy-3-methoxy-6'-isothiocyanato-6,7-2',3'-indolomorphinan, 17-allyl-6,7-didehydro-4,5α-epoxy-14β-hydroxy-3-methoxy-7'-isothiocyanato-6,7-2',3'-indolomorphinan, 17-allyl-6,7-didehydro-4,5α-epoxy-14β-hydroxy-3-methoxy-4'-nitro-6,7-2',3'-indolomorphinan, 17-allyl-6,7-didehydro-4,5α-epoxy-14β-hydroxy-3-methoxy-6'-nitro-6,7-2',3'-indolomorphinan, 17-allyl-6,7-didehydro-4,5α-epoxy-14β-hydroxy-3-methoxy-7'-nitro-6,7-2',3'-indolomorphinan, 3-acetoxy-17-cyclopropylmethyl-6,7-didehydro-4,5α-epoxy-14β-hydroxy-4'-methylthio-6,7-2',3'-indolomorphinan, 3-acetoxy-17-cyclopropylmethyl-6,7-didehydro-4,5α-epoxy-14β-hydroxy-5'-methylthio-6,7-2',3'-indolomorphinan, 3-acetoxy-17-cyclopropylmethyl-6,7-didehydro-4,5α-epoxy-14β-hydroxy-6'-methylthio-6,7-2',3'-indolomorphinan, 3-acetoxy-17-cyclopropylmethyl-6,7-didehydro-4,5α-epoxy-14β-hydroxy-7'-methylthio-6,7-2',3'-indolomorphinan, 3-acetoxy-17-cyclopropylmethyl-6,7-didehydro-4,5α-epoxy-14β-hydroxy-4'-methoxycarbonyl-6,7-2',3'-indolomorphinan, 3-acetoxy-17-cyclopropylmethyl-6,7-didehydro-4,5α-epoxy-14β-hydroxy-5'-ethoxycarbonyl-6,7-2',3'-indolomorphinan, 3-acetoxy-17-cyclopropylmethyl-6,7-didehydro-4,5α-epoxy-14β-hydroxy-6'-methoxycarbonyl-6,7-2',3'-indolomorphinan, 3-acetoxy-17-cyclopropylmethyl-6,7-didehydro-4,5α-epoxy-14β-hydroxy-7'-ethoxycarbonyl-6,7-2',3'-indolomorphinan, 3-acetoxy-17-cyclopropylmethyl-6,7-didehydro-4,5α-epoxy-14β-hydroxy-4'-(N-cyclopropylmethylcarbamoyl)-6,7-2',3'-indolomorphinan, 3-acetoxy-17-cyclopropylmethyl-6,7-didehydro-4,5α-epoxy-14β-hydroxy-5'-(N-cyclopropylmethylcarbamoyl)-6,7-2',3'-indolomorphinan, 3-acetoxy-17-cyclopropylmethyl-6,7-didehydro-4,5α-epoxy-14β-hydroxy-6'-(N-cyclopropylmethylcarbamoyl)-6,7-2',3'-indolomorphinan, 3-acetoxy-17-cyclopropylmethyl-6,7-didehydro-4,5α-epoxy-14β-hydroxy-7'-(N-cyclopropylmethylcarbamoyl)-6,7-2',3'-indolomorphinan, 3-acetoxy-17-cyclopropylmethyl-6,7-didehydro-4,5α-epoxy-14β-hydroxy-4'-cyano-6,7-2',3'-indolomorphinan, 3-acetoxy-17-cyclopropylmethyl-6,7-didehydro-4,5α-epoxy-14β-hydroxy-5'-cyano-6,7-2',3'-indolomorphinan, 3-acetoxy-17-cyclopropylmethyl-6,7-didehydro-4,5α-epoxy-14β-hydroxy-6'-cyano-6,7-2',3'-indolomorphinan, 3-acetoxy-17-cyclopropylmethyl-6,7-didehydro-4,5α-epoxy- 14β-hydroxy-4'-methylsulfonyl-6,7-2',3'-indolomorphinan, 3-acetoxy-17-cyclopropylmethyl-6,7-didehydro-4,5α-epoxy-14β-hydroxy-5'-methylsulfonyl-6,7-2',3'-indolomorphinan, 3-acetoxy-17-cyclopropylmethyl-6,7-didehydro-4,5α-epoxy-14β-hydroxy-6'-methylsulfonyl-6,7-2',3'-indolomorphinan, 3-acetoxy-17-cyclopropylmethyl-6,7-didehydro-4,5α-epoxy-14β-hydroxy-7'-methylsulfonyl-6,7-2',3'-indolomorphinan, 3-acetoxy-17-cyclopropylmethyl-6,7-didehydro-4,5α-epoxy-14β-hydroxy-4'-[2-(N,N-dimethylamino)ethyl)]-6,7-2',3'-indolomorphinan, 3-acetoxy-17-cyclopropylmethyl-6, 7-didehydro-4,5α-epoxy-14β-hydroxy-5'-[2-(N,N-dimethylamino)ethyl)]-6,7-2',3'-indolomorphinan, 3-acetoxy-17-cyclopropylmethyl-6,7-didehydro-4,5α-epoxy-14β-hydroxy-6'-[2-(N,N-dimethylamino)ethyl)]-6,7-2',3'-indolomorphinan, 3-acetoxy-17-cyclopropylmethyl-6,7-didehydro-4,5α-epoxy-14β-hydroxy-7'-[2-(N,N-dimethylamino)ethyl)]-6,7-2',3'-indolomorphinan, 3-acetoxy-17-cyclopropylmethyl-6,7-didehydro-4,5α-epoxy-14β-hydroxy-4'-(N,N-dimethylamino)methyl-6,7-2',3'-indolomorphinan, 3-acetoxy-17-cyclopropylmethyl-6,7-didehydro-4,5α-epoxy-14β-hydroxy-5'-(N,N-dimethylamino)methyl-6,7-2',3'-indolomorphinan, 3-acetoxy-17-cyclopropylmethyl-6,7-didehydro-4,5α-epoxy-14β-hydroxy-6,-(N,N-dimethylamino)methyl-6,7-2',3'-indolomorphinan, 3-acetoxy-17-cyclopropylmethyl-6,7-didehydro-4,5α-epoxy-14β-hydroxy-7'-(N,N-dimethylamino)methyl-6,7-2',3'-indolomorphinan, 3-acetoxy-17-cyclopropylmethyl-6,7-didehydro-4,5α-epoxy-14β-hydroxy-4'-isothiocyanato-6,7-2',3'-indolomorphinan, 3-acetoxy-17-cyclopropylmethyl-6,7-didehydro-4,5α-epoxy-14β-hydroxy-6'-isothiocyanato-6,7-2',3'-indolomorphinan, 3-acetoxy-17-cyclopropylmethyl-6,7-didehydro-4,5α-epoxy-14β-hydroxy-7'-isothiocyanato-6,7-2',3'-indolomorphinan, 3-acetoxy-17-cyclopropylmethyl-6,7-didehydro-4,5α-epoxy-14β-hydroxy-4'-nitro-6,7-2',3'-indolomorphinan, 3-acetoxy-17-cyclopropylmethyl-6,7-didehydro-4,5α-epoxy-14β-hydroxy-6'-nitro-6,7-2',3'-indolomorphinan, 3-acetoxy-17-cyclopropylmethyl-6,7-didehydro-4,5α-epoxy-14β-hydroxy-7'-nitro-6,7-2',3'-indolomorphinan, 17-allyl-3-acetoxy-6,7-didehydro-4,5α-epoxy-14β-hydroxy-4'-methoxycarbonyl-6,7-2',3'-indolomorphinan, 17-allyl-3-acetoxy-6,7-didehydro-4,5α-epoxy-14β-hydroxy-5'-ethoxycarbonyl-6,7-2',3'-indolomorphinan, 17-allyl-3-acetoxy-6,7-didehydro-4,5α-epoxy-14β-hydroxy-6'-methoxycarbonyl-6,7-2',3'-indolomorphinan, 17-allyl-3-acetoxy-6,7-didehydro-4,5α-epoxy-14β-hydroxy-7'-ethoxycarbonyl-6,7-2',3'-indolomorphinan, 17-allyl-3-acetoxy- 6,7-didehydro-4,5α-epoxy-14β-hydroxy-4'-(N-cyclopropylmethylcarbamoyl)-6,7-2',3'-indolomorphinan, 17-allyl-3-acetoxy-6,7-didehydro-4,5α-epoxy-14β-hydroxy-5'-(N-cyclopropylmethylcarbamoyl)-6,7-2',3'-indolomorphinan, 17-allyl-3-acetoxy-6,7-didehydro-4,5α-epoxy-14β-hydroxy-6'-(N-cyclopropylmethylcarbamoyl)-6,7-2',3'-indolomorphinan, 17-allyl-3-acetoxy-6,7-didehydro-4,5α-epoxy-14β-hydroxy-7'-(N-cyclopropylmethylcarbamoyl)-6,7-2',3'-indolomorphinan, 17-allyl-3-acetoxy-6,7-didehydro-4,5α-epoxy-14β-hydroxy-4'-cyano-6,7-2',3'-indolomorphinan, 17-allyl-3-acetoxy-6,7-didehydro-4,5α-epoxy-14β-hydroxy-5'-cyano-6,7-2',3'-indolomorphinan, 17-allyl-3-acetoxy-6,7-didehydro-4,5α-epoxy-14β-hydroxy-6'-cyano-6,7-2',3'-indolomorphinan, 17-allyl-3-acetoxy-6,7-didehydro-4,5α-epoxy-14β-hydroxy-4'-methylthio-6,7-2',3'-indolomorphinan, 17-allyl-3-acetoxy-6,7-didehydro-4,5α-epoxy-14β-hydroxy-5'-methylthio-6,7-2',3'-indolomorphinan, 17-allyl-3-acetoxy-6,7-didehydro-4,5α-epoxy-14β-hydroxy-6'-methylthio-6,7-2',3'-indolomorphinan, 17-allyl-3-acetoxy-6,7-didehydro-4,5α-epoxy-14β-hydroxy-7'-methylthio-6,7-2',3'-indolomorphinan, 17-allyl-3-acetoxy-6,7-didehydro-4,5α-epoxy-14β-hydroxy-4'-methylsulfonyl-6,7-2',3'-indolomorphinan, 17-allyl-3-acetoxy-6,7-didehydro-4,5α-epoxy-14β-hydroxy-5'-methylsulfonyl- 6,7-2',3'-indolomorphinan, 17-allyl-3-acetoxy-6,7-didehydro-4,5α-epoxy-14β-hydroxy-6'-methylsulfonyl-6,7-2',3'-indolomorphinan, 17-allyl-3-acetoxy-6,7-didehydro-4,5α-epoxy-14β-hydroxy-7'-methylsulfonyl-6,7-2',3'-indolomorphinan, 17-allyl-3-acetoxy-6,7-didehydro-4,5α-epoxy-14β-hydroxy-4'-[2-(N,N-dimethylamino)ethyl)]-6,7-2',3'-indolomorphinan, 17-allyl-3-acetoxy-6,7-didehydro-4,5α-epoxy-14β-hydroxy-5'-[2-(N,N-dimethylamino)ethyl)]-6,7-2',3'-indolomorphinan, 17-allyl-3-acetoxy-6,7-didehydro-4,5α-epoxy-14β-hydroxy-6'-[2-(N,N-dimethylamino)ethyl)]-6,7-2',3'-indolomorphinan, 17-allyl-3-acetoxy-6,7-didehydro-4,5α-epoxy-14β-hydroxy-7'-[2-(N,N-dimethylamino)ethyl)]-6,7-2',3'-indolomorphinan, 17-allyl-3-acetoxy-6,7-didehydro-4,5α-epoxy-14β-hydroxy-4'-(N,N-dimethylamino)methyl-6,7-2',3'-indolomorphinan, 17-allyl-3-acetoxy-6,7-didehydro-4,5α-epoxy-14β-hydroxy-5'-(N,N-dimethylamino)methyl-6,7-2',3'-indolomorphinan, 17-allyl-3-acetoxy-6,7-didehydro-4,5α-epoxy-14β-hydroxy-6'-(N,N-dimethylamino)methyl-6,7-2',3'-indolomorphinan, 17-allyl-3-acetoxy-6,7-didehydro-4,5α-epoxy-14β-hydroxy-7'-(N,N-dimethylamino)methyl-6,7-2',3'-indolomorphinan, 17-allyl-3-acetoxy-6,7-didehydro-4,5α-epoxy-14β-hydroxy-4'-isothiocyanato-6,7-2',3'-indolomorphinan, 17-allyl-3-acetoxy-6,7-didehydro-4,5α-epoxy-14β-hydroxy- 6'-isothiocyanato-6,7-2',3'-indolomorphinan, 17-allyl-3-acetoxy-6,7-didehydro-4,5α-epoxy-14β-hydroxy-7'-isothiocyanato-6,7-2',3'-indolomorphinan, 17-allyl-3-acetoxy-6,7-didehydro-4,5α-epoxy-14β-hydroxy-4'-nitro-6,7-2',3'-indolomorphinan, 17-allyl-3-acetoxy-6,7-didehydro-4,5α-epoxy-14β-hydroxy-6'-nitro-6,7-2',3'-indolomorphinan, 17-allyl-3-acetoxy-6,7-didehydro-4,5α-epoxy-14β-hydroxy-7'-nitro-6,7-2',3'-indolomorphinan, 14β-acetoxy-17-cyclopropylmethyl-6,7-didehydro-4,5α-epoxy-3-hydroxy-4'-methylthio-6,7-2',3'-indolomorphinan, 14β-acetoxy-17-cyclopropylmethyl-6,7-didehydro-4,5α-epoxy-3-hydroxy-5'-methylthio-6,7-2',3'-indolomorphinan, 14β-acetoxy-17-cyclopropylmethyl-6,7-didehydro-4,5α-epoxy-3-hydroxy-6'-methylthio-6,7-2',3'-indolomorphinan, 14β-acetoxy-17-cyclopropylmethyl-6,7-didehydro-4,5α-epoxy-3-hydroxy-7'-methylthio-6,7-2',3'-indolomorphinan, 14β-acetoxy-17-cyclopropylmethyl-6,7-didehydro-4,5α-epoxy-3-hydroxy-4'-methoxycarbonyl-6,7-2',3'-indolomorphinan, 14β-acetoxy-17-cyclopropylmethyl-6,7-didehydro-4,5α-epoxy-3-hydroxy-5'-ethoxycarbonyl-6,7-2',3'-indolomorphinan, 14β-acetoxy-17-cyclopropylmethyl-6,7-didehydro-4,5α-epoxy-3-hydroxy-6'-methoxycarbonyl-6,7-2',3'-indolomorphinan, 14β-acetoxy-17-cyclopropylmethyl-6,7-didehydro-4,5α-epoxy-3-hydroxy- 7'-ethoxycarbonyl-6,7-2',3'-indolomorphinan, 14β-acetoxy-17-cyclopropylmethyl-6,7-didehydro-4,5α-epoxy-3-hydroxy-4'-(N-cyclopropylmethylcarbamoyl)-6,7-2',3'-indolomorphinan, 14β-acetoxy-17-cyclopropylmethyl-6,7-didehydro-4,5α-epoxy-3-hydroxy-5'-(N-cyclopropylmethylcarbamoyl)-6,7-2',3'-indolomorphinan, 14β-acetoxy-17-cyclopropylmethyl-6,7-didehydro-4,5α-epoxy-3-hydroxy-6'-(N-cyclopropylmethylcarbamoyl)-6,7-2',3'-indolomorphinan, 14β-acetoxy-17-cyclopropylmethyl-6,7-didehydro-4,5α-epoxy-3-hydroxy-7'-(N-cyclopropylmethylcarbamoyl)-6,7-2',3'-indolomorphinan, 14β-acetoxy-17-cyclopropylmethyl-6,7-didehydro-4,5α-epoxy-3-hydroxy-4'-cyano-6,7-2',3'-indolomorphinan, 14β-acetoxy-17-cyclopropylmethyl-6,7-didehydro-4,5α-epoxy-3-hydroxy-5'-cyano-6,7-2',3'-indolomorphinan, 14β-acetoxy-17-cyclopropylmethyl-6,7-didehydro-4,5α-epoxy-3-hydroxy-6'-cyano-6,7-2',3'-indolomorphinan, 14β-acetoxy-17-cyclopropylmethyl-6,7-didehydro-4,5α-epoxy-3-hydroxy-4'-methylsulfonyl-6,7-2',3'-indolomorphinan, 14β-acetoxy-17-cyclopropylmethyl-6,7-didehydro-4,5α-epoxy-3-hydroxy-5'-methylsulfonyl-6,7-2',3'-indolomorphinan, 14β-acetoxy-17-cyclopropylmethyl-6,7-didehydro-4,5α-epoxy-3-hydroxy-6'-methylsulfonyl-6, 7-2',3'-indolomorphinan, 14β-acetoxy-17-cyclopropylmethyl-6,7-didehydro-4,5α-epoxy-3-hydroxy-7'-methylsulfonyl-6,7-2',3'-indolomorphinan, 14β-acetoxy-17-cyclopropylmethyl-6,7-didehydro-4,5α-epoxy-3-hydroxy-4'-[2-(N,N-dimethylamino)ethyl)]-6,7-2',3'-indolomorphinan, 14β-acetoxy-17-cyclopropylmethyl-6,7-didehydro-4,5α-epoxy-3-hydroxy-5'-[2-(N,N-dimethylamino)ethyl)]-6,7-2',3'-indolomorphinan, 14β-acetoxy-17-cyclopropylmethyl-6,7-didehydro-4,5α-epoxy-3-hydroxy-6'-[2-(N,N-dimethylamino)ethyl)]-6,7-2',3'-indolomorphinan, 14β-acetoxy-17-cyclopropylmethyl-6,7-didehydro-4,5α-epoxy-3-hydroxy-7'-[2-(N,N-dimethylamino)ethyl)]-6,7-2',3'-indolomorphinan, 14β-acetoxy-17-cyclopropylmethyl-6,7-didehydro-4,5α-epoxy-3-hydroxy-4,-(N,N-dimethylamino)methyl-6,7-2',3'-indolomorphinan, 14β-acetoxy-17-cyclopropylmethyl-6,7-didehydro-4,5α-epoxy-3-hydroxy-5'-(N,N-dimethylamino)methyl-6,7-2',3'-indolomorphinan, 14β-acetoxy-17-cyclopropylmethyl-6,7-didehydro-4,5α-epoxy-3-hydroxy-6'-(N,N-dimethylamino)methyl-6,7-2',3'-indolomorphinan, 14β-acetoxy-17-cyclopropylmethyl-6,7-didehydro-4,5α-epoxy-3-hydroxy-7'-(N,N-dimethylamino)methyl-6,7-2',3'-indolomorphinan, 14β-acetoxy-17-cyclopropylmethyl-6,7-didehydro-4,5α-epoxy-3-hydroxy-4'-isothiocyanato-6,7-2',3'-indolomorphinan, 14β-acetoxy-17-cyclopropylmethyl-6,7-didehydro-4,5α-epoxy-3-hydroxy-6'-isothiocyanato-6,7-2',3'-indolomorphinan, 14β-acetoxy-17-cyclopropylmethyl-6,7-didehydro-4,5α-epoxy-3-hydroxy-7'-isothiocyanato-6,7-2',3'-indolomorphinan, 14β-acetoxy-17-cyclopropylmethyl-6,7-didehydro-4,5α-epoxy-3-hydroxy-4'-nitro-6,7-2',3'-indolomorphinan, 14β-acetoxy-17-cyclopropylmethyl-6,7-didehydro-4,5α-epoxy-3-hydroxy-6'-nitro-6,7-2',3'-indolomorphinan, 14β-acetoxy-17-cyclopropylmethyl-6,7-didehydro-4,5α-epoxy-3-hydroxy-7'-nitro-6,7-2',3'-indolomorphinan, 17-allyl-14β-acetoxy-6,7-didehydro-4,5α-epoxy-3-hydroxy-4'-methoxycarbonyl-6,7-2',3'-indolomorphinan, 17-allyl-14β-acetoxy-6,7-didehydro-4,5α-epoxy-3-hydroxy-5'-ethoxycarbonyl-6,7-2',3'-indolomorphinan, 17-allyl-14β-acetoxy-6,7-didehydro-4,5α-epoxy-3-hydroxy-6'-methoxycarbonyl-6,7-2',3'-indolomorphinan, 17-allyl-14β-acetoxy-6,7-didehydro-4,5α-epoxy-3-hydroxy-7'-ethoxycarbonyl-6,7-2',3'-indolomorphinan, 17-allyl-14β-acetoxy-6,7-didehydro-4,5α-epoxy-3-hydroxy-4'-(N-cyclopropylmethylcarbamoyl)-6,7-2',3'-indolomorphinan, 17-allyl-14β-acetoxy-6,7-didehydro-4,5α-epoxy-3-hydroxy-5'-(N-cyclopropylmethylcarbamoyl)-6,7-2',3'-indolomorphinan, 17-allyl-14β-acetoxy-6,7-didehydro-4,5α-epoxy-3-hydroxy-6'-(N-cyclopropylmethylcarbamoyl)-6,7-2',3'-indolomorphinan, 17-allyl-14β-acetoxy-6,7-didehydro-4,5α-epoxy-3-hydroxy-7'-(N-cyclopropylmethylcarbamoyl)-6,7-2',3'-indolomorphinan, 17-allyl-14β-acetoxy- 6,7-didehydro-4,5α-epoxy-3-hydroxy-4'-cyano-6,7-2',3'-indolomorphinan, 17-allyl-14β-acetoxy-6,7-didehydro-4,5α-epoxy-3-hydroxy-5'-cyano-6,7-2',3'-indolomorphinan, 17-allyl-14β-acetoxy-6,7-didehydro-4,5α-epoxy-3-hydroxy-6'-cyano-6,7-2',3'-indolomorphinan, 17-allyl-14β-acetoxy-6,7-didehydro-4,5α-epoxy-3-hydroxy-4'-methylthio-6,7-2',3'-indolomorphinan, 17-allyl-14β-acetoxy-6,7-didehydro-4,5α-epoxy-3-hydroxy-5'-methylthio-6,7-2',3'-indolomorphinan, 17-allyl-14β-acetoxy-6,7-didehydro-4,5α-epoxy-3-hydroxy-6'-methylthio-6,7-2',3'-indolomorphinan, 17-allyl-14β-acetoxy-6,7-didehydro-4,5α-epoxy-3-hydroxy-7'-methylthio-6,7-2',3'-indolomorphinan, 17-allyl-14β-acetoxy-6,7-didehydro-4,5α-epoxy-3-hydroxy-4'-methylsulfonyl-6,7-2',3'-indolomorphinan, 17-allyl-14β-acetoxy-6,7-didehydro-4,5α-epoxy-3-hydroxy-5'-methylsulfonyl-6,7-2',3'-indolomorphinan, 17-allyl-14β-acetoxy-6,7-didehydro-4,5α-epoxy-3-hydroxy-6'-methylsulfonyl-6,7-2',3'-indolomorphinan, 17-allyl-14β-acetoxy-6,7-didehydro-4,5α-epoxy-3-hydroxy-7'-methylsulfonyl-6,7-2',3'-indolomorphinan, 17-allyl-14β-acetoxy-6,7-didehydro-4,5α-epoxy-3-hydroxy-4'-[2-(N,N-dimethylamino)ethyl)]-6,7-2,3 1-indolomorphinan, 17-allyl-14,-acetoxy-6,7-didehydro-4,5α-epoxy-3-hydroxy-5'-[2-(N,N-dimethylamino)ethyl)]-6,7-2',3'-indolomorphinan, 17-allyl-14β-acetoxy- 6,7-didehydro-4,5α-epoxy-3-hydroxy-6'-[2-(N,N-dimethylamino)ethyl)]-6,7-2',3'-indolomorphinan, 17-allyl-14β-acetoxy-6,7-didehydro-4,5α-epoxy-3-hydroxy-7'-[2-(N,N-dimethylamino)ethyl)]-6,7-2',3'-indolomorphinan, 17-allyl-14β-acetoxy-6,7-didehydro-4,5α-epoxy-3-hydroxy-4'-(N,N-dimethylamino)methyl-6,7-2',3'-indolomorphinan, 17-allyl-14β-acetoxy-6,7-didehydro-4,5α-epoxy-3-hydroxy-5'-(N,N-dimethylamino)methyl-6,7-2',3'-indolomorphinan, 17-allyl-14β-acetoxy-6,7-didehydro-4,5α-epoxy-3-hydroxy-6'-(N,N-dimethylamino)methyl-6,7-2',3'-indolomorphinan, 17-allyl-14β-acetoxy-6,7-didehydro-4,5α-epoxy-3-hydroxy-7'-(N,N-dimethylamino)methyl-6,7-2',3'-indolomorphinan, 17-allyl-14β-acetoxy-6,7-didehydro-4,5α-epoxy-3-hydroxy-4'-isothiocyanato-6,7-2',3'-indolomorphinan, 17-allyl-14β-acetoxy-6,7-didehydro-4,5α-epoxy-3-hydroxy-6'-isothiocyanato-6,7-2',3'-indolomorphinan, 17-allyl-14β-acetoxy-6,7-didehydro-4,5α-epoxy-3-hydroxy-7'-isothiocyanato-6,7-2',3'-indolomorphinan, 17-allyl-14β-acetoxy-6,7-didehydro-4,5α-epoxy-3-hydroxy-4'-nitro-6,7-2',3'-indolomorphinan, 17-allyl-14β-acetoxy-6,7-didehydro-4,5α-epoxy-3-hydroxy-6'-nitro-6,7-2',3'-indolomorphinan, 17-allyl-14β-acetoxy-6,7-didehydro-4,5α-epoxy-3-hydroxy-7'-nitro-6,7-2',3'-indolomorphinan and the like.

Among the compounds represented by the formula (II), the compound wherein $R^1$ is cyclopropylmethyl, $R^2$ is hydroxy, $R^3$ is hydrogen, $R^4$ is hydrogen, X is —$(CH_2)_4$— bonded to 6'- and 7'-positions, that is, the compound 2 represented by the following formula:

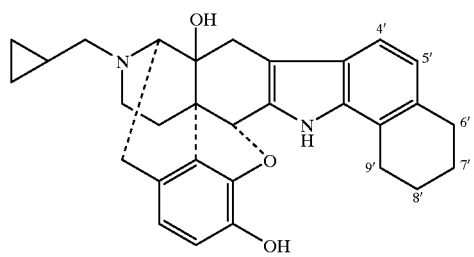

is named 17-cyclopropylmethyl-3,14β-dihydroxy-4,5α-epoxy-6,7-didehydromorphinano[6,7-b]cyclohexeno[g]indole. In accordance with this nomenclature, specific examples of the compounds according to the present invention include 17-cyclopropylmethyl-3,14β-dihydroxy-4,5α-epoxy-6'-ethoxycarbonyl-6,7-didehydromorphinano[6,7-b]cyclohexeno[g]indole, 17-cyclopropylmethyl-3,14β-dihydroxy-4,5α-epoxy-7'-ethoxycarbonyl-6,7-didehydromorphinano[6,7-b]cyclohexeno[g]indole, 17-cyclopropylmethyl-3,14β-dihydroxy-4,5α-epoxy-8'-ethoxycarbonyl-6,7-didehydromorphinano[6,7-b]cyclohexeno[g]indole, 17-cyclopropylmethyl-3,14β-dihydroxy-4,5α-epoxy-9'-ethoxycarbonyl-6,7-didehydromorphinano[6,7-b]cyclohexeno[g]indole, 17-cyclopropylmethyl-3,14β-dihydroxy-4,5α-epoxy-6'- sulfamoyl-6,7-didehydromorphinano[6,7-b]cyclohexeno[g]indole, 17-cyclopropylmethyl-3,14β-dihydroxy-4,5α-epoxy-7'-sulfamoyl-6,7-didehydromorphinano[6,7-b]cyclohexeno[g]indole, 17-cyclopropylmethyl-3,14β-dihydroxy-4,5α-epoxy-8'-sulfamoyl-6,7-didehydromorphinano[6,7-b]cyclohexeno[g]indole, 17-cyclopropylmethyl-3,14β-dihydroxy-4,5α-epoxy-9'-sulfamoyl-6,7-didehydromorphinano[6,7-b]cyclohexeno[g]indole, 17-cyclopropylmethyl-3,14β-dihydroxy-4,5α-epoxy-6'-carbamoyl-6,7-didehydromorphinano[6,7-b]cyclohexeno[g]indole, 17-cyclopropylmethyl-3, 14β-dihydroxy-4,5α-epoxy-7'-carbamoyl-6,7-didehydromorphinano[6,7-b]cyclohexeno[g]indole, 17-cyclopropylmethyl-3,14β-dihydroxy-4,5α-epoxy-8'-carbamoyl-6,7-didehydromorphinano[6,7-b]cyclohexeno[g]indole, 17-cyclopropylmethyl-3,14β-dihydroxy-4,5α-epoxy-9'-carbamoyl-6,7-didehydromorphinano[6,7-b]cyclohexeno[g]indole, 17-allyl-3,14β-dihydroxy-4,5α-epoxy-6'-ethoxycarbonyl-6,7-didehydromorphinano[6,7-b]cyclohexeno[g]indole, 17-allyl-3,14β-dihydroxy-4,5α-epoxy-7'-ethoxycarbonyl-6,7-didehydromorphinano[6,7-b]cyclohexeno[g]indole, 17-allyl-3,14β-dihydroxy-4,5α-epoxy-8'-ethoxycarbonyl-6,7-didehydromorphinano[6,7-b]cyclohexeno[g]indole, 17-allyl-3,14β-dihydroxy-4,5α-epoxy-9'-ethoxycarbonyl-6,7-didehydromorphinano[6,7-b]cyclohexeno[g]indole, 17-allyl-3,14β-dihydroxy-4,5α-epoxy-6'-sulfamoyl-6,7-didehydromorphinano[6,7-b]cyclohexeno[g]indole, 17-allyl-3,14β-dihydroxy-4,5α-epoxy-7'-sulfamoyl-6,7-didehydromorphinano[6,7-b]cyclohexeno[g]indole, 17-allyl-3,14β-dihydroxy-4,5α-epoxy-8'-sulfamoyl-6,7-didehydromorphinano[6,7-b]cyclohexeno[g]indole, 17-allyl-3,14β-dihydroxy-4,5α-epoxy-9'-sulfamoyl-6,7-didehydromorphinano[6,7-b]cyclohexeno[g]indole, 17-allyl-3,14β-dihydroxy-4,5α-epoxy-6'-carbamoyl-6,7-didehydromorphinano[6,7-b]cyclohexeno[g]indole, 17-allyl-3,14β-dihydroxy-4,5α-epoxy-7'-carbamoyl-6,7-didehydromorphinano[6,7-b]cyclohexeno[g]indole, 17-allyl-3,14β-dihydroxy-4,5α-epoxy-8'-carbamoyl-6,7-didehydromorphinano[6,7-b]cyclohexeno[g]indole, 17-allyl-3,14β-dihydroxy-4,5α-epoxy-9'-carbamoyl-6,7-didehydromorphinano[6,7-b]cyclohexeno[g]indole, 17-cyclopropylmethyl-3,14β-dihydroxy-4,5α-epoxy-6,7-didehydromorphinano[6,7-b]cyclohexeno[e]indole, 17-cyclopropylmethyl-3,14β-dihydroxy-4,5α-epoxy-6,7-didehydromorphinano[6,7-b]cyclohexeno[f]indole, 17-cyclopropylmethyl-3,14β-dihydroxy-4,5α-epoxy-6,7-didehydromorphinano[6,7-b]cyclopenteno[e]indole, 17-cyclopropylmethyl-3,14β-dihydroxy-4,5α-epoxy-6,7-didehydromorphinano[6,7-b]cyclopenteno[f]indole, 17-cyclopropylmethyl-3,14β-dihydroxy-4,5α-epoxy-6,7-didehydromorphinano[6,7-b]cyclopenteno[g]indole, 17-cyclopropylmethyl-3,14β-dihydroxy-4,5α-epoxy-6,7-didehydromorphinano[6,7-b]cyclohepteno[e]indole, 17-cyclopropylmethyl-3,14β-dihydroxy-4,5α-epoxy-6,7-didehydromorphinano[6,7-b]cyclohepteno[f]indole, 17-cyclopropylmethyl-3,14β-dihydroxy-4,5α-epoxy-6,7-didehydromorphinano[6,7-b]cyclohepteno[g]indole, 17-cyclopropylmethyl-3,14β-dihydroxy-4,5α-epoxy-6,7-didehydromorphinano[6,7-b]cyclooteno[e]indole, 17-cyclopropylmethyl-3,14β-dihydroxy-4,5α-epoxy-6,7-didehydromorphinano[6,7-b]cyclooteno[f]indole, 17-cyclopropylmethyl-3,14β-dihydroxy-4,5α-epoxy-6,7-didehydromorphinano[6,7-b]cyclooteno[g]indole, 17-allyl-3,14β-dihydroxy-4,5α-epoxy-6,7-didehydromorphinano[6,7-b]cyclohexeno[e]indole, 17-allyl-3,14β-dihydroxy-4,5α-epoxy-6,7-didehydromorphinano[6,7-b]cyclohexeno[f]indole, 17-allyl-3,14β-dihydroxy-4,5α-epoxy-6,7-didehydromorphinano[6,7-b]cyclohexeno[g]indole, 17-allyl-3,14β-dihydroxy-4,5α-epoxy-6,7-didehydromorphinano[6,7-b]cyclopenteno[e]indole, 17-allyl-3,14β-dihydroxy-4,5α-epoxy-6,7-didehydromorphinano[6,7-b]cyclopenteno[f]indole, 17-allyl-3,14β-dihydroxy-4,5α-epoxy-6,7-didehydromorphinano[6,7-b]cyclopenteno[g]indole, 17-allyl-3,14β-dihydroxy-4,5α-epoxy- 6,7-didehydromorphinano[6,7-b]cyclohepteno[e]indole, 17-allyl-3,14β-dihydroxy-4,5α-epoxy-6,7-didehydromorphinano[6,7-b]cyclohepteno[f]indole, 17-allyl-3,14β-dihydroxy-4,5α-epoxy-6,7-didehydromorphinano[6,7-b]cyclohepteno[g]indole, 17-allyl-3,14β-dihydroxy-4,5α-epoxy-6,7-didehydromorphinano[6,7-b]cyclooteno[e]indole, 17-allyl-3,14β-dihydroxy-4,5α-epoxy-6,7-didehydromorphinano[6,7-b]cyclooteno[f]indole, 17-allyl-3,14β-dihydroxy-4,5α-epoxy-6,7-didehydromorphinano[6,7-b]cyclooteno[g]indole, 17-cyclopropylmethyl-3,14β-dihydroxy-4,5α-epoxy-6,7-didehydromorphinano[6,7-b]pyrido[4,3-g]indole, 17-cyclopropylmethyl-3,14β-dihydroxy-4,5α-epoxy-6,7-didehydromorphinano[6,7-b]pyrido[2,3-g]indole, 17-cyclopropylmethyl-3,14β-dihydroxy-4,5α-epoxy-6,7-didehydromorphinano[6,7-b]pyrido[3,2-e]indole, 17-cyclopropylmethyl-3,14#-dihydroxy-4,5α-epoxy-6,7-didehydromorphinano[6,7-b]pyrido[2,3-f]indole, 17-cyclopropylmethyl-3,14β-dihydroxy-4,5α-epoxy-6,7-didehydromorphinano[6,7-b]pyrido[3,2-g]indole, 17-allyl-3,14β-dihydroxy-4,5α-epoxy-6,7-didehydromorphinano[6,7-b]pyrido[4,3-g]indole, 17-allyl-3,14β-dihydroxy-4,5α-epoxy-6,7-didehydromorphinano[6,7-b]pyrido[2,3-g]indole, 17-allyl-3,14β-dihydroxy-4,5α-epoxy-6,7-didehydromorphinano[6,7-b]pyrido[3,2-e]indole, 17-allyl-3,14β-dihydroxy-4,5α-epoxy-6,7-didehydromorphinano[6,7-b]pyrido[2,3-f]indole, 17-allyl-3,14β-dihydroxy-4,5α-epoxy-6,7-didehydromorphinano[6,7-b]pyrido[3,2-g]indole, 17-cyclopropylmethyl-4,5α-epoxy-14β-hydroxy-3-methoxy-6,7-didehydromorphinano[6,7-b]cyclohexeno[e]indole, 17-cyclopropylmethyl-4,5α-epoxy-14β-hydroxy-3-methoxy-6,7-didehydromorphinano[6,7-b]cyclohexeno[f]indole, 17-cyclopropylmethyl-4,5α-epoxy-14β-hydroxy-3-methoxy-6,7-didehydromorphinano[6,7-b]cyclohexeno[g]indole, 17-cyclopropylmethyl-4,5α-epoxy-14β-hydroxy-3-methoxy-6,7-didehydromorphinano [6,7-b]cyclopenteno[e]indole, 17-cyclopropylmethy-4,5α-epoxy-14β-hydroxy-3-methoxy-6,7-didehydromorphinano[6,7-b]cyclopenteno[f]indole, 17-cyclopropylmethyl-4,5α-epoxy-14β-hydroxy-3-methoxy-6,7-didehydromnorphinano[6,7-b) cyclopenteno[g]indole, 17-cyclopropylmethyl-4,5α-epoxy-14β-hydroxy-3-methoxy-6,7-didehydromorphinano[6,7-b]cyclohepteno[e]indole, 17-cyclopropylmnethyl-4,5α-epoxy-14β-hydroxy-3'-ethoxy-6,7-didehydronorphinano6,7-b]cyclohepteno[f]indole, 17-cyclopropylmethyl-4,5α-epoxy-14β-hydroxy-3-methoxy-6,7-didehydromorphinano[6,7-b]cyclohepteno[g]indole, 17-cyclopropylmethyl-4,5α-epoxy-14β-hydroxy-3-methoxy-6,7-didehydromorphinano[6,7-b]cyclooteno[e]indole, 17-cyclopropylmethyl-4,5α-epoxy-14β-hydroxy-3-methoxy-6,7-didehydromorphinano[6,7-b]cyclooteno[f]indole, 17-cyclopropylmethyl-4,5α-epoxy-14β-hydroxy-3-methoxy-6,7-didehydromorphinano[6,7-b]cyclooteno[g]indole, 17-cyclopropylmethyl-4,5α-epoxy-14β-hydroxy-3-methoxy-6,7-didehydromorphinano[6,7-b]pyrido[4,3-g]indole, 17-cyclopropylmethyl-4,5α-epoxy-14β-hydroxy-3-methoxy-6,7-didehydromorphinano[6,7-b]pyrido[2,3-g]indole, 17-cyclopropylmethyl-4,5α-epoxy-14β-hydroxy-3-methoxy-6,7-didehydromorphinano[6,7-b]

pyrido[3,2-e]indole, 17-cyclopropylmethyl-4,5α-epoxy-14β-hydroxy-3-methoxy-6,7-didehydromorphinano[6,7-b]pyrido[2,3-f]indole, 17-cyclopropylmethyl-4,5α-epoxy-14β-hydroxy-3-methoxy-6,7-didehydromorphinano[6,7-b]pyrido[3,2-g]indole, 17-allyl-4,5α-epoxy-14β-hydroxy-3-methoxy-6,7-didehydromorphinano[6,7-b]cyclohexeno[e]indole, 17-allyl-4,5α-epoxy-14β-hydroxy-3-methoxy-6,7-didehydromorphinano[6,7-b]cyclohexeno[f]indole, 17-allyl-4,5α-epoxy-14β-hydroxy-3-methoxy-6,7-didehydromorphinano[6,7-b]cyclohexeno[g]indole, 17-allyl-4,5α-epoxy-14β-hydroxy-3-methoxy-6,7-didehydromorphinano[6,7-b]cyclopenteno[e]indole, 17-allyl-4,5α-epoxy-14β-hydroxy-3-methoxy-6,7-didehydromorphinano[6,7-b]cyclopenteno[f]indole, 17-allyl-4,5α-epoxy-14β-hydroxy-3-methoxy-6,7-didehydromorphinano[6,7-b]cyclopenteno[g]indole, 17-allyl-4,5α-epoxy-14β-hydroxy-3-methoxy-6,7-didehydromorphinano[6,7-b]cyclohepteno[e]indole, 17-allyl-4,5α-epoxy-14β-hydroxy-3-methoxy-6,7-didehydromorphinano[6,7-b]cyclohepteno[f]indole, 17-allyl-4,5α-epoxy-14β-hydroxy-3-methoxy-6,7-didehydromorphinano[6,7-b]cyclohepteno[g]indole, 17-allyl-4,5α-epoxy-14β-hydroxy-3-methoxy-6,7-didehydromorphinano[6,7-b]cycloocteno[e]indole, 17-allyl-4,5α-epoxy-14β-hydroxy-3-methoxy-6,7-didehydromorphinano[6,7-b]cycloocteno[f]indole, 17-allyl-4,5α-epoxy-14β-hydroxy-3-methoxy-6,7-didehydromorphinano[6,7-b]cycloocteno[g]indole, 17-allyl-4,5α-epoxy-14β-hydroxy-3-methoxy-6,7-didehydromorphinano[6,7-b]pyrido[4,3-g]indole, 17-allyl-4,5α-epoxy-14β-hydroxy-3-methoxy-6,7-didehydromorphinano[6,7-b]pyrido[2,3-g]indole, 17-allyl-4,5α-epoxy-14β-hydroxy-3-methoxy-6,7-didehydromorphinano[6,7-b]pyrido[3,2-e]indole, 17-allyl-4,5α-epoxy-14β-hydroxy-3-methoxy-6,7-didehydromorphinano[6,7-b]pyrido[2,3-f]indole, 17-allyl-4,5α-epoxy-14β-hydroxy-3-methoxy-6,7-didehydromorphinano[6,7-b]pyrido[3,2-g]indole, 3-acetoxy-17-cyclopropylmethyl-4,5α-epoxy-14β-hydroxy-6,7-didehydromorphinano[6,7-b]cyclohexeno[e]indole, 3-acetoxy-17-cyclopropylmethyl-4,5α-epoxy-14β-hydroxy-6,7-didehydromorphinano[6,7-b]cyclohexeno[f]indole, 3-acetoxy-17-cyclopropylmethyl-4,5α-epoxy-14β-hydroxy-6,7-didehydromorphinano[6,7-b]cyclohexeno[g]indole, 3-acetoxy-17-cyclopropylmethyl-4,5α-epoxy-14β-hydroxy-6,7-didehydromorphinano[6,7-b]cyclopenteno[e]indole, 3-acetoxy-17-cyclopropylmethyl-4,5α-epoxy-14β-hydroxy-6,7-didehydromorphinano[6,7-b]cyclopenteno[f]indole, 3-acetoxy-17-cyclopropylmethyl-4,5α-epoxy-14β-hydroxy-6,7-didehydromorphinano[6,7-b]cyclopenteno[g]indole, 3-acetoxy-17-cyclopropylmethyl-4,5α-epoxy-14β-hydroxy-6,7-didehydromorphinano[6,7-b]cyclohepteno[e]indole, 3-acetoxy-17-cyclopropylmethyl-4,5α-epoxy-14β-hydroxy-6,7-didehydromorphinano[6,7-b]cyclohepteno[f]indole, 3-acetoxy-17-cyclopropylmethyl-4,5α-epoxy-14#-hydroxy-6,7-didehydromorphinano[6,7-b]cycloocteno[e]indole, 3-acetoxy-17-cyclopropylmethyl-4,5α-epoxy-14β-hydroxy-6,7-didehydromorphinano[6,7-b]cycloocteno[f]indole, 3-acetoxy-17-cyclopropylmethyl-4,5α-epoxy-14β-hydroxy-6,7-didehydromorphinano[6,7-b]cycloocteno[g]indole, 3-acetoxy-17-cyclopropylmethyl-4,5α-epoxy-14β-hydroxy-6,7-didehydromorphinano[6,7-b]pyrido[4,3-g]indole, 3-acetoxy-17-cyclopropylmethyl-4,5α-epoxy-14β-hydroxy-6,7-didehydromorphinano[6,7-b]pyrido[2,3-g]indole, 3-acetoxy-17-cyclopropylmethyl-4,5α-epoxy-14β-hydroxy-6,7-didehydromorphinano[6,7-b]pyrido[3,2-e]indole, 3-acetoxy-17-cyclopropylmethyl-4,5α-epoxy-14β-hydroxy-6,7-didehydromorphinano[6,7-b]pyrido[2,3-f]indole, 3-acetoxy-17-cyclopropylmethyl-4,5α-epoxy-14β-hydroxy-6,7-didehydromorphinano[6,7-b]pyrido[3,2-g]indole, 3-acetoxy-17-allyl-4,5α-epoxy-14β-hydroxy-6,7-didehydromorphinano[6,7-b]cyclohexeno[e]indole, 3-acetoxy-17-allyl-4,5α-epoxy-14β-hydroxy-6,7-didehydromorphinano[6,7-b]cyclohexeno[f]indole, 3-acetoxy-17-allyl-4,5α-epoxy-14β-hydroxy-6,7-didehydromorphinano[6,7-b]cyclohexeno[g]indole, 3-acetoxy-17-allyl-4,5α-epoxy-14β-hydroxy-6,7-didehydromorphinano[6,7-b]cyclopenteno[e]indole, 3-acetoxy-17-allyl-4,5α-epoxy-14β-hydroxy-6,7-didehydromorphinano[6,7-b]cyclopenteno[f]indole, 3-acetoxy-17-allyl-4,5α-epoxy-14β-hydroxy-6,7-didehydromorphinano[6,7-b]cyclopenteno[g]indole, 3-acetoxy-17-allyl-4,5α-epoxy-14β-hydroxy-6,7-didehydromorphinano[6,7-b]cyclohepteno[e]indole, 3-acetoxy-17-allyl-4,5α-epoxy-14β-hydroxy-6,7-didehydromorphinano[6,7-b]cyclohepteno[f]indole, 3-acetoxy-17-allyl-4,5α-epoxy-14β-hydroxy-6,7-didehydromorphinano[6,7-b]cyclohepteno[g]indole, 3-acetoxy-17-allyl-4,5α-epoxy-14β-hydroxy-6,7-didehydromorphinano[6,7-b]cycloocteno[e]indole, 3-acetoxy-17-allyl-4,5α-epoxy-14β-hydroxy-6,7-didehydromorphinano[6,7-b]cycloocteno[f]indole, 3-acetoxy-17-allyl-4,5α-epoxy-14β-hydroxy-6,7-didehydromorphinano[6,7-b]cycloocteno[g]indole, 3-acetoxy-17-allyl-4,5α-epoxy-14β-hydroxy-6,7-didehydromorphinano[6,7-b]pyrido[4,3-g]indole, 3-acetoxy-17-allyl-4,5α-epoxy-14β-hydroxy-6,7-didehydromorphinano[6,7-b]pyrido[2,3-g]indole, 3-acetoxy-17-allyl-4,5α-epoxy- 14β-hydroxy-6,7-didehydromorphinano[6,7-b]pyrido[3,2-e]indole, 3-acetoxy-17-allyl-4,5α-epoxy-14β-hydroxy-6,7-didehydromorphinano[6,7-b]pyrido[2,3-f]indole, 3-acetoxy-17-allyl-4,5α-epoxy-14β-hydroxy-6,7-didehydromorphinano[6,7-b]pyrido[3,2-g]indole, 14β-acetoxy-17-cyclopropylmethyl-4,5α-epoxy-3-hydroxy-6,7-didehydromorphinano[6,7-b]cyclohexeno[e]indole, 14β-acetoxy-17-cyclopropylmethyl-4,5α-epoxy-3-hydroxy-6,7-didehydromorphinano[6,7-b]cyclohexeno[f]indole, 14β-acetoxy-17-cyclopropylmethyl-4,5α-epoxy-3-hydroxy-6,7-didehydromorphinano[6,7-b]cyclohexeno[g]indole, 14β-acetoxy-17-cyclopropylmethyl-4,5α-epoxy-3-hydroxy-6,7-didehydromorphinano[6,7-b]cyclopenteno[e]indole, 14β-acetoxy-17-cyclopropylmethyl-4,5α-epoxy-3-hydroxy-6,7-didehydromorphinano[6,7-b]cyclopenteno[f]indole, 14β-acetoxy-17-cyclopropylmethyl-4,5α-epoxy-3-hydroxy-6,7-didehydromorphinano[6,7-b]cyclopenteno[g]indole, 14β-acetoxy-17-cyclopropylmethyl-4,5α-epoxy-3-hydroxy-6,7-didehydromorphinano[6,7-b]cyclohepteno[e]indole, 14β-acetoxy-17-cyclopropylmethyl-4,5α-epoxy-3-hydroxy-6,7-didehydromorphinano[6,7-b]cyclohepteno[f]indole, 14β-acetoxy-17-cyclopropylmethyl-4,5α-epoxy-3-hydroxy-6,7-didehydromorphinano[6,7-b]cyclohepteno[g]indole, 14β-acetoxy-17-cyclopropylmethyl-4,5α-epoxy-3-hydroxy-6,7-didehydromorphinano[6,7-b]cycloocteno[e]indole, 14β-acetoxy-17-cyclopropylmethyl-4,5α-epoxy-3-hydroxy-6,7-didehydromorphinano[6,7-b]cycloocteno[f]indole, 14β-acetoxy-17-cyclopropylmethyl-4,5α-epoxy-3-hydroxy-6,7-didehydromorphinano[6,7-b]cycloocteno[g]indole, 14β-acetoxy-17-cyclopropylmethyl-4,5α-epoxy-3-hydroxy-6,7-didehydromorphinano[6,7-b]pyrido[4,3-g]indole, 14β-acetoxy-17-cyclopropylmethyl-4,5α-epoxy-3-hydroxy-6,7-didehydromorphinano[6,7-b]pyrido[2,3-g]indole, 14β-acetoxy-17-cyclopropylmethyl-4,5α-epoxy-3-hydroxy-6,7-didehydromorphinano[6,7-b]pyrido[3,2-e]indole, 14β- acetoxy-17-cyclopropylmethyl-4,5α-epoxy-3-hydroxy-6,7-didehydromorphinano[6,7-b]pyrido[2,3-f]indole, 14β-acetoxy-17-cyclopropylmethyl-4,5α-epoxy-3-hydroxy-6,7-didehydromorphinano[6,7-b]pyrido[3,2-g]indole, 14β-acetoxy-17-allyl-4,5α-epoxy-3-hydroxy-6,7-didehydromorphinano[6,7-b]cyclohexeno[e]indole, 14β-acetoxy-17-allyl-4,5α-epoxy-3-hydroxy-6,7-didehydromorphinano[6,7-b]cyclohexeno[f]indole, 14β-acetoxy-17-allyl-4,5α-epoxy-3-hydroxy-6,7-didehydromorphinano[6,7-b]cyclohexeno[f]indole, 14β-acetoxy-17-allyl-4,5α-epoxy-3-hydroxy-6,7-didehydromorphinano[6,7-b]cyclopenteno[e]indole, 14β-acetoxy-17-allyl-4,5α-epoxy-3-hydroxy-6,7-didehydromorphinano[6,7-b]cyclopenteno[f]indole, 14β-acetoxy-17-allyl-4,5α-epoxy-3-hydroxy-6,7-didehydromorphinano[6,7-b]cyclopenteno[g]indole, 14β-acetoxy-17-allyl-4,5α-epoxy-3-hydroxy-6,7-didehydromorphinano[6,7-b]cyclohepteno[e]indole, 14β-acetoxy-17-allyl-4,5α-epoxy- 3-hydroxy-6,7-didehydromorphinano[6,7-b]cyclohepteno[f]indole, 14β-acetoxy-17-allyl-4,5α-epoxy-3-hydroxy-6,7-didehydromorphinano[6,7-b]cyclohepteno[g]indole, 14β-acetoxy-17-allyl-4,5α-epoxy-3-hydroxy-6,7-didehydromorphinano[6,7-b]cyclooocteno[e]indole, 14β-acetoxy-17-allyl-4,5α-epoxy-3-hydroxy-6,7-didehydromorphinano[6,7-b]cyclooocteno[f]indole, 14β-acetoxy-17-allyl-4,5α-epoxy-3-hydroxy-6,7-didehydromorphinano[6,7-b]cyclooocteno[g]indole, 14β-acetoxy-17-allyl-4,5α-epoxy-3-hydroxy-6,7-didehydromorphinano[6,7-b]pyrido[4,3-g]indole, 14β-acetoxy-17-allyl-4,5α-epoxy-3-hydroxy-6,7-didehydromorphinano[6,7-b]pyrido[2,3-g]indole, 14β-acetoxy-17-allyl-4,5α-epoxy-3-hydroxy-6,7-didehydromorphinano[6,7-b]pyrido[3,2-e]indole, 14β-acetoxy-17-allyl-4,5α-epoxy-3-hydroxy-6,7-didehydromorphinano[6,7-b]pyrido[2,3-f]indole and 14β-acetoxy-17-allyl-4,5α-epoxy-3-hydroxy-6,7-didehydromorphinano[6,7-b]pyrido[3,2-g]indole. Needless to say, the examples of the compounds according to the present invention are not limited to the compounds specifically mentioned above.

Among the compounds of the formula (I), those wherein $R^1$, $R^2$, $R^3$ and $R^4$ represent the meanings described above, respectively, and $R^5$ and $R^6$ independently represent hydrogen, trifluoromethyl, trifluoromethoxy, iodine, cyano, phenyl, $C_1$–$C_3$ hydroxyalkyl, $SR^7$, $SO_2R^7$, $(CH_2)_mCO_2R^7$ (wherein m represents an integer of 0–3 and $R^7$ represents $C_1$–$C_5$ alkyl), $SO_2NR^8R^9$, $CONR^8R^9$, $(CH_2)_nNR^8R^9$ (wherein n represents an integer of 1–3, $R^8$ and $R^9$ independently represent $C_1$–$C_5$ alkyl, $C_4$–$C_6$ cycloalkyl) or nitro (bonded to one of 4'-, 6'- and 7'-positions), that is, the compounds represented by the formula (Ia) (excluding the case wherein $R^5$ and $R^6$ simultaneously represent hydrogen), and the compounds represented by the formula (II) (wherein $R^1$, $R^2$, $R^3$, $R^4$ and X represent the same meanings as described above, respectively) can be obtained by the following method:

CHART 1

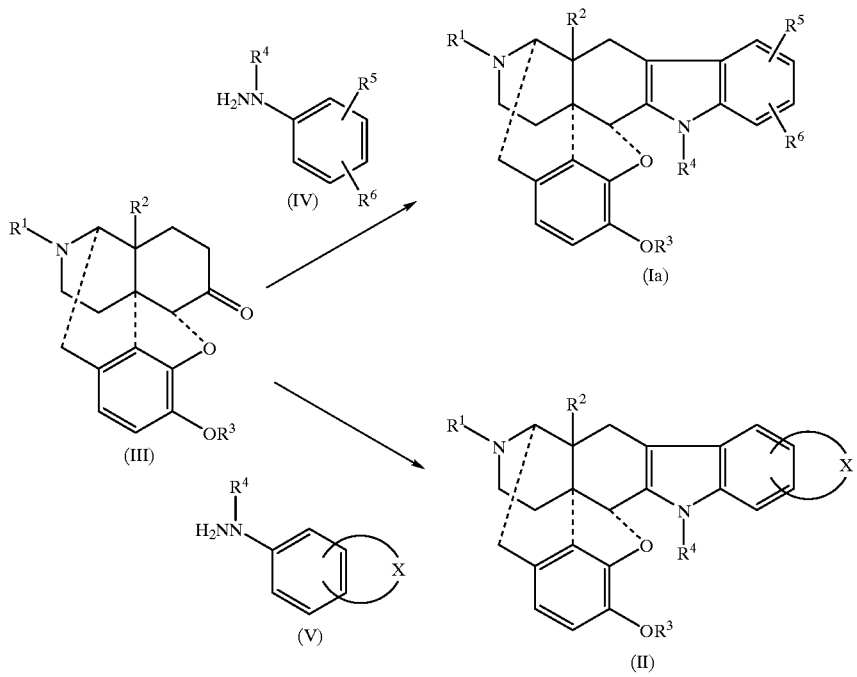

That is, these compounds can easily be obtained by reacting the compound represented by the formula (III) with the phenylhydrazine derivative represented by the formula (IV) or (V) (wherein $R^4$ and X represent the same meanings as described above, $R^5$ and $R^6$ independently represent hydrogen, trifluoromethyl, trifluoromethoxy, iodine, cyano, phenyl, $C_1$–$C_3$ hydroxyalkyl, $SR^7$, $SO_2R^7$, $(CH_2)_mCO_2R^7$ (wherein m represents an integer of 0–3, $R^7$ represents $C_1$–$C_5$ alkyl), $SO_2NR^8R^9$, $CONR^8R^9$, $(CH_2)_nNR^8R^9$ (wherein n represents an integer of 1–3, $R^8$ and $R^9$ independently represent hydrogen, $C_1$–$C_5$ alkyl or $C_4$–$C_6$ cycloalkylalkyl), or nitro (bonded to 2- or 3-position), with the proviso that $R^5$ and $R^6$ are not simultaneously hydrogen) in a solvent in the presence of an acid catalyst. Examples of the solvent include alcoholic solvents such as methanol and ethanol; aliphatic acid solvents such as acetic acid and propionic acid; and dipolar aprotic solvents such as DMF and DMSO. Among these, alcoholic solvents and aliphatic acid solvents are preferred, and ethanol and acetic acid are best preferred. Examples of the acid catalyst include inorganic acids such as hydrochloric acid, sulfuric acid, nitric acid, phosphoric acid, methanesulfonic acid, p-toluenesulfonic acid, acetic acid, formic acid and propionic acid. Among these, hydrochloric acid, sulfuric acid and methanesulfonic acid are preferred. The reaction may be carried out at 0–300° C., preferably 25–150° C., more preferably 60–120° C.

Among the compounds represented by the formula (I), the compounds wherein $R^1$, $R^2$ and $R^4$ represent the same meanings as described above, $R^3$ is hydrogen, $R^5$ is $(CH_2)_n NR^8 R^9$ (wherein n=1, $R^8$ and $R^9$ represent the same meanings described above), and $R^6$ is hydrogen, that is, the compounds represented by the formula (Id) can also be obtained from the compounds of the formula (I) wherein $R^1$, $R^2$ and $R^4$ represent the same meanings as described above, $R^3$ is hydrogen, $R^5$ is $CONR^8 R^9$ (wherein $R^8$ and $R^9$ represent the same meanings described above), and $R^6$ is hydrogen, that is, the compounds represented by the formula (Ib).

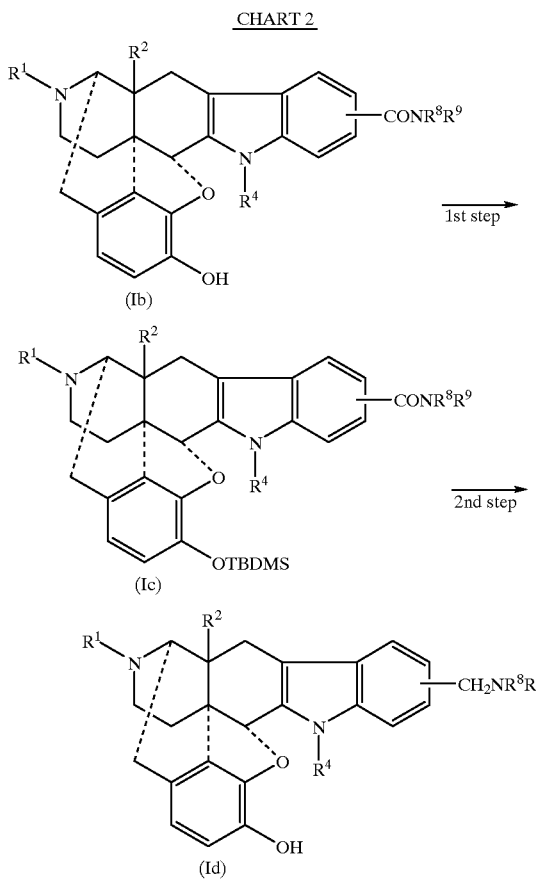

CHART 2

The first step is the step for protecting the phenolic hydroxyl group with tert-butyldimethylsilyl group in the presence of a base. As the base, triethylamine, diisopropylethylamine, imidazole and the like may be employed and satisfactory results are usually obtained by using imidazole. As the solvent, halogen-substituted solvents such as methylene chloride and chloroform, and DMF and the like may be employed. Among these, DMF is preferred. The reaction temperature range may be between −50 and 150° C. and satisfactory results are usually obtained at 0–30° C. The second step is the step for reducing amide to amine and for removing the protective group. As the reducing agent, lithium aluminum hydride, diborane, diisobutylaluminum hydride and the like may be employed, and diborane is best preferred. As the solvent, ether solvents such as ether, THF, DME and dioxane are preferred and satisfactory results are usually obtained by using THF. The reaction can be carried out at −50–150° C., and especially good results are obtained at 50–100° C. The removal of the protective group is carried out simultaneously when an acid is added for decomposition of the reducing reaction. The reaction is carried out by direct addition of an acid to the reaction solution. Examples of the acid used here include hydrochloric acid, sulfuric acid, nitric acid and the like, and hydrochloric acid is best preferred. The reaction can be carried out at 0–150° C., and especially good results are obtained at 50–100° C.

Among the compounds of the formula (I), those wherein $R^1$, $R^2$, $R^3$ and $R^4$ represent the same meanings as described above, $R^5$ represents isothiocyanato (bonded to one of 4'-, 6'- and 7'-positions), and $R^6$ is hydrogen, that is, the compounds represented by the formula (Ig) can be obtained through two steps from the compounds of the formula (I) wherein $R^1$, $R^2$, $R^3$ and $R^4$ represent the same meanings as described above, $R^5$ is nitro (bonded to one of 4'-, 6'- and 7'-positions), and $R^6$ is hydrogen, that is, the compounds represented by the formula (Ie).

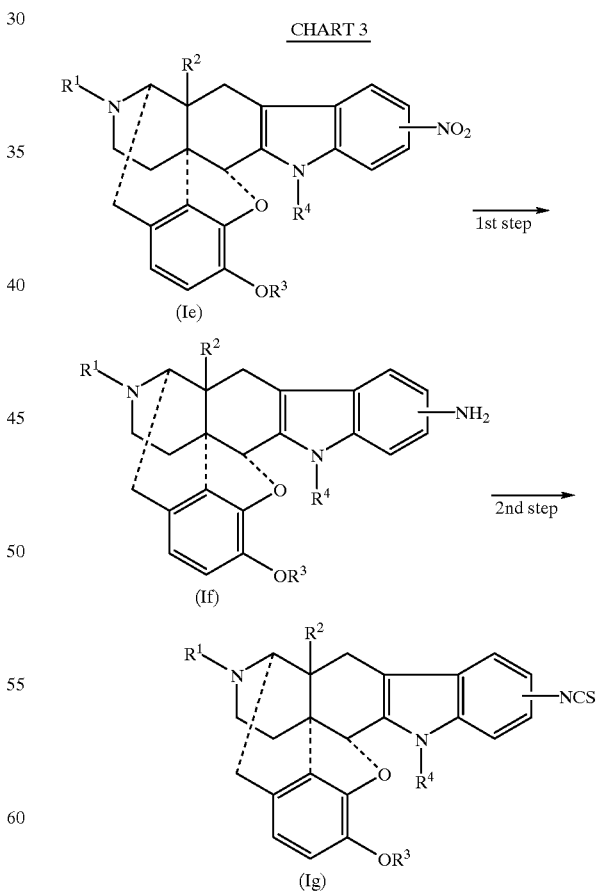

CHART 3

The first step is the step for reducing the nitro group to amino group. Methods for the reduction include a method wherein hydrogenation is carried out by using a catalyst such as palladium or platinum; a method wherein reduction is carried out by using a metal hydride such as lithium aluminum hydride; a method in which a metal such as iron, tin, zinc or the like and an acid are used; and a method in which the reduction is carried out by using stannous chloride. Satisfactory results are obtained by using stannous chloride. As the solvent, alcohols solvents such as methanol and ethanol are preferred, and ethanol is especially preferred. The reaction may be carried out at 0–80° C., preferably 50–80° C. The second step is the step for reaction of the amine with thiophosgene to convert the amine to isothiocyanate. As the solvent, two-phase systems between halogen-substituted solvents such as chloroform and methylene chloride, and aqueous sodium hydrogen carbonate solution or dilute hydrochloric acid are preferred, and chloroform-dilute hydrochloric acid is especially preferred. The reaction may be carried out at −50–60° C., preferably 0–30° C.

As the phenylhydrazine derivatives represented by the formula (IV) [wherein $R^4$ represents the same meanings as described above, $R^5$ and $R^6$ independently represent hydrogen, iodine, trifluoromethyl, trifluoromethoxy, cyano, phenyl, $C_1$–$C_3$ hydroxyalkyl, $SR^7$, $SO_2R^7$, $(CH_2)_mCO_2R^7$ (wherein m represents an integer of 0–3, $R^7$ represents $C_1$–$C_5$ alkyl), $SO_2NR^8R^9$, $CONR^8R^9$, $(CH_2)_nNR^8R^9$ (wherein n represents an integer of 1–3, $R^8$ and $R^9$ independently represents hydrogen, $C_1$–$C_5$ alkyl, or $C_4$–$C_6$ cycloalkylalkyl) or nitro (bonded to 2- or 3-position), with the proviso that $R^5$ and $R^6$ are not simultaneously hydrogen], commercially available compounds or synthesized products are used. The derivative (IVa) wherein $R^4$ is hydrogen is derived from a nitrobenzene derivative (VI) or an aniline derivative (VII) through the route shown in Chart 4.

methods may be employed. Satisfactory results are obtained by employing hydrogenation or the method using stannous chloride. As the catalyst for hydrogenation, platinum oxide, palladium-carbon or the like can be employed and the reaction normally proceeds under 1 atm of hydrogen atmosphere. As the solvent, alcoholic solvents such as methanol and ethanol are preferred and methanol is especially preferred. The reaction may be carried out at −20–60° C., preferably 0–30° C. The conditions of the reaction employing stannous chloride are the same as the first step in Chart 2. The second step is the step for reaction of the product with nitrite ion under acidic condition for conversion of the compound to diazonium ion and for reduction of the resultant to hydrazine. As the diazotization agent, sodium nitrite, potassium nitrite and the like may be employed, and satisfactory results are usually obtained by using sodium nitrite. The reaction is carried out using concentrated hydrochloric acid as the solvent. The reaction may be carried out at −30–100°C., preferably −10–30° C., and is usually carried out at 0° C. The reduction may be carried out using stannous chloride, tin, iron, zinc or the like in the presence of an acid, and satisfactory results are usually obtained by using stannous chloride. As the solvent, concentrated hydrochloric acid is used. The reaction temperature is preferably −30–50° C. and good results are usually obtained at 0° C.

Among the compounds represented by the formula (V), those wherein $R^4$ is hydrogen (i.e., Compound Va; wherein X represents the same meanings as described above) can also be obtained from (VIII) or (IX) similarly.

The phenylhydrazine derivative (IVf) wherein $R^4$ represents the same meanings as described above, $R^5$ is $CONR^8R^9$ (wherein $R^8$ and $R^9$ represent the same meanings as described above), and $R^6$ is hydrogen can also be synthesized from the phenylhydrazine derivative (IVb) wherein $R^4$ represents the same meanings as described above, $R^5$ is $CO_2R^7$ (wherein $R^7$ represents the same meanings as described above), and $R^6$ is hydrogen, by the method shown in Chart 5.

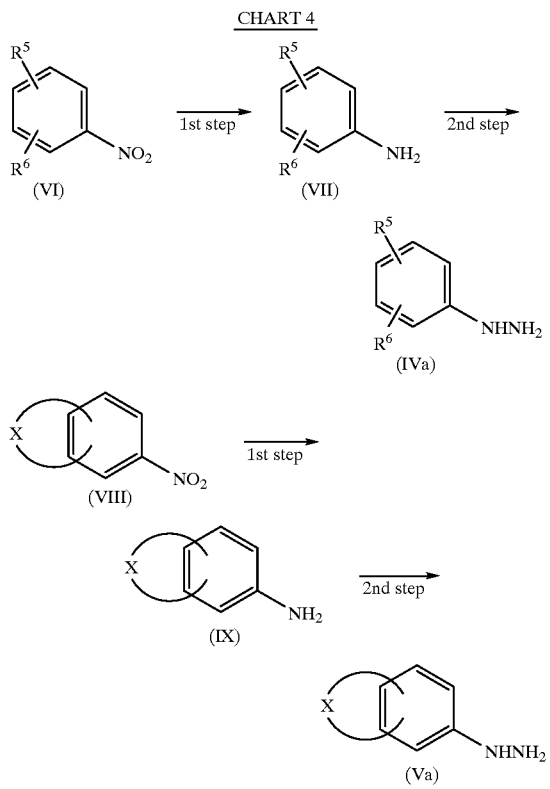

CHART 4

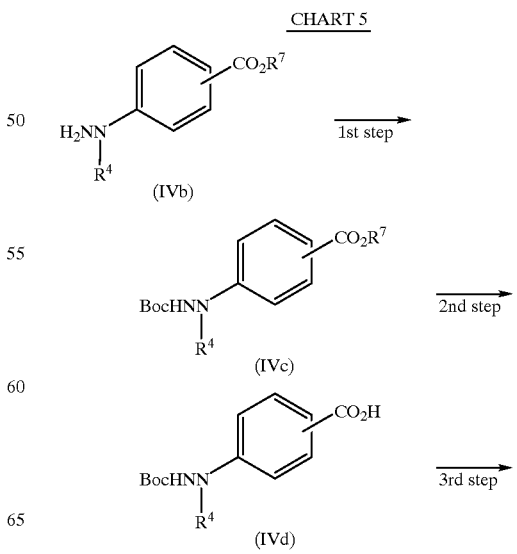

CHART 5

The first step is the step for reduction of nitro group to amino group. Similar to the first step in Chart 2, various -continued BocHN—N(R⁴)—[phenyl]—CONR⁸R⁹

(IVe)

→ 4th step →

H₂N—N(R⁴)—[phenyl]—CONR⁸R⁹

(IVf)

The first step is the step for protection of hydrazine with tert-butoxycarbonyl group. For this reaction, di-tert-butylcarbonate is employed. As the solvents, mixed solvents of an organic solvent-aqueous solvent are employed. As the organic solvent, halogen-substituted solvents such as chloroform and methylene chloride are preferred, and as the aqueous solvent, aqueous sodium hydrogen carbonate solution, aqueous potassium carbonate solution, aqueous sodium hydroxide solution, and aqueous potassium hydroxide solution are preferred. Mixed solvent of chloroform—aqueous sodium hydrogen carbonate solution is especially preferred, although the solvent is not restricted thereto. The reaction may be carried out at 0–150° C. and satisfactory results are usually obtained at 50–100° C. The second step is the step for hydrolyzing the ester under basic condition. As the base, sodium hydroxide, potassium hydroxide or the like may be employed. As the solvent, mixed solvents between an ether solvent such as dioxane or THF and water are preferably employed. The reaction may be carried out at 0–150° C., and satisfactory results are obtained at 50–100° C. The third step is the step for condensing the carboxylic acid with amine to form amide. As the condensing agent, DCC, 3-(3-dimethylaminopropyl)-1-ethylcarbodiimide hydrochloric acid salt and the like are employed. In view of the ease of post-treatment, 3-(3-dimethylaminopropyl)-1-ethylcarbodiimide hydrochloric acid salt is preferred. As the solvent, halogen-substituted solvents such as chloroform, methylene chloride and 1,2-dichloroethane are preferred. The reaction may be carried out at 0–150° C., preferably at 20–80° C. The fourth step is the step for removing the protective group of hydrazine under acidic condition. As the acid, hydrochloric acid, sulfuric acid, nitric acid and the like may be employed, and hydrochloric acid is preferred. As the solvent, alcoholic solvents such as ethanol and methanol, ether solvents such as THF and dioxane, and ethyl acetate and the like are preferred, and satisfactory results are usually obtained by using ethyl acetate. The reaction may be carried out at −20–100° C., preferably at 0–30° C.

When the compound of the present invention is clinically applied as an immunosuppressing agent, brain cell-protecting agent, antiallergic agent and anti-inflammatory agent, the free base or the acid addition salt thereof per se may be administered, or the active compound may be administered after mixing with an appropriate excipient such as a stabilizer, buffering agent, diluent, isotonic agent, antiseptic or the like. The compound may be formulated into various forms such as injection solutions, sublingual tablets, capsules, suppositories, formulations for oral administration and the like. The dose of administration is appropriately determined based on the object of administration, route of administration and conditions of the patient. In case of injection, 0.0001–1 g/day of the active compound is administered, and in case of oral administration, 0.001–10 g/day of the active compound is administered. The content of the compound of the present invention in a pharmaceutical formulation may be 0.05–99%. In case of injection solutions, the content may be 0.5–20%, and in case of formulations for oral administration, the content may be 0.1–50%.

EXAMPLES

The present invention will now be described by way of examples and reference examples. However, the present invention is not limited to the following examples.

Reference Example 1

N,N-dimethyl-2-(4-nitrophenyl)ethylamine

To 4.17 g of 2-(4-nitrophenyl)ethylamine (salt-free compound obtained by neutralization of commercially available hydrochloric acid salt), 1.1 ml of water was added. After cooling the mixture to 0° C., 4.8 ml of formic acid and 4.7 ml of aqueous 35% formalin solution were added to the mixture, and the resulting mixture was heated to reflux for 1 hour. The resulting mixture was cooled to 0° C. and 55 ml of 2N aqueous sodium hydroxide solution was added to make the mixture basic. The resultant was subjected to salting out and the resultant was extracted with ether (2×60 ml). The organic layers were combined, dried and concentrated, thereby obtaining 4.91 g of unpurified captioned compound.

NMR (90 MHz, CDCl3); δ 2.30 (6H, s), 2.43–2.67 (2H, m), 2.79–3.07 (2H, m), 7.38 (2H, d, J=9 Hz), 8.16 (2H, d, J=9 Hz).

By using 2-(3-nitrophenyl)ethylamine, 2-(2-nitrophenyl)ethylamine, 4-nitrobenzylamine, 3-nitrobenzylamine or 2-nitrobenzylamine in place of 2-(4-nitrophenyl)ethylamine, N,N-dimethyl-2-(3-nitrophenyl)ethylamine, N,N-dimethyl-2-( 2-nitrophenyl)ethylamine, N,N-dimethyl-4-nitrobenzylamine, N,N-dimethyl-3-nitrobenzylamine and N,N-dimethyl-2-nitrobenzylamine are obtained, respectively.

Reference Example 2

4-[2-(dimethylamino)ethyl]aniline

The 4.91 g of unpurified N,N-dimethyl-2-(4-nitrophenyl)ethylamine obtained in Reference Example 1 was dissolved in 70 ml of methanol and 96.1 mg of platinum oxide was added to the solution, followed by stirring the resulting mixture under hydrogen atmosphere (1 atm) at room temperature. After one hour from the beginning of the stirring, another 49.3 mg of platinum oxide was added and the mixture was stirred for a total of 4 hours. The reaction mixture was filtered through Celite, and the filtration residue was washed with methanol. The filtrate and the washing were combined and concentrated to obtain 4.11 g of unpurified captioned compound.

NMR (90 MHz, CDCl3); δ 2.28 (6H, s), 2.37–2.92 (4H, m), 3.55 (2H, br s, NH2), 6.63 (2H, d, J=9 Hz), 7.01 (2H, d, J=9 Hz).

Reference Example 3

4-dimethylaminomethylaniline

In 30 ml of ethanol, 2.93 g of N,N-dimethyl-4-nitrobenzylamine was dissolved, and 18.3 g of tin(II) chloride dihydrate was added to the solution, followed by stirring the resulting solution at 70° C. for 40 minutes. The reaction mixture was cooled to 0° C., and 100 ml of 2N aqueous sodium hydroxide solution was added to make the mixture basic. The resulting mixture was extracted with ethyl acetate (2×100 ml) and the organic layers were combined, dried and concentrated to obtain 2.46 g of unpurified captioned compound.

NMR (90 MHz, CDCl3); δ 2.20 (6H, s), 3.39 (2H, br s), 3.62 (2H, br s, NH2), 6.63 (2H, d, J=8.5 Hz), 7.08 (2H, d, J=8.5 Hz).

By using N,N-dimethyl-3-nitrobenzylamine or N,N-dimethyl-2-nitrobenzylamine in place of N,N-dimethyl-4-nitrobenzylamine, 3-dimethylaminomethylaniline and 2-dimethylaminomethylaniline are obtained, respectively.

Reference Example 4

4-[2-(dimethylamino)ethyl]phenylhydrazine

In 26 ml of concentrated hydrochloric acid, 2.18 g of the unpurified 4-[2-(dimethylamino)ethyl]aniline obtained in Reference Example 2 was dissolved at 0° C., and a solution containing 1.92 g of sodium nitrite in 8 ml of water was added dropwise, followed by stirring the resulting mixture at 0° C. for 1 hour. The resulting mixture was added to a solution containing 12.7 g of tin(II) chloride dihydrate in 5 ml of concentrated hydrochloric acid at 0° C. and the resulting mixture was stirred for 1 hour. To the reaction mixture, about 17 g of sodium hydroxide was added at 0° C. to make the mixture basic and the resultant was extracted with chloroform (2×50 ml). The organic layers were combined, dried and concentrated to obtain 1.90 g of an oily product. The obtained oily product was purified by column chromatography [silica gel; chloroform saturated with ammonia] to obtain 1.10 g of the captioned compound (yield 46%, 3 steps).

NMR (90 MHz, CDCl3); δ 2.28 (6H, s), 2.38–2.83 (4H, m), 3.38 (2H, br s, NH2), 5.10 (1H, br s, NH), 6.74 (2H, d, J=9 Hz), 7.08 (2H, d, J=9 Hz).

In accordance with Reference Examples 2 and 4, by using N,N-dimethyl-2-(3-nitrophenyl)ethylamine, N,N-dimethyl-2-(2-nitrophenyl)ethylamine, 3-nitrophenethyl alcohol, N-cyclopropylmethyl-4-nitrobenzenesulfonamide, N-cyclopropylmethyl-3-nitrobenzenesulfonamide, N-cyclopropylmethyl-2-nitrobenzenesulfonamide, ethyl 4-nitrophenylacetate, ethyl 3-nitrophenylacetate, ethyl 2-nitrophenylacetate, N,N-dimethyl-4-nitrobenzenesulfonamide, N,N-dimethyl-3-nitrobenzenesulfonamide, N,N-dimethyl-2-nitrobenzenesulfonamide or 3-nitrobenzenesulfonamide in place of N,N-dimethyl-2-(4-nitrophenyl)ethylamine, 3-[2-(dimethylamino)ethyl]phenylhydrazine, 2-[2-(dimethylamino)ethyl]phenylhydrazine, 3-(2-hydroxyethyl)phenylhydrazine, 4-(N-cyclopropylmethylsulfamoyl)phenylhydrazine, 3-(N-cyclopropylmethylsulfamoyl)phenylhydrazine, 2-(N-cyclopropylmethylsulfamoyl)phenylhydrazine, 4-ethoxycarbonylmethylphenylhydrazine, 3-ethoxycarbonylmethylphenylhydrazine, 2-ethoxycarbonylmethylphenylhydrazine, 4-(N,N-dimethylsulfamoyl)phenylhydrazine, 3-(N,N-dimethylsulfamoyl)phenylhydrazine, 2-(N,N-dimethylsulfamoyl)phenylhydrazine and 3-sulfamoylphenylhydrazine are obtained, respectively.

In accordance with Reference Example 4, by using 4-dimethylaminomethylaniline, 3-dimethylaminomethylaniline, 2-dimethylaminomethylaniline, 4-aminophenethyl alcohol, 2-aminophenethyl alcohol, 2-aminobenzenesulfonamide, 4-aminobenzonitrile, 3-aminobenzonitrile, 4-aminobiphenyl, 3-aminobiphenyl, 2-aminobiphenyl, 3-trifluoromethoxyaniline, 2-trifluoromethoxyaniline, 4-iodoaniline, 3-iodoaniline, 2-iodoaniline, ethyl 4-aminobenzoate, ethyl 3-aminobenzoate, ethyl 2-aminobenzoate, methyl 4-aminobenzoate, methyl 3-aminobenzoate, methyl 2-aminobenzoate, 1-amino-5,6,7,8-tetrahydronaphthalene, 2-amino-5,6,7,8-tetrahydronaphthalene, 5-aminoisoquinoline, 5-aminoquinoline, 6-aminoquinoline, 8-aminoquinoline, 4-aminoindan, 5-aminoindan, 1-amino-6,7,8,9-tetrahydro-5H-benzocycloheptene, 2-amino-6,7,8,9-tetrahydro-5H-benzocycloheptene, 1-amino-5,6,7,8,9,10-hexahydrobenzocyclooctene, 2-amino-5,6,7,8,9,10-hexahydrobenzocyclooctene, 1-amino-5-ethoxycarbonyl-5,6,7,8-tetrahydronaphthalene, 1-amino-6-ethoxycarbonyl-5,6,7,8-tetrahydronaphthalene, 1-amino-7-ethoxycarbonyl-5,6,7,8-tetrahydronaphthalene, 1-amino-8-ethoxycarbonyl-5,6,7,8-tetrahydronaphthalene, 1-amino-5-carbamoyl-5,6,7,8-tetrahydronaphthalene, 1-amino-6-carbamoyl-5,6,7,8-tetrahydronaphthalene, 1-amino-7-carbamoyl-5,6,7,8-tetrahydronaphthalene, 1-amino-8-carbamoyl-5,6,7,8-tetrahydronaphthalene, 1-amino-5-sulfamoyl-5,6,7,8-tetrahydronaphthalene, 1-amino-6-sulfamoyl-5,6,7,8-tetrahydronaphthalene, 1-amino-7-sulfamoyl-5,6,7,8-tetrahydronaphthalene or 1-amino-8-sulfamoyl-5,6,7,8-tetrahydronaphthalene in place of 4-[2-(dimethylamino)ethyl]aniline, 4-(N,N-dimethylaminomethyl)phenylhydrazine, 3-(N,N-dimethylaminomethyl)phenylhydrazine, 2-(N,N-dimethylaminomethyl)phenylhydrazine, 4-(2-hydroxyethyl)phenylhydrazine, 2-(2-hydroxyethyl)phenylhydrazine, 2-sulfamoylphenylhydrazine,4-cyanophenylhydrazine, 3-cyanophenylhydrazine, 4-phenylphenylhydrazine, 3-phenylphenylhydrazine, 2-phenylphenylhydrazine, 3-trifluoromethoxyphenylhydrazine, 2-trifluoromethoxyphenylhydrazine, 4-iodophenylhydrazine, 3-iodophenylhydrazine, 2-iodophenylhydrazine, 4-ethoxycarbonylphenylhydrazine, 3-ethoxycarbonylphenylhydrazine, 2-ethoxycarbonylphenylhydrazine, 4-methoxycarbonylphenylhydrazine, 3-methoxycarbonylphenylhydrazine, 2-methoxycarbonylphenylhydrazine, 1-hydrazino-5,6,7,8-tetrahydronaphthalene, 2-hydrazino-5,6,7,8-tetrahydronaphthalene, 5-hydrazinoisoquinoline, 5-hydrazinoquinoline, 6-hydrazinoquinoline, 8-hydrazinoquinoline, 4-hydrazinoindan, 5-hydrazinoindan, 1-hydrazino-6,7,8,9-tetrahydro-5H-benzocycloheptene, 2-hydrazino-6,7,8,9-tetrahydro-5H-benzocycloheptene, 1-hydrazino-5,6,7,8,9,10-hexahydrobenzocyclooctene, 2-hydrazino-5,6,7,8,9,10-hexahydrobenzocyclooctene, 1-hydrazino-5-ethoxycarbonyl-5,6,7,8-tetrahydronaphthalene, 1-hydrazino-6-ethoxycarbonyl-5,6,7,8-tetrahydronaphthalene, 1-hydrazino-7-ethoxycarbonyl-5,6,7,8-tetrahydronaphthalene, 1-hydrazino-8-ethoxycarbonyl-5,6,7,8-tetrahydronaphthalene, 1-hydrazino-5-carbamoyl-5,6,7,8-tetrahydronaphthalene, 1-hydrazino-6-carbamoyl-5,6,7,8-tetrahydronaphthalene, 1-hydrazino-7-carbamoyl-5,6,7,8-tetrahydronaphthalene, 1-hydrazino-8-carbamoyl-5,6,7,8-tetrahydronaphthalene, 1-hydrazino-5-sulfamoyl-5,6,7,8-tetrahydronaphthalene, 1-hydrazino-6-sulfamoyl-5,6,7,8-tetrahydronaphthalene, 1-hydrazino-7-sulfamoyl-5,6,7,8-tetrahydronaphthalene, and 1-hydrazino-8-sulfamoyl-5,6,7,8-tetrahydronaphthalene are obtained, respectively.

Reference Example 5

1-tert-butoxycarbonyl-2-(3-methoxycarbonylphenyl) hydrazine

In 40 ml of chloroform, 4.00 g of 3-methoxycarbonylphenylhydrazine methanesulfonic acid salt was dissolved.

To this solution, aqueous sodium hydrogen carbonate (1.31 g/30 ml) was added and then 3.6 ml of di-tert-butyldicarbonate was added to the mixture, followed by heating the resulting mixture to reflux for one hour. After leaving the mixture to cool to room temperature, the mixture was separated and the aqueous layer was extracted with chloroform (2×20 ml). The organic layers were combined, dried and concentrated to obtain 4.68 g of unpurified captioned compound.

NMR (90 MHz, CDCl3); δ 1.44 (9H, s), 3.90 (3H, s), 5.85 (1H, br s, NH), 6.44 (1H, m, NH), 7.00 (1H, ddd, J=8, 3, 2 Hz), 7.30 (1H, ddd, J=8, 8, 1 Hz), 7.47–7.63 (2H, m).

Reference Example 6

3-(2-tert-butoxycarbonylhydrazino)benzoic acid

The 4.68 g of unpurified 1-tert-butoxycarbonyl-2-(3-methoxycarbonylphenyl)hydrazine was dissolved in 75 ml of 1,4-dioxane, and 25 ml of aqueous 3N potassium hydroxide solution was added to the solution, followed by heating the mixture at reflux for one hour. The reaction mixture was cooled to 0° C., and about 25 ml of 3N hydrochloric acid was added to make the reaction mixture acidic. The mixture was subjected to salting out and the resultant was extracted with ethyl acetate (2×50 ml). The organic layers were combined, dried and concentrated to obtain 4.40 g of unpurified captioned compound.

NMR (90 MHz, CDCl3); δ 1.47 (9H, s), 5.5–6.4 (2H, br s, OH, NH), 6.60 (1H, m, NH), 7.05 (1H, m), 7.32 (1H, br dd, J=8, 8 Hz), 7.50–7.70 (2H, m).

Reference Example 7

1-tert-butoxycarbonyl-2-[3-(N-cyclopropylmethylcarbamoyl)phenyl]hydrazine

The 4.40 g of unpurified 3-(2-tert-butoxycarbonylhydrazino)benzoic acid was dissolved in 80 ml of dichloromethane. To this mixture, 1.78 g of cyclopropylmethylamine and 3.45 g of 3-(3-dimethylaminopropyl)-1-ethylcarbodiimide hydrochloric acid salt were added and the resulting mixture was heated at reflux for 2 hours. After leaving the reaction mixture to cool to room temperature, the mixture was sequentially washed with 50 ml of water, 50 ml of 1N hydrochloric acid and then 50 ml of aqueous saturated sodium hydrogen carbonate solution, dried and concentrated to obtain 3.42 g of crude crystals. The crude crystals were recrystallized twice from ethyl acetate-hexane to obtain 1.29 g (yield 40%, three steps) of the captioned compound.

NMR (90 MHz, CDCl3); δ 0.29 (2H, m), 0.58 (2H, m), 1.15 (1H, m), 1.46 (9H, s), 3.28 (2H, dd, J=7.0, 6.5 Hz), 5.58 (1H, m, NH), 6.21 (1H, m, NH), 6.47 (1H, br s, NH), 6.95 (1H, m), 7.15–7.38 (3H, m).

Reference Example 8

3-(N-cyclopropylmethylcarbamoyl)phenylhydrazine

In 5 ml of ethyl acetate, 1.92 g of 1-tert-butoxycarbonyl-2-[3-(N-cyclopropylmethylcarbamoyl)phenyl]hydrazine was dissolved and about 12 ml of 2N hydrochloric acid/ethyl acetate solution was added to the solution. The resulting suspension was stirred at room temperature for 4 hours. To the reaction mixture, 15 ml of aqueous 2N ammonia solution was added and the resultant was extracted with 20 ml of ethyl acetate. The extract was dried and concentrated to obtain 1.28 g of crude crystals. The crude crystals were recrystallized from ethyl acetate-hexane to obtain 1.20 g (yield 93%) of the captioned compound.

NMR (90 MHz, CDCl3); δ 0.30 (2H, m), 0.59 (2H, m), 1.15 (1H, m), 1.7–4.3 (3H, br s, NH2, NH), 3.31 (2H, dd, J=7.0, 5.5 Hz), 6.25 (1H, m, NH), 6.93 (1H, m), 7.05–7.38 (3H, m).

In accordance with Reference Examples 5–8, by using 4-methoxycarbonylphenylhydrazine or 2-methoxyphenylhydrazine in place of 3-methoxycarbonylphenylhydrazine, 4-(N-cyclopropylmethylcarbamoyl)phenylhydrazine and 2-(N-cyclopropylmethylcarbamoyl)phenylhydrazine are obtained, respectively.

Example 1

17-cyclopropylmethyl-6,7-didehydro-4,5α-epoxy-3,14β-dihydroxy-5'-iodo-6,7-2',3'-indolomorphinan 1

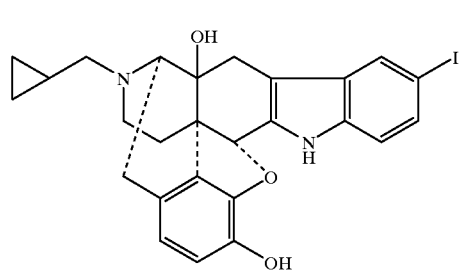

In 15 ml of ethanol, 950 mg of naltrexone hydrochloric acid salt and 590 mg of 4-iodophenylhydrazine were dissolved and then 0.36 ml of methanesulfonic acid was added to the solution, followed by heating the resulting mixture to reflux for 3 hours. After cooling the reaction mixture at room temperature, 20 ml of aqueous saturated sodium hydrogen carbonate solution was added while cooling the mixture in iced water to neutralize the mixture and the resultant was extracted three times with 30 ml of chloroform. The organic layers were combined and washed with 15 ml of aqueous saturated saline. The resultant was dried and concentrated and the obtained residue was purified by column chromatography [silica gel; chloroform:methanol:28% aqueous ammonia solution (97:3:0.3)]. The obtained powder was suspended in methanol and methanesulfonic acid was added to convert the compound to methanesulfonic acid salt. The resultant was purified by column chromatography [SEPHADEX LH-20; methanol] to obtain 492 mg of methanesulfonic acid salt of the captioned compound (yield 31%).

1 methanesulfonic acid salt mp.:220° C. (decomposed); NMR (400 MHz, DMSO-d6); δ 0.44 (1H, m), 0.49 (1H, m), 0.63 (1H, m), 0.72(1H, m), 1.10 (1H, m), 1.82 (1H, br d, J=11.7 Hz), 2.29 (3H, s), 2.50–2.63 (2H, m), 2.70 (1H, m), 2.91 (1H, d, J=16.1 Hz), 2.92 (1H, m), 3.11 (1H, m), 3.22 (1H, dd, J=19.5, 6.8 Hz), 3.36–3.47 (2H, m), 4.04, (1H, d, J=6.4 Hz), 5.68 (1H, s), 6.34 (1H, s), 6.60 (1H, d, J=8.3 Hz), 6.64 (1H, d, J=8.3 Hz), 7.22 (1H, d, J=8.3 Hz), 7.37 (1H, dd, 8.3, 1.7 Hz), 7.70 (1H, d, J=1.7 Hz), 8.94 (1H, br s), 9.25 (1H, s), 11.55 (1H, s). IR (KBr) υ 3350, 3220, 1510, 1195, 1048 cm$^1$. Mass (FAB) m/z 541 ((M+H))$^+$. Elementary Analysis: $C_{26}H_{25}N_2O_3I·CH_3SO_3H·0.4H_2O$; Calcd.:C, 50.38; H, 4.67; N, 4.35; I, 19.71; S, 4.98. Found:C, 50.39; H, 4.91; N, 4.35; I, 19.76; S, 4.92.

By using 4-ethoxycarbonylphenylhydrazine, 4-trifluoromethoxyphenylhydrazine, 4-sulfamoylphenylhydrazine, 4-methylsulfonylphenylhydrazine, 4-(N-cyclopropylmethylcarbamoyl)phenylhydrazine, 4-cyanophenylhydrazine, 4-[2-(N,N-dimethylamino)ethyl] phenylhydrazine, 4-(N,N-dimethylamino)methylphenylhydrazine, 4-phenylphenylhydrazine, 4-methylthiophenylhydrazine, 4-(N-cyclopropylmethylsulfamoyl)phenylhydrazine, 4-(N,N-dimethylsulfamoyl) phenylhydrazine, 4-(2-hydroxyethyl)phenylhydrazine, 4-ethoxycarbonylmethylphenylhydrazine, 1-methyl-1-[4-[2-(N,N-dimethylamino)ethyl]phenyl]hydrazine, 1-methyl-1-[4-(N,N-dimethylamino)methylphenyl]hydrazine, 1-methyl-1-(4-phenylphenyl)hydrazine or 1-methyl-1-(4-methylthiophenyl]hydrazine in place of 4-iodophenylhydrazine, 17-cyclopropylmethyl-6,7-didehydro-4,5α-epoxy-3,14β-dihydroxy-5'-ethoxycarbonyl-6,7-2',3'-indolomorphinan 3,17-cyclopropylmethyl-6,7-didehydro-4,5α-epoxy-3,14β-dihydroxy-5'-trifluoromethoxy-6,7-2',3'-indolomorphinan 4,17-cyclopropylmethyl-6,7-didehydro-4,5α-epoxy-3,14β-dihydroxy-5'-sulfamoyl-6,7-2',3'-indolomorphinan 5,17-cyclopropylmethyl-6,7-didehydro-4,5α-epoxy-3,14β-dihydroxy-5'-methylsulfonyl-6,7-2',3'-indolomorphinan 6,17-cyclopropylmethyl-6,7-didehydro-4,5α-epoxy-3,14β-dihydroxy-5'-(N-cyclopropylmethylcarbamoyl)-6,7-2',3'-indolomorphinan 7,17-cyclopropylmethyl-6,7-didehydro-4,5α-epoxy-3,14β-dihydroxy-5'-cyano-6,7-2',3'-indolomorphinan 8, 17-cyclopropylmethyl- 6,7-didehydro-4,5α-epoxy-3,14β-dihydroxy-5'-[2-(N,N-dimethylamino)ethyl]-6,7-2',3'-indolomorphinan 9, 17-cyclopropylmethyl-6,7-didehydro-4,5α-epoxy-3,14β-dihydroxy-5'-(N,N-dimethylamino)methyl-6,7-2',3'-indolomorphinan 10, 17-cyclopropylmethyl-6,7-didehydro-4,5α-epoxy-3,14β-dihydroxy-5'-phenyl-6,7-2',3'-indolomorphinan 11, 17-cyclopropylmethyl-6,7-didehydro-4,5α-epoxy-3,14β-dihydroxy-5'-methylthio-6,7-2',3'-indolomorphinan 12, 17-cyclopropylmethyl-6,7-didehydro-4,5α-epoxy-3,14β-dihydroxy-5'-(N-cyclopropylmethylsulfamoyl)-6,7-2',3'-indolomorphinan 13, 17-cyclopropylmethyl-6,7-didehydro-4,5α-epoxy-3,14β-dihydroxy-5'-(N,N-dimethylsulfamoyl)-6,7-2',3'-indolomorphinan 14, 17-cyclopropylmethyl-6,7-didehydro-4,5α-epoxy-3,14β-dihydroxy-5'-(2-hydroxyethyl)-6,7-2',3'-indolomorphinan 15, 17-cyclopropylmethyl-6,7-didehydro-4,5α-epoxy-3,14β-dihydroxy-5'-ethoxycarbonylmethyl-6,7-2',3'-indolomorphinan 16, 17-cyclopropylmethyl-6,7-didehydro-4,5α-epoxy-3,14β-dihydroxy-1'-methyl-5'-[2-(N,N-dimethylamino)ethyl]-6,7-2',3'-indolomorphinan 17, 17-cyclopropylmethyl-6,7-didehydro-4,5α-epoxy-3,14β-dihydroxy-1-methyl-5'-(N,N-dimethylamino)methyl-6,7-2',3'-indolomorphinan 18, 17-cyclopropylmethyl-6,7-didehydro-4,5α-epoxy-3,14β-dihydroxy-1'-methyl-5'-phenyl-6,7-2',3'-indolomorphinan 19 and 17-cyclopropylmethyl-6,7-didehydro-4,5α-epoxy-3,14β-dihydroxy-1'-methyl-5'-methylthio-6,7-2',3'-indolomorphinan 20 are obtained, respectively.

By using naloxone hydrochloric acid salt in place of naltrexone hydrochloric acid salt, and by using 4-iodophenylhydrazine, 4-ethoxycarbonylphenylhydrazine, 4-trifluoromethoxyphenylhydrazine, 4-sulfamoylphenylhydrazine, 4-methylsulfonylphenylhydrazine, 4-(N-cyclopropylmethylcarbamoyl)phenylhydrazine, 4-cyanophenylhydrazine, 4-[2-(N,N-dimethylamino)ethyl] phenylhydrazine, 4-(N,N-dimethylamino)methylphenylhydrazine, 4-phenylphenylhydrazine, 4-methylthiophenylhydrazine, 4-(N-cyclopropylmethylsulfamoyl) phenylhydrazine, 4-(N,N-dimethylsulfamoyl) phenylhydrazine, 4-(2-hydroxyethyl)phenylhydrazine, 4-ethoxycarbonylmethylphenylhydrazine, 1-methyl-1-[4-[2-(N,N-dimethylamino)ethyl]phenyl]hydrazine, 1-methyl-1-[4-(N,N-dimethylamino)methylphenyl]hydrazine, 1-methyl-1-(4-phenylphenyl)hydrazine or 1-methyl-1-(4-methylthiophenyl)hydrazine as the phenylhydrazine derivative, 17-allyl-6,7-didehydro-4,5α-epoxy-3,14β-dihydroxy-5'-iodo-6,7-2',3'-indolomorphinan 21, 17-allyl-6,7-didehydro-4,5α-epoxy-3,14β-dihydroxy-5'-ethoxycarbonyl-6,7-2',3'-indolomorphinan 22, 17-allyl-6,7-didehydro-4,5α-epoxy-3,14β-dihydroxy-5'-trifluoromethoxy-6,7-2',3'-indolomorphinan 23, 17-allyl-6,7-didehydro-4,5α-epoxy-3,14β-dihydroxy-5'-sulfamoyl-6,7-2',3'-indolomorphinan 24, 17-allyl-6,7-didehydro-4,5α-epoxy-3,14β-dihydroxy-5'-methylsulfonyl-6,7-2',3'-indolomorphinan 25, 17-allyl-6,7-didehydro-4,5α-epoxy-3,14β-dihydroxy-5'-(N-cyclopropylmethylcarbamoyl)-6,7-2',3'-indolomorphinan 26, 17-allyl-6,7-didehydro-4,5α-epoxy-3,14β-dihydroxy-5'-cyano-6,7-2',3'-indolomorphinan 27, 17-allyl-6,7-didehydro-4,5α-epoxy-3,14β-dihydroxy-5'-[2-(N,N-dimethylamino)ethyl]-6,7-2',3'-indolomorphinan 28, 17-allyl-6,7-didehydro-4,5α-epoxy-3,14β-dihydroxy-5'-(N,N-dimethylamino)methyl-6,7-2',3'-indolomorphinan 29, 17-allyl-6,7-didehydro-4,5α-epoxy-3,14β-dihydroxy-5'-phenyl-6,7-2',3'-indolomorphinan 30, 17-allyl-6,7-didehydro-4,5α-epoxy-3,14β-dihydroxy-5'-methylthio-6,7-2',3'-indolomorphinan 31, 17-allyl-6,7-didehydro-4,5α-epoxy-3,14β-dihydroxy-5'-(N-cyclopropylmethylsulfamoyl)-6,7-2',3'-indolomorphinan 32, 17-allyl-6,7-didehydro-4,5α-epoxy-3,14β-dihydroxy-5'-(N,N-dimethylsulfamoyl)-6,7-2',3'-indolomorphinan 33, 17-allyl-6,7-didehydro-4,5α-epoxy-3,14β-dihydroxy-5'-(2-hydroxyethyl)-6,7-2',3'-indolomorphinan 34, 17-allyl-6,7-didehydro-4,5α-epoxy-3,14β-dihydroxy-5'-ethoxycarbonylmethyl-6,7-2',3'-indolomorphinan 35, 17-allyl-6,7-didehydro-4,5α-epoxy-3,14β-dihydroxy-1'-methyl-5'-[2-(N,N-dimethylamino)ethyl]-6,7-2',3'-indolomorphinan 36, 17-allyl-6,7-didehydro-4,5α-epoxy-3,14β-dihydroxy-11-methyl-5'-(N,N-dimethylamino)methyl-6,7-2',3'-indolomorphinan 37, 17-allyl-6,7-didehydro-4,5α-epoxy-3,14β-dihydroxy-1'-methyl-5'-phenyl-6,7-2',3'-indolomorphinan 38 and 17-allyl-6,7-didehydro-4,5α-epoxy-3,14β-dihydroxy-1'-methyl-5'-methylthio-6,7-2',3'-indolomorphinan 39 are obtained, respectively.

3 methanesulfonic acid salt (yield 52%)

mp.>220° C. (decomposed). NMR (400 MHz, DMSO-d6); δ 0.44 (1H, m), 0.50 (1H, m), 0.63 (1H, m), 0.74 (1H, m), 1.14 (1H, m), 1.31 (3H, t, J=7.0 Hz), 1.83 (1H, m), 2.31 (3H, s), 2.60 (1H, d, J=16.1 Hz), 2.61 (1H, m), 2.72 (1H, m), 2.95 (1H, m), 3.02 (1H, d, J=16.1 Hz), 3.12 (1H, m), 3.26 (1H, dd, J=20.0, 6.8 Hz), 3.39 (1H, m), 3.45 (1H, d, J=20.0 Hz), 4.09 (1H, br d, J=6.4 Hz), 4.27 (2H, q, J=7.0 Hz), 5.71 (1H, s), 6.35 (1H, br s, OH), 6.61 (1H, d, J=8.3 Hz), 6.64 (1H, d, J=8.3 Hz), 7.44 (1H, d, J=8.8 Hz), 7.75 (1H, dd, J=8.8, 1.5 Hz), 8.07 (1H, br s), 8.95 (1H, m, NH$^+$), 9.26 (1H, br s, OH), 11.80 (1H, s, NH). IR (KBr); υ 3400, 1702, 1638, 1626, 1464, 1330, 1311, 1249, 1207, 1172, 1116, 1046, 870, 774 cm$^{-1}$. Mass (FAB); m/z 497 ((M+H)$^+$). Elementary Analysis: $C_{29}H_{30}N_2O_5 \cdot CH_3SO_3H \cdot 0.7H_2O$ Calcd.:C, 60.53; H, 5.99; N, 4.71; S, 5.36. Found:C, 60.53; H, 6.20; N, 4.65; S, 5.57.

4 hydrochloric acid salt (yield 57%)

mp.:235° C. (decomposed); NMR (500 MHz, DMSO-d6); δ 0.44 (1H, m), 0.51 (1H, m), 0.63 (1H, m), 0.73(1H, m), 1.11 (1H, m), 1.82 (1H, br d, J=11.6 Hz), 2.54 (1H, d,. J=15.9 Hz), 2.62 (1H, td, J=12.8, 4.3 Hz), 2.71 (1H, m), 2.97 (1H, m) 2.99 (1H, d, J=15.9 Hz), 3.12 (1H, m), 3.24 (1H, dd, J=19.5, 6.7 Hz), 3.36 (1H, m), 3.44 (1H, d, J=19.5 Hz),4.11, (1H, d, J=6.1 Hz), 5.70 (1H, s), 6.41 (1H, s), 6.60 (1H, d, J=8.3 Hz), 6.66 (1H, d, J=8.3 Hz), 7.08 (1H, d, J=8.5 Hz), 7.30 (1H, s), 7.44 (1H, d, J=8.5 Hz), 8.99(1H, br s), 9.27 (1H, s), 11.66 (1H, s). IR (KBr); υ 3270, 1508, 1460, 1267, 1205, 1152, 1116, 868, 801 cm$^{-1}$. Mass (FAB); m/z 499 ((M+H)$^+$). Elementary Analysis: $C_{27}H_{25}N_2O_4F·HCl$ Calcd.:C, 60.62; H, 4.90; N, 5.24; F, 10.65; Cl, 6.63. Found:C, 60.66; H, 5.06; N, 5.37; F, 10.40; Cl, 6.44.

5 methanesulfonic acid salt (yield 68%)

mp.:184° C. (decomposed); NMR (500 MHz, DMSO-d6); δ 0.44 (1H, m), 0.50 (1H, m), 0.64 (1H, m), 0.74(1H, m), 1.10 (1H, m), 1.83 (1H, br d, J=11.0 Hz), 2.30 (3H, s) 2.59 (1H, d,. J=15.9 Hz), 2.61 (1H, m), 2.72 (1H, m), 2.95 (1H, m) 2.98 (1H, d, J=15.9 Hz), 3.13 (1H, m), 3.28 (1H, m), 3.39 (1H,m), 3.44 (1H, d, J=19.5 Hz), 4.09 (1H, d, J=6.7 Hz), 5.72 (1H, s), 6.35 (1H, s), 6.60 (1H, d, J=7.9 Hz), 6.64 (1H, d, J=7.9 Hz), 7.10 (2H, s), 7.50 (1H, d, J=8.5 Hz), 7.59 (1H, dd, J=8.5, 1.8 Hz), 7.86 (1H, d, J=1.8 Hz), 8.93(1H, br s), 9.22 (1H, s), 11.79 (1H, s). IR (KBr); υ 3190, 1626, 1508, 1462, 1328, 1195, 1154, 1046, 774, 625 cm$^{-1}$. Mass (FAB); m/z 494 ((M+H)$^+$). Elementary Analysis: $C_{26}H_{27}N_3O_5S·CH_3SO_5H$ Calcd.:C, 54.17; H, 5.39; N, 7.02; S, 10.71 Found:C, 54.50; H, 5.51; N, 6.84; S, 10.39.

6 methanesulfonic acid salt (yield 75%)

mp.:205° C. (decomposed); NMR (400 MHz, DMSO-d6); δ 0.44 (1H, m), 0.50 (1H, m), 0.63 (1H, m), 0.73(1H, m), 1.11 (1H, m), 1.84 (1H, br d, J=11.2 Hz), 2.30 (3H, s) 2.60 (1H, d,. J=16.1 Hz), 2.63 (1H, m), 2.72 (1H, m), 2.95 (1H, m) 3.03 (1H, d, J=16.1 Hz), 3.10 (3H, s) 3.12 (1H, m), 3.24 (1H, m), 3.38 (1H,m), 3.46 (1H, d, J=20.0 Hz), 4.08 (1H, d, J=6.3 Hz), 5.74 (1H, s), 6.38 (1H, s), 6.61 (1H,d, J=7.8 Hz), 6.64 (1H, d, J=7.8 Hz), 7.57 (1H, d, J=8.8 Hz), 7.64 (1H, dd, J=8.8, 2.0 Hz), 7.96 (1H, d, J=2.0 Hz) 8.97(1H, br s), 9.27 (1H, s), 11.99 (1H, s). IR (KBr); v 3410, 1626, 1508, 1460, 1330, 1292, 1195, 1125, 1048, 774 cm$^{-1}$. Mass (FAB); m/z 493 ((M+H)$^+$). Elementary Analysis: $C_{27}H_{28}N_2O_5S·CH_3SO_3H·0.5H_2O$ Calcd.:C, 56.27; H, 5.56; N, 4.69; S, 10.73. Found:C, 56.30; H, 5.74; N, 4.62; S, 10.56.

7 methanesulfonic acid salt (yield 73%)

mp.>:240° C. (decomposed). NMR (400 MHz, DMSO-d6); δ 0.21 (2H, m), 0.41 (2H, m), 0.45 (1H, m), 0.50 (1H, m), 0.63 (1H,m), 0.73 (1H, m), 1.02 (1H, m), 1.11 (1H, m), 1.83 (1H, m), 2.30 (3H, s), 2.58 (1H, d, J=16.1 Hz), 2.60 (1H, m), 2.72 (1H, m), 2.94 (1H, m), 3.00 (1H, d, J=16.1 Hz), 3.09–3.18 (3H, m), 3.26 (1H, dd, J=19.6, 6.8 Hz), 3.37 (1H, m), 3.46 (1H, d, J=19.6 Hz), 4.08 (1H, br d, J=6.3 Hz), 5.70 (1H, s), 6.38 (1H, br s, OH), 6.60 (1H, d, J=8.1 Hz), 6.64 (1H, d, J=8.1 Hz), 7.37 (1H, d, J=8.8 Hz), 7.67 (1H, dd, J=8.8, 1.5 Hz), 8.00 (1H, br s), 8.34 (1H, t, J=5.6 Hz, NH), 8.95 (1H, m, NH$^+$), 9.25 (1H, br s, OH), 11.59, (1H, s, NH). IR (KBr); v 3420, 1630, 1620, 1543, 1466, 1328, 1209, 1197, 1116, 1048, 870, 818, 785 cm$^{-1}$. Mass (FAB); m/z 512 ((M+H)$^+$). Elementary Analysis: $C_{31}H_{33}N_3O_4·CH_3SO_3H·0.4H_2O$ Calcd.:C, 62.50; H, 6.20; N, 6.83; S, 5.21. Found:C, 62.10; H, 6.38; N, 7.00; S, 5.60.

8 methanesulfonic acid salt (yield 40%)

mp.:250° C. (decomposed, methanesulfonic acid salt); NMR (free, 400 MHz, acetone-d6-D$_2$O); δ 0.20 (2H, m), 0.54 (2H, m), 0.96 (1H, m), 1.72(1H, m), 2.30 (1H, m), 2.41 (1H, m), 2.48 (1H, d, J=6.4 Hz), 2.62 (1H, d, J=14.7 Hz) 2.79 (1H, m), 2.86 (1H, m) 2.88 (1H, d, J=15.6 Hz), 3.18 (1H, d, J=18.6 Hz), 3.41 (1H, d, J=6.4 Hz), 5.62 (1H, s), 6.54 (1H, d, J=8.3 Hz), 6.60 (1H, d, J=8.3 Hz), 7.39 (1H, dd, J=8.3, 1.5 Hz),7.55 (1H, d, J=7.8 Hz), 7.87 (1H, d, J=1.0 Hz) IR (KBr); v 3370, 2220, 1622, 1462, 1325, 1116, 870 cm$^{-1}$. Mass (EI); m/z 439 (M$^+$) Elementary Analysis: $C_{27}H_{25}N_3O_3·1.1CH_3SO_3H·0.5H_2O$ Calcd.:C, 60.90; H, 5.53; N, 7.58; S, 6.36 Found:C, 60.72; H, 5.82; N, 7.62; S, 6.31.

9 dimethanesulfonic acid salt (yield 35%)

mp.>210° C. (decomposed). NMR (500 MHz, DMSO-d6); δ 0.44 (1H, m), 0.50 (1H, m), 0.63 (1H, m), 0.72 (1H, m), 1.11 (1H, m), 1.83 (1H, m), 2.32 (6H, s), 2.52 (1H, m), 2.60 (1H, m), 2.71 (1H, m), 2.80 (6H, s), 2.90–3.01 (4H, m), 3.12 (1H, m), 3.18–3.50 (5H, m), 4.06 (1H, m), 5.68 (1H, s), 6.33 (1H, br s, OH), 6.58 (1H, d, J=7.9 Hz), 6.62 (1H, d, J=7.9 Hz), 7.03 (1H, br d, J=8.5 Hz), 7.25 (1H, s), 7.33 (1H, d, J=8.5 Hz), 8.92 (1H, m, NH$^+$), 9.20 (1H, br s, OH), 9.31 (1H, m, NH$^+$), 11.30 (1H, s, NH). IR (KBr); v 3410, 1649, 1638, 1626, 1460, 1330, 1197, 1052, 783 cm$^{-1}$. Mass (FAB); m/z 486 ((M+H)$^+$). Elementary Analysis: $C_{30}H_{35}N_3O_3·2CH_3SO_3H·1.1H_2O$ Calcd.:C, 55.09; H, 6.53; N, 6.02; S, 9.19. Found:C, 55.09; H, 6.91; N, 5.83; S, 9.18.

10 methanesulfonic acid salt (yield 55%)

mp.>180° C. (decomposed). NMR (400 MHz, DMSO-d6); δ 0.44 (1H, m), 0.51 (1H, m), 0.63 (1H, m), 0.73 (1H, m), 1.11 (1H,m), 1.84 (1H, m), 2.30 (6H, s), 2.48–2.78 (3H, m), 2.67 (3H, s), 2.69 (3H, s), 2.89–2.98 (2H, m), 3.14 (1H, m), 3.27 (1H, dd, J=20.0, 6.3 Hz), 3.39 (1H, m), 3.46 (1H, d, J=20.0 Hz), 4.07 (1H, m), 4.26–4.34 (2H, m), 5.70 (1H, s), 6.35 (1H, s, OH), 6.59 (1H, d, J=8.1 Hz), 6.63 (1H, d, J=8.1 Hz), 7.23 (1H, br d, J=8.3 Hz), 7.45 (1H, d, J=8.3 Hz), 7.46 (1H, s), 8.92 (1H, m, NH+), 9.23 (1H, s, OH), 9.39 (1H, m, NH$^+$), 11.59 (1H, s, NH). IR (KBr); v 3380, 1638, 1626, 1466, 1330, 1197, 1116, 1060, 936,785 cm$^{-1}$. Mass (FAB); m/z 472 ((M+H)$^+$). Elementary Analysis: $C_{29}H_{33}N_3O_3·2CH_3SO_3H·0.7H_2O$ Calcd.:C, 55.05; H, 6.32; N, 6.21; S, 9.48. Found:C, 54.90; H, 6.55; N, 6.17; S, 9.43.

Example 2

17-cyclopropylmethyl-6,7-didehydro-4,5α-epoxy-3, 14β-dihydroxy-4'-(2-hydroxyethyl)-6,7-2',3'-indolomorphinan 40 and 17-cyclopropylmethyl-6,7-didehydro-4,5α-epoxy-3,14β-dihydroxy-6'-(2-hydroxyethyl)-6,7-2',3'-indolomorphinan 41

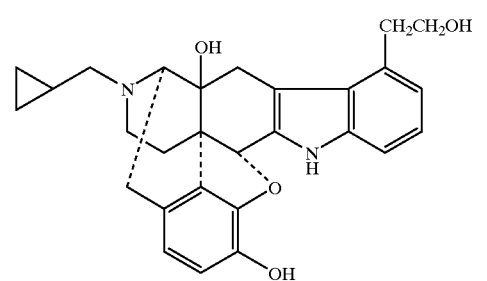

40

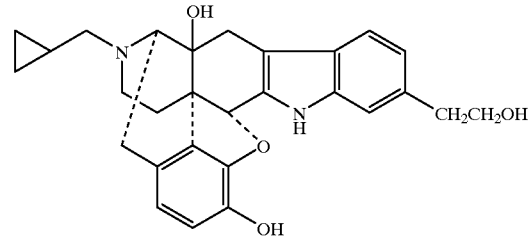

41

A reaction was carried out in the similar manner as in Example 1 using 1.64 g of naltrexone hydrochloric acid salt, 1.19 g of 3-(2-hydroxyethyl)phenylhydrazine, 0.59 ml of methanesulfonic acid and 33 ml of ethanol. The reaction product was purified by column chromatography [silica gel; chloroform:methanol:28% aqueous ammonia solution (90:10:0.1)] to obtain 503 mg (yield 27%) and 1200 mg (yield 60%) of the captioned compounds, respectively.

40 methanesulfonic acid salt mp.>228° C. (decomposed); NMR (400 MHz, DMSO-d6); δ 0.40–0.78 (4H, m), 1.07–1.18 (1H, m), 1.85 (1H, br d, J=21.0 Hz), 2.30 (3H, s), 2.53–2.78 (2H, m), 2.74 (1H, d, J=15.6 Hz), 2.89–2.98 (1H, m), 2.98 (2H, t, J=7.5 Hz), 3.11 (1H, br d, J=11.2 Hz), 3.19 (1H, d, J=16.1 Hz), 3.20–3.68 (5H, m), 4.05 (1H, br d, J=5.9 Hz), 4.55 (1H, br s), 5.66 (1H, s), 6.37 (1H, s), 6.60 (1H, d, J=8.3 Hz), 6.63 (1H, d, J=8.3 Hz), 6.73 (1H, d, J=7.3 Hz), 6.98 (1H, t, J=7.3 Hz), 7.18 (1H, t, J=7.3 Hz), 8.91 (1H, br s), 9.21 (1H, br s), 11.31 (1H, s). IR(KBr); ν 3400, 1620, 1508, 1462, 1332, 1195, 1116, 1050, 785 cm$^{-1}$. Mass (FAB); m/z 459 ((M+H)$^+$). Elementary Analysis: $C_{28}H_{30}N_2O_4 \cdot CH_3SO_3H \cdot 0.4H_2O$ Calcd.:C, 61.99; H, 6.24; N, 4.99; S, 5.71. Found:C, 61.96; H, 6.29; N, 5.13; S, 5.67.

41 methanesulfonic acid salt mp.>204° C. (decomposed); NMR (400 MHz, DMSO-d6); δ 0.38–0.55 (2H, m), 0.57–0.78 (2H, m), 1.04–1.15 (1H, m), 1.81 (1H, br d, J=11.2 Hz), 2.32 (3H, s), 2.48–2.80 (3H, m), 2.78 (2H, t, J=7.1 Hz), 2.92 (1H, d, J=16.1 Hz), 2.87–2.98 (1H, m), 3.11 (1H, br d, J=11.7 Hz), 3.25 (1H, dd, J=19.5, 6.8 Hz), 3.30–3.50 (3H, m), 3.57 (2H, t, J=7.1 Hz), 4.07 (1H, d, J=6.4 Hz), 5.66 (1H, s), 6.31 (1H, br s), 6.58 (1H, d, J=8.3 Hz), 6.62 (1H, d, J=8.3 Hz), 6.83 (1H, dd, J=7.8, 1.2 Hz), 7.18 (1H, br s), 7.23 (1H, d, J=7.8 Hz), 8.91 (1H, br s), 9.18 (1H, br s), 11.16 (1H, s). IR(KBr); ν 3420, 1620, 1510, 1462, 1330, 1199, 1116, 1048, 785 cm$^{-1}$. Mass (FAB); m/z 459 ((M+H)$^+$). Elementary Analysis: $C_{28}H_{30}N_2O_4 \cdot CH_3SO_3H \cdot 0.6H_2O$ Calcd.:C, 61.60; H, 6.27; N, 4.95; S. 5.67. Found:C, 61.62; H, 6.32; N, 4.93; S, 5.76.

By using 3-methylthiophenylhydrazine in place of 3-(2-hydroxyethyl)phenylhydrazine, 17-cyclopropylmethyl-6,7-didehydro-4,5α-epoxy-3,14β-dihydroxy-4'-methylthio-6,7-2',3'-indolomorphinan 42 and 17-cyclopropylmethyl-6,7-didehydro-4,5α-epoxy-3,14β-dihydroxy-6'-methylthio-6,7-2',3'-indolomorphinan 43 are obtained. By using 3-(N-cyclopropylmethylsulfamoyl)phenylhydrazine in place of 3-(2-hydroxyethyl)phenylhydrazine, 17-cyclopropylmethyl-6,7-didehydro-4,5α-epoxy-3,14β-dihydroxy-4'-(N-cyclopropylmethylsulfamoyl)-6,7-2',3'-indolomorphinan 44 and 17-cyclopropylmethyl-6,7-didehydro-4,5α-epoxy-3,14β-dihydroxy-6'-(N-cyclopropylmethylsulfamoyl)-6,7-2',3'-indolomorphinan 45 are obtained. By using 3-(N-cyclopropylmethylcarbamoyl)phenylhydrazine in place of 3-(2-hydroxyethyl)phenylhydrazine, 17-cyclopropylmethyl-6,7-didehydro-4,5α-epoxy-3,14β-dihydroxy-4'-(N-cyclopropylmethylcarbamoyl)-6,7-2',3'-indolomorphinan 46 and 17-cyclopropylmethyl-6,7-didehydro-4,5α-epoxy-3,14β-dihydroxy-6'-(N-cyclopropylmethylcarbamoyl)-6,7-2',3'-indolomorphinan 47 are obtained. By using 3-ethoxycarbonylmethylphenylhydrazine in place of 3-(2-hydroxyethyl)phenylhydrazine, 17-cyclopropylmethyl-6,7-didehydro-4,5α-epoxy-3,14β-dihydroxy-4'-ethoxycarbonylmethyl-6,7-2',3'-indolomorphinan 48 and 17-cyclopropylmethyl-6,7-didehydro-4,5α-epoxy-3,14β-dihydroxy-6'-ethoxycarbonylmethyl-6,7-2',3'-indolomorphinan 49 are obtained. By using 3-(N,N-dimethylsulfamoyl)phenylhydrazine in place of 3-(2-hydroxyethyl)phenylhydrazine, 17-cyclopropylmethyl-6,7-didehydro-4,5α-epoxy-3,14β-dihydroxy-4'-(N,N-dimethylsulfamoyl)-6,7-2',3'-indolomorphinan 50 and 17-cyclopropylmethyl-6,7-didehydro-4,5α-epoxy-3,14β-dihydroxy-6'-(N,N-dimethylsulfamoyl)-6,7-2',3'-indolomorphinan 51 are obtained. By using 3-cyanophenylhydrazine in place of 3-(2-hydroxyethyl) phenylhydrazine, 17-cyclopropylmethyl-6,7-didehydro-4,5α-epoxy-3,14β-dihydroxy-4'-cyano-6,7-2',3'-indolomorphinan 52 and 17-cyclopropylmethyl-6,7-didehydro-4,5α-epoxy-3,14β-dihydroxy-6'-cyano-6,7-2',3'-indolomorphinan 53 are obtained. By using 3-trifluoromethylphenylhydrazine in place of 3-(2-hydroxyethyl)phenylhydrazine, 17-cyclopropylmethyl-6,7-didehydro-4,5α-epoxy-3,14β-dihydroxy-4'-trifluoromethyl-6,7-2',3'-indolomorphinan 54 and 17-cyclopropylmethyl-6,7-didehydro-4,5α-epoxy-3,14β-dihydroxy-6'-trifluoromethyl-6,7-2',3'-indolomorphinan 55 are obtained. By using 3-phenylphenylhydrazine in place of 3-(2-hydroxyethyl)phenylhydrazine, 17-cyclopropylmethyl-6,7-didehydro-4,5α-epoxy-3,14β-dihydroxy-4'-phenyl-6,7-2',3'-indolomorphinan 56 and 17-cyclopropylmethyl-6,7-didehydro-4,5α-epoxy-3,14β-dihydroxy-6'-phenyl-6,7-2',3'-indolomorphinan 57 are obtained. By using 3-trifluoromethoxyphenylhydrazine in place of 3-(2-hydroxyethyl)phenylhydrazine, 17-cyclopropylmethyl-6,7-didehydro-4,5α-epoxy-3,14β-dihydroxy-4'-trifluoromethoxy-6,7-2',3'-indolomorphinan 58 and 17-cyclopropylmethyl-6,7-didehydro-4,5α-epoxy-3,14β-dihydroxy-6'-trifluoromethoxy-6,7-2',3'-indolomorphinan 59 are obtained. By using 3-sulfamoylphenylhydrazine in place of 3-(2-hydroxyethyl)phenylhydrazine, 17-cyclopropylmethyl-6,7-didehydro-4,5α-epoxy-3,14β-dihydroxy-4'-sulfamoyl-6,7-2',3'-indolomorphinan 60 and 17-cyclopropylmethyl-6,7-didehydro-4,5α-epoxy-3,14β-dihydroxy-6'-sulfamoyl-6,7-2',3'-indolomorphinan 61 are obtained. By using 3-iodophenylhydrazine in place of 3-(2-hydroxyethyl)phenylhydrazine, 17-cyclopropylmethyl-6,7-didehydro-4,5α-epoxy-3,14β-dihydroxy-4'-iodo-6,7-2',3'-indolomorphinan 62 and 17-cyclopropylmethyl-6,7-didehydro-4,5α-epoxy-3,14β-dihydroxy-6'-iodo-6,7-2',3'-indolomorphinan 63 are obtained. By using 3-[2-(N,N-dimethylamino)ethyl)]phenylhydrazine in place of 3-(2-hydroxyethyl)phenylhydrazine, 17-cyclopropylmethyl-6,7-didehydro-4,5α-epoxy-3,14β-dihydroxy-4'-[2-(N,N-dimethylamino)ethyl)]-6,7-2',3'-indolomorphinan 64 and 17-cyclopropylmethyl-6,7-didehydro-4,5α-epoxy-3,14β-dihydroxy-6'-[2-(N,N-dimethylamino)ethyl)]-6,7-2',3'-indolomorphinan 65 are obtained. By using 3-(N,N-dimethylamino)methylphenylhydrazine in place of 3-(2-hydroxyethyl)phenylhydrazine, 17-cyclopropylmethyl-6,7-didehydro-4,5α-epoxy-3,14β-dihydroxy-4'-(N,N-dimethylamino)methyl-6,7-2',3'-indolomorphinan 66 and 17-cyclopropylmethyl-6,7-didehydro-4,5α-epoxy-3,14β-dihydroxy-6'-(N,N-dimethylamino)methyl-6,7-2',3'-indolomorphinan 67 are obtained. By using 1-methyl-1-(3-methylthiophenyl)hydrazine in place of 3-(2-hydroxyethyl) phenylhydrazine, 17-cyclopropylmethyl-6,7-didehydro-4,5α-epoxy-3,14β-dihydroxy-1'-methyl-4'-methylthio-6,7-2',3'-indolomorphinan 68 and 17-cyclopropylmethyl-6,7-didehydro-4,5α-epoxy-3,14β-dihydroxy-1'-methyl-6'-methylthio-6,7- 2',3'-indolomorphinan 69 are obtained. By using 1-methyl-1-(3-phenylphenyl)hydrazine in place of 3-(2-hydroxyethyl)phenylhydrazine, 17-cyclopropylmethyl-6,7-didehydro-4,5α-epoxy-3,14β-dihydroxy-1'-methyl-4'-phenyl-6,7-2',3'-indolomorphinan 70 and 17-cyclopropylmethyl-6,7-didehydro-4,5α-epoxy-3,14β-dihydroxy-1'-methyl-6'-phenyl-6,7-2',3'-indolomorphinan 71 are obtained. By using 1-methyl-1-[3-[2-(N,N-dimethylamino)ethyl)]phenyl]hydrazine in place of 3-(2-hydroxyethyl)phenylhydrazine, 17-cyclopropylmethyl-6,7-didehydro-4,5α-epoxy-3,14β-dihydroxy-11-methyl-4'-[2-(N,N-dimethylamino)ethyl)]-6,7-2',3'-indolomorphinan 72 and 17-cyclopropylmethyl-6,7-didehydro-4,5α-epoxy-3, 14β-dihydroxy-1'-methyl-6'-[2-(N,N-dimethylamino) ethyl)]-6,7-2',3'-indolomorphinan 73 are obtained. By using 1-methyl-[3-(N,N-dimethylamino)methylphenyl]hydrazine in place of 3-(2-hydroxyethyl)phenylhydrazine, 17-cyclopropylmethyl-6,7-didehydro-4,5α-epoxy-3,14β-dihydroxy-1'-methyl-4'-(N,N-dimethylamino)methyl-6,7-2',3'-indolomorphinan 74 and 17-cyclopropylmethyl-6,7-didehydro-4,5α-epoxy-3,14β-dihydroxy-1'-methyl-6'-(N,N-dimethylamino)methyl-6,7-2',3'-indolomorphinan 75 are obtained.

By using 3-methoxycarbonylphenylhydrazine in place of 3-(2-hydroxyethyl)phenylhydrazine and by using methanol in place of ethanol, 17-cyclopropylmethyl- 6,7-didehydro-4,5α-epoxy-3,14β-dihydroxy-4'-methoxycarbonyl-6,7-2',3'-indolomorphinan 76 and 17-cyclopropylmethyl-6,7-didehydro-4,5α-epoxy-3,14β-dihydroxy-6'-methoxycarbonyl-6,7-2',3'-indolomorphinan 77 are obtained.

By using 3-nitrophenylhydrazine in place of 3-(2-hydroxyethyl)phenylhydrazine and by using acetic acid-12N hydrochloric acid (4:1) in place of ethanol-methanesulfonic acid, 17-cyclopropylmethyl-6,7-didehydro-4,5α-epoxy-3,14β-dihydroxy-4'-nitro-6,7-2',3'-indolomorphinan 78 and 17-cyclopropylmethyl-6,7-didehydro-4,5α-epoxy-3,14β-dihydroxy-6'-nitro-6,7-2',3'-indolomorphinan 79 are obtained.

By using naloxone hydrochloric acid salt in place of naltrexone hydrochloric acid salt and by using 3-(2-hydroxyethyl)phenylhydrazine, 3-methylthiophenylhydrazine, 3-(N-cyclopropylmethylsulfamoyl)phenylhydrazine, 3-(N-cyclopropylmethylcarbamoyl)phenylhydrazine, 3-ethoxycarbonylmethylphenylhydrazine, 3-(N,N-dimethylsulfamoyl)phenylhydrazine, 3-cyanophenylhydrazine, 3-trifluoromethylphenylhydrazine, 3-phenylphenylhydrazine, 3-trifluoromethoxyphenylhydrazine, 3-sulfamoylphenylhydrazine, 3-iodophenylhydrazine, 3-[2-(N,N-dimethylamino)ethyl)] phenylhydrazine, 3-(N,N-dimethylamino)methylphenylhydrazine, 1-methyl-1-(3-methylthiophenyl)hydrazine, 1-methyl-1-(3-phenylphenyl)hydrazine, 1-methyl-1-[3-[2-(N,N-dimethylamino)ethyl)]phenyl]hydrazine or 1-methyl-[3-(N,N-dimethylamino)methylphenyl]hydrazine as the phenylhydrazine derivative, 17-allyl-6,7-didehydro-4,5α-epoxy-3,14β-dihydroxy-4'-methylthio-6,7-2',3'-indolomorphinan 80, 17-allyl-6,7-didehydro-4,5α-epoxy-3,14β-dihydroxy-6'-methylthio-6,7-2',3'-indolomorphinan 81, 17-allyl-6,7-didehydro-4,5α-epoxy-3,14β-dihydroxy-4'-(N-cyclopropylmethylsulfamoyl)-6,7-2',3'-indolomorphinan 82, 17-allyl-6,7-didehydro-4,5α-epoxy-3,14β-dihydroxy-6'-(N-cyclopropylmethylsulfamoyl)-6,7-2',3'-indolomorphinan 83, 17-allyl-6,7-didehydro-4,5α-epoxy-3,14β-dihydroxy-4'-(N-cyclopropylmethylcarbamoyl)-6,7-2',3'-indolomorphinan 84, 17-allyl-6,7-didehydro-4,5α-epoxy-3,14β-dihydroxy-6'-(N-cyclopropylmethylcarbamoyl)-6,7-2',3'-indolomorphinan 85, 17-allyl-6,7-didehydro-4,5α-epoxy-3,14β-dihydroxy-4'-ethoxycarbonylmethyl-6,7-2',3'-indolomorphinan 86, 17-allyl-6,7-didehydro-4,5α-epoxy-3,14β-dihydroxy-6'-ethoxycarbonylmethyl-6,7-2',3'-indolomorphinan 87, 17-allyl-6,7-didehydro-4,5α-epoxy-3,14β-dihydroxy-4'-(N,N-dimethylsulfamoyl)-6,7-2',3'-indolomorphinan 88, 17-allyl-6,7-didehydro-4,5α-epoxy-3,14β-dihydroxy-6'-(N,N-dimethylsulfamoyl)-6,7-2',3'-indolomorphinan 89, 17-allyl-6,7-didehydro-4,5α-epoxy-3,14β-dihydroxy-4'-cyano-6,7-2',3'-indolomorphinan 90, 17-allyl-6,7-didehydro-4,5α-epoxy-3,14β-dihydroxy-6'-cyano-6,7-2',3'-indolomorphinan 91, 17-allyl-6,7-didehydro-4,5α-epoxy-3,14β-dihydroxy-4'-trifluoromethyl-6,7-2',3'-indolomorphinan 92, 17-allyl-6,7-didehydro-4,5α-epoxy-3,14β-dihydroxy-6'-trifluoromethyl-6,7-2',3'-indolomorphinan 93, 17-allyl-6,7-didehydro-4,5α-epoxy-3,14β-dihydroxy-4'-phenyl-6,7-2',3'-indolomorphinan 94, 17-allyl-6,7-didehydro-4,5α-epoxy-3,14β-dihydroxy-6'-phenyl-6,7-2',3'-indolomorphinan 95, 17-allyl-6,7-didehydro-4,5α-epoxy-3,14β-dihydroxy-4'-trifluoromethoxy-6,7-2',3'-indolomorphinan 96, 17-allyl-6,7-didehydro-4,5α-epoxy-3,14β-dihydroxy-6'-trifluoromethoxy-6,7-2',3'-indolomorphinan 97, 17-allyl-6,7-didehydro-4,5α-epoxy-3,14β-dihydroxy-4'-sulfamoyl-6,7-2',3'-indolomorphinan 98, 17-allyl-6,7-didehydro-4,5α-epoxy-3,14β-dihydroxy-6'-sulfamoyl-6,7-2',3'-indolomorphinan 99, 17-allyl-6,7-didehydro-4,5α-epoxy-3,14β-dihydroxy-4'-iodo-6,7-2',3'-indolomorphinan 100, 17-allyl-6,7-didehydro-4,5α-epoxy-3,14β-dihydroxy-6'-iodo-6,7-2',3'-indolomorphinan 101, 17-allyl-6,7-didehydro-4,5α-epoxy-3,14β-dihydroxy-4'-[2-(N,N-dimethylamino)ethyl)]-6,7-2',3'-indolomorphinan 102, 17-allyl-6,7-didehydro-4,5α-epoxy- 3,14β-dihydroxy-6'-[2-(N,N-dimethylamino)ethyl)]-6,7-2',3'-indolomorphinan 103, 17-allyl-6,7-didehydro-4,5α-epoxy-3,14β-dihydroxy-4'-(N,N-dimethylamino)methyl-6,7-2',3'-indolomorphinan 104, 17-allyl-6,7-didehydro-4,5α-epoxy-3,14β-dihydroxy-6'-(N,N-dimethylamino)methyl-6,7-2',3'-indolomorphinan 105, 17-allyl-6,7-didehydro-4,5α-epoxy-3,14β-dihydroxy-1'-methyl-4'-methylthio-6,7-2',3'-indolomorphinan 106, 17-allyl-6,7-didehydro-4,5α-epoxy-3,14β-dihydroxy-1'-methyl-6'-methylthio-6,7-2',3'-indolomorphinan 107, 17-allyl-6,7-didehydro-4,5α-epoxy-3,14β-dihydroxy-1'-methyl-4'-phenyl-6,7-2',3'-indolomorphinan 108, 17-allyl-6,7-didehydro-4,5α-epoxy-3,14β-dihydroxy-1'-methyl-6'-phenyl-6,7-2',3'-indolomorphinan 109, 17-allyl-6,7-didehydro-4,5α-epoxy-3,14β-dihydroxy-1'-methyl-4'-[2-(N,N-dimethylamino)ethyl)]-6,7-2',3'-indolomorphinan 110, 17-allyl-6,7-didehydro-4,5α-epoxy-3,14β-dihydroxy-1'-methyl-6'-[2-(N,N-dimethylamino)ethyl)]-6,7-2',3'-indolomorphinan 111, 17-allyl-6,7-didehydro-4,5α-epoxy-3,14β-dihydroxy-1'-methyl-4'-(N,N-dimethylamino)methyl-6,7-2',3'-indolomorphinan 112 and 17-allyl-6,7-didehydro-4,5α-epoxy-3,14β-dihydroxy-1'-methyl-6'-(N,N-dimethylamino)methyl-6,7-2',3'-indolomorphinan 113 are obtained, respectively.

By using naloxone hydrochloric acid salt and 3-methoxycarbonylphenylhydrazine in place of naltrexone hydrochloric acid salt and 3-(2-hydroxyethyl)phenylhydrazine, and by using methanol in place of ethanol, 17-allyl-6,7-didehydro-4,5α-epoxy-3,14β-dihydroxy-4'-methoxycarbonyl-6,7-2',3'-indolomorphinan 114 and 17-allyl-6,7-didehydro-4,5α-epoxy-3,14β-dihydroxy-6'-methoxycarbonyl-6,7-2',3'-indolomorphinan 115 are obtained.

By using naloxone hydrochloric acid salt and 3-nitrophenylhydrazine in place of naltrexone hydrochloric acid and 3-(2-hydroxyethyl)phenylhydrazine, and by using acetic acid—12N hydrochloric acid (4:1) in place of ethanol-methanesulfonic acid, 17-allyl-6,7-didehydro-4,5α-epoxy-3,14β-dihydroxy-4'-nitro-6,7-2',3'-indolomorphinan 116 and 17-allyl-6,7-didehydro-4,5α-epoxy-3,14β-dihydroxy-6'-nitro-6,7-2',3'-indolomorphinan 117 are obtained.

43 methanesulfonic acid salt (yield 57%)

mp.>225° C. (decomposed); NMR (400 MHz, CDCl3, data for free base); δ 0.11–0.21 (2H, m), 0.51–0.62 (2H, m), 0.83–0.93 (1H, m), 1.71 (1H, br d, J=11.2 Hz), 2.19–2.47 (4H, m), 2.47 (1H, br s), 2.47 (3H, s), 2.60 (1H, d, J=15.6

Hz), 2.63–2.71 (1H, m), 2.78 (1H, dd, J=6.4, 18.6 Hz), 2.85 (1H, d, J=15.6 Hz), 3.09 (1H, d, J=18.6 Hz), 3.36 (1H, d, J=6.4 Hz), 5.48 (1H, br s), 5.68 (1H, s), 6.42 (1H, d, J=8.1 Hz), 6.51 (1H, d, J=8.1 Hz), 6.97 (1H, dd, J=1.5, 8.1 Hz), 7.10 (1H, br s), 7.26 (1H, d, J=8.3 Hz), 8.18 (1H, s). IR (KBr); ν 3400, 1620, 1510, 1460, 1328, 1209, 1048 cm$^{-1}$ Mass (EI); m/z 460 (M$^+$). Elementary Analysis: $C_{27}H_{28}N_2O_3S·CH_3SO_3H·0.6H_2O$ Calcd.: C, 59.26; H, 5.90; N, 4.94; S, 11.30. Found C, 59.21; H, 5.86; N, 4.90; S, 11.38.

45 methanesulfonic acid salt (yield 45%)

mp.>300° C. (decomposed, ether); NMR (400MHz, DMSO-d6); δ 0.03 (2H, m), 0.3 (2H, m), 0.44 (1H, m), 0.50 (1H, m), 0.63 (1H, m), 0.74 (2H, m), 1.09 (1H, m), 1.84 (1H, br d, J=12.7 Hz), 2.30 (3H, s), 2.50 (2H, m), 2.54–2.58 (2H, m), 2.63 (1H, m), 2.72 (1H, m), 2.95 (1H, m), 2.99 (1H, d, J=16.1 Hz), 3.12 (1H, br d, J=8.8 Hz), 3.26 (1H, dd, J=20.0, 7.3 Hz), 3.45 (1H, d, J=20.0 Hz), 4.09 (1H, d, J=9.4 Hz), 5.75 (1H, s), 6.37 (1H, s), 6.61 (1H, d, J=8.3 Hz), 6.64 (1H, d, J=8.3 Hz), 7.40 (1H, dd, J=8.3, 1.2 Hz), 7.52 (1H, d, J=8.3 Hz), 7.55 (1H, t, J=5.9 Hz), 7.82 (1H, d, J=1.2 Hz), 8.95 (1H, br s), 9.26 (1H, s), 11.87 (1H, s). IR (KBr); ν 3400, 1635, 1626, 1506, 1480, 1311, 1210, 1190, 1149, 1050, 872, 785 cm$^{-1}$. Mass (FAB); m/z 548 ((M+H)$^+$). Elementary Analysis: $C_{31}H_{37}N_3O_8S_2·0.3H_2O$ Calcd.: C, 57,35; H, 5.84; N, 6.47; S, 9.89. Found: C, 57,17; H, 5.99; N, 6.38; S, 9.79.

46 methanesulfonic acid salt (yield 18%) mp.>235° C. (decomposed). NMR (500 MHz, DMSO-d6); δ 0.23 (2H, m), 0.39–0.47 (3H, m), 0.49 (1H, m), 0.63 (1H, m), 0.72 (1H, m), 1.02 (1H, m), 1.13 (1H, m), 1.81 (1H, m), 2.30 (3H, s), 2.58 (1H, d, J=16.5 Hz), 2.61 (1H, m), 2.72 (1H, m), 2.92 (1H, m), 2.97 (1H, m), 3.02 (1H, d, J=16.5 Hz), 3.08–3.16 (2H, m), 3.23 (1H, m), 3.39 (1H, m), 3.46 (1H, d, J=20.1 Hz), 3.98 (1H, br d, J=6.1 Hz), 5.69 (1H, s), 6.25 (1H, br s, OH), 6.61 (1H, d, J=8.3 Hz), 6.64 (1H, d, J=8.3 Hz), 7.04 (1H, dd, J=7.3, 1.2 Hz), 7.12 (1H, dd, J=7.9, 7.3 Hz), 7.44 (1H, dd, J=7.9, 1.2 Hz), 8.31 (1H, t, J=5.5 Hz, NH), 8.87 (1H, m, NH$^+$), 9.21 (1H, br s, OH), 11.55 (1H, s, NH). IR (KBr); ν 3332, 1638, 1620, 1535, 1460, 1328, 1197, 1164, 1116, 1050, 803, 779 cm$^{-1}$. Mass (FAB); m/z 512 ((M+H)$^+$). Elementary Analysis: $C_{31}H_{33}N_3O_4·CH_3SO_3H·0.3H_2O$ Calcd.: C, 62.69; H, 6.18; N. 6.85; S, 5.23. Found: C, 62.60; H, 6.10; N, 7.01; S, 5.55.

47 methanesulfonic acid salt (yield 25%)

mp.>220° C. (decomposed). NMR (500 MHz, DMSO-d6); δ 0.23 (2H, m), 0.40–0.47 (3H, m), 0.50 (1H, m), 0.63 (1H, m), 0.73 (1H, m), 1.05 (1H, m), 1.10 (1H, m), 1.83 (1H, m), 2.30 (3H, s), 2.56 (1H, d, J=15.9 Hz), 2.61 (1H, m), 2.72 (1H, m), 2.94 (1H, m), 2.98 (1H, d, J=15.9 Hz), 3.09–3.18 (3H, m), 3.26 (1H, dd, J=19.5, 6.7 Hz), 3.39 (1H, m), 3.44 (1H, d, J=19.5 Hz), 4.08 (1H, br d, J=6.7 Hz), 5.72 (1H, s), 6.37 (1H, br s, OH), 6.60 (1H, d, J=7.9 Hz), 6.64 (1H, d, J=7.9 Hz), 7.39 (1H, d, J=8.5 Hz), 7.53 (1H, dd, J=8.5, 1.2 Hz), 7.93 (1H, br s), 8.45 (1H, t, J=5.8 Hz, NH), 8.93 (1H, m, NH$^+$), 9.23 (1H, s, OH), 11.63, (1H, s, NH). IR (KBr); ν 3400, 1620, 1545, 1462, 1330, 1195, 1116, 1048, 820, 772 cm$^{-1}$. Mass (FAB); m/z 512 ((M+H)$^+$). Elementary Analysis: $C_{31}H_{33}N_3O_4·CH_3SO_3H·0.4H_2O$ Calcd.: C, 62.50; H, 6.20; N, 6.83; S, 5.21. Found: C, 62.29; H, 6.41; N, 7.04; S, 5.18.

48 methanesulfonic acid salt (yield 14%)

mp.>180° C. (decomposed); NMR (400 MHz, DMSO-d6); δ 0.38–0.77 (4H, m), 1.10 (3H, t, J=6.6 Hz), 1.08–1.18 (1H, m), 1.81 (1H, br d, J=11.7 Hz), 2.32 (3H, s), 2.53–2.79 (2H, m), 2.70 (1H, d, J=15.6 Hz), 2.87–2.97 (1H, m), 3.08–3.23 (2H, m), 3.15 (1H, d, J=15.6 Hz), 3.27–3.50 (2H, m), 3.82 (1H, d, J=15.6 Hz), 3.96 (1H, d, J=15.6 Hz), 3.95–4.07 (3H, m), 5.67 (1H, s), 6.38 (1H, br s), 6.59 (1H, d, J=8.1 Hz), 6.64 (1H, d, J=8.1 Hz), 6.76 (1H, d, J=7.3 Hz), 7.02 (1H, t, br s), 7.26 (1H, d, J=7.3 Hz), 8.93 (1H, br s), 9.21(1H, br s), 11.41 (1H, s). IR (KBr); ν 3420, 1719, 1620, 1508, 1466, 1330, 1183, 1116, 1048 cm$^{-1}$ Mass (FAB); m/z 501 (M+H).$^+$ Elementary Analysis: $C_{30}H_{32}N_2O_5·CH_3SO_3H·0.5H_2O$ Calcd.: C, 61.11; H, 6.19; N, 4.60; S, 5.26. Found: C, 60.87; H, 6.40; N, 4.60; S, 5.61.

49 methanesulfonic acid salt (yield 43%)

mp.>160° C. (decomposed); NMR (free, 400 MHz, CDCl3); δ 0.11–0.22 (2H, m), 0.51–0.62 (2H, m), 0.83–0.93 (1H, m), 1.20 (3H, t, J=7.1 Hz), 1.73 (1H, br d, J=11.5 Hz), 2.27 (1H, dt, J=2.9, 11.5 Hz), 2.33–2.44 (2H, m), 2.44 (1H, dd, J=6.6, 12.5 Hz), 2.60 (1H, d, J=15.6 Hz), 2.70 (1H, dd, J=4.1, 11.5 Hz), 2.77 (1H, dd, J=6.4, 18.6 Hz), 2.86 (1H, d, J=16.1 Hz), 3.09 (1H,d, J=18.6 Hz), 3.35 (1H, d, J=6.4 Hz), 3.63 (2H, s), 4.10 (2H, q, J=7.1 Hz), 5.00 (2H, br s), 5.67 (1H, s), 6.44 (1H, d, J=8.3 Hz), 6.52 (1H, d, J=8.3 Hz), 6.91 (1H, dd, J=1.0, 8.3 Hz), 7.12 (1H, br s), 7.32 (1H, d, J=8.3 Hz), 8.33 (1H, s). IR (KBr); ν 3420, 1720, 1630, 1510, 1460, 1330, 1116, 1048 cm$^{-1}$. Mass (FAB); m/z 501 ((M+H)$^+$). Elementary Analysis: $C_{30}H_{32}N_2O_5·CH_3SO_3H·0.5H_2O$ Calcd.: C, 61.47; H, 6.16; N, 4.62; S, 5.29. Found: C, 61.45; H, 6.13; N, 4.74; S, 5.48.

51 methanesulfonic acid salt (yield 24%)

mp.: 270.0–272.0° C. (decomposed, ether) NMR (400 MHz,DMSO d6); δ 0.44 (1H, m), 0.50 (1H, m), 0.64 (1H, m), 0.74 (1H, m), 1.10 (1H,m), 1.85 (1H, d, J=11.0 Hz), 2.30 (3H, s), 2.56 (6H, s), 2.57–2.65 (2H, m), 2.72 (1H, m), 2.96 (1H, m), 3.01 (1H, d, J=16.9 Hz), 3.13 (1H, br d, J=11.6 Hz), 3.26 (1H, dd, J=19.8, 7.3 Hz), 3.35–3.49 (2H, m), 4.10 (1H, d, J=7.3 Hz), 5.75 (1H, s), 6.38 (1H, s), 6.61 (1H, d, J=7.9 Hz), 6.64 (1H, d, J=7.9 Hz), 7.33 (1H, dd, J=8.2, 1.5 Hz), 7.59 (1H, d, J=8.2 Hz), 7.76 (1H, d, J=1.5 Hz), 9.00 (1H, br s), 9.26 (1H, s), 11.92 (1H, s). IR (KBr); ν 3400, 1626, 1508, 1325, 1152, 951, 770, 721 cm$^{-1}$. Mass (FAB); m/z 522 ((M+H)$^+$). Elementary Analysis: $C_{29}H_{35}N_3O_8S_2·1.0H2O$ Calcd.:C, 54.79; H, 5.55; N, 6.61; S, 10.09. Found:C, 54.67; H, 5.79; N, 6.66; S, 9.87.

53 methanesulfonic acid salt (yield 18%)

mp.: 250° C. (decomposed); NMR (free, 400 MHz, acetone-d6-D2O); δ 0.23 (2H, m), 0.59 (2H, m), 0.98 (1H, m), 1.76(1H, m), 2.34 (1H, m), 2.46 (1H, m), 2.51 (1H, d,. J=6.3 Hz), 2.65 (1H, d, J=15.6 Hz) 2.82 (1H, m), 2.90 (1H, m) 2.89 (1H, d, J=15.6 Hz), 3.23 (1H, d, J=18.6 Hz), 3.43 (1H, d, J=6.3 Hz), 5.66 (1H, s), 6.59 (1H, d, J=8.3 Hz), 6.65 (1H, d, J=8.3 Hz), 7.28 (1H, dd, J=8.3, 1.5 Hz), 7.55 (1H, d, J=8.3 Hz), 7.76 (1H, s) IR (KBr); 3320, 2220, 1620, 1502, 1332, 1116, 820 cm$^{-1}$. Mass (EI); m/z 439 (M$^+$). Elementary Analysis: $C_{27}H_{25}N_3O_3·1.2CH_3SO_3H·0.7H_2O$ Calcd.: C, 59.69; H, 5.54; N, 7.40; S, 6.78. Found: C, 59.79; H, 5.67; N, 7.45; S, 6.57.

76 methanesulfonic acid salt (yield 32%)

mp.>230° C. (decomposed). NMR (400 MHz, DMSO-d6); δ 0.44 (1H, m), 0.52 (1H, m), 0.63 (1H, m), 0.73 (1H, m), 1.12 (1H, m), 1.83 (1H, m), 2.30 (3H, s), 2.57 (1H, m), 2.64 (1H, d, J=16.6 Hz), 2.73 (1H, m), 2.86 (1H, m), 3.10 (1H, m), 3.17 (1H, d, J=16.6 Hz), 3.24 (1H, dd, J=20.0, 7.3 Hz), 3.37–3.48 (2H, m), 3.83 (3H, m), 4.03 (1H, br d, J=7.8 Hz), 5.70 (1H, s), 6.20 (1H, br s, OH), 6.62 (1H, d, J=8.3 Hz), 6.65 (1H, d, J=8.3 Hz), 7.19 (1H, dd, J=7.8, 7.8 Hz), 7.52 (1H, d, J=7.8 Hz), 7.63 (1H, d, J=7.8 Hz), 8.89 (1H, br s, NH$^+$), 9.26 (1H, br s, OH), 11.82 (1H, s, NH). IR (KBr); ν 3400, 1709, 1638, 1620, 1508, 1462, 1437, 1330, 1303, 1270, 1205, 1118, 1046, 926, 870, 814, 770, 756 cm$^{-1}$. Mass (FAB); m/z 473 ((M+H)$^+$). Elementary Analysis: $C_{28}H_{28}N_2O_5·CH_3SO_3H·0.6H_2O$ Calcd.: C, 60.11; H, 5.77; N, 4.83; S, 5.53. Found: C, 60.04; H, 5.80; N, 4.88; S, 5.63.

77 methanesulfonic acid salt (yield 47%)

mp.>240° C. (decomposed). NMR (400 MHz, DMSO-d6); δ 0.44 (1H, m), 0.50 (1H, m), 0.63 (1H, m), 0.74 (1H, m), 1.10 (1H, m), 1.84 (1H, m), 2.31 (3H, s), 2.56 (1H, d, J=16.1 Hz), 2.61 (1H, m), 2.72 (1H, m), 2.94 (1H, m), 2.99 (1H, d, J=16.1 Hz), 3.12 (1H, m), 3.26 (1H, dd, J=19.8, 6.5 Hz), 3.39 (1H, m), 3.45 (1H, d, J=19.8 Hz), 3.85 (3H, s), 4.08 (1H, br d, J=7.8 Hz), 5.75 (1H, s), 6.39 (1H, br s, OH), 6.61 (1H, d, J=8.1 Hz), 6.64 (1H, d, J=8.1 Hz), 7.46 (1H, d, J=8.3 Hz), 7.61 (1H, dd, J=8.3, 1.5 Hz), 8.02 (1H, br s), 8.95 (1H, m, NH$^+$), 9.28 (1H, br s, OH), 11.81 (1H, s, NH). IR (KBr); ν 3382, 1698, 1626, 1508, 1460, 1437, 1330, 1212, 1116, 1044, 872, 774 cm$^{-1}$. Mass (FAB); m/z 473 ((M+H)$^+$). Elementary Analysis: $C_{28}H_{28}N_2O_5 \cdot CH_3SO_3H$ Calcd.: C, 61.25; H, 5.67; N, 4.93; S, 5.64. Found: C, 61.04; H, 5.93; N, 4.93; S, 5.58.

78 methanesulfonic acid salt (yield 10%)

mp.: 220° C. (decomposed) NMR (400 MHz, DMSO-d6); δ 0.44 (1H, m), 0.50 (1H, m), 0.63 (1H, m), 0.74(1H, m), 1.12 (1H,m), 1.85 (1H, br d, J=10.7 Hz), 2.30 (3H, s), 2.59 (1H, m), 2.67 (1H, d,. J=16.6 Hz), 2.74 (1H, m), 2.89 (1H, m), 3.06 (1H, d, J=16.6 Hz), 3.11 (1H, m), 3.25 (1H, dd, J=19.5, 6.8 Hz), 3.40–3.48 (2H,m), 4.07 (1H, d, J=6.8 Hz), 5.75 (1H, s), 6.23 (1H, s), 6.64 (1H, d, J=8.3 Hz), 6.67 (1H, d, J=8.3 Hz), 7.29(1H, dd, J=8.3, 7.8 Hz), 7.77 (1H, dd, J=8.3, 1.0 Hz), 7.81 (1H, dd, J=7.8, 1.0 Hz), 8.90 (1H, br s), 9.29 (1H, br s), 12.31 (1H, s). IR (KBr); ν 3420, 1510, 1350, 1328, 1197, 1040, 557 cm$^{-1}$. Mass (FAB); m/z 458 ((M–H)$^-$). Elementary Analysis: $C_{26}H_{25}N_3O_5 \cdot CH_3SO_3H \cdot 0.5H_2O$ Calcd.: C, 57.44; H, 5.36; N, 7.44; S, 5.68. Found: C, 57.51; H, 5.25; N, 7.24; S, 5.65.

79 methanesulfonic acid salt (yield 38%) mp.: 250° C. (decomposed); NMR (400 MHz, DMSO-d6); δ 0.44 (1H, m), 0.50 (1H, m), 0.63 (1H, m), 0.73(1H, m), 1.10 (1H, m), 1.85 (1H, br d, J=11.7 Hz), 2.29 (3H, s) 2.58 (1H, d,. J=16.1 Hz), 2.60 (1H, m), 2.73 (1H, m), 2.94 (1H, m) 3.02 (1H, d, J=16.1 Hz), 3.12 (1H, m), 3.26 (1H, dd, J=20.0, 6.8 Hz), 3.40 (1H,m), 3.46 (1H, d, J=20.0 Hz), 4.09 (1H, d, J=6.8 Hz), 5.78 (1H, s), 6.42 (1H, s), 6.62 (1H, d, J=8.3 Hz), 6.65 (1H, d, J=8.3 Hz), 7.57 (1H, d, J=8.8 Hz), 7.88 (1H, dd, J=8.8, 2.0 Hz), 8.30 (1H, d, J=2.0 Hz), 8.97(1H, br s) 9.29 (1H, s), 12.21 (1H, s). IR (KBr); ν 3390, 1510, 1466, 1328, 1197, 1116, 1060, 820, 785cm$^{-1}$. Mass (FAB); m/z 458 ((M−H)$^-$). Elementary Analysis: $C_{26}H_{25}N_3O_5 \cdot CH_3SO_3H \cdot 0.7H_2O$ Calcd.: C, 57.07; H. 5.39; N, 7.39; S, 5.64. Found: C, 57.20; H, 5.69; N, 7.24; S, 5.67.

114 methanesulfonic acid salt (yield 28%)

mp.: 220° C. (decomposed); NMR (free, 500 MHz, CDCl$_3$-D$_2$O); δ 1.64 (1H, d, J=11.6 Hz), 2.23 (2H, m), 2.51 (1H, m), 2.73 (1H, d, J=15.9 Hz), 2.75 (1H, m), 3.03 (1H, d, J=18.3 Hz), 3.09 (3H, m), 3.15 (1H, d, J=17.1 Hz), 3.79 (3H, s), 5.12 (2H, m), 5.53 (1H, s), 5.75 (1H, m), 6.36 (1H, d, J=7.9 hz), 6.43 (1H, d, J=7.9 Hz), 6.98 (1H, t, J=7.9 Hz), 7.24 (1H, d, J=9.2), 7.49 (1H, dd, J=7.3, 1.2 Hz); IR (KBr); ν 3320, 1702, 1502, 1294, 1137, 752 cm$^{-1}$. Mass (FAB); m/z 459 ((M+H)$^+$). Elementary Analysis: $C_{27}H_{26}N_2O_5 \cdot CH_3SO_3H \cdot 0.5H_2O$ Calcd.: C, 59.67; H, 5.54; N, 4.97; S, 5.69. Found: C, 59.62; H, 5.68; N, 4.87; S, 5.83.

115 methanesulfonic acid salt (yield 42%)

mp.: 200° C. (decomposed); NMR (free, 500 MHz, CDCl$_3$-D$_2$O) δ 2.28 (2H, m), 2.51 (1H, d, J=15.8 Hz), 2.55 (1H, m), 2.78 (1H, d, J=15.8 Hz), 2.80 (1H, m), 3.15 (4H, m), 3.89 (3H, s), 5.21 (2H, m), 5.64 (1H, s), 5.82 (1H, m), 6.50 (1H, d, J=8.4 Hz), 6.56 (1H, d, J=8.1 Hz), 7.52 (1H, d, J=8.4 Hz), 7.53 (1H, dd, J=8.4, 1.5 Hz), 7.56 (1H, s) IR (KBr); ν 3320, 1698, 1626, 1504, 1212, 1096,768 cm$^{-1}$. Mass (FAB); m/z 458 ((M+H)$^+$); Elementary Analysis: $C_{27}H_{26}N_2O_5 \cdot CH_3SO_3H \cdot 0.5H_2O$ Calcd.: C, 59.67; H, 5.54; N, 4.97; S, 5.69. Found: C, 59.65; H, 5.81; N, 4.77; S, 5.69.

Example 3

17-cyclopropylmethyl-6,7-didehydro-4,5α-epoxy-3, 14β-dihydroxy-7'-trifluoromethyl-6,7-2',3'-indolomorphinan 118

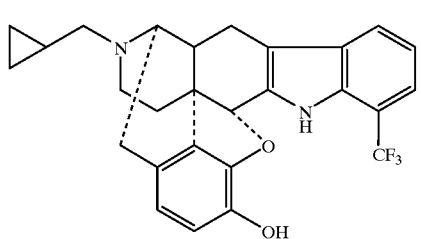

Using 2.00 g of naltrexone hydrochloric acid salt, 1.02 g of 2-trifluoromethylphenylhydrazine, 3.44 ml of methanesulfonic acid and 40 ml of ethanol, the reaction and purification as in Example 1 were carried out to obtain 1.07 g of methanesulfonic acid salt of the captioned compound (yield 35%).

118 methanesulfonic acid salt mp.: 256.0–261° C. (decomposed, ether); NMR (400 Hz, DMSO-d6); δ 0.45 (1H, m), 0.50 (1H, m), 0.64 (1H, m), 0.73 (1H, m), 1.10 (1H, m), 1.86 (1H, br d, J=11.2 Hz), 2.30 (3H, s), 2.50 (1H, m), 2.56 (1H, d, J=16.1 Hz), 2.61 (1H, m), 2.74 (1H, m), 2.94 (1H, m), 2.99 (1H, d, J=16.1 Hz), 3.12 (1H, m), 3.26 (1H, dd, J=19.7, 6.6 Hz), 3.40 (1H, m), 3.46 (1H, d, J=19.7 Hz), 4.10 (1H, br d, J=6.4 Hz), 5.70 (1H, s), 6.40 (1H, s), 6.61 (1H, d, J=8.3 Hz), 6.66 (1H, d, J=8.3 Hz), 7.16 (1H, dd, J=7.8, 7.3 Hz), 7.48 (1H, d, J=7.3 Hz), 7.68 (1H, d, J=7.8 Hz), 8.95 (1H, br s), 9.27 (1H, s), 11.76 (1H, s). IR (KBr); ν 3400, 1638, 1628, 1508, 1466, 1317, 1200, 1120, 1048, 872, 781, 748 cm$^{-1}$. Mass (FAB); m/z 483 ((M+H)$^+$). Elementary Analysis: $C_{28}H_{29}F_3N_2O_6S_1 \cdot 0.3H_2O$ Calcd.:C, 57.59; H, 5.11; N, 4.80; F. 9.76; S, 5.49. Found:C, 57.59; H, 5.24; N, 4.80; F, 9.80; S, 5.42.

By using 2-ethoxycarbonylphenylhydrazine, 2-phenylphenylhydrazine, 2-methylthiophenylhydrazine, 2-(2-hydroxyethyl)phenylhydrazine, 2-(N-cyclopropylmethylsulfamoyl)phenylhydrazine, 2-(N,N-dimethylsulfamoyl)phenylhydrazine, 2-sulfamoylphenylhydrazine, 2-ethoxycarbonylmethylphenylhydrazine, 2-(N-cyclopropylmethylcarbamoyl) phenylhydrazine, 2-trifluoromethoxyphenylhydrazine, 2-iodophenylhydrazine, 2-(N,N-dimethylamino) methylphenylhydrazine, 2-[2-(N,N-dimethylamino)ethyl] phenylhydrazine, 1-methyl-1-(2-methylthiophenyl) hydrazine, 1-methyl-1-(2-phenylphenyl)hydrazine, 1-methyl-1-[2-[2-(N,N-dimethylamino)ethyl)]phenyl] hydrazine or 1-methyl-[2-(N,N-dimethylamino) methylphenyl]hydrazine in place of 2-trifluoromethylphenylhydrazine, 17-cyclopropylmethyl-6,7-didehydro-4,5α-epoxy-3,14β-dihydroxy-7'-ethoxycarbonyl-6,7-2',3'-indolomorphinan 119, 17-cyclopropylmethyl-6,7-didehydro-4,5α-epoxy-3,14β-dihydroxy-7'-phenyl-6,7-2',3'-indolomorphinan 120, 17-cyclopropylmethyl-6,7-didehydro-4,5α-epoxy-3,14β-dihydroxy-7'-methylthio-6,7-2',3'-indolomorphinan 121, 17-cyclopropylmethyl-6,7-didehydro-4,5α-epoxy-3,14β-dihydroxy-7'-(2-hydroxyethyl)-6,7-2',3'-indolomorphinan 122, 17-cyclopropylmethyl-6,7-didehydro-4,5α-epoxy-3, 14β-dihydroxy-7'-(N-cyclopropylmethylsulfamoyl)-6,7-2',3'-indolomorphinan 123, 17-cyclopropylmethyl-6,7-didehydro-4,5α-epoxy-3,14β-dihydroxy-7'-(N,N-dimethylsulfamoyl)-6,7-2',3'-indolomorphinan 124, 17-cyclopropylmethyl-6,7-didehydro-4,5α-epoxy-3,14β-dihydroxy-7'-sulfamoyl-6,7-2',3'-indolomorphinan 125, 17-cyclopropylmethyl-6,7-didehydro-4,5α-epoxy-3,14β-dihydroxy-7'-ethoxycarbonylmethyl-6,7-2',3'-indolomorphinan 126, 17-cyclopropylmethyl-6,7-didehydro-4,5α-epoxy-3,14β-dihydroxy-7'-(N-cyclopropylmethylcarbamoyl)-6,7-2',3'-indolomorphinan 127, 17-cyclopropylmethyl-6,7-didehydro-4,5α-epoxy-3,14β-dihydroxy-7'-trifluoromethoxy-6,7-2',3'-indolomorphinan 128, 17-cyclopropylmethyl-6,7-didehydro-4,5α-epoxy-3,14β-dihydroxy-7'-iodo-6,7-2',3'-indolomorphinan 129, 17-cyclopropylmethyl-6,7-didehydro-4,5α-epoxy-3,14β-dihydroxy-7'-(N,N-dimethylamino)methyl-6,7-2',3'-indolomorphinan 130, 17-cyclopropylmethyl-6,7-didehydro-4,5α-epoxy-3,14β-dihydroxy-7'-[2-(N,N-dimethylamino)ethyl]-6,7-2',3'-indolomorphinan 131, 17-cyclopropylmethyl-6,7-didehydro-4,5α-epoxy-3,14β-dihydroxy-1'-methyl-7'-methylthio-6,7-2',3'-indolomorphinan 132, 17-cyclopropylmethyl-6,7-didehydro-4,5α-epoxy-3,14β-dihydroxy-1'-methyl-7'-phenyl-6,7-2',3'-indolomorphinan 133, 17-cyclopropylmethyl-6,7-didehydro-4,5α-epoxy-3,14β-dihydroxy-1'-methyl-7'-[2-(N,N-dimethylamino)ethyl]-6,7-2',3'-indolomorphinan 134 and 17-cyclopropylmethyl-6,7-didehydro-4,5α-epoxy-3,14β-dihydroxy-1'-methyl-7'-(N,N-dimethylamino)methyl-6,7-2',3'-indolomorphinan 135 are obtained, respectively.

By using 2-nitrophenylhydrazine in place of 2-trifluoromethylphenylhydrazine and by using acetic acid—12N hydrochloric acid (4:1) in place of ethanol-methanesulfonic acid, 17-cyclopropylmethyl-6,7-didehydro-4,5α-epoxy-3,14β-dihydroxy-7'-nitro-6,7-2',3'-indolomorphinan 136 is obtained.

By using naloxone hydrochloric acid salt in place of naltrexone hydrochloric acid salt, and by using 2-trifluoromethylphenylhydrazine, 2-ethoxycarbonylphenylhydrazine, 2-phenylphenylhydrazine, 2-methylthiophenylhydrazine, 2-(2-hydroxyethyl)phenylhydrazine, 2-(N-cyclopropylmethylsulfamoyl)phenylhydrazine, 2-(N,N-dimethylsulfamoyl)phenylhydrazine, 2-sulfamoylphenylhydrazine, 2-ethoxycarbonylmethylphenylhydrazine, 2-(N-cyclopropylmethylcarbamoyl)phenylhydrazine, 2-trifluoromethoxyphenylhydrazine, 2-iodophenylhydrazine, 2-(N,N-dimethylamino)methylphenylhydrazine, 2-[2-(N,N-dimethylamino)ethyl]phenylhydrazine, 1-methyl-1-(2-methylthiophenyl)hydrazine, 1-methyl-1-(2-phenylphenyl)hydrazine, 1-methyl-1-[2-[2-(N,N-dimethylamino)ethyl)]phenyl]hydrazine or 1-methyl-[2-(N,N-dimethylamino)methylphenyl]hydrazine as the phenylhydrazine derivative, 17-allyl-6,7-didehydro-4,5α-epoxy-3,14β-dihydroxy-7'-trifluoromethyl-6,7-2',3'-indolomorphinan 137, 17-allyl-6,7-didehydro-4,5α-epoxy-3,14β-dihydroxy-7'-ethoxycarbonyl-6,7-2',3'-indolomorphinan 138, 17-allyl-6,7-didehydro-4,5α-epoxy-3,14β-dihydroxy-7'-phenyl-6,7-2',3'-indolomorphinan 139, 17-allyl-6,7-didehydro-4,5α-epoxy-3,14β-dihydroxy-7'-methylthio-6,7-2',3'-indolomorphinan 140, 17-allyl-6,7-didehydro-4,5α-epoxy-3,14β-dihydroxy-7'-(2-hydroxyethyl)-6,7-2',3'-indolomorphinan 141, 17-allyl-6,7-didehydro-4,5α-epoxy-3,14β-dihydroxy-7'-(N-cyclopropylmethylsulfamoyl)-6,7-2',3'-indolomorphinan 142, 17-allyl-6,7-didehydro-4,5α-epoxy-3,14β-dihydroxy-7'-(N,N-dimethylsulfamoyl)-6,7-2', 3'-indolomorphinan 143, 17-allyl-6,7-didehydro-4,5α-epoxy-3,14β-dihydroxy-7'-sulfamoyl-6,7-2',3'-indolomorphinan 144, 17-allyl-6,7-didehydro-4,5α-epoxy-3,14β-dihydroxy-7'-ethoxycarbonylmethyl-6,7-2',3'-indolomorphinan 145, 17-allyl-6,7-didehydro-4,5α-epoxy-3,14β-dihydroxy-7'-(N-cyclopropylmethylcarbamoyl)-6,7-2',3'-indolomorphinan 146, 17-allyl-6,7-didehydro-4,5α-epoxy-3,14β-dihydroxy-7'-trifluoromethoxy-6,7-2',3'-indolomorphinan 147, 17-allyl-6,7-didehydro-4,5α-epoxy-3,14β-dihydroxy-7'-iodo-6,7-2',3'-indolomorphinan 148, 17-allyl-6,7-didehydro-4,5α-epoxy-3,14β-dihydroxy-7'-(N,N-dimethylamino)methyl-6,7-2',3'-indolomorphinan 149, 17-allyl-6,7-didehydro-4,5α-epoxy-3,14β-dihydroxy-7'-[2-(N,N-dimethylamino)ethyl]-6,7-2',3'-indolomorphinan 150, 17-allyl-6,7-didehydro-4,5α-epoxy-3,14β-dihydroxy-1'-methyl-7'-methylthio-6,7-2',3'-indolomorphinan 151, 17-allyl-6,7-didehydro-4,5α-epoxy-3,14β-dihydroxy-1'-methyl-7'-phenyl-6,7-2',3'-indolomorphinan 152, 17-allyl-6,7-didehydro-4,5α-epoxy-3,14β-dihydroxy-1'-methyl-7'-[2-(N,N-dimethylamino)ethyl]-6,7-2',3'-indolomorphinan 153 and 17-allyl-6,7-didehydro-4,5α-epoxy-3,14β-dihydroxy-1'-methyl-7'-(N,N-dimethylamino)methyl-6,7-2',3'-indolomorphinan 154 are obtained, respectively.

By using naloxone hydrochloric acid salt and 2-nitrophenylhydrazine in place of naltrexone hydrochloric acid salt and 2-trifluoromethylphenylhydrazine and by using acetic acid—12N hydrochloric acid (4:1) in place of ethanol-methanesulfonic acid, 17-allyl-6,7-didehydro-4,5α-epoxy-3,14β-dihydroxy-7'-nitro-6,7-2',3'-indolomorphinan 155 is obtained.

119 methanesulfonic acid salt (yield 38%)

mp.>200° C. (decomposed). NMR (400 MHz, DMSO-d6); δ 0.44 (1H, m), 0.50 (1H, m), 0.63 (1H, m), 0.74 (1H, m), 1.14 (1H, m), 1.31 (3H, t, J=6.8 Hz), 1.85 (1H, m), 2.30 (3H, s), 2.57 (1H, d, J=16.1 Hz), 2.59 (1H, m), 2.73 (1H, m), 2.94 (1H, m), 2.98 (1H, d, J=16.1 Hz), 3.12 (1H, m), 3.26 (1H, dd, J=20.0, 6.8 Hz), 3.38 (1H, m), 3.45 (1H, d, J=20.0 Hz), 4.08 (1H, br d, J=6.3 Hz), 4.43 (1H, dq, J=10.7, 6.8 Hz), 4.49 (1H, dq, J=10.7, 6.8 Hz), 5.79 (1H, s), 6.38 (1H, br s, OH), 6.60 (1H, d, J=8.3 Hz), 6.64 (1H, d, J=8.3 Hz), 7.12 (1H, dd, J=7.8, 7.3 Hz), 7.68 (1H, br d, J=7.8 Hz), 7.81 (1H, dd, J=7.3, 1.0 Hz), 8.95 (1H, m, NH$^+$), 9.25 (1H, br s, OH), 11.24 (1H, s, NH). IR (KBr); ν 3420, 1690, 1638, 1620, 1508, 1466, 1435, 1290, 1207, 1166, 1116, 1044, 866,756 cm$^{-1}$. Mass (negative FAB); m/z 485 ((M–H)$^-$). Elementary Analysis: $C_{29}H_{30}N_2O_5 \cdot CH_3SO_3H \cdot 0.6H_2O$ Calcd.: C, 60.71; H, 5.98; N, 4.72; S. 5.40. Found: C, 60.56; H, 5.93; N, 4.74; S, 5.68.

120 methanesulfonic acid salt (yield 35%)

mp.>300° C. (decomposed, ether); NMR (400MHz, DMSO-d6); δ 0.45 (1H, m), 0.50 (1H, m), 0.64 (1H, m), 0.74 (1H, m), 1.10 (1H, m), 1.83 (1H, br d, J=10.7 Hz), 2.30 (3H, s), 2.50 (1H, m), 2.56 (1H, d, J=16.1 Hz), 2.60 (1H, m), 2.73 (1H, m), 2.94 (1H, m), 2.98 (1H, d, J=16.1 Hz), 3.10 (1H, br d, J=12.7 Hz), 3.24~3.34 (2H, m), 4.10 (1H, br d, J=6.8 Hz), 5.66 (1H, s), 6.37 (1H, s), 6.60 (1H, d, J=8.3 Hz), 6.64 (1H, d, J=8.3 Hz), 7.09 (1H, dd, J=7.3, 6.8 Hz), 7.15 (1H, dd, J=7.3, 1.5 Hz), 7.37 (1H, dd, J=6.8, 1.5 Hz), 7.45 (1H, t, J=7.3 Hz), 7.55 (2H, t, J=7.3 Hz), 7.63 (2H, d, J=7.3 Hz), 8.93 (1H, br s), 9.20 (1H, s), 11.20 (1H, s). IR (KBr); ν 3400, 1682, 1506, 1464, 1323, 1278, 1149, 1044, 901, 768, 557 cm$^{-1}$ Mass (FAB); m/z 491 ((M+H)$^+$). Elementary Analysis: $C_{33}H_{34}N_2O_6S \cdot 0.1H_2O$ Calcd.: C, 67.35; H, 5.86; N, 4.76; S, 5.45. Found: C, 67.07; H, 6.02; N, 4.76; S, 5.49.

121 methanesulfonic acid salt (yield 61%)

mp.>205° C. (decomposed); NMR (400 MHz, DMSO-d6); δ 0.39–0.78 (4H, m), 1.03–1.15 (1H, m), 1.84 (1H, br d, J=11.2 Hz), 2.33 (3H, s), 2.52 (3H,s), 2.50–2.80 (3H, m), 2.87–3.02 (2H, m), 3.06–3.17 (1H, m), 3.25 (1H, dd, J=19.5, 6.8 Hz), 3.30–3.48 (2H,m), 4.08 (1H, d, J=6.4 Hz), 5.67 (1H, s), 6.35 (1H,br s), 6.59 (1H, d, J=7.8 Hz), 6.64 (1H, d, J=7.8 Hz), 6.99 (1H, t,J=7.8 Hz), 7.11 (1H, d, J=7.8 Hz), 7.24 (1H, d, J=7.8 Hz), 8.30 (1H, br s), 8.93 (1H, br s), 11.36 (1H, s). IR(KBr); ν 3420, 1620, 1508, 1462, 1421, 1319, 1207, 1116, 783 cm$^{-1}$. Mass (FAB); m/z 461 (M+H).$^{+}$ Elementary Analysis: $C_{27}H_{28}N_2O_3S \cdot CH_3SO_3H \cdot 0.6H_2O$ Calcd.: C, 59.26; H, 5.90; N, 4.94; S, 11.30. Found: C, 59.23; H, 5.91; N, 4.92; S, 11.45.

136 methanesulfonic acid salt (yield 24%)

mp.: 235° C. (decomposed); NMR (400 MHz, DMSO-d6); δ 0.45 (1H, m), 0.50 (1H, m), 0.63 (1H, m), 0.74 (1H, m), 1.09 (1H, m), 1.87 (1H, br d, J=10.7 Hz), 2.29 (3H, s), 2.58 (1H, d, J=16.6 Hz), 2.60 (1H, m), 2.75 (1H, m), 2.95 (1H, m), 3.01 (1H, d, J=16.6 Hz), 3.13 (1H, m), 3.25 (1H, dd, J=20.0, 6.8 Hz), 3.40 (1H,m), 3.47 (1H, J=20.0 Hz), 4.10 (1H, d, J=6.8 Hz), 5.75 (1H, s), 6.44 (1H, s), 6.61 (1H, d, J=8.3 Hz), 6.65 (1H, d, J=8.3 Hz), 7.23(1H, dd, J=8.3, 7.8 Hz), 7.90 (1H, d, J=7.8 Hz), 8.14 (1H, d, J=8.3 Hz), 8.96 (1H, br s), 9.26 (1H, br s), 12.17 (1H, s). IR (KBr); ν 3410, 1632, 1510, 1466, 1348, 1317, 1158, 1038, 741 cm$^{-1}$. Mass (FAB); m/z 458 ((M–H)$^{-1}$). Elementary Analysis: $C_{26}H_{25}N_3O_5 \cdot CH_3SO_3H \cdot 0.8H_2O$ Calcd.: C, 56.89; H, 5.41; N, 7.37; S, 5.62. Found C, 56.91; H, 5.58; N, 7.25; S, 5.60.

Example 4

17-cyclopropylmethyl-3,14β-dihydroxy-4,5α-epoxy-6,7-didehydromorphinano[6,7-b]pyrido[4,3-g]indole 156

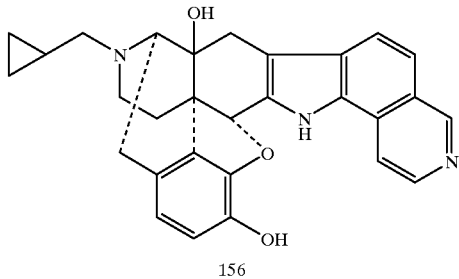

156

Using 1.34 g of naltrexone hydrochloric acid salt, 0.64 g of 5-hydrazinoisoquinoline, 0.71 ml of methanesulfonic acid and 21 ml of ethanol, the reaction and purification as in Example 1 were carried out to obtain 1.53 g of methanesulfonic acid salt of the captioned compound (yield 64%).

156 methanesulfonic acid salt mp.>280° C. (decomposed); NMR (400 MHz, DMSO-d6); δ 0.42–0.80 (4H, m), 1.07–1.18 (1H, m), 1.90 (1H, br d, J=11.7 Hz), 2.36 (6H, s), 2.64–2.83 (2H, m), 2.67 (1H, d, J=16.1 Hz), 2.95–3.05 (1H, m), 3.13–3.24 (1H, m), 3.19 (1H, d, J=16.1 Hz), 3.29 (1H, dd, J=6.8, 20.0 Hz), 3.30–3.53 (2H, m), 3.50 (1H, d, J=20.0 Hz), 4.16 (1H, d, J=6.8 Hz), 5.92 (1H, s), 6.47 (1H, br s), 6.64 (1H, d, J=8.3 Hz), 6.67 (1H, d, J=8.3 Hz), 7.97 (1H, d, J=8.8 Hz), 8.00 (1H, d, J=8.8 Hz), 8.75 (1H, d, J=6.8 Hz), 8.83 (1H, d, J=6.8 Hz), 9.00 (1H, br s), 9.32 (1H, br s), 9.74 (1H, s), 13.37 (1H, s). IR (KBr); ν 3400, 1638, 1388, 1330, 1199, 1116, 1052, 785 cm$^{-1}$ Mass (FAB); m/z 466 ((M+H)+). Elementary Analysis: $C_{29}H_{27}N_3O_3 \cdot 2.1CH_3SO_3H \cdot 0.4H_2O$ Calcd.:C, 55.37; H, 5.41; N, 6.23; S, 9.98. Found:C, 55.54; H, 5.71; N, 6.32; S, 9.71.

By using 5-hydrazinoquinoline or 8-hydrazinoquinoline in place of 5-hydrazinoisoquinoline, 17-cyclopropylmethyl-3,14β-dihydroxy-4,5α-epoxy-6,7-didehydromorphinano[6,7-b]pyrido[2,3-g]indole 157 and 17-cyclopropylmethyl-3,14β-dihydroxy-4,5α-epoxy-6,7-didehydromorphinano[6,7-b]pyrido[3,2-g]indole 158 are obtained, respectively. By using 6-hydrazinoquinoline in place of 5-hydrazinoisoquinoline, 17-cyclopropylmethyl-3,14β-dihydroxy-4,5α-epoxy-6,7-didehydromorphinano[6,7-b]pyrido[3,2-e]indole 159 and 17-cyclopropylmethyl-3,14β-dihydroxy-4,5α-epoxy-6,7-didehydromorphinano[6,7-b]pyrido[2,3-f]indole 160 are obtained.

By using naloxone hydrochloric acid salt in place of naltrexone hydrochloric acid salt, and by using 5-hydrazinoisoquinoline, 5-hydrazinoquinoline or 8-hydrazinoquinoline as the hydrazine derivative, 17-allyl-3,14β-dihydroxy-4,5α-epoxy-6,7-didehydromorphinano[6,7-b]pyrido[4,3-g]indole 161, 17-allyl-3,14β-dihydroxy-4,5α-epoxy-6,7-didehydromorphinano[6,7-b]pyrido[2,3-g]indole 163 and 17-allyl-3,14β-dihydroxy-4,5α-epoxy-6,7-didehydromorphinano[6,7-b]pyrido[3,2-g]indole 164 are obtained, respectively. By using 6-hydrazinoquinoline as the hydrazine derivative, 17-allyl-3,14β-dihydroxy-4,5α-epoxy-6,7-didehydromorphinano[6,7-b]pyrido[3,2-e]indole 165 and 17-allyl-3,14β-dihydroxy-4,5α-epoxy-6,7-didehydromorphinano{6,7-b]pyrido[2,3-f]indole 166 are obtained.

Example 5

17-cyclopropylmethyl-3,14β-dihydroxy-4,5α-epoxy-6,7-didehydromorphinano[6,7-b]cyclohexeno[g]indole 2

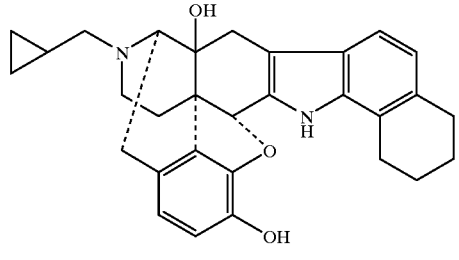

2

Using 966 mg of naltrexone hydrochloric acid salt, 770 mg of 1-hydrazino-5,6,7,8-tetrahydronaphthalene, 0.46 ml of methanesulfonic acid and 15 ml of ethanol, the reaction and purification as in Example 1 were carried out to obtain 525 mg of methanesulfonic acid salt of the captioned compound (yield 32%).

2 methanesulfonic acid salt mp.>235° C. (decomposed); NMR (500 MHz, CDCl3, data for free base); δ 0.13–0.20 (2H, m), 0.53–0.61 (2H, m), 0.85–0.93 (1H, m), 1.77–1.89(5H, m), 2.30 (1H, dt, J=3.5, 12.5 Hz), 2.38–2.47 (2H, m), 2.46 (1H, dd, J=6.4, 12.5 Hz), 2.60 (1H, dd, J=1.1, 15.7 Hz), 2.67–2.86 (6H, m), 2.86 (1H, d, J=15.6 Hz), 3.12 (1H, d, J=18.3 Hz), 3.36 (1H, d, J=6.6 Hz), 5.04 (2H, br s), 5.71 (1H, s), 6.53 (1H, d, J=8.1 Hz), 6.60 (1H, d, J=8.1 Hz), 6.74 (1H, d, J=8.1 Hz), 7.14 (1H, d, J=8.1 Hz), 8.06 (1H, s). IR(KBr); ν 3400, 1510, 1460, 1207, 1048 cm$^{-1}$; Mass (EI); m/z 468 (M$^+$). Elementary Analysis: $C_{30}H_{32}N_2O_3 \cdot CH_3SO_3H \cdot 0.6H_2O$; Calcd.:C, 64.70; H, 6.51; N, 4.87; S, 5.57. Found: C, 64.33; H, 6.54; N, 4.95; S, 5.83.

By using 1-hydrazino-5-ethoxycarbonyl-5,6,7,8-tetrahydronaphthalene, 1-hydrazino-6-ethoxycarbonyl-5,6,7,8-tetrahydronaphthalene, 1-hydrazino-7-ethoxycarbonyl-5,6,7,8-tetrahydronaphthalene, 1-hydrazino-8- ethoxycarbonyl-5,6,7,8-tetrahydronaphthalene, 1-hydrazino-5-carbamoyl-5,6,7,8-tetrahydronaphthalene, 1-hydrazino-6-carbamoyl-5,6,7,8-tetrahydronaphthalene, 1-hydrazino-7-carbamoyl-5,6,7,8-tetrahydronaphthalene, 1-hydrazino-8-carbamoyl-5,6,7,8-tetrahydronaphthalene, 1-hydrazino-5-sulfamoyl-5,6,7,8-tetrahydronaphthalene, 1-hydrazino-6-sulfamoyl-5,6,7,8-tetrahydronaphthalene, 1-hydrazino-7-sulfamoyl-5,6,7,8-tetrahydronaphthalene or 1-hydrazino-8-sulfamoyl-5,6,7,8-tetrahydronaphthalene in place of 1-hydrazino-5,6,7,8-tetrahydronaphthalene, 17-cyclopropylmethyl-3,14β-dihydroxy-4,5α-epoxy-6'-ethoxycarbonyl-6,7-didehydromorphinano[6,7-b]cyclohexeno[g]indole 401, 17-cyclopropylmethyl-3,14β-dihydroxy-4,5α-epoxy-7'-ethoxycarbonyl-6,7-didehydromorphinano[6,7-b]cyclohexeno[g]indole 402, 17-cyclopropylmethyl-3,14β-dihydroxy-4,5α-epoxy-8'-ethoxycarbonyl-6,7-didehydromorphinano[6,7-b]cyclohexeno[g]indole 403, 17-cyclopropylmethyl-3,14β-dihydroxy-4,5α-epoxy-9'-ethoxycarbonyl-6,7-didehydromorphinano[6,7-b]cyclohexeno[g]indole 404, 17-cyclopropylmethyl-3,14β-dihydroxy-4,5α-epoxy-6'-carbamoyl-6,7-didehydromorphinano[6,7-b]cyclohexeno[g]indole 405, 17-cyclopropylmethyl-3,14β-dihydroxy-4,5α-epoxy-7'-carbamoyl-6,7-didehydromorphinano[6,7-b]cyclohexeno[g]indole 406, 17-cyclopropylmethyl-3,14β-dihydroxy-4,5α-epoxy-8'-carbamoyl-6,7-didehydromorphinano[6,7-b]cyclohexeno[g]indole 407, 17-cyclopropylmethyl-3,14β-dihydroxy-4,5α-epoxy-9'-carbamoyl-6,7-didehydromorphinano[6,7-b]cyclohexeno[g]indole 408, 17-cyclopropylmethyl-3,14β-dihydroxy-4,5α-epoxy-6'-sulfamoyl-6,7-didehydromorphinano[6,7-b]cyclohexeno[g]indole 409, 17-cyclopropylmethyl-3,14β-dihydroxy-4,5α-epoxy-7'-sulfamoyl-6,7-didehydromorphinano[6,7-b]cyclohexeno[g]indole 410, 17-cyclopropylmethyl-3,14β-dihydroxy-4,5α-epoxy-8'-sulfamoyl-6,7-didehydromorphinano[6,7-b]cyclohexeno[g]indole 411 and 17-cyclopropylmethyl-3,14β-dihydroxy-4,5α-epoxy-9'-sulfamoyl-6,7-didehydromorphinano[6,7-b]cyclohexeno[g]indole 412 are obtained, respectively.

By using 2-hydrazino-5,6,7,8-tetrahydronaphthalene in place of 1-hydrazino-5,6,7,8-tetrahydronaphthalene, 17-cyclopropylmethyl-3,14β-dihydroxy-4,5α-epoxy-6,7-didehydromorphinano[6,7-b]cyclohexeno[e]indole 413 and 17-cyclopropylmethyl-3,14β-dihydroxy-4,5α-epoxy-6,7-didehydromorphinano[6,7-b]cyclohexeno[f]indole 414 are obtained. By using 4-hydrazinoindan in place of 1-hydrazino-5,6,7,8-tetrahydronaphthalene, 17-cyclopropylmethyl-3,14β-dihydroxy-4,5α-epoxy-6,7-didehydromorphinano[6,7-b]cyclopenteno[g]indole 415 is obtained. By using 5-hydrazinoindan in place of 1-hydrazino-5,6,7,8-tetrahydronaphthalene, 17-cyclopropylmethyl-3,14β-dihydroxy-4,5α-epoxy-6,7-didehydromorphinano[6,7-b]cyclopenteno[e]indole 416 and 17-cyclopropylmethyl-3,14β-dihydroxy-4,5α-epoxy-6,7-didehydromorphinano[6,7-b]cyclopenteno[f]indole 417 are obtained. By using 1-hydrazino-6,7,8,9-tetrahydro-5H-benzocycloheptene in place of 1-hydrazino-5,6,7,8-tetrahydronaphthalene, 17-cyclopropylmethyl-3,14β-dihydroxy-4,5α-epoxy-6,7-didehydromorphinano[6,7-b]cyclohepteno[g]indole 418 is obtained. By using 2-hydrazino-6,7,8,9-tetrahydro-5H-benzocycloheptene in place of 1-hydrazino-5,6,7,8-tetrahydronaphthalene, 17-cyclopropylmethyl-3,14β-dihydroxy-4,5α-epoxy-6,7-didehydromorphinano[6,7-b]cyclohepteno[e]indole 419 and 17-cyclopropylmethyl-3,14β-dihydroxy-4,5α-epoxy-6,7-didehydromorphinano[6,7-b]cyclohepteno[f]indole 420 are obtained. By using 1-hydrazino-5,6,7,8,9,10-hexahydrobenzocyclooctene in place of 1-hydrazino-5,6,7,8-tetrahydronaphthalene, 17-cyclopropylmethyl-3,14β-dihydroxy-4,5α-epoxy-6,7-didehydromorphinano[6,7-b]cycloocteno[g]indole 421 is obtained. By using 2-hydrazino-5,6,7,8,9,10-hexahydrobenzocyclooctene in place of 1-hydrazino-5,6,7,8-tetrahydronaphthalene, 17-cyclopropylmethyl-3,14β-dihydroxy-4,5α-epoxy-6,7-didehydromorphinano[6,7-b]cycloocteno[e]indole 422 and 17-cyclopropylmethyl-3,14β-dihydroxy-4,5α-epoxy-6,7-didehydromorphinano[6,7-b]cycloocteno[f]indole 423 are obtained.

By using naloxone hydrochloric acid salt in place of naltrexone hydrochloric acid salt and by using 1-hydrazino-5,6,7,8-tetrahydronaphthalene, 1-hydrazino-5-ethoxycarbonyl-5,6,7,8-tetrahydronaphthalene, 1-hydrazino-6-ethoxycarbonyl-5,6,7,8-tetrahydronaphthalene, 1-hydrazino-7-ethoxycarbonyl-5,6,7,8-tetrahydronaphthalene, 1-hydrazino-8-ethoxycarbonyl-5,6,7,8-tetrahydronaphthalene, 1-hydrazino-5-carbamoyl-5,6,7,8-tetrahydronaphthalene, 1-hydrazino-6-carbamoyl-5,6,7,8-tetrahydronaphthalene, 1-hydrazino-7-carbamoyl-5,6,7,8-tetrahydronaphthalene, 1-hydrazino-8-carbamoyl-5,6,7,8-tetrahydronaphthalene, 1-hydrazino-5-sulfamoyl-5,6,7,8-tetrahydronaphthalene, 1-hydrazino-6-sulfamoyl-5,6,7,8-tetrahydronaphthalene, 1-hydrazino-7-sulfamoyl-5,6,7,8-tetrahydronaphthalene or 1-hydrazino-8-sulfamoyl-5,6,7,8-tetrahydronaphthalene as the hydrazine derivative, 17-allyl-3,14β-dihydroxy-4,5α-epoxy-6,7-didehydromorphinano[6,7-b]cyclohexeno[g]indole 162, 17-allyl-3,14β-dihydroxy-4,5α-epoxy-6'-ethoxycarbonyl-6,7-didehydromorphinano[6,7-b]cyclohexeno[g]indole 424, 17-allyl-3,14β-dihydroxy-4,5α-epoxy-7'-ethoxycarbonyl-6,7-didehydromorphinano[6,7-b]cyclohexeno[g]indole 425, 17-allyl-3,14β-dihydroxy-4,5α-epoxy-8'-ethoxycarbonyl-6,7-didehydromorphinano[6,7-b]cyclohexeno[g]indole 426, 17-allyl-3,14β-dihydroxy-4,5α-epoxy-9'-ethoxycarbonyl-6,7-didehydromorphinano[6,7-b]cyclohexeno[g]indole 427, 17-allyl-3,14β-dihydroxy-4,5α-epoxy-6'-carbamoyl-6,7-didehydromorphinano[6,7-b]cyclohexeno[g]indole 428, 17-allyl-3,14β-dihydroxy-4,5α-epoxy-7'-carbamoyl-6,7-didehydromorphinano[6,7-b]cyclohexeno[g]indole 429, 17-allyl-3,14β-dihydroxy-4,5α-epoxy-8'-carbamoyl-6,7-didehydromorphinano[6,7-b]cyclohexeno[g]indole 430, 17-allyl-3,14β-dihydroxy-4,5α-epoxy-9'-carbamoyl-6,7-didehydromorphinano[6,7-b]cyclohexeno[g]indole 431, 17-allyl-3,14β-dihydroxy-4,5α-epoxy-6'-sulfamoyl-6,7-didehydromorphinano[6,7-b]cyclohexeno[g]indole 432, 17-allyl-3,14β-dihydroxy-4,5α-epoxy-7'-sulfamoyl-6,7-didehydromorphinano[6,7-b]cyclohexeno[g]indole 433, 17-allyl-3,14β-dihydroxy-4,5α-epoxy-8'-sulfamoyl-6,7-didehydromorphinano[6,7-b]cyclohexeno[g]indole 434 and 17-allyl-3,14β-dihydroxy-4,5α-epoxy-9'-sulfamoyl-6,7-didehydromorphinano[6,7-b]cyclohexeno[g]indole 435 are obtained, respectively. By using 2-hydrazino-5,6,7,8-tetrahydronaphthalene as the hydrazine derivative, 17-allyl-3,14β-dihydroxy-4,5α-epoxy-6,7-didehydromorphinano[6,7-b]cyclohexeno[e]indole 436 and 17-allyl-3,14β-dihydroxy-4,5α-epoxy-6,7-didehydromorphinano[6,7-b]cyclohexeno[f]indole 437 are obtained. By using 4-hydrazinoindan as the hydrazine derivative, 17-allyl-3,14β-dihydroxy-4,5α-epoxy-6,7-didehydromorphinano[6,7-b]cyclopenteno[g]indole 438 is obtained. By using 5-hydrazinoindan as the hydrazine derivative, 17-allyl-3,14β-dihydroxy-4,5α-epoxy-6,7-didehydromorphinano[6,7-b]cyclopenteno[e]indole 439 and 17-allyl-3,14β-dihydroxy-4,5α-epoxy-6,7-didehydromorphinano[6,7-b]cyclopenteno[f]indole 440 are obtained. By using 1-hydrazino-6,7,8,9-tetrahydro-5H- benzocycloheptene as the hydrazine derivative, 17-allyl-3,14β-dihydroxy-4,5α-epoxy-6,7-didehydromorphinano[6,7-b]cyclohepteno[g]indole 441 is obtained. By using 2-hydrazino-6,7,8,9-tetrahydro-5H-benzocycloheptene as the hydrazine derivative, 17-allyl-3,14β-dihydroxy-4,5α-epoxy-6,7-didehydromorphinano[6,7-b]cyclohepteno[e]indole 442 and 17-allyl-3,14β-dihydroxy-4,5α-epoxy-6,7-didehydromorphinano[6,7-b]cyclohepteno[f]indole 443 are obtained. By using 1-hydrazino-5,6,7,8,9,10-hexahydrobenzocyclooctene as the hydrazine derivative, 17-allyl-3,14β-dihydroxy-4,5α-epoxy-6,7-didehydromorphinano[6,7-b]cycloocteno[g]indole 444 is obtained. By using 2-hydrazino-5,6,7,8,9,10-hexahydrobenzocyclooctene as the hydrazine derivative, 17-allyl-3,14β-dihydroxy-4,5α-epoxy-6,7-didehydromorphinano[6,7-b]cycloocteno[e]indole 445 and 17-allyl-3,14β-dihydroxy-4,5α-epoxy-6,7-didehydromorphinano[6,7-b]cycloocteno[f]indole 446 are obtained.

Example 6

17-cyclopropylmethyl-6,7-didehydro-4,5α-epoxy-3,14β-dihydroxy-7'-amino-6,7-2',3'-indolomorphinan 167

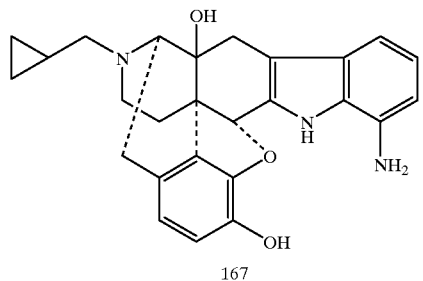

167

In 20 ml of ethanol, 1.00 g of 17-cyclopropylmethyl-6,7-didehydro-4,5α-epoxy-3,14β-dihydroxy-7'-nitro-6,7-2',3'-indolomorphinan 136 and 3.50 g of stannous chloride dihydrate were dissolved and the resulting mixture was heated at 70° C. for 3 hours under stirring. After leaving the reaction mixture to cool to room temperature, 2N aqueous sodium hydroxide solution was added while cooling the mixture in iced water to neutralize the mixture, and the generated precipitates were removed by filtration. The filtrate was extracted with ethyl acetate and the combined organic layers were washed with saturated saline. After drying and concentration, obtained unpurified captioned compound was converted to 680 mg of dihydrochloride (yield 62%).
167 dihydrochloride
Mass (FAB); m/z 430 ((M+H)$^+$).
By using 17-cyclopropylmethyl-6,7-didehydro-4,5α-epoxy-3,14β-dihydroxy-6'-nitro-6,7-2',3'-indolomorphinan 79, 17-cyclopropylmethyl-6,7-didehydro-4,5α-epoxy-3,14,8-dihydroxy-4'-nitro-6,7-2',3'-indolomorphinan 78, 17-allyl-6,7-didehydro-4,5α-epoxy-3,14β-dihydroxy-7'-nitro-6,7-2',3'-indolomorphinan 155, 17-allyl-6,7-didehydro-4,5α-epoxy-3,14β-dihydroxy-6'-nitro-6,7-2',3'-indolomorphinan 117 or 17-allyl-6,7-didehydro-4,5α-epoxy-3,14β-dihydroxy-4'-nitro-6,7-2',3'-indolomorphinan 116 in place of 17-cyclopropylmethyl-6,7-didehydro-4,5α-epoxy-3,14β-dihydroxy-7'-nitro-6,7-2',3'-indolomorphinan 136, 17-cyclopropylmethyl-6,7-didehydro-4,5α-epoxy-3,14β-dihydroxy-6'-amino-6,7-2',3'-indolomorphinan 168, 17-cyclopropylmethyl-6,7-didehydro-4,5α-epoxy-3,14β-dihydroxy-4'-amino-6,7-2',3'-indolomorphinan 169, 17-allyl-6,7-didehydro-4,5α-epoxy-3,14β-dihydroxy-7'-amino-6,7-2',3'-indolomorphinan 170, 17-allyl-6,7-didehydro-4,5α-epoxy-3,14β-dihydroxy-6'-amino-6,7-2',3'-indolomorphinan 171 and 17-allyl-6,7-didehydro-4,5α-epoxy-3,14β-dihydroxy-4'-nitro-6,7-2',3'-indolomorphinan 172 are obtained, respectively.
168 dihydrochloride
Mass (FAB); m/z 430 ((M+H)$^+$).
169 dihydrochloride
Mass (FAB); m/z 430 ((M+H)$^+$).

Example 7

17-cyclopropylmethyl-6,7-didehydro-4,5α-epoxy-3,14β-dihydroxy-7'-isothiocyanato-6,7-2',3'-indolomorphinan 173

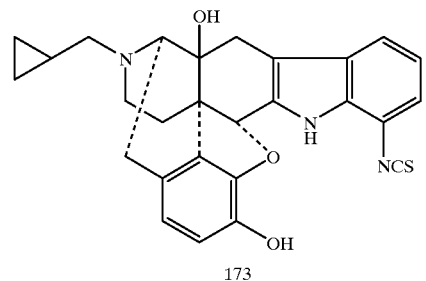

173

In 20 ml of water, 600 mg of 17-cyclopropylmethyl-6,7-didehydro-4,5α-epoxy-3,14β-dihydroxy-7'-amino-6,7-2',3'-indolomorphinan 167-dihydrochloride was dissolved and the solution was cooled in iced water. To this solution, a solution containing 95 μl of thiophosgene in 10 ml of chloroform was added dropwise and the mixture was warmed to room temperature, followed by stirring the mixture for 5 hours at room temperature. The mixture was neutralized by adding saturated aqueous sodium hydrogen carbonate solution while cooling the mixture in iced water and chloroform-methanol (3:1) was added to dissolve insoluble matters, followed by separating the generated two layers. The resultant was extracted twice with 20 ml of chloroform-methanol (3:1) and the combined organic layers were washed with saturated saline. After drying and concentration, the obtained residue was purified by column chromatography [silica gel; chloroform:methanol (95:5)] to obtain the captioned compound which was then converted to 353 mg of methane sulfonic acid salt (yield 52%).
173 methanesulfonic acid salt
mp.: 170° C. (decomposed); NMR (500 MHz, DMSO-d6); δ 0.44 (1H, m), 0.50 (1H, m), 0.63 (1H, m), 0.73 (1H, m), 1.09 (1H, m), 1.85 (1H, br d, J=11.0 Hz), 2.30 (3H, s), 2.54 (1H, d, J=15.9 Hz), 2.60 (1H, m), 2.73 (1H, m), 2.94 (1H, m), 2.95 (1H, d, J=15.9 Hz), 3.11 (1H, m), 3.25 (1H, m), 3.38 (1H,m), 3.44 (1H, J=20.1 Hz), 4.08 (1H, d, J=6.7 Hz), 5.68 (1H, s), 6.37 (1H, s), 6.60 (1H, d, J=7.9 Hz), 6.65 (1H, d, J=7.9 Hz), 7.03(1H, t, J=7.9 Hz), 7.30 (1H, d, J=7.9 Hz), 7.40 (1H, d, J=7.9 Hz), 8.93 (1H, br s), 9.24 (1H, br s), 12.14 (1H, s). IR (KBr); ν3410, 2122, 1462, 1323, 1195, 1048, 785 cm$^{-1}$. Mass (FAB); m/z 472 ((M+H)$^+$). Elementary Analysis: $C_{27}H_{25}N_3O_3S \cdot CH_3SO_3H \cdot 1.3H_2O$; Calcd.:C, 56.90; H, 5.39; N, 7.11; S, 10.85. Found: C, 56.89; H, 5.54; N, 7.04; S, 10.83.

By using 17-cyclopropylmethyl-6,7-didehydro-4,5α-epoxy-3,14β-dihydroxy-6'-amino-6,7-2',3'-indolomorphinan 168.dihydrochloride, 17-cyclopropylmethyl-6,7-didehydro-4,5α-epoxy-3,14β-dihydroxy-4'-amino-6,7-2',3'-indolomorphinan 169.dihydrochloride, 17-allyl-6,7-didehydro-4,5α-epoxy-3,14β-dihydroxy-7'-amino-6,7-2',3'-indolomorphinan 170, 17-allyl-6,7-didehydro-4,5α-epoxy-3,14β-dihydroxy-6'-amino-6,7-2',3'-indolomorphinan 171 or 17-allyl-6,7-didehydro-4,5α-epoxy-3,14β-dihydroxy-4'-amino-6,7-2',3'-indolomorphinan 172 in place of 17-cyclopropylmethyl-6,7-didehydro-4,5α-epoxy-3,14β-dihydroxy-7'-amino-6,7-2',3'-indolomorphinan 167.dihydrochloride, 17-cyclopropylmethyl-6,7-didehydro-4,5α-epoxy-3,14β-dihydroxy-6'-isothiocyanato-6,7-2',3'-indolomorphinan 174, 17-cyclopropylmethyl-6,7-didehydro-4,5α-epoxy-3,14β-dihydroxy-4'-isothiocyanato-6,7-2',3'-indolomorphinan 175, 17-allyl-6,7-didehydro-4,5α-epoxy-3,14β-dihydroxy-7'-isothiocyanato-6,7-2',3'-indolomorphinan 176, 17-allyl-6,7-didehydro-4,5α-epoxy-3,14β-dihydroxy-6'-isothiocyanato-6,7-2',3'-indolomorphinan 177, and 17-allyl-6,7-didehydro-4,5α-epoxy-3,14β-dihydroxy-4'-isothiocyanato-6,7-2',3'-indolomorphinan 178 are obtained, respectively.

174 methanesulfonic acid salt (yield 23 %)

mp.: 200° C. (decomposed); NMR (400 MHz, DMSO-d6); δ 0.44 (1H, m), 0.49 (1H, m), 0.63 (1H, m), 0.73 (1H, m), 1.09 (1H, m), 1.82 (1H, br d, J=11.7 Hz), 2.30 (3H, s), 2.52–2.64 (2H, m), 2.71 (1H, m), 2.93 (1H, m), 2.95 (1H, d, J=16.1 Hz), 3.11 (1H, m), 3.25 (1H, dd, J=20.0, 6.8 Hz), 3.38 (1H,m), 3.44 (1H, J=20.0 Hz), 4.07 (1H, d, J=6.4 Hz), 5.69 (1H, s), 6.36 (1H, s), 6.60 (1H, d, J=7.8 Hz), 6.64 (1H, d, J=7.8 Hz), 7.04(1H, dd, J=8.3, 1.5 Hz), 7.41 (1H, d, J=8.3 Hz), 7.44 (1H, d, J=1.5 Hz), 8.93 (1H, br s), 9.24 (1H, br s), 11.69 (1H, s). IR (KBr); ν 3380, 2122, 1462, 1332, 1195, 1116, 1048, 855, 799, 785 cm$^{-1}$. Mass (FAB); m/z 472 ((M+H)$^+$). Elementary Analysis: $C_{27}H_{25}N_3O_3S \cdot CH_3SO_3H \cdot 0.7H_2O$ Calcd.:C, 57.96; H, 5.28; N, 7.24; S, 11.05. Found :C, 57.94; H, 5.59; N, 7.20; S, 10.97.

175 methanesulfonic acid salt (yield 46%) mp.: 175° C. (decomposed); NMR (500 MHz, DMSO-d6); δ 0.44 (1H, m), 0.52 (1H, m), 0.65 (1H, m), 0.72 (1H, m), 1.16 (1H, m), 1.84 (1H, br d, J=10.4 Hz), 2.29 (3H, s), 2.61 (1H, m), 2.67 (1H, d, J=15.9 Hz), 2.73 (1H, m), 2.90 (1H, m), 3.13 (1H, m), 3.23 (1H, d, J=16.5 Hz), 3.28 (1H,m), 3.45 (1H, m), 3.47 (1H, d, J=19.5 Hz), 4.04 (1H, d, J=6.7 Hz), 5.70 (1H, s), 6.40 (1H, s), 6.62 (1H, d, J=8.5 Hz), 6.65 (1H, d, J=8.5 Hz), 7.09(1H, d, J=7.9 Hz), 7.14 (1H, t, J=7.9 Hz), 7.39 (1H, d, J=7.9 Hz), 8.95 (1H, br s), 9.24 (1H, br s), 11.83 (1H, s). IR (KBr); ν 3390, 2120, 1462, 1332, 1199, 1116, 1050, 783 cm$^{-1}$. Mass (FAB); m/z 472 ((M+H)$^+$). Elementary Analysis: $C_{27}H_{25}N_3O_3S \cdot CH_3SO_3H \cdot 0.5H_2O$; Calcd.:C, 58.32; H, 5.24; N, 7.28; S, 11.12. Found: C, 58.19; H, 5.34; N, 7.23; S, 11.22.

Example 8
3-(tert-butyldimethylsiloxy)-17-cyclopropylmethyl-6,7-didehydro-4,5α-epoxy-14β-hydroxy-5'-(N-cyclopropylmethylcarbamoyl)-6,7-2',3'-indolomorphinan 179

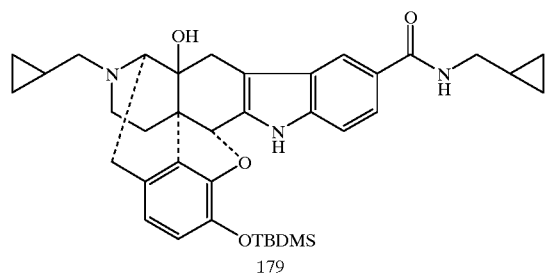

179

In 2.6 ml of anhydrous DMF, 379.1 mg of 17-cyclopropylmethyl-6,7-didehydro-4,5α-epoxy-3,14β-dihydroxy-5'-(N-cyclopropylmethylcarbamoyl)-6,7-2',3'-indolomorphinan 7 was dissolved. To this solution, 204.4 mg of imidazole and 228.6 mg of tert-butylchlorodimethylsilane were added and the resulting mixture was stirred at room temperature for 1 hour. To the reaction mixture, 30 ml of water was added and the resultant was extracted with ether (3×30 ml). The organic layers were combined, dried and concentrated to obtain 536 mg of an oily product. The obtained oily product was purified by column chromatography [silica gel; hexane-ethyl acetate-methanol (7:7:1)] to obtain 446.7 mg (yield 96%) of the captioned compound. A part of the obtained crude crystals were recrystallized from ethyl acetate to obtain crystals in the form of plate (recrystallization yield 75%).

mp.: 174–184° C. (ethyl acetate); NMR (400 MHz, CDCl3); δ −0.01 (3H, s), 0.02 (3H, s), 0.17 (2H, m), 0.27 (2H, m), 0.52–0.61(4H, m), 0.87 (9H, s), 0.89 (1H, m), 1.06 (1H, m), 1.78 (1H, m), 2.27–2.48 (4H, m), 2.64 (1H, br d, J=15.6 Hz), 2.75 (1H, m), 2.81 (1H, dd, J=19.0, 6.3 Hz), 2.90 (1H, d, 15.6 Hz), 3.14 (1H, d, 19.0 Hz), 3.30 (2H, m), 3.36 (1H, m), 4.95 (1H, br s, OH), 5.60 (1H, s), 6.20 (1H, m, NH), 6.53 (1H, d, J=8.3 Hz), 6.57 (1H, d, J=8.3 Hz), 7.19 (1H, d, J=8.3 Hz), 7.56 (1H, dd, J=8.3, 2.0 Hz), 7.84 (1H, br s), 8.25 (1H, s, NH). IR (KBr); ν 3400, 3080, 1638, 1620, 1522, 1497, 1473, 1446, 1336, 1259, 1166, 1035, 955, 853, 801, 783 cm$^{-1}$. Mass (EI); m/z 625 (M$^+$).

Example 9
17-cyclopropylmethyl-6,7-didehydro-4,5α-epoxy-3,14β-dihydroxy-5'-(N-cyclopropylmethylamino)methyl-6,7-2',3'-indolomorphinan 180

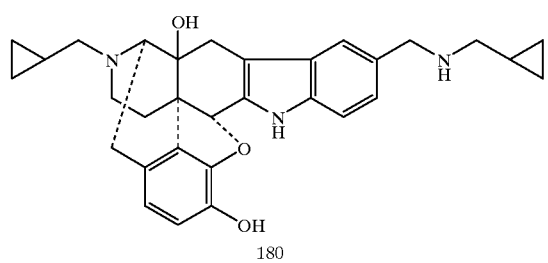

180

In 4.5 ml of anhydrous THF, 403.3 mg of 3-(tert-butyldimethylsiloxy)-17-cyclopropylmethyl-6,7-didehydro-4,5α-epoxy-14β-hydroxy-5'-(N-cyclopropylmethylcarbamoyl)-6,7-2',3'-indolomorphinan 179 was dissolved under argon gas flow. To this solution, 1.7 ml of 2.0M diborane dimethylsulfide complex solution in anhydrous THF was added dropwise at 0° C. and the resulting mixture was heated to reflux for 2.7 hours. After cooling the reaction mixture to 0° C., 4 ml of 6N hydrochloric acid was added and the resulting mixture was again heated to reflux for 1 hour. After cooling the reaction mixture to 0° C., 40 ml of saturated aqueous sodium hydrogen carbonate solution was added to make the mixture basic, and the resultant was extracted with chloroform-methanol (3:1) (3×20 ml). The organic layers were combined and dried to condense the extract to obtain 403 mg of an oily product. This oily product was purified by column chromatography [① silica gel; chloroform-methanol saturated with ammonia (20:1→15:1); ② silica gel for flush column chromatography; chloroform-methanol saturated with ammonia (25:1→15:1); ③ SEPHADEX gel; methanol] to obtain 165.2 mg (yield 47%, two steps) of methanesulfonic acid salt of free base of the captioned compound. The obtained free base was dissolved in methanol and 0.045 ml of methanesulfonic acid was added thereto. Excess ethyl acetate was then added to precipitate the product to obtain 224.1 mg (yield 46%, two steps) of the captioned compound.
180 methanesulfonic acid salt mp.>190° C. (decomposed). NMR (400 MHz, DMSO-d6) δ 0.30 (2H, m), 0.44 (1H, m), 0.51 (1H, m), 0.55 (2H, m), 0.64 (1H, m), 0.73 (1H, m), 1.02 (1H, m), 1.12 (1H, m), 1.83 (1H, m), 2.32 (6H, s), 2.48–2.78 (5H, m), 2.94 (1H, d, J=16.1 Hz), 2.95 (1H, m), 3.14 (1H, m), 3.24 (1H, dd, J=20.0, 6.8 Hz), 3.34 (1H, m), 3.45 (1H, d, J=20.0 Hz), 4.08 (1H, br d, J=6.3 Hz), 4.15–4.21 (2H, m), 5.70 (1H, s), 6.34 (1H,br s, OH), 6.59 (1H, d, J=8.3 Hz), 6.63 (1H, d, J=8.3 Hz), 7.24 (1H, dd, J=8.3, 1.5 Hz), 7.42 (1H, d, J=8.3 Hz), 7.47 (1H, br s), 8.73 (2H, m, NH2+), 8.91 (1H, m, NH+), 9.24 (1H, br s, OH), 11.51 (1H, s, NH). IR (KBr); 3386, 1638, 1626, 1462, 1328, 1197, 1116, 1060, 866, 785 cm⁻¹. Mass (FAB); m/z 498 ((M+H)⁺). Elementary Analysis: $C_{31}H_{35}N_3O_3 \cdot 2CH_3SO_3H \cdot 1.5H_2O$; Calcd.:C, 55.29; H, 6.47; N, 5.86; S, 8.95. Found: C, 55.49; H, 6.37; N, 5.60; S, 8.79.

In accordance with Examples 7 and 8, by using 17-cyclopropylmethyl-6,7-didehydro-4,5α-epoxy-3,14β-dihydroxy-4'-(N-cyclopropylmethylcarbamoyl)-6,7-2',3'-indolomorphinan 46, 17-cyclopropylmethyl-6,7-didehydro-4,5α-epoxy-3,14β-dihydroxy-6'-(N-cyclopropylmethylcarbamoyl)-6,7-2',3'-indolomorphinan 47, 17-cyclopropylmethyl-6,7-didehydro-4,5α-epoxy-3,14β-dihydroxy-7'-(N-cyclopropylmethylcarbamoyl)-6,7-2',3'-indolomorphinan 127, 17-allyl-6,7-didehydro-4,5α-epoxy-3,14β-dihydroxy-4'-(N-cyclopropylmethylcarbamoyl)-6,7-2',3'-indolomorphinan 84, 17-allyl-6,7-didehydro-4,5α-epoxy-3,14β-dihydroxy-5'-(N-cyclopropylmethylcarbamoyl)-6,7-2',3'-indolomorphinan 26, 17-allyl-6,7-didehydro-4,5α-epoxy-3,14β-dihydroxy-6'-(N-cyclopropylmethylcarbamoyl)-6,7-2',3'-indolomorphinan 85 or 17-allyl-6,7-didehydro-4,5α-epoxy-3,14β-dihydroxy-7'-(N-cyclopropylmethylcarbamoyl)-6,7-2',3'-indolomorphinan 146 in place of 17-cyclopropylmethyl-6,7-didehydro-4,5α-epoxy-3,14β-dihydroxy-5'-(N-cyclopropylmethylcarbamoyl)-6,7-2',3'-indolomorphinan 7, 17-cyclopropylmethyl-6,7-didehydro-4,5α-epoxy-3,14β-dihydroxy-4'-(N-cyclopropylmethylamino)methyl-6,7-2',3'-indolomorphinan 181, 17-cyclopropylmethyl-6,7-didehydro-4,5α-epoxy-3,14β-dihydroxy-6'-(N-cyclopropylmethylamino)methyl-6,7-2',3'-indolomorphinan 182, 17-cyclopropylmethyl-6,7-didehydro-4,5α-epoxy-3,14β-dihydroxy-7'-(N-cyclopropylmethylamino)methyl-6,7-2',3'-indolomorphinan 183, 17-allyl-6,7-didehydro-4,5α-epoxy-3,14β-dihydroxy-4'-(N-cyclopropylmethylamino)methyl-6,7-2',3'-indolomorphinan 184, 17-allyl-6,7-didehydro-4,5α-epoxy-3,14β-dihydroxy-5'-(N-cyclopropylmethylamino)methyl-6,7-2',3'-indolomorphinan 185, 17-allyl-6,7-didehydro-4,5α-epoxy-3,14β-dihydroxy-6'-(N-cyclopropylmethylamino)methyl-6,7-2',3'-indolomorphinan 186, and 17-allyl-6,7-didehydro-4,5α-epoxy-3,14β-dihydroxy-7'-(N-cyclopropylmethylamino)methyl-6,7-2',3'-indolomorphinan 187 are obtained, respectively.

Example 10

17-cyclopropylmethyl-6,7-didehydro-4,5α-epoxy-3,14β-dihydroxy-6'-methylsulfonyl-6,7-2',3'-indolomorphinan 188

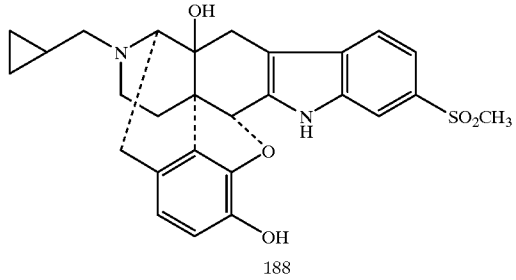

188

In 14 ml of acetic acid, 459.6 mg of 17-cyclopropylmethyl-6,7-didehydro-4,5α-epoxy-3,14β-dihydroxy-6'-methylthio-6,7-2',3'-indolomorphinan 43 was dissolved. To this solution, 0.57 ml of 30% aqueous hydrogen peroxide solution was added and the resulting mixture was stirred at 50° C. for 4 hours. After cooling the reaction mixture to room temperature, 10 ml of aqueous saturated sodium thiosulfate solution was added to the mixture and the mixture was stirred for 10 minutes, followed by concentration of the mixture. To the residue, 15 ml of chloroform and 15 ml of 3N aqueous sodium hydroxide solution were added and generated layers were separated. The aqueous layer was further extracted twice with 10 ml of chloform. The obtained organic layers were dried over anhydrous sodium sulfate and then concentrated. The obtained residue was purified by column chromatography [silica gel; chloroform saturated with ammonia/methanol (15:1)] to obtain 310.2 mg of the captioned compound. The thus obtained compound was dissolved in 4 ml of methanol and 41 µl of methanesulfonic acid was added thereto, followed by concentration of the mixture. The obtained residue was purified by column chromatography [SEPHADEX-LH-20; methanol] and excess ether was added. The solids were collected by filtration and washed to obtain 210 mg (yield 38%) of white methanesulfonic acid salt.
188 methanesulfonic acid salt mp.: 255–260° C. (decomposed); NMR(free, 400 MHz, CDCl₃); δ 0.10–0.22 (2H, m), 0.50–0.62 (2H, m), 0.82–0.93 (1H, m), 1.80 (1H,br d, J=11.2 Hz), 1.95 (1H, br s), 2.25–2.50 (5H, m), 2.64 (1H, d, J=16.1 Hz), 2.72–2.83 (1H, m), 2.92 (3H, s), 2.89–3.00 (1H, m), 3.12 (1H, d, J=18.6 Hz), 3.32 (1H, d, J=6.3 Hz), 5.64 (1H, s), 6.55 (1H, br d, J=8.3 Hz), 6.68 (1H, d, J=8.1 Hz), 6.84 (1H, br d, J=8.3 Hz), 9.24 (1H, br s). IR (KBr); v 3450, 1510, 1460, 1294, 1210, 1141, 1122, 1048, 779 cm⁻¹; Mass (FAB); m/z 493 ((M+H)⁺). Elementary Analysis: $C_{27}H_{28}N_2O_5S \cdot CH_3SO_3H \cdot 0.6H_2O$; Calcd.:C, 56.10; H. 5.58; N, 4.67; S, 10.70. Found: C, 56.19; H, 5.76; N, 4.61; S, 10.32.

By using 17-cyclopropylmethyl-6,7-didehydro-4,5α-epoxy-3,14β-dihydroxy-4'-methylthio-6,7-2',3'- indolomorphinan 42, 17-cyclopropylmethyl-6,7-didehydro-4,5α-epoxy-3,14β-dihydroxy-5'-methylthio-6,7-2',3'-indolomorphinan 12, 17-cyclopropylmethyl-6,7-didehydro-4,5α-epoxy-3,14β-dihydroxy-7'-methylthio-6,7-2',3'-indolomorphinan 121, 17-allyl-6,7-didehydro-4,5α-epoxy-3,14β-dihydroxy-4'-methylthio-6,7-2',3'-indolomorphinan 80, 17-allyl-6,7-didehydro-4,5α-epoxy-3,14β-dihydroxy-5'-methylthio-6,7-2',3'-indolomorphinan 31, 17-allyl-6,7-didehydro-4,5α-epoxy-3,14β-dihydroxy-6'-methylthio-6,7-2',3'-indolomorphinan 81 or 17-allyl-6,7-didehydro-4,5α-epoxy-3,14β-dihydroxy-7'-methylthio-6,7-2',3'-indolomorphinan 140 in place of 17-cyclopropylmethyl-6,7-didehydro-4,5α-epoxy-3,14β-dihydroxy-6'-methylthio-6,7-2',3'-indolomorphinan 43, 17-cyclopropylmethyl-6,7-didehydro-4,5α-epoxy-3,14β-dihydroxy-4'-methylsulfonyl-6,7-2',3'-indolomorphinan 189, 17-cyclopropylmethyl-6,7-didehydro-4,5α-epoxy-3,14β-dihydroxy-5'-methylsulfonyl-6,7-2',3'-indolomorphinan 6, 17-cyclopropylmethyl-6,7-didehydro-4,5α-epoxy-3,14β-dihydroxy-7'-methylsulfonyl-6,7-2',3'-indolomorphinan 190, 17-allyl-6,7-didehydro-4,5α-epoxy-3,14β-dihydroxy-4'-methylsulfonyl-6,7-2',3'-indolomorphinan 191, 17-allyl-6,7-didehydro-4,5α-epoxy-3,14β-dihydroxy-5'-methylsulfonyl-6,7-2',3'-indolomorphinan 25, 17-allyl-6,7-didehydro-4,5α-epoxy-3,14β-dihydroxy-6'-methylsulfonyl-6,7-2',3'-indolomorphinan 192 and 17-allyl-6,7-didehydro-4,5α-epoxy-3,14β-dihydroxy-7'-methylsulfonyl-6,7-2',3'-indolomorphinan 193 are obtained, respectively.

190 methanesulfonic acid salt (yield 25%)

mp.>215° C. (decomposed); NMR (400 MHz, DMSO-d6); δ 0.40–0.54 (2H, m), 0.59–0.77 (2H, m), 1.04–1.17 (1H, m), 1.86 (1H,br d, J=10.7 Hz), 2.30 (3H, s), 2.50–2.79 (2H, m), 2.57 (1H, d, J=16.1 Hz), 2.90–3.00 (1H, m), 3.00 (1H, d, J=16.1 Hz), 3.06–3.50 (3H, m), 3.31 (3H, s), 4.09 (1H, d, J=6.4 Hz), 5.75 (1H, s), 6.41 (1H,s), 6.61 (1H, d, J=7.8 Hz), 6.65 (1H, d, J=7.8 Hz), 7.22 (1H, t, J=7.6 Hz), 7.65 (1H, dd, J=7.3, 1.0 Hz), 7.76 (1H, d, J=7.8 Hz), 8.95 (1H, br s), 9.27 (1H, s), 11.66 (1H, s). IR (KBr); ν 3420, 1620, 1462, 1299, 1205, 1125, 1048 cm$^{-1}$ Mass (FAB); m/z 493 (M+H)$^+$; Elementary Analysis: $C_{27}H_{28}N_2O_5S \cdot CH_3SO_3H \cdot 0.8H_2O$; Calcd.:C, 55.76; H, 5.62; N, 4.64; S, 10.63. Found: C, 55.78; H, 5.65; N, 4.55; S, 10.56.

Example 11

17-cyclopropylmethyl-6,7-didehydro-4,5α-epoxy-14β-hydroxy-3-methoxy-6'-methoxycarbonyl-6,7-2',3'-indolomorphinan 194

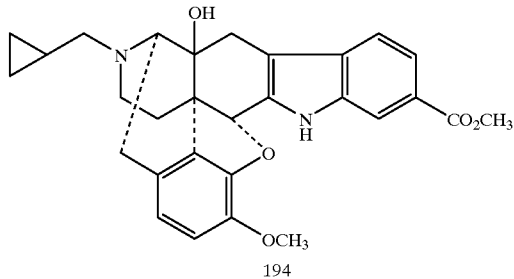

194

In 20 ml of methanol, 600 mg of 17-cyclopropylmethyl-6,7-didehydro-4,5α-epoxy-3,14β-dihydroxy-6'-methoxycarbonyl-6,7-2',3'-indolomorphinan 77 was dissolved and the solution was cooled to 0° C. To this solution, diazomethane solution in ether was added dropwise until the starting material disappeared. The reaction was monitored by TLC. After completion of the reaction, the solvent was evaporated and the obtained crude crystals were recrystallized from methanol to obtain 515 mg of the captioned compound (yield 83%). Four hundred fifty milligrams of this product was converted to methanesulfonic acid salt and the salt was recovered by filtration after adding ether to obtain 502 mg of methanesulfonic acid salt of the captioned compound.

194 methanesulfonic acid salt mp.: 220–227° C. (decomposed); NMR(free, 400 MHz, CDCL3); δ 0.15–0.23 (2H,m), 0.54–0.64 (2H, m), 0.93 (1H, m), 1.82 (1H, m), 2.32 (1H, m), 2.37–2.52 (3H, m), 2.64 (1H, d, J=15.1 Hz) 2.74–2.90 (2H, m), 2.92 (1H, d, J=15.1 Hz), 3.17 (1H, d, J=18.6 Hz), 3.43 (1H, m), 3.77 (3H, m), 3.90 (3H, m), 5.05 (1H, br s), 5.69 (1H, s), 6.64 (1H, d, J=8.3 Hz), 6.67 (1H, d, J=8.3 Hz), 7.38 (1H, d, J=8.3 Hz), 7.69 (1H, dd, J=8.3, 1.5 Hz), 7.97 (1H, s), 8.60 (1H, br s). Mass (EI); m/z 486 (M$^+$). Elementary Analysis: $C_{29}H_{30}N_2O_5 \cdot CH_3SO_3H \cdot 0.8H_2O$; Calcd.:C, 60.35; H, 6.01; N, 4.69; S, 5.37. Found: C, 60.23; H, 6.30; N, 4.72; S, 5.38.

By using 17-cyclopropylmethyl-6,7-didehydro-4,5α-epoxy-3,14β-dihydroxy-4'-methoxycarbonyl-6,7-2',3'-indolomorphinan 76, 17-cyclopropylmethyl-6,7-didehydro-4,5α-epoxy-3,14β-dihydroxy-5'-ethoxycarbonyl-6,7-2',3'-indolomorphinan 3,17-cyclopropylmethyl-6,7-didehydro-4,5α-epoxy-3,14β-dihydroxy-7'-ethoxycarbonyl- 6,7-2',3'-indolomorphinan 119, 17-cyclopropylmethyl-6,7-didehydro-4,5α-epoxy-3,14β-dihydroxy-4'-(N-cyclopropylmethylcarbamoyl)-6,7-2',3'-indolomorphinan 46, 17-cyclopropylmethyl-6,7-didehydro-4,5α-epoxy-3,14β-dihydroxy-5'-(N-cyclopropylmethylcarbamoyl)-6,7-2',3'-indolomorphinan 7, 17-cyclopropylmethyl-6,7-didehydro-4,5α-epoxy-3,14β-dihydroxy-6'-(N-cyclopropylmethylcarbamoyl)-6,7-2',3'-indolomorphinan 47, 17-cyclopropylmethyl-6,7-didehydro-4,5α-epoxy-3,14β-dihydroxy-7'-(N-cyclopropylmethylcarbamoyl)-6,7-2',3'-indolomorphinan 127, 17-cyclopropylmethyl-6,7-didehydro-4,5α-epoxy-3,14β-dihydroxy-4'-cyano-6,7-2',3'-indolomorphinan 52, 17-cyclopropylmethyl-6,7-didehydro-4,5α-epoxy-3,14β-dihydroxy-5'-cyano-6,7-2',3'-indolomorphinan 8, 17-cyclopropylmethyl-6,7-didehydro-4,5α-epoxy-3,14β-dihydroxy-6'-cyano-6,7-2',3'-indolomorphinan 53, 17-cyclopropylmethyl-6,7-didehydro-4,5α-epoxy-3,14β-dihydroxy-4'-methylthio-6,7-2',3'-indolomorphinan 42, 17-cyclopropylmethyl-6,7-didehydro-4,5α-epoxy-3,14β-dihydroxy-5'-methylthio-6,7-2',3'-indolomorphinan 12, 17-cyclopropylmethyl-6,7-didehydro-4,5α-epoxy-3,14β-dihydroxy-6'-methylthio-6,7-2',3'-indolomorphinan 43, 17-cyclopropylmethyl-6,7-didehydro-4,5α-epoxy-3,14β-dihydroxy-7'-methylthio-6,7-2',3'-indolomorphinan 121, 17-cyclopropylmethyl-6,7-didehydro-4,5α-epoxy-3,14β-dihydroxy-4'-methylsulfonyl-6,7-2',3'-indolomorphinan 189, 17-cyclopropylmethyl- 6,7-didehydro-4,5α-epoxy-3,14β-dihydroxy-5'-methylsulfonyl-6,7-2',3'-indolomorphinan 6, 17-cyclopropylmethyl-6,7-didehydro-4,5α-epoxy-3,14β-dihydroxy-6'-methylsulfonyl-6,7-2',3'-indolomorphinan 188, 17-cyclopropylmethyl-6,7-didehydro-4,5α-epoxy-3,14β-dihydroxy-7'-methylsulfonyl-6,7-2',3'-indolomorphinan 190, 17-cyclopropylmethyl-6,7-didehydro-4,5α-epoxy-3,14β-dihydroxy-4'-[2-(N,N-dimethylamino)ethyl)]-6,7-2',3'-indolomorphinan 64, 17-cyclopropylmethyl-6,7-didehydro-4,5α-epoxy-3,14β-dihydroxy-5'-[2-(N,N-dimethylamino)ethyl)]-6,7-2',3'-indolomorphinan 9, 17-cyclopropylmethyl-6,7-didehydro-4,5α-epoxy-3,14β-dihydroxy-6'-[2-(N,N-dimethylamino)ethyl)]-6,7-2',3'-indolomorphinan 65, 17-cyclopropylmethyl-6,7-didehydro-4,5α-epoxy-3,14β-dihydroxy-7'-[2-(N,N-dimethylamino)ethyl)]-6,7-2',3'-indolomorphinan 131, 17-cyclopropylmethyl-6,7-didehydro-4,5α-epoxy-3,14β-dihydroxy-4'-(N,N-dimethylamino)methyl-6,7-2',3'-indolomorphinan 66, 17-cyclopropylmethyl-6,7-didehydro-4,5α-epoxy-3,14β-dihydroxy-5'-(N,N-dimethylamino)methyl-6,7-2',3'-indolomorphinan 10, 17-cyclopropylmethyl-6,7-didehydro-4,5α-epoxy-3,14β-dihydroxy-6'-(N,N-dimethylamino)methyl-6,7-2',3'-indolomorphinan 67, 17-cyclopropylmethyl-6,7-didehydro-4,5α-epoxy-3,14β-dihydroxy-7'-(N,N-dimethylamino)methyl-6,7-2',3'-indolomorphinan 130, 17-cyclopropylmethyl-6,7-didehydro-4,5α-epoxy-3,14β-dihydroxy- 4'-isothiocyanato-6,7-2',3'-indolomorphinan 175, 17-cyclopropylmethyl-6,7-didehydro-4,5α-epoxy-3,14β-dihydroxy-6'-isothiocyanato-6,7-2',3'-indolomorphinan 174, 17-cyclopropylmethyl-6,7-didehydro-4,5α-epoxy-3,14β-dihydroxy-7'-isothiocyanato-6,7-2',3'-indolomorphinan 173, 17-cyclopropylmethyl-6,7-didehydro-4,5α-epoxy-3,14β-dihydroxy-4'-nitro-6,7-2',3'-indolomorphinan 78, 17-cyclopropylmethyl-6,7-didehydro-4,5α-epoxy-3,14β-dihydroxy-6'-nitro-6,7-2',3'-indolomorphinan 79, 17-cyclopropylmethyl-6,7-didehydro-4,5α-epoxy-3,14β-dihydroxy-7'-nitro-6,7-2',3'-indolomorphinan 136, 17-allyl-6,7-didehydro-4,5α-epoxy-3,14β-dihydroxy-4'-methoxycarbonyl-6,7-2',3'-indolomorphinan 114, 17-allyl-6,7-didehydro-4,5α-epoxy-3,14β-dihydroxy-5'-ethoxycarbonyl-6,7-2',3'-indolomorphinan 22, 17-allyl-6,7-didehydro-4,5α-epoxy-3,14β-dihydroxy-6'-methoxycarbonyl-6,7-2',3'-indolomorphinan 115, 17-allyl-6,7-didehydro-4,5α-epoxy-3,14β-dihydroxy-7'-ethoxycarbonyl-6,7-2',3'-indolomorphinan 138, 17-allyl-6,7-didehydro-4,5α-epoxy-3,14β-dihydroxy-4'-(N-cyclopropylmethylcarbamoyl)-6,7-2',3'-indolomorphinan 84, 17-allyl-6,7-didehydro-4,5α-epoxy-3,14β-dihydroxy-5'-(N-cyclopropylmethylcarbamoyl)-6,7-2',3'-indolomorphinan 26, 17-allyl-6,7-didehydro-4,5α-epoxy-3,14β-dihydroxy-6'-(N-cyclopropylmethylcarbamoyl)-6,7-2',3'-indolomorphinan 85, 17-allyl-6,7-didehydro-4,5α-epoxy-3,14β-dihydroxy-7'-(N-cyclopropylmethylcarbamoyl)-6,7-2',3'-indolomorphinan 146, 17-allyl-6,7-didehydro-4,5α-epoxy-3,14β-dihydroxy-4'-cyano-6,7-2',3'-indolomorphinan 90, 17-allyl-6,7-didehydro-4,5α-epoxy-3,14β-dihydroxy-5'-cyano-6,7-2',3'-indolomorphinan 27, 17-allyl-6,7-didehydro-4,5α-epoxy-3,14β-dihydroxy-6'-cyano-6,7-2',3'-indolomorphinan 91, 17-allyl-6,7-didehydro-4,5α-epoxy-3,14β-dihydroxy-4'-methylthio-6,7-2',3'-indolomorphinan 80, 17-allyl-6,7-didehydro-4,5α-epoxy-3,14β-dihydroxy-5'-methylthio-6,7-2',3'-indolomorphinan 31, 17-allyl-6,7-didehydro-4,5α-epoxy-3,14β-dihydroxy-6'-methylthio-6,7-2',3'-indolomorphinan 81, 17-allyl-6,7-didehydro-4,5α-epoxy-3,14β-dihydroxy-7'-methylthio-6,7-2',3'-indolomorphinan 140, 17-allyl-6,7-didehydro-4,5α-epoxy-3,14β-dihydroxy-4'-methylsulfonyl-6,7-2',3'-indolomorphinan 191, 17-allyl-6,7-didehydro-4,5α-epoxy-3,14β-dihydroxy-5'-ethylsulfonyl-6,7-2',3'-indolomorphinan 25, 17-allyl-6,7-didehydro-4,5α-epoxy-3,14β-dihydroxy-6'-methylsulfonyl-6,7-2',3'-indolomorphinan 192, 17-allyl-6,7-didehydro-4,5α-epoxy-3,14β-dihydroxy-7'-methylsulfonyl-6,7-2',3'-indolomorphinan 193, 17-allyl-6,7-didehydro-4,5α-epoxy-3,14β-dihydroxy-4'-[2-(N,N-dimethylamino)ethyl)]-6,7-2',3'-indolomorphinan 102, 17-allyl-6,7-didehydro-4,5α-epoxy-3,14β-dihydroxy-5'-[2-(N,N-dimethylamino)ethyl)]-6,7-2',3'-indolomorphinan 28, 17-allyl-6,7-didehydro-4,5α-epoxy-3,14β-dihydroxy- 6'-[2-(N,N-dimethylamino)ethyl)]-6,7-2',3'-indolomorphinan 103, 17-allyl-6,7-didehydro-4,5α-epoxy-3,14β-dihydroxy-7'-[2-(N,N-dimethylamino)ethyl)]-6,7-2',3'-indolomorphinan 150, 17-allyl-6,7-didehydro-4,5α-epoxy-3,14β-dihydroxy-4'-(N,N-dimethylamino)methyl-6,7-2',3'-indolomorphinan 104, 17-allyl-6,7-didehydro-4,5α-epoxy-3,14β-dihydroxy-5'-(N,N-dimethylamino)methyl-6,7-2',3'-indolomorphinan 29, 17-allyl-6,7-didehydro-4,5α-epoxy-3,14β-dihydroxy-6'-(N,N-dimethylamino)methyl-6,7-2',3'-indolomorphinan 105, 17-allyl-6,7-didehydro-4,5α-epoxy-3,14β-dihydroxy-7'-(N,N-dimethylamino)methyl-6,7-2',3'-indolomorphinan 149, 17-allyl-6,7-didehydro-4,5α-epoxy-3,14β-dihydroxy-4'-isothiocyanato-6,7-2',3'-indolomorphinan 178, 17-allyl-6,7-didehydro-4,5α-epoxy-3,14β-dihydroxy-6'-isothiocyanato-6,7-2',3'-indolomorphinan 177, 17-allyl-6,7-didehydro-4,5α-epoxy-3,14β-dihydroxy-7'-isothiocyanato-6,7-2',3'-indolomorphinan 176, 17-allyl-6,7-didehydro-4,5α-epoxy-3,14β-dihydroxy-4'-nitro-6,7-2',3'-indolomorphinan 116, 17-allyl-6,7-didehydro-4,5α-epoxy-3,14β-dihydroxy-6'-nitro-6,7-2',3'-indolomorphinan 117 or 17-allyl-6,7-didehydro-4,5α-epoxy-3,14β-dihydroxy-7'-nitro-6,7-2',3'-indolomorphinan 155 in place of 17-cyclopropylmethyl-6,7-didehydro-4,5α-epoxy-3,14β-dihydroxy-6'-methoxycarbonyl-6,7-2',3'-indolomorphinan 77, 17-cyclopropylmethyl-6,7-didehydro-4,5α-epoxy-14β-hydroxy-3-methoxy-4'-methoxycarbonyl-6,7-2',3'-indolomorphinan 195, 17-cyclopropylmethyl-6,7-didehydro-4,5α-epoxy-14β-hydroxy-3-methoxy-5'-ethoxycarbonyl-6,7-2',3'-indolomorphinan 196, 17-cyclopropylmethyl-6,7-didehydro-4,5α-epoxy-14β-hydroxy-3-methoxy-7'-ethoxycarbonyl-6,7-2',3'-indolomorphinan 197, 17-cyclopropylmethyl-6,7-didehydro-4,5α-epoxy-14β-hydroxy-3-methoxy-4'-(N-cyclopropylmethylcarbamoyl)-6,7-2',3'-indolomorphinan 198, 17-cyclopropylmethyl-6,7-didehydro-4,5α-epoxy-14β-hydroxy-3-methoxy-5'-(N-cyclopropylmethylcarbamoyl)-6,7-2',3'-indolomorphinan 199, 17-cyclopropylmethyl-6,7-didehydro-4,5α-epoxy-14β-hydroxy-3-methoxy-6'-(N-cyclopropylmethylcarbamoyl)-6,7-2',3'-indolomorphinan 200, 17-cyclopropylmethyl-6,7-didehydro-4,5α-epoxy-14β-hydroxy-3-methoxy-7'-(N-cyclopropylmethylcarbamoyl)-6,7-2',3'-indolomorphinan 201, 17-cyclopropylmethyl-6,7-didehydro-4,5α-epoxy-14β-hydroxy-3-methoxy-4'-cyano-6,7-2',3'-indolomorphinan 202, 17-cyclopropylmethyl-6,7-didehydro-4,5α-epoxy-14β-hydroxy-3-methoxy-5'-cyano-6,7-2',3'-indolomorphinan 203, 17-cyclopropylmethyl-6,7-didehydro-4,5α-epoxy-14β-hydroxy-3-methoxy-6'-cyano-6,7-2',3'-indolomorphinan 204, 17-cyclopropylmethyl-6,7-didehydro-4,5α-epoxy-14β-hydroxy-3-methoxy-4'-methylthio-6,7-2',3'-indolomorphinan 205, 17-cyclopropylmethyl-6,7-didehydro-4,5α-epoxy- 14β-hydroxy-3-methoxy-5'-methylthio-6,7-2',3'-indolomorphinan 206, 17-cyclopropylmethyl-6,7-didehydro-4,5α-epoxy-14β-hydroxy-3-methoxy-6'-methylthio-6,7-2',3'-indolomorphinan 207, 17-cyclopropylmethyl-6,7-didehydro-4,5α-epoxy-14β-hydroxy-3-methoxy-7'-methylthio-6,7-2',3'-indolomorphinan 208, 17-cyclopropylmethyl-6,7-didehydro-4,5α-epoxy-14β-hydroxy-3-methoxy-4'-methylsulfonyl-6,7-2',3'-indolomorphinan 209, 17-cyclopropylmethyl-6,7-didehydro-4,5α-epoxy-14β-hydroxy-3-methoxy-5'-methylsulfonyl-6,7-2',3'-indolomorphinan 210, 17-cyclopropylmethyl-6,7-didehydro-4,5α-epoxy-14β-hydroxy-3-methoxy-6'-methylsulfonyl-6,7-2',3'-indolomorphinan 211, 17-cyclopropylmethyl-6,7-didehydro-4,5α-epoxy-14β-hydroxy-3-methoxy-7'-methylsulfonyl-6,7-2',3'-indolomorphinan 212, 17-cyclopropylmethyl-6,7-didehydro-4,5α-epoxy-14β-hydroxy-3-methoxy-4'-[2-(N, N-dimethylamino)ethyl)]-6,7-2',3'-indolomorphinan 213, 17-cyclopropylmethyl-6,7-didehydro-4,5α-epoxy-14β-hydroxy-3-methoxy-5'-[2-(N,N-dimethylamino)ethyl)]-6,7-2',3'-indolomorphinan 214, 17-cyclopropylmethyl-6,7-didehydro-4,5α-epoxy-14β-hydroxy-3-methoxy-6'-[2-(N,N-dimethylamino)ethyl)]-6,7-2',3'-indolomorphinan 215, 17-cyclopropylmethyl-6,7-didehydro-4,5α-epoxy-14β-hydroxy-3-methoxy-7'-[2-(N,N-dimethylamino)ethyl)]-6,7-2',3'-indolomorphinan 216, 17-cyclopropylmethyl-6,7-didehydro-4,5α-epoxy-14β-hydroxy-3-methoxy-4'-(N,N-dimethylamino)methyl- 6,7-2',3'-indolomorphinan 217, 17-cyclopropylmethyl-6,7-didehydro-4,5α-epoxy-14β-hydroxy-3-methoxy-5'-(N,N-dimethylamino)methyl-6,7-2',3'-indolomorphinan 218, 17-cyclopropylmethyl-6,7-didehydro-4,5α-epoxy-14β-hydroxy-3-methoxy-6'-(N,N-dimethylamino)methyl-6,7-2',3'-indolomorphinan 219, 17-cyclopropylmethyl-6,7-didehydro-4,5α-epoxy-14β-hydroxy-3-methoxy-7'-(N,N-dimethylamino)methyl-6,7-2',3'-indolomorphinan 220, 17-cyclopropylmethyl-6,7-didehydro-4,5α-epoxy-14β-hydroxy-3-methoxy-4'-isothiocyanato-6,7-2',3'-indolomorphinan 221, 17-cyclopropylmethyl-6,7-didehydro-4,5α-epoxy-14β-hydroxy-3-methoxy-6'-isothiocyanato-6,7-2',3'-indolomorphinan 222, 17-cyclopropylmethyl-6,7-didehydro-4,5α-epoxy-14β-hydroxy-3-methoxy-7'-isothiocyanato-6,7-2',3'-indolomorphinan 223, 17-cyclopropylmethyl-6,7-didehydro-4,5α-epoxy-14β-hydroxy-3-methoxy-4'-nitro-6,7-2',3'-indolomorphinan 224, 17-cyclopropylmethyl-6,7-didehydro-4,5α-epoxy-14β-hydroxy-3-methoxy-6'-nitro-6,7-2',3'-indolomorphinan 225, 17-cyclopropylmethyl-6,7-didehydro-4,5α-epoxy-14β-hydroxy-3-methoxy-7'-nitro-6,7-2',3'-indolomorphinan 226, 17-allyl-6,7-didehydro-4,5α-epoxy-14β-hydroxy-3-methoxy-4'-methoxycarbonyl-6,7-2',3'-indolomorphinan 227, 17-allyl-6,7-didehydro-4,5α-epoxy-14β-hydroxy-3-methoxy-51-ethoxycarbonyl-6,7-2',3'-indolomorphinan 228, 17-allyl-6,7-didehydro-4,5α-epoxy-14β-hydroxy-3-methoxy-6'-methoxycarbonyl-6,7-2',3'-indolomorphinan 229, 17-allyl-6,7-didehydro-4,5α-epoxy-14β-hydroxy-3-methoxy-7'-ethoxycarbonyl-6,7-2',3'-indolomorphinan 230, 17-allyl-6,7-didehydro-4,5α-epoxy-14β-hydroxy-3-methoxy-4'-(N-cyclopropylmethylcarbamoyl)-6,7-2',3'-indolomorphinan 231, 17-allyl-6,7-didehydro-4,5α-epoxy-14β-hydroxy-3-methoxy-5'-(N-cyclopropylmethylcarbamoyl)-6,7-2',3'-indolomorphinan 232, 17-allyl-6,7-didehydro-4,5α-epoxy-14β-hydroxy-3-methoxy-6'-(N-cyclopropylmethylcarbamoyl)-6,7-2',3'-indolomorphinan 233, 17-allyl-6,7-didehydro-4,5α-epoxy-14β-hydroxy-3-methoxy-7'-(N-cyclopropylmethylcarbamoyl)-6,7-2',3'-indolomorphinan 234, 17-allyl-6,7-didehydro-4,5α-epoxy-14β-hydroxy-3-methoxy-4'-cyano-6,7-2',3'-indolomorphinan 235, 17-allyl-6,7-didehydro-4,5α-epoxy-14β-hydroxy-3-methoxy-5'-cyano-6,7-2',3'-indolomorphinan 236, 17-allyl-6,7-didehydro-4,5α-epoxy-14β-hydroxy-3-methoxy-6'-cyano-6,7-2',3'-indolomorphinan 237, 17-allyl-6,7-didehydro-4,5α-epoxy-14β-hydroxy-3-methoxy-4'-methylthio-6,7-2',3'-indolomorphinan 238, 17-allyl-6,7-didehydro-4,5α-epoxy-14β-hydroxy-3-methoxy-5'-methylthio-6,7-2',3'-indolomorphinan 239, 17-allyl-6,7-didehydro-4,5α-epoxy-14β-hydroxy-3-methoxy-6'-methylthio-6,7-2',3'-indolomorphinan 240, 17-allyl-6,7-didehydro-4,5α-epoxy-14β-hydroxy-3-methoxy-7'-methylthio-6,7-2',3'-indolomorphinan 241, 17-allyl-6,7-didehydro- 4,5α-epoxy-14β-hydroxy-3-methoxy-4'-methylsulfonyl-6,7-2',3'-indolomorphinan 242, 17-allyl-6,7-didehydro-4,5α-epoxy-14β-hydroxy-3-methoxy-5'-methylsulfonyl-6,7-2',3'-indolomorphinan 243, 17-allyl-6,7-didehydro-4,5α-epoxy-14β-hydroxy-3-methoxy-6'-methylsulfonyl-6,7-2',3'-indolomorphinan 244, 17-allyl-6,7-didehydro-4,5α-epoxy-14β-hydroxy-3-methoxy-7'-methylsulfonyl-6,7-2',3'-indolomorphinan 245, 17-allyl-6,7-didehydro-4,5α-epoxy-14β-hydroxy-3-methoxy-4'-[2-(N,N-dimethylamino)ethyl)]-6,7-2',3'-indolomorphinan 246, 17-allyl-6,7-didehydro-4,5α-epoxy-14β-hydroxy-3-methoxy-5'-[2-(N,N-dimethylamino)ethyl)]-6,7-2',3'-indolomorphinan 247, 17-allyl-6,7-didehydro-4,5α-epoxy-14β-hydroxy-3-methoxy-6'-[2-(N,N-dimethylamino)ethyl)]-6,7-2',3'-indolomorphinan 248, 17-allyl-6,7-didehydro-4,5α-epoxy-14β-hydroxy-3-methoxy-7'-[2-(N,N-dimethylamino)ethyl)]-6,7-2',3'-indolomorphinan 249, 17-allyl-6,7-didehydro-4,5α-epoxy-14β-hydroxy-3-methoxy-4'-(N,N-dimethylamino)methyl-6,7-2',3'-indolomorphinan 250, 17-allyl-6,7-didehydro-4,5α-epoxy-14β-hydroxy-3-methoxy-5'-(N,N-dimethylamino)methyl-6,7-2',3'-indolomorphinan 251, 17-allyl-6,7-didehydro-4,5α-epoxy-14β-hydroxy-3-methoxy-6'-(N,N-dimethylamino)methyl-6,7-2',3'-indolomorphinan 252, 17-allyl-6,7-didehydro-4,5α-epoxy-14β-hydroxy-3-methoxy-7'-(N,N-dimethylamino)methyl-6,7-2',3'-indolomorphinan 253, 17-allyl-6,7-didehydro-4,5α-epoxy-14β-hydroxy-3-methoxy-4'-isothiocyanato-6,7-2',3'-indolomorphinan 254, 17-allyl-6,7-didehydro-4,5α-epoxy-14β-hydroxy-3-methoxy-6'-isothiocyanato-6,7-2',3'-indolomorphinan 255, 17-allyl-6,7-didehydro-4,5α-epoxy-14β-hydroxy-3-methoxy-7'-isothiocyanato-6,7-2',3'-indolomorphinan 256, 17-allyl-6,7-didehydro-4,5α-epoxy-14β-hydroxy-3-methoxy-4'-nitro-6,7-2',3'-indolomorphinan 257, 17-allyl-6,7-didehydro-4,5α-epoxy-14β-hydroxy-3-methoxy-6'-nitro-6,7-2',3'-indolomorphinan 258 and 17-allyl-6,7-didehydro-4,5α-epoxy-14β-hydroxy-3-methoxy-7'-nitro-6,7-2',3'-indolomorphinan 259 are obtained, respectively.

By using 17-cyclopropylmethyl-3,14β-dihydroxy-4,5α-epoxy-6,7-didehydromorphinano[6,7-b]cyclohexeno[g] indole 2, 17-cyclopropylmethyl-3,14β-dihydroxy-4,5α-epoxy-6'-ethoxycarbonyl-6,7-didehydromorphinano[6,7-b]cyclohexeno[g]indole 401, 17-cyclopropylmethyl-3,14β-dihydroxy-4,5α-epoxy-7'-ethoxycarbonyl-6,7-didehydromorphinano[6,7-b]cyclohexeno[g]indole 402, 17-cyclopropylmethyl-3,14β-dihydroxy-4,5α-epoxy-8'-ethoxycarbonyl-6,7-didehydromorphinano[6,7-b]cyclohexeno[g]indole 403, 17-cyclopropylmethyl-3,14β-dihydroxy-4,5α-epoxy-9'-ethoxycarbonyl-6,7-didehydromorphinano[6,7-b]cyclohexeno[g]indole 404, 17-cyclopropylmethyl-3,14β-dihydroxy-4,5α-epoxy-6'-carbamoyl- 6,7-didehydromorphinano[6,7-b]cyclohexeno[g]indole 405, 17-cyclopropylmethyl-3,14β-dihydroxy-4,5α-epoxy-7'-carbamoyl-6,7-didehydromorphinano[6,7-b]cyclohexeno[g]indole 406, 17-cyclopropylmethyl-3,14β-dihydroxy-4,5α-epoxy-8'-carbamoyl-6,7-didehydromorphinano[6,7-b]cyclohexeno[g]indole 407, 17-cyclopropylmethyl-3,14β-dihydroxy-4,5α-epoxy-9'-carbamoyl-6,7-didehydromorphinano[6,7-b]cyclohexeno[g]indole 408, 17-cyclopropylmethyl-3,14β-dihydroxy-4,5α-epoxy-6'-sulfamoyl-6,7-didehydromorphinano[6,7-b]cyclohexeno[g]indole 409, 17-cyclopropylmethyl-3,14β-dihydroxy-4,5α-epoxy-7'-sulfamoyl-6,7-didehydromorphinano[6,7-b]cyclohexeno[g]indole 410, 17-cyclopropylmethyl-3,14β-dihydroxy-4,5α-epoxy-8'-sulfamoyl-6,7-didehydromorphinano[6,7-b]cyclohexeno[g]indole 411 or 17-cyclopropylmethyl-3,14β-dihydroxy-4,5α-epoxy-9'-sulfamoyl-6,7-didehydromorphinano[6,7-b]cyclohexeno[g]indole 412 in place of 17-cyclopropylmethyl-6,7-didehydro-4,5α-epoxy-3,14β-dihydroxy- 6'-methoxycarbonyl-6,7-2',3'-indolomorphinan 77, 17-cyclopropylmethyl-4,5α-epoxy-14β-hydroxy-3-methoxy-6,7-didehydromorphinano[6,7-b]cyclohexeno[g]indole 447, 17-cyclopropylmethyl-4,5α-epoxy-14β-hydroxy-3-methoxy-6'-ethoxycarbonyl-6,7-didehydromorphinano[6,7-b]cyclohexeno[g]indole 448, 17-cyclopropylmethyl-4,5α-epoxy-14β-hydroxy-3-methoxy- 7'-ethoxycarbonyl-6,7-didehydromorphinano[6,7-b]cyclohexeno[g]indole 449, 17-cyclopropylmethyl-4,5α-epoxy-14β-hydroxy-3-methoxy-8'-ethoxycarbonyl-6,7-didehydromorphinano[6,7-b]cyclohexeno[g]indole 450, 17-cyclopropylmethyl-4,5α-epoxy-14β-hydroxy-3-methoxy-9'-ethoxycarbonyl-6,7-didehydromorphinano[6,7-b]cyclohexeno[g]indole 451, 17-cyclopropylmethyl-4,5α-epoxy-14β-hydroxy-3-methoxy-6'-carbamoyl-6,7-didehydromorphinano[6,7-b]cyclohexeno[g]indole 452, 17-cyclopropylmethyl-4,5α-epoxy-14β-hydroxy-3-methoxy-7'-carbamoyl-6,7-didehydromorphinano[6,7-b]cyclohexeno[g]indole 453, 17-cyclopropylmethyl-4,5α-epoxy-14β-hydroxy-3-methoxy-8'-carbamoyl-6,7-didehydromorphinano[6,7-b]cyclohexeno[g]indole 454, 17-cyclopropylmethyl-4,5α-epoxy-14β-hydroxy-3-methoxy-9'-carbamoyl-6,7-didehydromorphinano[6,7-b]cyclohexeno[g]indole 455, 17-cyclopropylmethyl-4,5α-epoxy-14β-hydroxy-3-methoxy-6'-sulfamoyl-6,7-didehydromorphinano[6,7-b]cyclohexeno[g]indole 456, 17-cyclopropylmethyl-4,5α-epoxy-14β-hydroxy-3-methoxy-7'-sulfamoyl-6,7-didehydromorphinano[6,7-b]cyclohexeno[g]indole 457, 17-cyclopropylmethyl-4,5α-epoxy-14β-hydroxy-3-methoxy-8'-sulfamoyl-6,7-didehydromorphinano[6,7-b]cyclohexeno[g]indole 458 and 17-cyclopropylmethyl-4,5α-epoxy-14β-hydroxy-3-methoxy-9'-sulfamoyl-6,7-didehydromorphinano[6,7-b]cyclohexeno[g]indole 459 are obtained, respectively.

By using 17-cyclopropylmethyl-3,14β-dihydroxy-4,5α-epoxy-6,7-didehydromorphinano[6,7-b]cyclohexeno[e]indole 413, 17-cyclopropylmethyl-3,14β-dihydroxy-4,5α-epoxy-6,7-didehydromorphinano[6,7-b]cyclohexeno[f]indole 414, 17-cyclopropylmethyl-3,14β-dihydroxy-4,5α-epoxy-6,7-didehydromorphinano[6,7-b]cyclopenteno[g]indole 415, 17-cyclopropylmethyl-3,14β-dihydroxy-4,5α-epoxy-6,7-didehydromorphinano[6,7-b]cyclopenteno[e]indole 416, 17-cyclopropylmethyl-3,14β-dihydroxy-4,5α-epoxy-6,7-didehydromorphinano[6,7-b]cyclopenteno[f]indole 417, 17-cyclopropylmethyl-3,14β-dihydroxy-4,5α-epoxy-6,7-didehydromorphinano[6,7-b]cyclohepteno[g]indole 418, 17-cyclopropylmethyl-3,14β-dihydroxy-4,5α-epoxy-6,7-didehydromorphinano[6,7-b]cyclohepteno[e]indole 419, 17-cyclopropyl-ethyl-3,14β-dihydroxy-4,5α-epoxy-6,7-didehydromorphinano[6,7-b]cyclohepteno[f]indole 420, 17-cyclopropylmethyl-3,14β-dihydroxy-4,5α-epoxy-6,7-didehydromorphinano[6,7-b]cycloocteno[g]indole 421, 17-cyclopropylmethyl-3,14β-dihydroxy-4,5α-epoxy-6,7-didehydromorphinano[6,7-b]cycloocteno[e]indole 422 or 17-cyclopropylmethyl-3,14β-dihydroxy-4,5α-epoxy-6,7-didehydromorphinano[6,7-b]cycloocteno[f]indole 423 in place of 17-cyclopropylmethyl-6,7-didehydro-4,5α-epoxy-3,14β-dihydroxy-6'-methoxycarbonyl-6,7-2',3'-indolomorphinan 77, 17-cyclopropylmethyl-4,5α-epoxy-14β-hydroxy-3-methoxy-6,7-didehydromorphinano[6,7-b]cyclohexeno[e]indole 460, 17-cyclopropylmethyl-4,5α-epoxy-14β-hydroxy-3-methoxy-6,7-didehydromorphinano[6,7-b]cyclohexeno[f]indole 461, 17-cyclopropylmethyl-4,5α-epoxy-14β-hydroxy-3-methoxy-6,7-didehydromorphinano[6,7-b]cyclopenteno[g]indole 462, 17-cyclopropylmethyl-4,5α-epoxy-14β-hydroxy-3-methoxy-6,7-didehydromorphinano[6,7-b]cyclopenteno[e]indole 463, 17-cyclopropylmethyl-4,5α-epoxy-14β-hydroxy-3-methoxy-6,7-didehydromorphinano[6,7-b]cyclopenteno[f]indole 464, 17-cyclopropylmethyl-4,5α-epoxy-14β-hydroxy-3-methoxy-6,7-didehydromorphinano[6,7-b]cyclohepteno[g]indole 465, 17-cyclopropylmethyl-4,5α-epoxy-14β-hydroxy-3-methoxy-6,7-didehydromorphinano[6,7-b]cyclohepteno[e]indole 466, 17-cyclopropylmethyl-4,5α-epoxy-14β-hydroxy-3-methoxy-6,7-didehydromorphinano[6,7-b]cyclohepteno[f]indole 467, 17-cyclopropylmethyl-4,5α-epoxy-14β-hydroxy-3-methoxy-6,7-didehydromorphinano[6,7-b]cycloocteno[g]indole 468, 17-cyclopropylmethyl-4,5α-epoxy-14β-hydroxy-3-methoxy-6,7-didehydromorphinano[6,7-b]cycloocteno[e]indole 469 and 17-cyclopropylmethyl-4,5α-epoxy-14β-hydroxy-3-methoxy-6,7-didehydromorphinano[6,7-b]cycloocteno[f]indole 470 are obtained, respectively.

By using 17-allyl-3,14β-dihydroxy-4,5α-epoxy-6,7-didehydromorphinano[6,7-b]cyclohexeno[g]indole 162, 17-allyl-3,14β-dihydroxy-4,5α-epoxy-6'-ethoxycarbonyl-6,7-didehydromorphinano[6,7-b]cyclohexeno[g]indole 424, 17-allyl-3,14β-dihydroxy-4,5α-epoxy-7'-ethoxycarbonyl-6,7-didehydromorphinano[6,7-b]cyclohexeno[g]indole 425, 17-allyl-3,14β-dihydroxy-4,5α-epoxy-8'-ethoxycarbonyl-6,7-didehydromorphinano[6,7-b]cyclohexeno[g]indole 426, 17-allyl-3,14β-dihydroxy-4,5α-epoxy-9'-ethoxycarbonyl-6,7-didehydromorphinano[6,7-b]cyclohexeno[g]indole 427, 17-allyl-3,14β-dihydroxy-4,5α-epoxy-6'-carbamoyl-6,7-didehydromorphinano[6,7-b]cyclohexeno[g]indole 428, 17-allyl-3,14β-dihydroxy-4,5α-epoxy-7'-carbamoyl-6,7-didehydromorphinano[6,7-b]cyclohexeno[g]indole 429, 17-allyl-3,14β-dihydroxy-4,5α-epoxy-8'-carbamoyl-6,7-didehydromorphinano[6,7-b]cyclohexeno[g]indole 430, 17-allyl-3,14β-dihydroxy-4,5α-epoxy-9'-carbamoyl-6,7-didehydromorphinano[6,7-b]cyclohexeno[g]indole 431, 17-allyl-3,14β-dihydroxy-4,5α-epoxy-6'-sulfamoyl-6,7-didehydromorphinano[6,7-b]cyclohexeno[g]indole 432, 17-allyl-3,14β-dihydroxy-4,5α-epoxy-7'-sulfamoyl-6,7-didehydromorphinano[6,7-b]cyclohexeno[g]indole 433, 17-allyl-3,14β-dihydroxy-4,5α-epoxy-8'-sulfamoyl-6,7-didehydromorphinano[6,7-b]cyclohexeno[g]indole 434 or 17-allyl-3,14 i-dihydroxy-4,5α-epoxy-9'-sulfamoyl-6,7-didehydromorphinano[6,7-b]cyclohexeno[g]indole 435 in place of 17-cyclopropylmethyl-6,7-didehydro-4,5α-epoxy-3,14β-dihydroxy-6'-methoxycarbonyl-6,7-2',3'-indolomorphinan 77, 17-allyl-4,5α-epoxy-14β-hydroxy-3-methoxy- 6,7-didehydromorphinano[6,7-b]cyclohexeno[g]indole 471, 17-allyl-4,5α-epoxy-14β-hydroxy-3-methoxy-6'-ethoxycarbonyl-6,7-didehydromorphinano[6,7-b]cyclohexeno[g]indole 472, 17-allyl-4,5α-epoxy-14β-hydroxy-3-methoxy-7'-ethoxycarbonyl-6,7-didehydromorphinano[6,7-b]cyclohexeno[g]indole 473, 17-allyl-4,5α-epoxy-14β-hydroxy-3-methoxy-8'-ethoxycarbonyl-6,7-didehydromorphinano[6,7-b]cyclohexeno[g]indole 474, 17-allyl-4,5α-epoxy-14β-hydroxy-3-methoxy-9'-ethoxycarbonyl-6,7-didehydromorphinano[6,7-b]cyclohexeno[g]indole 475, 17-allyl-4,5α-epoxy-14β-hydroxy-3-methoxy-6'-carbamoyl-6,7-didehydromorphinano[6,7-b]cyclohexeno[g]indole 476, 17-allyl-4,5α-epoxy-14β-hydroxy-3-methoxy-7'-carbamoyl-6,7-didehydromorphinano[6,7-b]cyclohexeno[g]indole 477, 17-allyl-4,5α-epoxy-14β-hydroxy-3-methoxy-8'-carbamoyl-6,7-didehydromorphinano[6,7-b]cyclohexeno[g]indole 478, 17-allyl-4,5α-epoxy-14β-hydroxy-3-methoxy-9'-carbamoyl-6,7-didehydromorphinano[6,7-b]cyclohexeno[g]indole 479, 17-allyl-4,5α-epoxy-14β-hydroxy-3-methoxy-6'-sulfamoyl-6,7-didehydromorphinano[6,7-b]cyclohexeno[g]indole 480, 17-allyl-4,5α-epoxy-14β-hydroxy-3-methoxy-7'-sulfamoyl-6,7-didehydromorphinano[6,7-b]cyclohexeno[g]indole 481, 17-allyl-4,5α-epoxy-14β-hydroxy-3-methoxy-8'-sulfamoyl-6,7-didehydromorphinano[6,7-b]cyclohexeno[g]indole 482 and 17-allyl-4,5α-epoxy-14β-hydroxy-3-methoxy-9'- sulfamoyl-6,7-didehydromorphinano[6,7-b]cyclohexeno[g] indole 483 are obtained, respectively.

By using 17-allyl-3,14β-dihydroxy-4,5α-epoxy-6,7-didehydromorphinano[6,7-b]cyclohexeno[e]indole 436, 17-allyl-3,14β-dihydroxy-4,5α-epoxy-6,7-didehydromorphinano[6,7-b]cyclohexeno[f]indole 437, 17-allyl-3,14β-dihydroxy-4,5α-epoxy-6,7-didehydromorphinano[6,7-b]cyclopenteno[g]indole 438, 17-allyl-3,14β-dihydroxy-4,5α-epoxy-6,7-didehydromorphinano[6,7-b]cyclopenteno[e]indole 439, 17-allyl-3,14β-dihydroxy-4,5α-epoxy-6,7-didehydromorphinano[6,7-b]cyclopenteno[f]indole 440, 17-allyl-3,14β-dihydroxy-4,5α-epoxy-6,7-didehydromorphinano[6,7-b]cyclohepteno[g]indole 441, 17-allyl-3,14β-dihydroxy-4,5α-epoxy-6,7-didehydromorphinano[6,7-b]cyclohepteno[e]indole 442, 17-allyl-3,14β-dihydroxy-4,5α-epoxy-6,7-didehydromorphinano[6,7-b]cyclohepteno[f]indole 443, 17-allyl-3,14β-dihydroxy-4,5α-epoxy-6,7-didehydromorphinano[6,7-b]cycloocteno[g]indole 444, 17-allyl-3,14β-dihydroxy-4,5α-epoxy-6,7-didehydromorphinano[6,7-b]cycloocteno[e]indole 445 or 17-allyl-3,14β-dihydroxy-4,5α-epoxy-6,7-didehydromorphinano[6,7-b]cycloocteno[f]indole 446 in place of 17-cyclopropylmethyl-6,7-didehydro-4,5α-epoxy-3,14β-dihydroxy-6'-methoxycarbonyl-6,7-2',3'-indolomorphinan 77, 17-allyl-4,5α-epoxy-14β-hydroxy-3-methoxy-6,7-didehydromorphinano[6,7-b]cyclohexeno[e] indole 484, 17-allyl-4,5α-epoxy-14β-hydroxy-3-methoxy-6,7-didehydromorphinano[6,7-b]cyclohexeno[f]indole 485, 17-allyl-4,5α-epoxy-14β-hydroxy-3-methoxy-6,7-didehydromorphinano[6,7-b]cyclopenteno[g]indole 486, 17-allyl-4,5α-epoxy-14β-hydroxy-3-methoxy-6,7-didehydromorphinano[6,7-b]cyclopenteno[e]indole 487, 17-allyl-4,5α-epoxy-14β-hydroxy-3-methoxy-6,7-didehydromorphinano[6,7-b]cyclopenteno[f]indole 488, 17-allyl-4,5α-epoxy-14β-hydroxy-3-methoxy-6,7-didehydromorphinano[6,7-b]cyclohepteno[g]indole 489, 17-allyl-4,5α-epoxy-14β-hydroxy-3-methoxy-6,7-didehydromorphinano[6,7-b]cyclohepteno[e]indole 490, 17-allyl-4,5α-epoxy-14β-hydroxy-3-methoxy-6,7-didehydromorphinano[6,7-b]cyclohepteno[f]indole 491, 17-allyl-4,5α-epoxy-14β-hydroxy-3-methoxy-6,7-didehydromorphinano[6,7-b]cycloocteno[g]indole 492, 17-allyl-4,5α-epoxy-14β-hydroxy-3-methoxy-6,7-didehydromorphinano[6,7-b]cycloocteno[e]indole 493 and 17-allyl-4,5α-epoxy-14β-hydroxy-3-methoxy-6,7-didehydromorphinano[6,7-b]cycloocteno[f]indole 494 are obtained, respectively.

Example 12

3-acetoxy-17-cyclopropylmethyl-6,7-didehydro-4,5α-epoxy-14β-hydroxy-6'-methylthio-6,7-2',3'-indolomorphinan

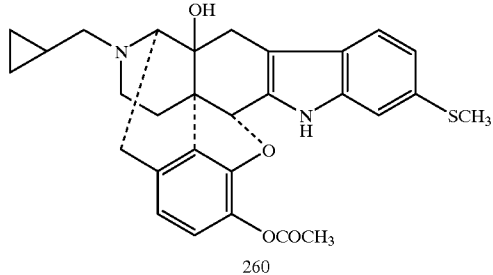

260

In 5 ml of pyridine, 500 mg of 17-cyclopropylmethyl-6,7-didehydro-4,5α-epoxy-3,14β-dihydroxy-6'-methylthio-6,7-2',3'-indolomorphinan 43 hydrochloric acid salt was dissolved and 0.20 ml of acetic anhydride was added to the solution, followed by stirring the mixture at room temperature for 10 minutes. The reaction mixture was concentrated to dryness to obtain 540 mg of hydrochloric acid salt of the captioned compound.

260 hydrochloric acid salt IR(KBr); ν 1754 cm$^{-1}$. Mass (FAB); m/z 503 (M+H)$^+$ By using 17-cyclopropylmethyl-6,7-didehydro-4,5α-epoxy-3,14β-dihydroxy-4'-methylthio-6,7-2',3'-indolomorphinan 42, 17-cyclopropylmethyl-6,7-didehydro-4,5α-epoxy-3,14β-dihydroxy-5'-methylthio-6,7-2',3'-indolomorphinan 12, 17-cyclopropylmethyl-6,7-didehydro-4,5α-epoxy-3,14β-dihydroxy-7'-methylthio-6,7-2',3'-indolomorphinan 121, 17-cyclopropylmethyl-6,7-didehydro-4,5α-epoxy-3,14β-dihydroxy-4'-methoxycarbonyl-6,7-2',3'-indolomorphinan 76, 17-cyclopropylmethyl-6,7-didehydro-4,5α-epoxy-3,14β-dihydroxy-5'-ethoxycarbonyl-6,7-2',3'-indolomorphinan 3, 17-cyclopropylmethyl-6,7-didehydro-4,5α-epoxy-3,14β-dihydroxy-6'-methoxycarbonyl-6,7-2',3'-indolomorphinan 77, 17-cyclopropylmethyl-6,7-didehydro-4,5α-epoxy-3,14β-dihydroxy-7'-ethoxycarbonyl-6,7-2',3'-indolomorphinan 119, 17-cyclopropylmethyl-6,7-didehydro-4,5α-epoxy-3,14β-dihydroxy-4'-(N-cyclopropylmethylcarbamoyl)-6,7-2',3'-indolomorphinan 46, 17-cyclopropylmethyl-6,7-didehydro-4,5α-epoxy-3,14β-dihydroxy-5'-(N-cyclopropylmethylcarbamoyl)-6,7-2',3'-indolomorphinan 7, 17-cyclopropylmethyl-6,7-didehydro-4,5α-epoxy-3,14β-dihydroxy-6'-(N-cyclopropylmethylcarbamoyl)-6,7-2',3'-indolomorphinan 47, 17-cyclopropylmethyl-6,7-didehydro-4,5α-epoxy-3,14β-dihydroxy-7'-(N-cyclopropylmethylcarbamoyl)-6,7-2',3'-indolomorphinan 127, 17-cyclopropylmethyl-6,7-didehydro-4,5α-epoxy-3,14β-dihydroxy-4'-cyano-6,7-2',3'-indolomorphinan 52, 17-cyclopropylmethyl-6,7-didehydro-4,5α-epoxy-3,14β-dihydroxy-5'-cyano-6,7-2',3'-indolomorphinan 8, 17-cyclopropylmethyl-6,7-didehydro-4,5α-epoxy-3,14β-dihydroxy-6'-cyano-6,7-2',3'-indolomorphinan 53, 17-cyclopropylmethyl-6,7-didehydro-4,5α-epoxy-3,14β-dihydroxy-4'-methylsulfonyl-6,7-2',3'-indolomorphinan 189, 17-cyclopropylmethyl-6,7-didehydro-4,5α-epoxy-3,14β-dihydroxy-5'-methylsulfonyl-6,7-2',3'-indolomorphinan 6, 17-cyclopropylmethyl-6,7-didehydro-4,5α-epoxy-3,14β-dihydroxy-6'-methylsulfonyl-6,7-2',3'-indolomorphinan 188, 17-cyclopropylmethyl-6,7-didehydro-4,5α-epoxy-3,14β-dihydroxy-7'-methylsulfonyl-6,7-2',3'-indolomorphinan 190, 17-cyclopropylmethyl-6,7-didehydro-4,5α-epoxy-3,14β-dihydroxy-4'-[2-(N,N-dimethylamino)ethyl)]-6,7-2',3'-indolomorphinan 64, 17-cyclopropylmethyl-6,7-didehydro-4,5α-epoxy-3,14β-dihydroxy-5'-[2-(N,N-dimethylamino)ethyl)]-6,7-2',3'-indolomorphinan 9, 17-cyclopropylmethyl-6,7-didehydro-4,5α-epoxy-3,14β-dihydroxy-6'-[2-(N,N-dimethylamino)ethyl)]-6,7-2',3'-indolomorphinan 65, 17-cyclopropylmethyl-6,7-didehydro-4,5α-epoxy-3,14β-dihydroxy-7'-[2-(N,N-dimethylamino)ethyl)]-6,7-2',3'-indolomorphinan 131, 17-cyclopropylmethyl-6,7-didehydro-4,5α-epoxy-3,14β-dihydroxy-4'-(N,N-dimethylamino)methyl-6,7-2',3'-indolomorphinan 66, 17-cyclopropylmethyl-6,7-didehydro-4,5α-epoxy-3,14β-dihydroxy-5'-(N,N-dimethylamino)methyl-6,7-2',3'-indolomorphinan 10, 17-cyclopropylmethyl-6,7-didehydro-4,5α-epoxy-3,14β-dihydroxy-6'-(N,N-dimethylamino)methyl-6,7-2',3'-indolomorphinan 67, 17-cyclopropylmethyl-6,7-didehydro-4,5α-epoxy-3,14β-dihydroxy-7'-(N,N-dimethylamino)methyl-6,7-2',3'-indolomorphinan 130, 17-cyclopropylmethyl-6,7-didehydro-4,5α-epoxy-3,14β-dihydroxy-4'-isothiocyanato-6,7-2',3'-indolomorphinan 175, 17-cyclopropylmethyl-6,7-didehydro-4,5α-epoxy-3,14β-dihydroxy-6'-isothiocyanato-6,7-2',3'-indolomorphinan 174, 17-cyclopropylmethyl-6,7-didehydro-4,5α-epoxy-3,14β-dihydroxy-7'-isothiocyanato-6,7-2',3'-indolomorphinan 173, 17-cyclopropylmethyl-6,7-didehydro-4,5α-epoxy-3,14β-dihydroxy-4'-nitro-6,7-2',3'-indolomorphinan 78, 17-cyclopropylmethyl-6,7-didehydro-4,5α-epoxy-3,14β-dihydroxy-6'-nitro-6,7-2',3'-indolomorphinan 79, 17-cyclopropylmethyl-6,7-didehydro-4,5α-epoxy-3,14β-dihydroxy-7'-nitro-6,7-2',3'-indolomorphinan 136, 17-allyl-6,7-didehydro-4,5α-epoxy-3,14β-dihydroxy-4'-methoxycarbonyl-6,7-2',3'-indolomorphinan 114, 17-allyl-6,7-didehydro-4,5α-epoxy-3,14β-dihydroxy-5'-ethoxycarbonyl-6,7-2',3'-indolomorphinan 22, 17-allyl-6,7-didehydro-4,5α-epoxy-3,14β-dihydroxy-6'-methoxycarbonyl-6,7-2',3'-indolomorphinan 115, 17-allyl-6,7-didehydro-4,5α-epoxy-3,14β-dihydroxy-7'-ethoxycarbonyl-6,7-2',3'-indolomorphinan 138, 17-allyl-6,7-didehydro-4,5α-epoxy-3,14β-dihydroxy-4'-(N-cycopropylmethylcarbamoyl)-6,7-2',3'-indolomorphinan 84, 17-allyl-6,7-didehydro-4,5α-epoxy-3,14β-dihydroxy-5'-(N-cycopropylmethylcarbamoyl)-6,7-2',3'-indolomorphinan 26, 17-allyl-6,7-didehydro-4,5α-epoxy-3,14β-dihydroxy-6'-(N-cyclopropylmethylcarbamoyl)- 6,7-2',3'-indolomorphinan 85, 17-allyl-6,7-didehydro-4,5α-epoxy-3,14β-dihydroxy-7'-(N-cyclopropylmethylcarbamoyl)-6,7-2',3'-indolomorphinan 146, 17-allyl-6,7-didehydro-4,5α-epoxy-3,14β-dihydroxy-4'-cyano-6,7-2',3'-indolomorphinan 90, 17-allyl-6,7-didehydro-4,5α-epoxy-3,14β-dihydroxy-5'-cyano-6,7-2',3'-indolomorphinan 27, 17-allyl-6,7-didehydro-4,5α-epoxy-3,14β-dihydroxy-6'-cyano-6,7-2',3'-indolomorphinan 91, 17-allyl-6,7-didehydro-4,5α-epoxy-3,14β-dihydroxy-4'-methylthio-6,7-2',3'-indolomorphinan 80, 17-allyl-6,7-didehydro-4,5α-epoxy-3,14β-dihydroxy-5'-methylthio-6,7-2',3'-indolomorphinan 31, 17-allyl-6,7-didehydro-4,5α-epoxy-3,14β-dihydroxy-6'-methylthio-6,7-2',3'-indolomorphinan 81, 17-allyl-6,7-didehydro-4,5α-epoxy-3,14β-dihydroxy-7'-methylthio-6,7-2',3'-indolomorphinan 140, 17-allyl-6,7-didehydro-4,5α-epoxy-3,14β-dihydroxy-4'-methylsulfonyl-6,7-2',3'-indolomorphinan 191, 17-allyl-6,7-didehydro-4,5α-epoxy-3,14β-dihydroxy-5'-methylsulfonyl-6,7-2',3'-indolomorphinan 25, 17-allyl-6,7-didehydro-4,5α-epoxy-3,14β-dihydroxy-6'-methylsulfonyl-6,7-2',3'-indolomorphinan 192, 17-allyl-6,7-didehydro-4,5α-epoxy-3,14β-dihydroxy-7'-methylsulfonyl-6,7-2',3'-indolomorphinan 193, 17-allyl-6,7-didehydro-4,5α-epoxy-3,14β-dihydroxy-4'-[2-(N,N-dimethylamino)ethyl)]-6,7-2',3'-indolomorphinan 102, 17-allyl-6,7-didehydro-4,5α-epoxy-3,14β-dihydroxy-5'-[2-(N,N-dimethylamino)ethyl)]-6,7-2',3'-indolomorphinan 28, 17-allyl-6,7-didehydro-4,5α-epoxy-3,14β-dihydroxy-6'-[2-(N,N-dimethylamino)ethyl)]-6,7-2',3'-indolomorphinan 103, 17-allyl-6,7-didehydro-4,5α-epoxy-3,14β-dihydroxy-7'-[2-(N,N-dimethylamino)ethyl)]-6,7-2',3'-indolomorphinan 150, 17-allyl-6,7-didehydro-4,5α-epoxy-3,14β-dihydroxy-4'-(N,N-dimethylamino)methyl-6,7-2',3'-indolomorphinan 104, 17-allyl-6,7-didehydro-4,5α-epoxy-3,14β-dihydroxy-5'-(N,N-dimethylamino)methyl-6,7-2',3'-indolomorphinan 29, 17-allyl-6,7-didehydro-4,5α-epoxy-3,14β-dihydroxy-6'-(N,N-dimethylamino)methyl-6,7-2',3'-indolomorphinan 105, 17-allyl-6,7-didehydro-4,5α-epoxy-3,14β-dihydroxy-7'-(N,N-dimethylamino)methyl-6,7-2',3'-indolomorphinan 149, 17-allyl-6,7-didehydro-4,5α-epoxy-3,14β-dihydroxy-4'-isothiocyanato-6,7-2',3'-indolomorphinan 178, 17-allyl-6,7-didehydro-4,5α-epoxy-3,14β-dihydroxy-6'-isothiocyanato-6,7-2',3'-indolomorphinan 177, 17-allyl-6,7-didehydro-4,5α-epoxy-3,14β-dihydroxy-7'-isothiocyanato-6,7-2',3'-indolomorphinan 176, 17-allyl-6,7-didehydro-4,5α-epoxy-3,14β-dihydroxy-4'-nitro-6,7-2',3'-indolomorphinan 116, 17-allyl-6,7-didehydro-4,5α-epoxy-3,14β-dihydroxy-6'-nitro-6,7-2',3'-indolomorphinan 117 or 17-allyl-6,7-didehydro-4,5α-epoxy-3,14β-dihydroxy-7'-nitro-6,7-2',3'-indolomorphinan 155 in place of 17-cyclopropylmethyl-6,7-didehydro-4,5α-epoxy-3,14β-dihydroxy-6'-methylthio-6,7-2',3'-indolomorphinan 43, 3-acetoxy-17-cyclopropylmethyl-6,7-didehydro-4,5α-epoxy-14β-hydroxy-4'-methylthio-6,7-2',3'-indolomorphinan 261, 3-acetoxy-17-cyclopropylmethyl-6,7-didehydro-4,5α-epoxy-14β-hydroxy-5'-methylthio-6,7-2',3'-indolomorphinan 262, 3-acetoxy-17-cyclopropylmethyl-6,7-didehydro-4,5α-epoxy-14β-hydroxy-7'-methylthio-6,7-2',3'-indolomorphinan 263, 3-acetoxy-17-cyclopropylmethyl-6,7-didehydro-4,5α-epoxy-14β-hydroxy-4'-methoxycarbonyl-6,7-2',3'-indolomorphinan 264, 3-acetoxy-17-cyclopropylmethyl-6,7-didehydro-4,5α-epoxy-14β-hydroxy-5'-ethoxycarbonyl-6,7-2',3'-indolomorphinan 265, 3-acetoxy-17-cyclopropylmethyl-6,7-didehydro-4,5α-epoxy-14β-hydroxy-6'-methoxycarbonyl-6,7-2',3'-indolomorphinan 266, 3-acetoxy-17-cyclopropylmethyl-6,7-didehydro-4,5α-epoxy-14β-hydroxy-7'-ethoxycarbonyl-6,7-2',3'-indolomorphinan 267, 3-acetoxy-17-cyclopropylmethyl-6,7-didehydro-4,5α-epoxy-14β-hydroxy-4'-(N-cyclopropylmethylcarbamoyl)-6,7-2',3'-indolomorphinan 268, 3-acetoxy-17-cyclopropylmethyl-6,7-didehydro-4,5α-epoxy-14β-hydroxy-5'-(N-cyclopropylmethylcarbamoyl)-6,7-2',3'-indolomorphinan 269, 3-acetoxy-17-cyclopropylmethyl-6,7-didehydro-4,5α-epoxy- 14β-hydroxy-6'-(N-cyclopropylmethylcarbamoyl)-6,7-2',3'-indolomorphinan 270, 3-acetoxy-17-cyclopropylmethyl-6,7-didehydro-4,5α-epoxy-14β-hydroxy-7'-(N-cyclopropylmethylcarbamoyl)-6,7-2',3'-indolomorphinan 271, 3-acetoxy-17-cyclopropylmethyl-6,7-didehydro-4,5α-epoxy-14β-hydroxy-4'-cyano-6,7-2',3'-indolomorphinan 272, 3-acetoxy-17-cyclopropylmethyl-6,7-didehydro-4,5α-epoxy-14β-hydroxy-5'-cyano-6,7-2',3'-indolomorphinan 273, 3-acetoxy-17-cyclopropylmethyl-6,7-didehydro-4,5α-epoxy-14β-hydroxy-6'-cyano-6,7-2',3'-indolomorphinan 274, 3-acetoxy-17-cyclopropylmethyl-6,7-didehydro-4,5α-epoxy-14β-hydroxy-4'-methylsulfonyl-6,7-2',3'-indolomorphinan 275, 3-acetoxy-17-cyclopropylmethyl-6,7-didehydro-4,5α-epoxy-14β-hydroxy-5'-methylsulfonyl-6,7-2',3'-indolomorphinan 276, 3-acetoxy-17-cyclopropylmethyl-6,7-didehydro-4,5α-epoxy-14β-hydroxy-6'-methylsulfonyl-6,7-2',3'-indolomorphinan 277, 3-acetoxy-17-cyclopropylmethyl-6,7-didehydro-4,5α-epoxy-14β-hydroxy-7'-methylsulfonyl-6,7-2',3'-indolomorphinan 278, 3-acetoxy-17-cyclopropylmethyl-6,7-didehydro-4,5α-epoxy-14β-hydroxy-4'-[2-(N,N-dimethylamino)ethyl)]-6,7-2',3'-indolomorphinan 279, 3-acetoxy-17-cyclopropylmethyl-6,7-didehydro-4,5α-epoxy-14β-hydroxy-5'-[2-(N,N-dimethylamino)ethyl)]-6,7-2',3'-indolomorphinan 280, 3-acetoxy-17-cyclopropylmethyl-6,7-didehydro-4,5α-epoxy- 14β-hydroxy-6'-[2-(N,N-dimethylamino)ethyl)]-6,7-2',3'-indolomorphinan 281, 3-acetoxy-17-cyclopropylmethyl-6,7-didehydro-4,5α-epoxy-14β-hydroxy-7'-[2-(N,N-dimethylamino)ethyl)]-6,7-2',3'-indolomorphinan 282, 3-acetoxy-17-cyclopropylmethyl-6,7-didehydro-4,5α-epoxy-14β-hydroxy-4'-(N,N-dimethylamino)methyl-6,7-2',3'-indolomorphinan 283, 3-acetoxy-17-cyclopropylmethyl-6,7-didehydro-4,5α-epoxy-14β-hydroxy-5'-(N,N-dimethylamino)methyl-6,7-2',3'-indolomorphinan 284, 3-acetoxy-17-cyclopropylmethyl-6,7-didehydro-4,5α-epoxy-14β-hydroxy-6'-(N,N-dimethylamino)methyl-6,7-2',3'-indolomorphinan 285, 3-acetoxy-17-cyclopropylmethyl-6,7-didehydro-4,5α-epoxy-14β-hydroxy-7'-(N,N-dimethylamino)methyl-6,7-2',3'-indolomorphinan 286, 3-acetoxy-17-cyclopropylmethyl-6,7-didehydro-4,5α-epoxy-14β-hydroxy-4'-isothiocyanato-6,7-2',3'-indolomorphinan 287, 3-acetoxy-17-cyclopropylmethyl-6,7-didehydro-4,5α-epoxy-14β-hydroxy-6'-isothiocyanato-6,7-2',3'-indolomorphinan 288, 3-acetoxy-17- cyclopropylmethyl-6,7-didehydro-4,5α-epoxy-14β-hydroxy-7'-isothiocyanato-6,7-2',3'-indolomorphinan 289, 3-acetoxy-17-cyclopropylmethyl-6,7-didehydro-4,5α-epoxy-14β-hydroxy-4'-nitro-6,7-2',3'-indolomorphinan 290, 3-acetoxy-17-cyclopropylmethyl-6,7-didehydro-4,5α-epoxy-14β-hydroxy-6'-nitro-6,7-2',3'-indolomorphinan 291, 3-acetoxy-17-cyclopropylmethyl-6,7-didehydro-4,5α-epoxy-14β-hydroxy-7'-nitro-6,7- 2',3'-indolomorphinan 292, 17-allyl-3-acetoxy-6,7-didehydro-4,5α-epoxy-14β-hydroxy-4'-methoxycarbonyl-6,7-2',3'-indolomorphinan 293, 17-allyl-3-acetoxy-6,7-didehydro-4,5α-epoxy-14β-hydroxy-5'-ethoxycarbonyl-6,7-2',3'-indolomorphinan 294, 17-allyl-3-acetoxy-6,7-didehydro-4,5α-epoxy-14β-hydroxy-6'-methoxycarbonyl-6,7-2',3'-indolomorphinan 295, 17-allyl-3-acetoxy-6,7-didehydro-4,5α-epoxy-14β-hydroxy-7'-ethoxycarbonyl-6,7-2',3'-indolomorphinan 296, 17-allyl-3-acetoxy-6,7-didehydro-4,5α-epoxy-14β-hydroxy-4'-(N-cyclopropylmethylcarbamoyl)-6,7-2',3'-indolomorphinan 297, 17-allyl-3-acetoxy-6,7-didehydro-4,5α-epoxy-14β-hydroxy-5'-(N-cyclopropylmethylcarbamoyl)-6,7-2',3'-indolomorphinan 298, 17-allyl-3-acetoxy-6,7-didehydro-4,5α-epoxy-14β-hydroxy-6'-(N-cyclopropylmethylcarbamoyl)-6,7-2',3'-indolomorphinan 299, 17-allyl-3-acetoxy-6,7-didehydro-4,5α-epoxy-14β-hydroxy-7'-(N-cyclopropylmethylcarbamoyl)-6,7-2',3'-indolomorphinan 300, 17-allyl-3-acetoxy-6,7-didehydro-4,5α-epoxy-14β-hydroxy-4'-cyano-6,7-2',3'-indolomorphinan 301, 17-allyl-3-acetoxy-6,7-didehydro-4,5α-epoxy-14β-hydroxy-5'-cyano-6,7-2',3'-indolomorphinan 302, 17-allyl-3-acetoxy-6,7-didehydro-4,5α-epoxy-14β-hydroxy-6'-cyano-6,7-2',3'-indolomorphinan 303, 17-allyl-3-acetoxy-6,7-didehydro-4,5α-epoxy-14β-hydroxy-4'-methylthio-6,7-2',3'-indolomorphinan 304, 17-allyl-3-acetoxy- 6,7-didehydro-4,5α-epoxy-14β-hydroxy-5'-methylthio-6,7-2',3'-indolomorphinan 305, 17-allyl-3-acetoxy-6,7-didehydro-4,5α-epoxy-14β-hydroxy-6'-methylthio-6,7-2',3'-indolomorphinan 306, 17-allyl-3-acetoxy-6,7-didehydro-4,5α-epoxy-14β-hydroxy-7'-methylthio-6,7-2',3'-indolomorphinan 307, 17-allyl-3-acetoxy-6,7-didehydro-4,5α-epoxy-14β-hydroxy-4'-methylsulfonyl-6,7-2',3'-indolomorphinan 308, 17-allyl-3-acetoxy-6,7-didehydro-4,5α-epoxy-14β-hydroxy-5'-methylsulfonyl-6,7-2',3'-indolomorphinan 309, 17-allyl-3-acetoxy-6,7-didehydro-4,5α-epoxy-14β-hydroxy-6'-methylsulfonyl-6,7-2',3'-indolomorphinan 310, 17-allyl-3-acetoxy-6,7-didehydro-4,5α-epoxy-14β-hydroxy-7'-methylsulfonyl-6,7-2',3'-indolomorphinan 311, 17-allyl-3-acetoxy-6,7-didehydro-4,5α-epoxy-14β-hydroxy-4'-[2-(N,N-dimethylamino)ethyl)]-6,7-2',3'-indolomorphinan 312, 17-allyl-3-acetoxy-6,7-didehydro-4,5α-epoxy-14β-hydroxy-5'-[2-(N,N-dimethylamino)ethyl)]-6,7-2',3'-indolomorphinan 313, 17-allyl-3-acetoxy-6,7-didehydro-4,5α-epoxy-14β-hydroxy-6'-[2-(N,N-dimethylamino)ethyl)]-6,7-2',3'-indolomorphinan 314, 17-allyl-3-acetoxy-6,7-didehydro-4,5α-epoxy-14β-hydroxy-7'-[2-(N,N-dimethylamino)ethyl)]-6,7-2',3'-indolomorphinan 315, 17-allyl-3-acetoxy-6,7-didehydro-4,5α-epoxy-14β-hydroxy-4'-(N,N-dimethylamino)methyl-6,7-2',3'-indolomorphinan 316, 17-allyl-3-acetoxy-6,7-didehydro-4,5α-epoxy-14β-hydroxy-5'-(N,N-dimethylamino)methyl- 6,7-2',3'-indolomorphinan 317, 17-allyl-3-acetoxy-6,7-didehydro-4,5α-epoxy-14β-hydroxy-6'-(N,N-dimethylamino)methyl-6,7-2',3'-indolomorphinan 318, 17-allyl-3-acetoxy-6,7-didehydro-4,5α-epoxy-14β-hydroxy-7'-(N,N-dimethylamino)methyl-6,7-2',3'-indolomorphinan 319, 17-allyl-3-acetoxy-6,7-didehydro-4,5α-epoxy-14β-hydroxy-4'-isothiocyanato-6 7-2',3'-indolomorphinan 320, 17-allyl-3-acetoxy-6,7-didehydro-4,5α-epoxy-14β-hydroxy-6'-isothiocyanato-6,7-2',3'-indolomorphinan 321, 17-allyl-3-acetoxy-6,7-didehydro-4,5α-epoxy-14β-hydroxy-7'-isothiocyanato-6,7-2',3'-indolomorphinan 322, 17-allyl-3-acetoxy-6,7-didehydro-4,5α-epoxy-14β-hydroxy-4'-nitro-6,7-2',3'-indolomorphinan 323, 17-allyl-3-acetoxy-6,7-didehydro-4,5α-epoxy-14β-hydroxy-6'-nitro-6,7-2',3'-indolomorphinan 324 and 17-allyl-3-acetoxy-6,7-didehydro-4,5α-epoxy-14β-hydroxy-7'-nitro-6,7-2',3'-indolomorphinan 325 are obtained, respectively.

By using 17-cyclopropylmethyl-3,14β-dihydroxy-4,5α-epoxy-6,7-didehydromorphinano[6,7-b]cyclohexeno[g]indole 2, 17-cyclopropylmethyl-3,14β-dihydroxy-4,5α-epoxy-6'-ethoxycarbonyl-6,7-didehydromorphinano[6,7-b]cyclohexeno[g]indole 401, 17-cyclopropylmethyl-3,14β-dihydroxy-4,5α-epoxy-7'-ethoxycarbonyl-6,7-didehydromorphinano[6,7-b]cyclohexeno[g]indole 402, 17-cyclopropylmethyl-3,14β-dihydroxy-4,5α-epoxy-8'-ethoxycarbonyl- 6,7-didehydromorphinano[6,7-b]cyclohexeno[g]indole 403, 17-cyclopropylmethyl-3,14β-dihydroxy-4,5α-epoxy-9'-ethoxycarbonyl-6,7-didehydromorphinano[6,7-b]cyclohexeno[g]indole 404, 17-cyclopropylmethyl-3,14β-dihydroxy-4,5α-epoxy-6'-carbamoyl-6,7-didehydromorphinano[6,7-b]cyclohexeno[g]indole 405, 17-cyclopropylmethyl-3,14β-dihydroxy-4,5α-epoxy-7'-carbamoyl-6,7-didehydromorphinano[6,7-b]cyclohexeno[g]indole 406, 17-cyclopropylmethyl-3,14β-dihydroxy-4,5α-epoxy-8'-carbamoyl-6,7-didehydromorphinano[6,7-b]cyclohexeno[g]indole 407, 17-cyclopropylmethyl-3,14β-dihydroxy-4,5α-epoxy-9'-carbamoyl-6,7-didehydromorphinano[6,7-b]cyclohexeno[g]indole 408, 17-cyclopropylmethyl-3,14β-dihydroxy-4,5α-epoxy-6'-sulfamoyl-6,7-didehydromorphinano[6,7-b]cyclohexeno[g]indole 409, 17-cyclopropylmethyl-3,14β-dihydroxy-4,5α-epoxy-7'-sulfamoyl-6,7-didehydromorphinano[6,7-b]cyclohexeno[g]indole 410, 17-cyclopropylmethyl-3,14β-dihydroxy-4,5α-epoxy-8'-sulfamoyl-6,7-didehydromorphinano[6,7-b]cyclohexeno[g]indole 411 or 17-cyclopropylmethyl-3,14β-dihydroxy-4,5α-epoxy-9'-sulfamoyl-6,7-didehydromorphinano[6,7-b]cyclohexeno[g]indole 412 in place of 17-cyclopropylmethyl-6,7-didehydro-4,5α-epoxy-3,14β-dihydroxy-6'-methylthio-6,7-2',3'-indolomorphinan 43, 3-acetoxy-17-cyclopropylmethyl- 4,5α-epoxy-14β-hydroxy-6,7-didehydromorphinano[6,7-b]cyclohexeno[g]indole 495, 3-acetoxy-17-cyclopropylmethyl-4,5α-epoxy-14β-hydroxy-6'-ethoxycarbonyl-6,7-didehydromorphinano[6,7-b]cyclohexeno[g]indole 496, 3-acetoxy-17-cyclopropylmethyl-4,5α-epoxy-14β-hydroxy-7'-ethoxycarbonyl-6,7-didehydromorphinano[6,7-b]cyclohexeno[g]indole 497, 3-acetoxy-17-cyclopropylmethyl-4,5α-epoxy-14β-hydroxy-8'-ethoxycarbonyl-6,7-didehydromorphinano[6,7-b]cyclohexeno[g]indole 498, 3-acetoxy-17-cyclopropylmethyl-4,5α-epoxy-14β-hydroxy-9'-ethoxycarbonyl-6,7-didehydromorphinano[6,7-b]cyclohexeno[g]indole 499, 3-acetoxy-17-cyclopropylmethyl-4,5α-epoxy-14β-hydroxy-6'-carbamoyl-6,7-didehydromorphinano[6,7-b]cyclohexeno[g]indole 500, 3-acetoxy-17-cyclopropylmethyl-4,5α-epoxy-14β-hydroxy-7'-carbamoyl -6,7-didehydromorphinano[6,7-b]cyclohexeno[g]indole 501, 3-acetoxy-17-cyclopropylmethyl-4,5α-epoxy-14β-hydroxy-8'-carbamoyl-6,7-didehydromorphinano[6,7-b]cyclohexeno[g]indole 502, 3-acetoxy-17-cyclopropylmethyl-4,5α-epoxy-14β-hydroxy-9'-carbamoyl-6,7-didehydromorphinano[6,7-b]cyclohexeno[g]indole 503, 3-acetoxy-17-cyclopropylmethyl-4,5α-epoxy-14β-hydroxy-6'-sulfamoyl-6,7-didehydromorphinano[6,7-b]cyclohexeno[g]indole 504, 3-acetoxy-17-cyclopropylmethyl-4,5α-epoxy- 14β-hydroxy-7'-sulfamoyl-6,7-didehydromorphinano[6,7-b]cyclohexeno[g]indole 505, 3-acetoxy-17- cyclopropylmethyl-4,5α-epoxy-14β-hydroxy-8'-sulfamoyl-6,7-didehydromorphinano[6,7-b]cyclohexeno[g]indole 506 and 3-acetoxy-17-cyclopropylmethyl-4,5α-epoxy-14β-hydroxy-9'-sulfamoyl-6,7-didehydromorphinano[6,7-b]cyclohexeno[g]indole 507 are obtained, respectively.

By using 17-cyclopropylmethyl-3,14β-dihydroxy-4,5α-epoxy-6,7-didehydromorphinano[6,7-b]cyclohexeno[e]indole 413, 17-cyclopropylmethyl-3,14β-dihydroxy-4,5α-epoxy-6,7-didehydromorphinano[6,7-b]cyclohexeno[f]indole 414, 17-cyclopropylmethyl-3,14β-dihydroxy-4,5α-epoxy-6,7-didehydromorphinano[6,7-b]cyclopenteno[g]indole 415, 17-cyclopropylmethyl-3,14β-dihydroxy-4,5α-epoxy-6,7-didehydromorphinano[6,7-b]cyclopenteno[e]indole 416, 17-cyclopropylmethyl-3,14β-dihydroxy-4,5α-epoxy-6,7-didehydromorphinano[6,7-b]cyclopenteno[f]indole 417, 17-cyclopropylmethyl-3,14β-dihydroxy-4,5α-epoxy-6,7-didehydromorphinano[6,7-b]cyclohepteno[g]indole 418, 17-cyclopropylmethyl-3,14β-dihydroxy-4,5α-epoxy-6,7-didehydromorphinano[6,7-b]cyclohepteno[e]indole 419, 17-cyclopropylmethyl-3,14β-dihydroxy-4,5α-epoxy-6,7-didehydromorphinano[6,7-b]cyclohepteno[f]indole 420, 17-cyclopropylmethyl-3,14β-dihydroxy-4,5α-epoxy-6,7-didehydromorphinano[6,7-b]cycloocteno[g]indole 421, 17-cyclopropylmethyl-3,14β-dihydroxy-4,5α-epoxy-6,7-didehydromorphinano[6,7-b]cycloocteno[e]indole 422 or 17-cyclopropylmethyl-3,14β-dihydroxy-4,5α-epoxy-6,7-didehydromorphinano[6,7-b]cycloocteno[f]indole 423 in place of 17-cyclopropylmethyl-6,7-didehydro-4,5α-epoxy-3,14β-dihydroxy-6'-methylthio-6,7-2',3'-indolomorphinan 43, 3-acetoxy-17-cyclopropylmethyl-4,5α-epoxy-14β-hydroxy-6,7-didehydromorphinano[6,7-b]cyclohexeno[e]indole 508, 3-acetoxy-17-cyclopropylmethyl-4,5α-epoxy-14β-hydroxy-6,7-didehydromorphinano[6,7-b]cyclohexeno[f]indole 509, 3-acetoxy-17-cyclopropylmethyl-4,5α-epoxy-14β-hydroxy-6,7-didehydromorphinano[6,7-b]cyclopenteno[g]indole 510, 3-acetoxy-17-cyclopropylmethyl-4,5α-epoxy-14β-hydroxy-6,7-didehydromorphinano[6,7-b]cyclopenteno[e]indole 511, 3-acetoxy-17-cyclopropylmethyl-4,5α-epoxy-14β-hydroxy-6,7-didehydromorphinano[6,7-b]cyclopenteno[f]indole 512, 3-acetoxy-17-cyclopropylmethyl-4,5α-epoxy-14β-hydroxy-6,7-didehydromorphinano[6,7-b]cyclohepteno[g]indole 513, 3-acetoxy-17-cyclopropylmethyl-4,5α-epoxy-14β-hydroxy-6,7-didehydromorphinano[6,7-b]cyclohepteno[e]indole 514, 3-acetoxy-17-cyclopropylmethyl-4,5α-epoxy-14β-hydroxy-6,7-didehydromorphinano[6,7-b]cyclohepteno[f]indole 515, 3-acetoxy-17-cyclopropylmethyl-4,5α-epoxy-14β-hydroxy-6,7-didehydromorphinano[6,7-b]cycloocteno[g]indole 516, 3-acetoxy-17-cyclopropylmethyl-4,5α-epoxy-14β-hydroxy-6,7-didehydromorphinano[6,7-b]cycloocteno[e]indole 517 and 3-acetoxy-17-cyclopropylmethyl-4,5α-epoxy-14β-hydroxy-6,7-didehydromorphinano[6,7-b]cycloocteno[f]indole 518 are obtained, respectively.

By using 17-allyl-3,14β-dihydroxy-4,5α-epoxy-6,7-didehydromorphinano[6,7-b]cyclohexeno[g]indole 162, 17-allyl-3,14β-dihydroxy-4,5α-epoxy-6'-ethoxycarbonyl-6,7-didehydromorphinano[6,7-b]cyclohexeno[g]indole 424, 17-allyl-3,14β-dihydroxy-4,5α-epoxy-7'-ethoxycarbonyl-6,7-didehydromorphinano[6,7-b]cyclohexeno[g]indole 425, 17-allyl-3,14β-dihydroxy-4,5α-epoxy-8'-ethoxycarbonyl-6,7-didehydromorphinano[6,7-b]cyclohexeno[g]indole 426, 17-allyl-3,14β-dihydroxy-4,5α-epoxy-9'-ethoxycarbonyl-6,7-didehydromorphinano[6,7-b]cyclohexeno[g]indole 427, 17-allyl-3,14β-dihydroxy-4,5α-epoxy-6'-carbamoyl-6,7-didehydromorphinano[6,7-b]cyclohexeno[g]indole 428, 17-allyl-3,14β-dihydroxy-4,5α-epoxy-7'-carbamoyl-6,7-didehydromorphinano[6,7-b]cyclohexeno[g]indole 429, 17-allyl-3,14β-dihydroxy-4,5α-epoxy-8'-carbamoyl-6,7-didehydromorphinano[6,7-b]cyclohexeno[g]indole 430, 17-allyl-3,14β-dihydroxy-4,5α-epoxy-9'-carbamoyl-6,7-didehydromorphinano[6,7-b]cyclohexeno[g]indole 431, 17-allyl-3,14β-dihydroxy-4,5α-epoxy-6'-sulfamoyl-6,7-didehydromorphinano[6,7-b]cyclohexeno[g]indole 432, 17-allyl-3,14β-dihydroxy-4,5α-epoxy-7'-sulfamoyl-6,7-didehydromorphinano[6,7-b]cyclohexeno[g]indole 433, 17-allyl-3,14β-dihydroxy-4,5α-epoxy-8'-sulfamoyl-6,7-didehydromorphinano[6,7-b]cyclohexeno[g]indole 434 or 17-allyl-3,14β-dihydroxy-4,5α-epoxy-9'-sulfamoyl-6,7-didehydromorphinano[6,7-b]cyclohexeno[g]indole 435 in place of 17-cyclopropylmethyl-6,7-didehydro-4,5α-epoxy-3,14β-dihydroxy-6'-methylthio-6,7-2',3'-indolomorphinan 43, 3-acetoxy-17-allyl-4,5α-epoxy-14β-hydroxy-6,7-didehydromorphinano[6,7-b]cyclohexeno[g]indole 519, 3-acetoxy-17-allyl-4,5α-epoxy-14β-hydroxy-6'-ethoxycarbonyl-6,7-didehydromorphinano[6,7-b]cyclohexeno[g]indole 520, 3-acetoxy-17-allyl-4,5α-epoxy-14β-hydroxy-7'-ethoxycarbonyl-6,7-didehydromorphinano[6,7-b]cyclohexeno[g]indole 521, 3-acetoxy-17-allyl-4,5α-epoxy-14β-hydroxy-8'-ethoxycarbonyl-6,7-didehydromorphinano[6,7-b]cyclohexeno[g]indole 522, 3-acetoxy-17-allyl-4,5α-epoxy-14β-hydroxy-9'-ethoxycarbonyl-6,7-didehydromorphinano[6,7-b]cyclohexeno[g]indole 523, 3-acetoxy-17-allyl-4,5α-epoxy-14β-hydroxy-6'-carbamoyl-6,7-didehydromorphinano[6,7-b]cyclohexeno[g]indole 524, 3-acetoxy-17-allyl-4,5α-epoxy-14β-hydroxy-7'-carbamoyl-6,7-didehydromorphinano[6,7-b]cyclohexeno[g]indole 525, 3-acetoxy-17-allyl-4,5α-epoxy-14β-hydroxy-8'-carbamoyl-6,7-didehydromorphinano[6,7-b]cyclohexeno[g]indole 526, 3-acetoxy-17-allyl-4,5α-epoxy-14β-hydroxy-9'-carbamoyl-6,7-didehydromorphinano[6,7-b]cyclohexeno[g]indole 527, 3-acetoxy-17-allyl-4,5α-epoxy-14β-hydroxy-6'-sulfamoyl-6,7-didehydromorphinano[6,7-b]cyclohexeno[g]indole 528, 3-acetoxy-17-allyl-4,5α-epoxy-14β-hydroxy-7'-sulfamoyl-6,7-didehydromorphinano[6,7-b]cyclohexenog]indole 529, 3-acetoxy-17-allyl-4,5α-epoxy-14β-hydroxy-8'-sulfamoyl-6,7-didehydromorphinano[6,7-b]cyclohexeno[g]indole 530 and 3-acetoxy-17-allyl-4,5α-epoxy-14β-hydroxy-9'-sulfamoyl-6,7-didehydromorphinano[6,7-b]cyclohexeno[g]indole 531 are obtained, respectively.

By using 17-allyl-3,14β-dihydroxy-4,5α-epoxy-6,7-didehydromorphinano[6,7-b]cyclohexeno[e]indole 436, 17-allyl-3,14β-dihydroxy-4,5α-epoxy-6,7-didehydromorphinano[6,7-b]cyclohexeno[f]indole 437, 17-allyl-3,14β-dihydroxy-4,5α-epoxy-6,7-didehydromorphinano[6,7-b]cyclopenteno[g]indole 438, 17-allyl-3,14β-dihydroxy-4,5α-epoxy-6,7-didehydromorphinano[6,7-b]cyclopenteno[e]indole 439, 17-allyl-3,14β-dihydroxy-4,5α-epoxy-6,7-didehydromorphinano[6,7-b]cyclopenteno[f]indole 440, 17-allyl-3,14β-dihydroxy-4,5α-epoxy-6,7-didehydromorphinano[6,7-b]cyclohepteno[g]indole 441, 17-allyl-3,14β-dihydroxy-4,5α-epoxy-6,7-didehydromorphinano[6,7-b]cyclohepteno[e]indole 442, 17-allyl-3,14β-dihydroxy-4,5α-epoxy-6,7-didehydromorphinano[6,7-b]cyclohepteno[f]indole 443, 17-allyl-3,14β-dihydroxy-4,5α-epoxy-6,7-didehydromorphinano[6,7-b]cycloocteno[g]indole 444, 17-allyl-3,14β-dihydroxy-4,5α-epoxy-6,7-didehydromorphinano[6,7-b]cycloocteno[e]indole 445 or 17-allyl-3,14β-dihydroxy-4,5α-epoxy-6,7-didehydromorphinano[6,7-b]cycloocteno[f]indole 446 in place of 17-cyclopropylmethyl-6,7-didehydro-4,5α-epoxy-3,14β-dihydroxy-6l-methylthio-6,7-2',3'-indolomorphinan 43, 3-acetoxy-17-allyl-4,5α-epoxy-14β-hydroxy-6,7-didehydromorphinano[6,7-b]cyclohexeno[e]indole 532, 3-acetoxy-17-allyl-4,5α-epoxy-14β-hydroxy-6,7-didehydromorphinano[6,7-b]cyclohexeno[f]indole 533, 3-acetoxy-17-allyl-4,5α-epoxy-14β-hydroxy-6,7-didehydromorphinano[6,7-b]cyclopenteno[g]indole 534, 3-acetoxy-17-allyl-4,5α-epoxy-14β-hydroxy-6,7-didehydromorphinano[6,7-b]cyclopenteno[e]indole 535, 3-acetoxy-17-allyl-4,5α-epoxy-14β-hydroxy-6,7-didehydromorphinano[6,7-b]cyclopenteno[f]indole 536, 3-acetoxy-17-allyl-4,5α-epoxy-14β-hydroxy-6,7-didehydromorphinano[6,7-b]cyclohepteno[g]indole 537, 3-acetoxy-17-allyl-4,5α-epoxy-14β-hydroxy-6,7-didehydromorphinano[6,7-b]cyclohepteno[e]indole 538, 3-acetoxy-17-allyl-4,5α-epoxy-14β-hydroxy-6,7-didehydromorphinano[6,7-b]cyclohepteno[f]indole 539, 3-acetoxy-17-allyl-4,5α-epoxy-14β-hydroxy-6,7-didehydromorphinano[6,7-b]cycloocteno[g]indole 540, 3-acetoxy-17-allyl-4,5α-epoxy-14β-hydroxy-6,7-didehydromorphinano[6,7-b]cycloocteno[e]indole 541 and 3-acetoxy-17-allyl-4,5α-epoxy-14β-hydroxy-6,7-didehydromorphinano[6,7-b]cycloocteno[f]indole 542 are obtained, respectively.

Example 13

17-cyclopropylmethyl-3,14β-diacetoxy-6,7-didehydro-4,5α-epoxy-6'-methylthio-6,7-2',3'-indolomorphinan 326

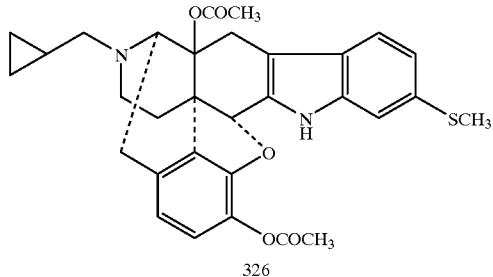

326

In 50 ml of acetic anhydride, 1.00 g of 17-cyclopropylmethyl-6,7-didehydro-4,5α-epoxy-3,14β-dihydroxy-6'-methylthio-6,7-2',3'-indolomorphinan 43 was dissolved and the solution was heated to reflux for 1 hour. After cooling the mixture to room temperature, the solvent was evaporated to obtain 1.29 g of unpurified captioned compound.

IR(KBr); ν 1760, 1727 cm$^{-1}$.

Example 14

14β-acetoxy-17-cyclopropylmethyl-6,7-didehydro-4,5α-epoxy-3-hydroxy-6'-methylthio-6,7-2',3'-indolomorphinan 327

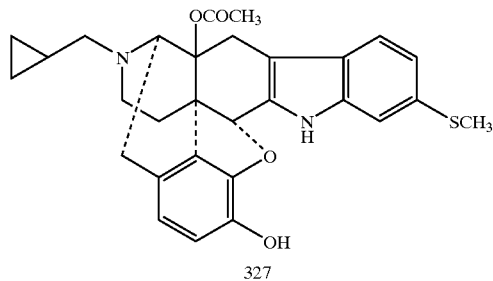

327

The 1.29 g of 17-cyclopropylmethyl-3,14β-diacetoxy-6,7-didehydro-4,5α-epoxy-6'-methylthio-6,7-2',3'-indolomorphinan 326 obtained in Example 13 was dissolved in 24 ml of 4% sulfuric acid and 24 ml of acetic acid, and the resulting solution was stirred at room temperature for 4 days. To the solution, 10% sodium hydroxide solution was added to make the solution basic and the resultant was extracted three times with 50 ml of chloform. The organic layers were combined and washed with saturated saline, followed by drying and concentration. The obtained residue was purified by column chromatography [silica gel; chloroform-chlorform/methanol (99:1)] to obtain 612 mg of the captioned compound. The obtained compound was suspended in methanol and methanesulfonic acid was added to the suspension to convert the compound to methanesulfonic acid salt. The salt was purified by column chromatograph [SEPHADEX-LH-20; methanol] to obtain 595 mg of methanesulfonic acid salt of the captioned compound (yield 46%, two steps).

327 methanesulfonic acid salt

IR(KBr); ν 1736 cm$^{-1}$. Mass (FAB); m/z 503 (M+H)$^+$

In accordance with Examples 13 and 14, by using 17-cyclopropylmethyl-6,7-didehydro-4,5α-epoxy-3,14β-dihydroxy-4'-methylthio-6,7-2',3'-indolomorphinan 42, 17-cyclopropylmethyl-6,7-didehydro-4,5α-epoxy-3,14β-dihydroxy-57-methylthio-6,7-2',3'-indolomorphinan 12, 17-cyclopropylmethyl-6,7-didehydro-4,5α-epoxy-3,14β-dihydroxy-7'-methylthio-6,7-2',3'-indolomorphinan 121, 17-cyclopropylmethyl-6,7-didehydro-4,5α-epoxy-3,14β-dihydroxy-4'-methoxycarbonyl-6,7-2',3'-indolomorphinan 76, 17-cyclopropylmethyl-6,7-didehydro-4,5α-epoxy-3,14β-dihydroxy-5'-ethoxycarbonyl-6,7-2',3'-indolomorphinan 3, 17-cyclopropylmethyl-6,7-didehydro-4,5α-epoxy-3,14β-dihydroxy-6'-methoxycarbonyl-6,7-2',3'-indolomorphinan 77, 17-cyclopropylmethyl-6,7-didehydro-4,5α-epoxy-3,14β-dihydroxy-7'-ethoxycarbonyl-6,7-2',3'-indolomorphinan 119, 17-cyclopropylmethyl-6,7-didehydro-4,5α-epoxy-3,14β-dihydroxy-4'-(N-cyclopropylmethylcarbamoyl)-6,7-2',3'-indolomorphinan 46, 17-cyclopropylmethyl-6,7-didehydro-4,5α-epoxy-3,14β-dihydroxy-5'-(N-cyclopropylmethylcarbamoyl)-6,7-2',3'-indolomorphinan 7, 17-cyclopropylmethyl-6,7-didehydro-4,5α-epoxy- 3,14β-dihydroxy-6'-(N-cyclopropylmethylcarbamoyl)-6,7-2',3'-indolomorphinan 47, 17-cyclopropylmethyl-6,7-didehydro-4,5α-epoxy-3,14β-dihydroxy-7'-(N-cyclopropylmethylcarbamoyl)-6,7-2',3'-indolomorphinan 127, 17-cyclopropylmethyl-6,7- didehydro-4,5α-epoxy-3,14β-dihydroxy-4'-cyano-6,7-2',3'-indolomorphinan 52, 17-cyclopropylmethyl-6,7-didehydro-4,5α-epoxy-3,14β-dihydroxy-5'-cyano-6,7-2',3'-indolomorphinan 8, 17-cyclopropylmethyl-6,7-didehydro-4,5α-epoxy-3,14β-dihydroxy-6'-cyano-6,7-2',3'-indolomorphinan 53, 17-cyclopropylmethyl-6,7-didehydro-4,5α-epoxy-3,14β-dihydroxy-4'-methylsulfonyl-6,7-2',3'-indolomorphinan 189, 17-cyclopropylmethyl-6,7-didehydro-4,5α-epoxy-3,14β-dihydroxy-5'-methylsulfonyl-6,7-2',3'-indolomorphinan 6, 17-cyclopropylmethyl-6,7-didehydro-4,5α-epoxy-3,14β-dihydroxy-6'-methylsulfonyl-6,7-2',3'-indolomorphinan 188, 17-cyclopropylmethyl-6,7-didehydro-4,5α-epoxy-3,14β-dihydroxy-7'-methylsulfonyl-6,7-2',3'-indolomorphinan 190, 17-cyclopropylmethyl-6,7-didehydro-4,5α-epoxy-3,14β-dihydroxy-4'-[2-(N,N-dimethylamino)ethyl)]-6,7-2',3'-indolomorphinan 64, 17-cyclopropylmethyl-6,7-didehydro-4,5α-epoxy-3,14β-dihydroxy-5'-[2-(N,N-dimethylamino)ethyl)]-6,7-2',3'-indolomorphinan 9, 17-cyclopropylmethyl-6,7-didehydro-4,5α-epoxy-3,14β-dihydroxy-6'-[2-(N,N-dimethylamino)ethyl)]-6,7-2',3'-indolomorphinan 65, 17-cyclopropylmethyl-6,7-didehydro-4,5α-epoxy-3,14β-dihydroxy-7'-[2-(N,N-dimethylamino)ethyl)]-6,7-2',3'-indolomorphinan 131, 17-cyclopropylmethyl-6,7-didehydro-4,5α-epoxy-3,14β-dihydroxy-4'-(N,N-dimethylamino)methyl-6,7-2',3'-indolomorphinan 66, 17-cyclopropylmethyl-6,7-didehydro-4,5α-epoxy-3,14β-dihydroxy-5'-(N,N-dimethylamino)methyl-6,7-2',3'-indolomorphinan 10, 17-cyclopropylmethyl-6,7-didehydro-4,5α-epoxy-3,14β-dihydroxy-6'(N,N-dimethylamino)methyl-6,7-2',3'-indolomorphinan 67, 17-cyclopropylmethyl-6,7-didehydro-4,5α-epoxy-3,14β-dihydroxy-7'-(N,N-dimethylamino)methyl-6,7-2',3'-indolomorphinan 130, 17-cyclopropylmethyl-6,7-didehydro-4,5α-epoxy-3,14β-dihydroxy-4'-isothiocyanato-6,7-2',3'-indolomorphinan 175, 17-cyclopropylmethyl-6,7-didehydro-4,5α-epoxy-3,14β-dihydroxy-6'-isothiocyanato-6,7-2',3'-indolomorphinan 174, 17-cyclopropylmethyl-6,7-didehydro-4,5α-epoxy-3,14β-dihydroxy-7'-isothiocyanato-6,7-2',3'-indolomorphinan 173, 17-cyclopropylmethyl-6,7-didehydro-4,5α-epoxy-3,14β-dihydroxy-4'-nitro-6,7-2',3'-indolomorphinan 78, 17-cyclopropylmethyl-6,7-didehydro-4,5α-epoxy-3,14β-dihydroxy-6'-nitro-6,7-2',3'-indolomorphinan 79, 17-cyclopropylmethyl-6,7-didehydro-4,5α-epoxy-3,14β-dihydroxy-7'-nitro-6,7-2',3'-indolomorphinan 136, 17-allyl-6,7-didehydro-4,5α-epoxy-3,14β-dihydroxy-4'-methoxycarbonyl-6,7-2',3'-indolomorphinan 114, 17-allyl-6,7-didehydro-4,5α-epoxy-3,14β-dihydroxy-5'-ethoxycarbonyl-6,7-2',3'-indolomorphinan 22, 17-allyl-6,7-didehydro-4,5α-epoxy-3,14β-dihydroxy-6'-methoxycarbonyl-6,7-2',3'-indolomorphinan 115, 17-allyl-6,7-didehydro-4,5α-epoxy-3,14β-dihydroxy-7'-ethoxycarbonyl-6,7-2',3'-indolomorphinan 138, 17-allyl-6,7-didehydro-4,5α-epoxy-3,14β-dihydroxy-4'-(N-cyclopropylmethylcarbamoyl)-6,7-2',3'-indolomorphinan 84, 17-allyl-6,7-didehydro-4,5α-epoxy-3,14β-dihydroxy-5'-(N-cyclopropylmethylcarbamoyl)-6,7-2',3'-indolomorphinan 26, 17-allyl-6,7-didehydro-4,5α-epoxy-3,14β-dihydroxy-6'-(N-cyclopropylmethylcarbamoyl)-6,7-2',3'-indolomorphinan 85, 17-allyl-6,7-didehydro-4,5α-epoxy-3,14β-dihydroxy-7'-(N-cyclopropylmethylcarbamoyl)-6,7-2',3'-indolomorphinan 146, 17-allyl-6,7-didehydro-4,5α-epoxy-3,14β-dihydroxy-4'-cyano-6,7-2',3'-indolomorphinan 90, 17-allyl-6,7-didehydro-4,5α-epoxy-3,14β-dihydroxy-5'-cyano-6,7-2',3'-indolomorphinan 27, 17-allyl-6,7-didehydro-4,5α-epoxy-3,14β-dihydroxy-6'-cyano-6,7-2',3'-indolomorphinan 91, 17-allyl-6,7-didehydro-4,5α-epoxy-3, 14β-dihydroxy-4'-methylthio-6,7-2',3'-indolomorphinan 80, 17-allyl-6,7-didehydro-4,5α-epoxy-3,14β-dihydroxy-5'-methylthio-6,7-2',3'-indolomorphinan 31, 17-allyl-6,7-didehydro-4,5α-epoxy-3,14β-dihydroxy-6'-methylthio-6,7-2',3'-indolomorphinan 81, 17-allyl-6,7-didehydro-4,5α-epoxy-3,14β-dihydroxy-7'-methylthio-6,7-2',3'-indolomorphinan 140, 17-allyl-6,7-didehydro-4,5α-epoxy-3,14β-dihydroxy-4'-methylsulfonyl-6,7-2',3'-indolomorphinan 191, 17-allyl-6,7-didehydro-4,5α-epoxy-3,14β-dihydroxy-5'-methylsulfonyl-6,7-2',3'-indolomorphinan 25, 17-allyl-6,7-didehydro-4,5α-epoxy-3,14β-dihydroxy-6'-methylsulfonyl-6,7-2',3'-indolomorphinan 192, 17-allyl-6,7-didehydro-4,5α-epoxy-3,14β-dihydroxy-7'-methylsulfonyl-6,7-2',3'-indolomorphinan 193, 17-allyl-6,7-didehydro-4,5α-epoxy-3,14β-dihydroxy-4'-[2-(N,N-dimethylamino)ethyl)]-6,7-2',3'-indolomorphinan 102, 17-allyl-6,7-didehydro-4,5α-epoxy-3,14β-dihydroxy-5'-[2-(N,N-dimethylamino)ethyl)]-6,7-2',3'-indolomorphinan 28, 17-allyl-6,7-didehydro-4,5α-epoxy-3,14β-dihydroxy-6'-[2-(N,N-dimethylamino)ethyl)]-6,7-2',3'-indolomorphinan 103, 17-allyl-6,7-didehydro-4,5α-epoxy-3,14β-dihydroxy-7'-[2-(N,N-dimethylamino)ethyl)]-6,7-2',3'-indolomorphinan 150, 17-allyl-6,7-didehydro-4,5α-epoxy-3,14β-dihydroxy-4'-(N,N-dimethylamino)methyl-6,7-2',3'-indolomorphinan 104, 17-allyl-6,7-didehydro-4,5α-epoxy-3,14β-dihydroxy-5'-(N,N-dimethylamino)methyl-6,7-2',3'-indolomorphinan 29, 17-allyl-6,7-didehydro-4,5α-epoxy-3,14β-dihydroxy-6'-(N,N-dimethylamino)methyl-6,7-2',3'-indolomorphinan 105, 17-allyl-6,7-didehydro-4,5α-epoxy-3,14β-dihydroxy-7'-(N,N-dimethylamino)methyl-6,7-2',3'-indolomorphinan 149, 17-allyl-6,7-didehydro-4,5α-epoxy-3,14β-dihydroxy-4'-isothiocyanato-6,7-2',3'-indolomorphinan 178, 17-allyl-6,7-didehydro-4,5α-epoxy-3,14β-dihydroxy-6'-isothiocyanato-6,7-2',3'-indolomorphinan 177, 17-allyl-6,7-didehydro-4,5α-epoxy-3,14β-dihydroxy-7'-isothiocyanato-6,7-2',3'-indolomorphinan 176, 17-allyl-6,7-didehydro-4,5α-epoxy-3,14β-dihydroxy-4'-nitro-6,7-2',3'-indolomorphinan 116, 17-allyl-6,7-didehydro-4,5α-epoxy-3,14β-dihydroxy-6'-nitro-6,7-2',3'-indolomorphinan 117 or 17-allyl-6,7-didehydro-4,5α-epoxy-3,14β-dihydroxy-7'-nitro-6,7-2',3'-indolomorphinan 155 in place of 17-cyclopropylmethyl-6,7-didehydro-4,5α-epoxy-3,14β-dihydroxy-6'-methylthio-6,7-2',3'-indolomorphinan 43, 14β-acetoxy-17-cyclopropylmethyl-6,7-didehydro-4,5α-epoxy-3-hydroxy-4'-methylthio-6,7-2',3'-indolomorphinan 328, 14β-acetoxy-17-cyclopropylmethyl-6,7-didehydro-4,5α-epoxy-3-hydroxy-5'-methylthio-6,7-2',3'-indolomorphinan 329, 14β-acetoxy-17-cyclopropylmethyl-6,7-didehydro-4,5α-epoxy-3-hydroxy-7'-methylthio-6,7-2',3'-indolomorphinan 330, 14β-acetoxy-17-cyclopropylmethyl-6,7-didehydro-4,5α-epoxy-3-hydroxy-4'-methoxycarbonyl-6,7-2',3'-indolomorphinan 331, 146-acetoxy-17-cyclopropylmethyl-6,7-didehydro-4,5α-epoxy-3-hydroxy-5'-ethoxycarbonyl-6,7-2',3'-indolomorphinan 332, 14β-acetoxy-17-cyclopropylmethyl-6,7-didehydro-4,5α-epoxy-3-hydroxy-6'-methoxycarbonyl-6,7-2',3'-indolomorphinan 333, 14β-acetoxy-17-cyclopropylmethyl-6,7-didehydro-4,5α-epoxy-3-hydroxy-7'-ethoxycarbonyl-6,7-2',3'-indolomorphinan 334, 14β-acetoxy-17-cyclopropylmethyl-6,7-didehydro-4,5α-epoxy-3-hydroxy-4'-(N-cyclopropylmethylcarbamoyl)-6,7-2',3'-indolomorphinan 335, 14β-acetoxy-17-cyclopropylmethyl-6,7-didehydro-4,5α-epoxy-3-hydroxy-5'-(N-cyclopropylmethylcarbamoyl)-6,7-2',3'-indolomorphinan 336, 14β-acetoxy-17-cyclopropylmethyl-6,7-didehydro-4,5α-epoxy-3-hydroxy-6'-(N-cyclopropylmethylcarbamoyl)-6,7-2',3'-indolomorphinan 337, 14β-acetoxy-17-cyclopropylmethyl-6,7-didehydro-4,5α-epoxy-3-hydroxy-7'-(N-cyclopropylmethylcarbamoyl)-6,7-2',3'-indolomorphinan 338, 14β-acetoxy-17-cyclopropylmethyl-6,7-didehydro-4,5α-epoxy-3-hydroxy-4'-cyano-6,7-2',3'-indolomorphinan 339, 14β-acetoxy-17-cyclopropylmethyl-6,7-didehydro-4,5α-epoxy-3-hydroxy-5'-cyano-6,7-2',3'-indolomorphinan 340, 14β-acetoxy-17-cyclopropylmethyl-6,7-didehydro-4,5α-epoxy-3-hydroxy-6'-cyano-6,7-2',3'-indolomorphinan 341, 14β-acetoxy-17-cyclopropylmethyl-6,7-didehydro-4,5α-epoxy-3-hydroxy-4'-methylsulfonyl-6,7-2',3'-indolomorphinan 342, 14β-acetoxy-17-cyclopropylmethyl-6,7-didehydro-4,5α-epoxy-3-hydroxy-5'-methylsulfonyl-6,7-2',3'-indolomorphinan 343, 14β-acetoxy-17-cyclopropylmethyl-6,7-didehydro-4,5α-epoxy-3-hydroxy-6'-methylsulfonyl-6,7-2',3'-indolomorphinan 344, 14β-acetoxy-17-cyclopropylmethyl-6,7-didehydro-4,5α-epoxy-3-hydroxy-7'-methylsulfonyl-6,7-2',3'-indolomorphinan 345, 14β-acetoxy-17-cyclopropylmethyl-6,7-didehydro-4,5α-epoxy-3-hydroxy-4'-[2-(N,N-dimethylamnino)ethyl)]-6,7-2',3'-indolomorphinan 346, 14β-acetoxy-17-cyclopropylmethyl-6,7-didehydro-4,5α-epoxy-3-hydroxy-5'-[2-(N,N-dimethylamino)ethyl)]-6,7-2',3'-indolomorphinan 347, 14β-acetoxy-17-cyclopropylmethyl-6,7-didehydro-4,5α-epoxy-3-hydroxy-6'-[2-(N,N-dimethylamnino)ethyl)]-6,7-2',3'-indolomorphinan 348, 14β-acetoxy-17-cyclopropylmethyl-6,7-didehydro-4,5α-epoxy-3-hydroxy-7'-[2-(N,N-dimethylamnino)ethyl)]-6,7-2',3'-indolomorphinan 349, 14β-acetoxy-17-cyclopropylmethyl-6,7-didehydro-4,5α-epoxy-3-hydroxy-4'-(N,N-dimethylamino)methyl-6,7-2',3'-indolomorphinan 350, 14β-acetoxy-17-cyclopropylmethyl-6,7-didehydro-4,5α-epoxy-3-hydroxy-5'-(N,N-dimethylamino)methyl-6,7-2',3'-indolomorphinan 351, 14β-acetoxy-17-cyclopropylmethyl-6,7-didehydro-4,5α-epoxy-3-hydroxy-6'-(N,N-dimethylamino)methyl-6,7-2',3'-indolomorphinan 352, 14β-acetoxy-17-cyclopropylmnethyl-6,7-didehydro-4,5α-epoxy-3-hydroxy-7'-(N,N-dimethylamino)methyl-6,7-2',3'-indolomorphinan 353, 14β-acetoxy-17-cyclopropylmethyl-6,7-didehydro-4,5α-epoxy-3-hydroxy-4'-isothiocyanato-6,7-2',3'-indolomorphinan 354, 14β-acetoxy-17-cyclopropylmethyl-6,7-didehydro-4,5α-epoxy-3-hydroxy-6'-isothiocyanato-6,7-2',3'-indolomorphinan 355, 14β-acetoxy-17-cyclopropylmethyl-6,7-didehydro-4,5α-epoxy-3-hydroxy-7'-isothiocyanato-6,7-2',3'-indolomorphinan 356, 14β-acetoxy-17-cyclopropylmethyl-6,7-didehydro-4,5α-epoxy-3-hydroxy-4'-nitro-6,7-2',3'-indolomorphinan 357, 14β-acetoxy-17-cyclopropylmethyl-6,7-didehydro-4,5α-epoxy-3-hydroxy-6'-nitro-6,7-2',3'-indolomorphinan 358, 14β-acetoxy-17-cyclopropylmethyl-6,7-didehydro-4,5α-epoxy-3-hydroxy-7'-nitro-6,7-2',3'-indolomorphinan 359, 17-allyl-14β-acetoxy-6,7-didehydro-4,5α-epoxy-3-hydroxy-4'-methoxycarbonyl-6,7-2',3'-indolomorphinan 360, 17-allyl-14β-acetoxy-6,7-didehydro-4,5α-epoxy-3-hydroxy-5'-ethoxycarbonyl-6,7-2',3'-indolomorphinan 361, 17-allyl-14β-acetoxy-6,7-didehydro-4,5α-epoxy-3-hydroxy-6'-methoxycarbonyl-6,7-2',3'-indolomorphinan 362, 17-allyl-14β-acetoxy-6,7-didehydro-4,5α-epoxy-3-hydroxy-7'-ethoxycarbonyl-6,7-2',3'-indolomorphinan 363, 17-allyl-14β-acetoxy-6,7-didehydro-4,5α-epoxy-3-hydroxy-4'-(N-cyclopropylmethylcarbamoyl)-6,7-2',3'-indolomorphinan 364, 17-allyl-14β-acetoxy-6,7-didehydro-4,5α-epoxy-3-hydroxy-5'-(N-cyclopropylmethylcarbamoyl)-6,7-2',3'-indolomorphinan 365, 17-allyl-14β-acetoxy-6,7-didehydro-4,5α-epoxy-3-hydroxy-6'-(N-cyclopropylmethylcarbamoyl)-6,7-2',3'-indolomorphinan 366, 17-allyl-14β-acetoxy-6,7-didehydro-4,5α-epoxy-3-hydroxy-7'-(N-cyclopropylmethylcarbamoyl)- 6,7-2',3'-indolomorphinan 367, 17-allyl-14β-acetoxy-6,7-didehydro-4,5α-epoxy-3-hydroxy-4'-cyano-6,7-2',3'-indolomorphinan 368, 17-allyl-14β-acetoxy-6,7-didehydro-4,5α-epoxy-3-hydroxy-5'-cyano-6,7-2',3'-indolomorphinan 369, 17-allyl-14β-acetoxy-6,7-didehydro-4,5α-epoxy-3-hydroxy-6'-cyano-6,7-2',3'-indolomorphinan 370, 17-allyl-14β-acetoxy-6,7-didehydro-4,5α-epoxy-3-hydroxy-4'-methylthio-6,7-2',3'-indolomorphinan 371, 17-allyl-14β-acetoxy-6,7-didehydro-4,5α-epoxy-3-hydroxy-5'-methylthio-6,7-2',3'-indolomorphinan 372, 17-allyl-14β-acetoxy-6,7-didehydro-4,5α-epoxy-3-hydroxy-6'-methylthio-6,7-2',3'-indolomorphinan 373, 17-allyl-14β-acetoxy-6,7-didehydro-4,5α-epoxy-3-hydroxy-7'-methylthio-6,7-2',3'-indolomorphinan 374, 17-allyl-14β-acetoxy-6,7-didehydro-4,5α-epoxy-3-hydroxy-4'-methylsulfonyl-6,7-2',3'-indolomorphinan 375, 17-allyl-14β-acetoxy-6,7-didehydro-4,5α-epoxy-3-hydroxy-5'-methylsulfonyl-6,7-2',3'-indolomorphinan 376, 17-allyl-14β-acetoxy-6,7-didehydro-4,5α-epoxy-3-hydroxy-6'-methylsulfonyl-6,7-2',3'-indolomorphinan 377, 17-allyl-14β-acetoxy-6,7-didehydro-4,5α-epoxy-3-hydroxy-7'-methylsulfonyl-6,7-2',3'-indolomorphinan 378, 17-allyl-14β-acetoxy-6,7-didehydro-4,5α-epoxy-3-hydroxy-4'-[2-(N,N-dimethylamino)ethyl)]-6,7-2',3'-indolomorphinan 379, 17-allyl-14β-acetoxy-6,7-didehydro-4,5α-epoxy-3-hydroxy-5'-[2-(N,N-dimethylamino)ethyl)]-6,7- 2',3'-indolomorphinan 380, 17-allyl-14β-acetoxy-6,7-didehydro-4,5α-epoxy-3-hydroxy-6'-[2-(N,N-dimethylamino)ethyl)]-6,7-2',3'-indolomorphinan 381, 17-allyl-14β-acetoxy-6,7-didehydro-4,5α-epoxy-3-hydroxy-7'-[2-(N,N-dimethylamino)ethyl)]-6,7-2',3'-indolomorphinan 382, 17-allyl-14β-acetoxy-6,7-didehydro-4,5α-epoxy-3-hydroxy-4'-(N,N-dimethylamino)methyl-6,7-2',3'-indolomorphinan 383, 17-allyl-14β-acetoxy-6,7-didehydro-4,5α-epoxy-3-hydroxy-5'-(N,N-dimethylamino)methyl-6,7-2',3'-indolomorphinan 384, 17-allyl-14β-acetoxy-6,7-didehydro-4,5α-epoxy-3-hydroxy-6'-(N,N-dimethylamino)methyl-6,7-2',3'-indolomorphinan 385, 17-allyl-14β-acetoxy-6,7-didehydro-4,5α-epoxy-3-hydroxy-7'-(N,N-dimethylamino)methyl-6,7-2',3'-indolomorphinan 386, 17-allyl-14β-acetoxy-6,7-didehydro-4,5α-epoxy-3-hydroxy-4'-isothiocyanato-6,7-2',3'-indolomorphinan 387, 17-allyl-14β-acetoxy-6,7-didehydro-4,5α-epoxy-3-hydroxy-6'-isothiocyanato-6,7-2',3'-indolomorphinan 388, 17-allyl-14β-acetoxy-6,7-didehydro-4,5α-epoxy-3-hydroxy-7'-isothiocyanato-6,7-2',3'-indolomorphinan 389, 17-allyl-14β-acetoxy-6,7-didehydro-4,5α-epoxy-3-hydroxy-4'-nitro-6,7-2',3'-indolomorphinan 390, 17-allyl-14β-acetoxy-6,7-didehydro-4,5α-epoxy-3-hydroxy-6'-nitro-6,7-2',3'-indolomorphinan 391 and 17-allyl-14β-acetoxy-6,7-didehydro-4,5α-epoxy-3-hydroxy-7'-nitro-6,7-2',3'-indolomorphinan 392 are obtained, respectively.

By using 17-cyclopropylmethyl-3,14β-dihydroxy-4,5α-epoxy-6,7-didehydromorphinano[6,7-b]cyclohexeno[g]indole 2, 17-cyclopropylmethyl-3,14β-dihydroxy-4,5α-epoxy-6'-ethoxycarbonyl-6,7-didehydromorphinano[6,7-b]cyclohexeno[g]indole 401, 17-cyclopropylmethyl-3,14β-dihydroxy-4,5α-epoxy-7'-ethoxycarbonyl-6,7-didehydromorphinano[6,7-b]cyclohexeno[g]indole 402, 17-cyclopropylmethyl-3,14β-dihydroxy-4,5α-epoxy-8'-ethoxycarbonyl-6,7-didehydromorphinano[6,7-b]cyclohexeno[g]indole 403, 17-cyclopropylmethyl-3,14β-dihydroxy-4,5α-epoxy-9'-ethoxycarbonyl-6,7-didehydromorphinano[6,7-b]cyclohexeno[g]indole 404, 17-cyclopropylmethyl-3,14β-dihydroxy-4,5α-epoxy-6'-carbamoyl-6,7-didehydromorphinano[6,7-b]cyclohexeno[g]

indole 405, 17-cyclopropylmethyl-3,14β-dihydroxy-4,5α-epoxy-7'-carbamoyl-6,7-didehydromorphinano[6,7-b]cyclohexeno[g]indole 406, 17-cyclopropylmethyl-3,14β-dihydroxy-4,5α-epoxy-8'-carbamoyl-6,7-didehydromorphinano[6,7-b]cyclohexeno[g]indole 407, 17-cyclopropylmethyl-3,14β-dihydroxy-4,5α-epoxy-9'-carbamoyl-6,7-didehydromorphinano[6,7-b]cyclohexeno[g]indole 408, 17-cyclopropylmethyl-3,14β-dihydroxy-4,5α-epoxy-6'-sulfamoyl-6,7-didehydromorphinano[6,7-b]cyclohexeno[g]indole 409, 17-cyclopropylmethyl-3,14β-dihydroxy-4,5α-epoxy-7'-sulfamoyl-6,7-didehydromorphinano[6,7-b]cyclohexeno[g]indole 410, 17-cyclopropylmethyl-3,14β-dihydroxy-4,5α-epoxy-8'-sulfamoyl-6,7-didehydromorphinano[6,7-b]cyclohexeno[g]indole 411 or 17-cyclopropylmethyl-3,14β-dihydroxy-4,5α-epoxy-9'-sulfamoyl-6,7-didehydromorphinano[6,7-b]cyclohexeno[g]indole 412 in place of 17-cyclopropylmethyl-6,7-didehydro-4,5α-epoxy-3,14β-dihydroxy-6'-methylthio-6,7-2',3'-indolomorphinan 43, 14β-acetoxy-17-cyclopropylmethyl-4,5α-epoxy-3-hydroxy-6,7-didehydromorphinano[6,7-b]cyclohexeno[g]indole 543, 14β-acetoxy-17-cyclopropylmethyl-4,5α-epoxy-3-hydroxy-6'-ethoxycarbonyl-6,7-didehydromorphinano[6,7-b]cyclohexeno[g]indole 544, 14β-acetoxy-17-cyclopropylmethyl-4,5α-epoxy-3-hydroxy-7'-ethoxycarbonyl-6,7-didehydromorphinano[6,7-b]cyclohexeno[g]indole 545, 14β-acetoxy-17-cyclopropylmethyl-4,5α-epoxy-3-hydroxy-8'-ethoxycarbonyl-6,7-didehydromorphinano[6,7-b]cyclohexeno[g]indole 546, 14β-acetoxy-17-cyclopropylmethyl-4,5α-epoxy-3-hydroxy-9'-ethoxycarbonyl-6,7-didehydromorphinano[6,7-b]cyclohexeno[g]indole 547, 14β-acetoxy-17-cyclopropylmethyl-4,5α-epoxy-3-hydroxy-6'-carbamoyl-6,7-didehydromorphinano[6,7-b]cyclohexeno[g]indole 548, 14β-acetoxy-17-cyclopropylmethyl-4,5α-epoxy-3-hydroxy-7'-carbamoyl-6,7-didehydromorphinano[6,7-b]cyclohexeno[g]indole 549, 14β-acetoxy-17-cyclopropylmethyl-4,5α-epoxy-3-hydroxy-8'-carbamoyl-6,7-didehydromorphinano[6,7-b]cyclohexeno[g]indole 550, 14β-acetoxy-17-cyclopropylmethyl-4,5α-epoxy-3-hydroxy-9'-carbamoyl-6,7-didehydromorphinano[6,7-b]cyclohexeno[g]indole 551, 14β-acetoxy-17-cyclopropylmethyl-4,5α-epoxy-3-hydroxy-6'-sulfamoyl-6,7-didehydromorphinano[6,7-b]cyclohexeno[g]indole 552, 14β-acetoxy-17-cyclopropylmethyl-4,5α-epoxy-3-hydroxy-7'-sulfamoyl-6,7-didehydromorphinano[6,7-b]cyclohexeno[g]indole 553, 14β-acetoxy-17-cyclopropylmethyl-4,5α-epoxy-3-hydroxy-8'-sulfamoyl-6,7-didehydromorphinano[6,7-b]cyclohexeno[g]indole 554 and 14β-acetoxy-17-cyclopropylmethyl-4,5α-epoxy-3-hydroxy-9'-sulfamoyl-6,7-didehydromorphinano[6,7-b]cyclohexeno[g]indole 555 are obtained, respectively.

By using 17-cyclopropylmethyl-3,14β-dihydroxy-4,5α-epoxy-6,7-didehydromorphinano[6,7-b]cyclohexeno[e]indole 413, 17-cyclopropylmethyl-3,14β-dihydroxy-4,5α-epoxy-6,7-didehydromorphinano[6,7-b]cyclohexeno[f]indole 414, 17-cyclopropylmethyl-3,14β-dihydroxy-4,5α-epoxy-6,7-didehydromorphinano[6,7-b]cyclopenteno[g]indole 415, 17-cyclopropylmethyl-3,14β-dihydroxy-4,5α-epoxy-6,7-didehydromorphinano[6,7-b]cyclopenteno[e]indole 416, 17-cyclopropylmethyl-3,14β-dihydroxy-4,5α-epoxy-6,7-didehydromorphinano[6,7-b]cyclopenteno[f]indole 417, 17-cyclopropylmethyl-3,14β-dihydroxy-4,5α-epoxy-6,7-didehydromorphinano[6,7-b]cyclohepteno[g]indole 418, 17-cyclopropylmethyl-3,14β-dihydroxy-4,5α-epoxy-6,7-didehydromorphinano[6,7-b]cyclohepteno[e]indole 419, 17-cyclopropylmethyl-3,14β-dihydroxy-4,5α-epoxy-6,7-didehydromorphinano[6,7-b]cyclohepteno[f]indole 420, 17-cyclopropylmethyl-3,14β-dihydroxy-4,5α-epoxy-6,7-didehydromorphinano[6,7-b]cyclooocteno[g]indole 421, 17-cyclopropylmethyl-3,14β-dihydroxy-4,5α-epoxy-6,7-didehydromorphinano[6,7-b]cyclooocteno[e]indole 422 or 17-cyclopropylmethyl-3,14β-dihydroxy-4,5α-epoxy-6,7-didehydromorphinano[6,7-b]cyclooocteno[f]indole 423 in place of 17-cyclopropylmethyl-6,7-didehydro-4,5α-epoxy-3,14β-dihydroxy-6'-methylthio-6,7-2',3'-indolomorphinan 43, 14β-acetoxy-17-cyclopropylmethyl-4,5α-epoxy-3-hydroxy-6,7-didehydromorphinano[6,7-b]cyclohexeno[e]indole 556, 14β-acetoxy-17-cyclopropylmethyl-4,5α-epoxy-3-hydroxy-6,7-didehydromorphinano[6,7-b]cyclohexeno[f]indole 557, 14β-acetoxy-17-cyclopropylmethyl-4,5α-epoxy-3-hydroxy-6,7-didehydromorphinano[6,7-b]cyclopenteno[g]indole 558, 14β-acetoxy-17-cyclopropylmethyl-4,5α-epoxy-3-hydroxy-6,7-didehydromorphinano[6,7-b]cyclopenteno[e]indole 559, 14β-acetoxy-17-cyclopropylmethyl-4,5α-epoxy-3-hydroxy-6,7-didehydromorphinano[6,7-b]cyclopenteno[f]indole 560, 14β-acetoxy-17-cyclopropylmethyl-4,5α-epoxy-3-hydroxy-6,7-didehydromorphinano[6,7-b]cyclohepteno[g]indole 561, 14β-acetoxy-17-cyclopropylmethyl-4,5α-epoxy-3-hydroxy-6,7-didehydromorphinano[6,7-b]cyclohepteno[e]indole 562, 14β-acetoxy-17-cyclopropylmethyl-4,5α-epoxy-3-hydroxy-6,7-didehydromorphinano[6,7-b]cyclohepteno[f]indole 563, 14β-acetoxy-17-cyclopropylmethyl-4,5α-epoxy-3-hydroxy-6,7-didehydromorphinano[6,7-b]cyclooocteno[g]indole 564, 14β-acetoxy-17-cyclopropylmethyl-4,5α-epoxy-3-hydroxy-6,7-didehydromorphinano[6,7-b]cyclooocteno[e]indole 565 and 14β-acetoxy-17-cyclopropylmethyl-4,5α-epoxy-3-hydroxy-6,7-didehydromorphinano[6,7-b]cyclooocteno[f]indole 566 are obtained, respectively.

By using 17-allyl-3,14β-dihydroxy-4,5α-epoxy-6,7-didehydromorphinano[6,7-b]cyclohexeno[g]indole 162, 17-allyl-3,14β-dihydroxy-4,5α-epoxy-6'-ethoxycarbonyl-6,7-didehydromorphinano[6,7-b]cyclohexeno[g]indole 424, 17-allyl-3,14β-dihydroxy-4,5α-epoxy-7'-ethoxycarbonyl-6,7-didehydromorphinano[6,7-b]cyclohexeno[g]indole 425, 17-allyl-3,14β-dihydroxy-4,5α-epoxy-8'-ethoxycarbonyl-6,7-didehydromorphinano[6,7-b]cyclohexeno[g]indole 426, 17-allyl-3,14β-dihydroxy-4,5α-epoxy-9'-ethoxycarbonyl-6,7-didehydromorphinano[6,7-b]cyclohexeno[g]indole 427, 17-allyl-3,14β-dihydroxy-4,5α-epoxy-6'-carbamoyl-6,7-didehydromorphinano[6,7-b]cyclohexeno[g]indole 428, 17-allyl-3,14β-dihydroxy-4,5α-epoxy-7'-carbamoyl-6,7-didehydromorphinano[6,7-b]cyclohexeno[g]indole 429, 17-allyl-3,14β-dihydroxy-4,5α-epoxy-8'-carbamoyl-6,7-didehydromorphinano[6,7-b]cyclohexeno[g]indole 430, 17-allyl-3,14β-dihydroxy-4,5α-epoxy-9'-carbamoyl-6,7-didehydromorphinano[6,7-b]cyclohexeno[g]indole 431, 17-allyl-3,14β-dihydroxy-4,5α-epoxy-6'-sulfamoyl-6,7-didehydromorphinano[6,7-b]cyclohexeno[g]indole 432, 17-allyl-3,14β-dihydroxy-4,5α-epoxy-7'-sulfamoyl-6,7-didehydromorphinano[6,7-b]cyclohexeno[g]indole 433, 17-allyl-3,14β-dihydroxy-4,5α-epoxy-8'-sulfamoyl-6,7-didehydromorphinano[6,7-b]cyclohexeno[g]indole 434 or 17-allyl-3,14β-dihydroxy-4,5α-epoxy-9'-sulfamoyl-6,7-didehydromorphinano[6,7-b]cyclohexeno[g]indole 435 in place of 17-cyclopropylmethyl-6,7-didehydro-4,5α-epoxy-3,14β-dihydroxy-6'-methylthio-6,7-2',3'-indolomorphinan 43, 14β-acetoxy-17-allyl-4,5α-epoxy-3-hydroxy-6,7-didehydromorphinano[6,7-b]cyclohexeno[g]indole 567, 14β-acetoxy-17-allyl-4,5α-epoxy-3-hydroxy-6'-ethoxycarbonyl-6,7-didehydromorphinano[6,7-b]cyclohexeno[g]indole 568, 14β-acetoxy-17-allyl-4,5α-epoxy-3-hydroxy-7'-ethoxycarbonyl-6,7-didehydromorphinano[6,7-b]cyclohexeno[g]indole 569, 14β-acetoxy-17-allyl-4,5α-epoxy-3-hydroxy-8'-ethoxycarbonyl-6,7-didehydromorphinano[6,7-b]cyclohexeno[g]indole 570, 14β-acetoxy-17-allyl-4,5α-epoxy-3-hydroxy-9'-ethoxycarbonyl-6,7-didehydromorphinano[6,7-b]cyclohexeno[g]indole 571, 14β-acetoxy-17-allyl-4,5α-epoxy-3-hydroxy-6'-carbamoyl-6,7-didehydromorphinano[6,7-b]cyclohexeno[g]indole 572, 14β-acetoxy-17-allyl-4,5α-epoxy-3-hydroxy-7'-carbamoyl-6,7-didehydromorphinano[6,7-b]cyclohexeno[g]indole 573, 14β-acetoxy-17-allyl-4,5α-epoxy-3-hydroxy-8'-carbamoyl-6,7-didehydromorphinano[6,7-b]cyclohexeno[g]indole 574, 14β-acetoxy-17-allyl-4,5α-epoxy-3-hydroxy-9'-carbamoyl-6,7-didehydromorphinano[6,7-b]cyclohexeno[g]indole 575, 14β-acetoxy-17-allyl-4,5α-epoxy-3-hydroxy-6'-sulfamoyl-6,7-didehydromorphinano[6,7-b]cyclohexeno[g]indole 576, 14β-acetoxy-17-allyl-4,5α-epoxy-3-hydroxy-7'-sulfamoyl-6,7-didehydromorphinano[6,7-b]cyclohexeno[g]indole 577, 14β-acetoxy-17-allyl-4,5α-epoxy-3-hydroxy-8'-sulfamoyl-6,7-didehydromorphinano[6,7-b]cyclohexeno[g]indole 578 and 14β-acetoxy-17-allyl-4,5α-epoxy-3-hydroxy-9'-sulfamoyl-6,7-didehydromorphinano[6,7-b]cyclohexeno[g]indole 579 are obtained, respectively. By using 17-allyl-3,14β-dihydroxy-4,5α-epoxy-6,7-didehydromorphinano[6,7-b]cyclohexeno[e]indole 436, 17-allyl-3,14β-dihydroxy-4,5α-epoxy-6,7-didehydromorphinano[6,7-b]cyclohexeno[f]indole 437, 17-allyl-3,14β-dihydroxy-4,5α-epoxy-6,7-didehydromorphinano[6,7-b]cyclopenteno[g]indole 438, 17-allyl-3,14β-dihydroxy-4,5α-epoxy-6,7-didehydromorphinano[6,7-b]cyclopenteno[e]indole 439, 17-allyl-3,14β-dihydroxy-4,5α-epoxy-6,7-didehydromorphinano[6,7-b]cyclopenteno[f]indole 440, 17-allyl-3,14β-dihydroxy-4,5α-epoxy-6,7-didehydromorphinano[6,7-b]cyclohepteno[g]indole 441, 17-allyl-3,14β-dihydroxy-4,5α-epoxy-6,7-didehydromorphinano[6,7-b]cyclohepteno[e]indole 442, 17-allyl-3,14β-dihydroxy-4,5α-epoxy-6,7-didehydromorphinano[6,7-b]cyclohepteno[f]indole 443, 17-allyl-3,14β-dihydroxy-4,5α-epoxy-6,7-didehydromorphinano[6,7-b]cyclooteno[g]indole 444, 17-allyl-3,14β-dihydroxy-4,5α-epoxy-6,7-didehydromorphinano[6,7-b]cycloocteno[e]indole 445 or 17-allyl-3,14β-dihydroxy-4,5α-epoxy-6,7-didehydromorphinano[6,7-b]cycloocteno[f]indole 446 in place of 17-cyclopropylmethyl-6,7-didehydro-4,5α-epoxy-3,14β-dihydroxy-6'-methylthio-6,7-2',3'-indolomorphinan 43, 14β-acetoxy-17-allyl-4,5α-epoxy-3-hydroxy-6,7-didehydromorphinano[6,7-b]cyclohexeno[e]indole 580, 14β-acetoxy-17-allyl-4,5α-epoxy-3-hydroxy-6,7-didehydromorphinano[6,7-b]cyclohexeno[f]indole 581, 14β-acetoxy-17-allyl-4,5α-epoxy-3-hydroxy-6,7-didehydromorphinano[6,7-b]cyclopenteno[g]indole 582, 14β-acetoxy-17-allyl-4,5α-epoxy-3-hydroxy-6,7-didehydromorphinano[6,7-b]cyclopenteno[e]indole 583, 14β-acetoxy-17-allyl-4,5α-epoxy-3-hydroxy-6,7-didehydromorphinano[6,7-b]cyclopenteno[f]indole 584, 14β-acetoxy-17-allyl-4,5α-epoxy-3-hydroxy-6,7-didehydromorphinano[6,7-b]cyclohepteno[g]indole 585, 14β-acetoxy-17-allyl-4,5α-epoxy-3-hydroxy-6,7-didehydromorphinano[6,7-b]cyclohepteno[e]indole 586, 14β-acetoxy-17-allyl-4,5α-epoxy-3-hydroxy-6,7-didehydromorphinano[6,7-b]cyclohepteno[f]indole 587, 14β-acetoxy-17-allyl-4,5α-epoxy-3-hydroxy-6,7-didehydromorphinano[6,7-b]cycloocteno[g]indole 588, 14β-acetoxy-17-allyl-4,5α-epoxy-3-hydroxy-6,7-didehydromorphinano[6,7-b]cycloocteno[e]indole 589 and 14β-acetoxy-17-allyl-4,5α-epoxy-3-hydroxy-6,7-didehydromorphinano[6,7-b]cycloocteno[f]indole 590 are obtained, respectively.

Example 15

17-cyclopropylmethyl-6,7-didehydro-4,5α-epoxy-3,14β-dihydroxy-6'-propoxycarbonyl-6,7-2',3'-indolomorphinan 393

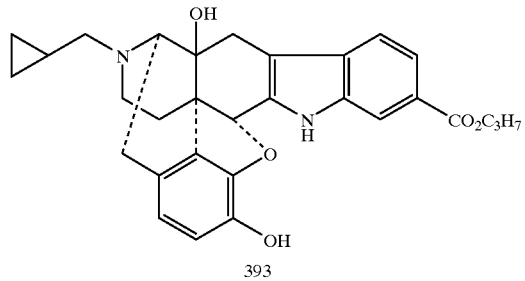

393

In 9 ml of n-propanol, 517 mg (1.09 mmol) of 17-cyclopropylmethyl-6,7-didehydro-4,5α-epoxy-3,14β-dihydroxy-6'-methoxycarbonyl-6,7-2',3'-indolomorphinan 77 was dissolved. To this solution, 11 ml of 1M sodium n-propoxide solution in n-propanol was added and the resulting mixture was stirred at 60° C. for 2 hours. After cooling the reaction mixture to room temperature, 70 ml of water was added and the resultant was extracted with 70 ml of chloroform and chloform-methanol (3:1) 2×50 ml. The organic layers were combined, dried and concentrated to obtain 542 mg of crude product. The obtained crude product was purified by column chromatography [silica gel 30 g; hexane-ethyl acetate-methanol (7:7:1)] to obtain 490.6 mg (yield 90%) of the captioned compound. The obtained compound was dissolved in ethyl acetate and 0.065 ml of methanesulfonic acid solution in ethyl acetate was added thereto. The precipitates were collected by filtration and washed with ethyl acetate to obtain 516.7 mg (yield 79%) of methanesulfonic acid salt of the captioned compound.

393 methanesulfonic acid salt mp.: 175–220° C. (decomposed). NMR (400 MHz, DMSO-d6); δ 0.44 (1H, m), 0.50 (1H, m), 0.63 (1H, m), 0.73 (1H, m), 0.99 (3H, t, J=7.3 Hz), 1.09 (1H, m), 1.74 (2H, tq, J=6.8, 7.3 Hz), 1.83 (1H, m), 2.30 (3H, s), 2.56 (1H, d, J=16.1 Hz), 2.61 (1H, m), 2.72 (1H, m), 2.95 (1H, m), 2.99 (1H, d, J=16.1 Hz), 3.22 (1H, m), 3.26 (1H, dd, J=20.0, 6.8 Hz), 3.38 (1H, m), 3.45 (1H, d, J=20.0 Hz), 4.09 (1H, brd, J=6.3 Hz), 4.22 (2H, t, J=6.8 Hz), 5.74 (1H, s), 6.38 (1H, br s, OH), 6.60 (1H, d, J=8.1 Hz), 6.64 (1H, d, J=8.1 Hz), 7.46 (1H, d, J=8.3 Hz), 7.61 (1H, dd, J=8.3, 1.5 Hz), 8.07 (1H, br s), 8.94 (1H, m, NH$^+$), 9.26 (1H, br s, OH), 11.76 (1H, s, NH). IR (KBr); ν 3422, 1688, 1638, 1626, 1508, 1462, 1330, 1212, 1116, 1046, 872, 774 cm$^{-1}$. Mass (FAB); m/z 501 ((M+H)$^+$). Elementary Analysis: $C_{30}H_{32}N_2O_5 \cdot CH_3SO_3H \cdot 0.6H_2O$; Calcd.:C, 61.29; H, 6.17; N, 4.61; S, 5.28. Found: C, 61.06; H, 6.31; N, 4.64; S, 5.53.

By using 17-cyclopropylmethyl-6,7-didehydro-4,5α-epoxy-3,14β-dihydroxy-4'-methoxycarbonyl-6,7-2',3'-indolomorphinan 76, 17-cyclopropylmethyl-6,7-didehydro-4,5α-epoxy-3,14β-dihydroxy-5'-ethoxycarbonyl-6,7-2',3'-indolomorphinan 3, 17-cyclopropylmethyl-6,7-didehydro-4,5α-epoxy-3,14β-dihydroxy-7'-ethoxycarbonyl-6,7-2',3'- indolomorphinan 119, 17-allyl-6,7-didehydro-4,5α-epoxy-3,14β-dihydroxy-4'-methoxycarbonyl-6,7-2',3'-indolomorphinan 114, 17-allyl-6,7-didehydro-4,5α-epoxy-3,14β-dihydroxy-5'-ethoxycarbonyl-6,7-2',3'-indolomorphinan 22, 17-allyl-6,7-didehydro-4,5α-epoxy-3,14β-dihydroxy-6'-methoxycarbonyl-6,7-2',3'-indolomorphinan 115 or 17-allyl-6,7-didehydro-4,5α-epoxy-3,14β-dihydroxy-7'-ethoxycarbonyl-6,7-2',3'-indolomorphinan 138 in place of 17-cyclopropylmethyl-6,7-didehydro-4,5α-epoxy-3,14β-dihydroxy-6'-methoxycarbonyl-6,7-2',3'-indolomorphinan 77, 17-cyclopropylmethyl-6,7-didehydro-4,5α-epoxy-3,14β-dihydroxy-4'-propoxycarbonyl-6,7-2',3'-indolomorphinan 394, 17-cyclopropylmethyl-6,7-didehydro-4,5α-epoxy-3,14β-dihydroxy-5'-propoxycarbonyl-6,7-2',3'-indolomorphinan 395, 17-cyclopropylmethyl-6,7-didehydro-4,5α-epoxy-3,14β-dihydroxy-7'-propoxycarbonyl-6,7-2',3'-indolomorphinan 396, 17-allyl-6,7-didehydro-4,5α-epoxy-3,14β-dihydroxy-4'-propoxycarbonyl-6,7-2',3'-indolomorphinan 397, 17-allyl-6,7-didehydro-4,5α-epoxy-3,14β-dihydroxy-5'-propoxycarbonyl-6,7-2',3'-indolomorphinan 398, 17-allyl-6,7-didehydro-4,5α-epoxy-3,14β-dihydroxy-6'-propoxycarbonyl-6,7-2',3'-indolomorphinan 399 and 17-allyl-6,7-didehydro-4,5α-epoxy- 3,14β-dihydroxy-7'-propoxycarbonyl-6,7-2',3'-indolomorphinan 400 are obtained, respectively.

Example 16

17-cyclopropylmethyl-6,7-didehydro-4,5α-epoxy-3,14β-dihydroxy-7'-methylsulfinyl-6,7-2',3'-indolomorphinan 591, 592

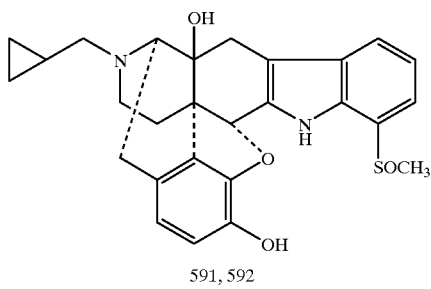

591, 592

In 20 ml of acetic acid, 1.00 g of 17-cyclopropylmethyl-6,7-didehydro-4,5α-epoxy-3,14β-dihydroxy-7'-methylthio-6,7-2',3'-indolomorphinan 121 was dissolved. To this solution, a solution containing 0.45 g of m-chloroperbenzoic acid (85%) in 10 ml of acetic acid was added dropwise and the resulting mixture was stirred at room temperature for 1.5 hours. To this mixture, 1 ml of aqueous saturated sodium thiosulfate solution was added and the resulting mixture was stirred for 1 hour, followed by concentration of the mixture. The obtained residue was neutralized by adding aqueous saturated sodium hydrogen carbonate solution and the resultant was extracted with chloroform:methanol (4:1). The organic layers were washed with saturated saline, dried over anhydrous magnesium sulfate and concentrated. The obtained residue was purified by column chromatography [silica gel; chloroform/methanol/28% aqueous ammonia (50:1:0.1–20:1:0.1)]. The low polar component was recrystallized from methylene chloride:ethyl acetate and the high polar component was recrystallized from methylene chloride:methanol to obtain two types of isomers 591 and 592 of the captioned compound in amounts of 306 mg and 402 mg, respectively. These isomers were separately suspended in methanol and equivalent methanesulfonic acid was added to the suspensions to convert the compounds to salts. Each of the resulting mixtures was concentrated and excess ethyl acetate was added to the residue. The obtained precipitates were collected by filtration to obtain methanesulfonic acid salts in amounts of 337 mg (yield 27%) and 463 mg (yield 37%), respectively.

591 free mp.: 225–227° C.

591 methanesulfonic acid salt;

mp.: 230° C. (decomposed); NMR (500 MHz, DMSO-d6); δ 0.44 (1H, m), 0.50 (1H, m), 0.63 (1H, m), 0.74 (1H, m), 1.09 (1H, m), 1.85 (1H, br d, J=10.4 Hz), 2.30 (3H, s), 2.56 (1H, d, J=15.9 Hz), 2.60 (1H, m), 2.73 (1H, m), 2.92 (3H, s), 2.94 (1H, m), 2.99 (1H, d, J=15.9 Hz), 3.12 (1H, m), 3.26 (1H, dd, J=20.1, 6.7 Hz), 3.37 (1H,m), 3.45 (1H, J=19.5 Hz), 4.09 (1H, d, J=6.1 Hz), 5.72 (1H, s), 6.38 (1H, s), 6.60 (1H, d, J=7.9 Hz), 6.65 (1H, d, J=7.9 Hz), 7.18 (1H, dd, J=7.9, 7.3 Hz), 7.47 (1H, d, J=7.3 Hz), 7.56 (1H, d, J=7.9 Hz), 8.94 (1H, br s), 9.25 (1H, br s), 11.66 (1H, s). IR (KBr); ν 3410, 1638, 1504, 1462, 1423, 1323, 1195, 1060, 785, 561 cm$^{-1}$. Mass (FAB); m/z 477 (M+H). Elementary Analysis: $C_{27}H_{28}N_2O_4S \cdot CH_3SO_3H \cdot 0.4H_2O \cdot 0.2AcOEt$; Calcd.:C, 57.89; H, 5.80; N, 4.69; S, 10.73. Found: C, 58.16; H, 5.91; N, 4.66; S, 10.35.

592 free mp.: 216–218° C.

592 methanesulfonic acid salt mp.: 240° C. (decomposed); NMR (500 MHz, DMSO-d6); δ 0.44 (1H, m), 0.50 (1H, m), 0.63 (1H, m), 0.74 (1H, m), 1.10 (1H, m), 1.84 (1H, br d, J=11.0 Hz), 2.30 (3H, s), 2.57 (1H, d, J=15.9 Hz), 2.60 (1H, m), 2.73 (1H, m), 2.85 (3H, s), 2.94 (1H, m), 2.99 (1H, d, J=15.9 Hz), 3.11 (1H, m), 3.26 (1H, dd, J=20.1, 6.7 Hz), 3.36 (1H,m), 3.45 (1H, J=19.5 Hz), 4.09 (1H, d, J=6.1 Hz), 5.71 (1H, s), 6.37 (1H, br s), 6.60 (1H, d, J=7.9 Hz), 6.65 (1H, d, J=7.9 Hz), 7.22 (1H, dd, J=7.9, 7.3 Hz), 7.51 (1H, d, J=7.3 Hz), 7.54 (1H, d,J=7.9 Hz), 8.94 (1H, br s), 9.24 (1H, br s), 11.71 (1H, s). IR (KBr); ν 3410, 1620, 1508, 1460, 1423, 1325, 1195, 1060, 785, 561 cm$^{-1}$. Mass (FAB); m/z 477 (M+H). Elementary Analysis: $C_{27}H_{28}N_2O_4S \cdot CH_3SO_3H \cdot 1.7H_2O$; Calcd.:C, 55.74; H, 5.91; N, 4.64; S, 10.63. Found: C, 55.57; H, 5.87; N, 4.60; S, 10.76.

By using 17-cyclopropylmethyl-6,7-didehydro-4,5α-epoxy-3,14β-dihydroxy-4'-methylthio-6,7-2',3'-indolomorphinan 42, 17-cyclopropylmethyl-6,7-didehydro-4,5α-epoxy-3,14β-dihydroxy-5'-methylthio-6,7-2',3'-indolomorphinan 12, 17-cyclopropylmethyl-6,7-didehydro-4,5α-epoxy-3,14β-dihydroxy-6'-methylthio-6,7-2',3'-indolomorphinan 43, 17-allyl-6,7-didehydro-4,5α-epoxy-3,14β-dihydroxy-4'-methylthio-6,7-2',3'-indolomorphinan 80, 17-allyl-6,7-didehydro-4,5α-epoxy-3,14β-dihydroxy-5'-methylthio-6,7-2',3'-indolomorphinan 31, 17-allyl-6,7-didehydro-4,5α-epoxy-3,14β-dihydroxy-6'-methylthio-6,7-2',3'-indolomorphinan 81 or 17-allyl-6,7-didehydro-4,5α-epoxy-3,14β-dihydroxy-7'-methylthio-6,7-2',3'-indolomorphinan 140 in place of 17-cyclopropylmethyl-6,7-didehydro-4,5α-epoxy-3,14β-dihydroxy-7'-methylthio-6,7-2',3'-indolomorphinan 121, 17-cyclopropylmethyl-6,7-didehydro-4,5α-epoxy- 3,14β-dihydroxy-4'-methylsulfinyl-6,7-2',3'-indolomorphinan 593, 594, 17-cyclopropylmethyl- 6,7-dihydro-4,5α-epoxy-3,14β-dihydroxy-5'-methylsulfinyl-6,7-2',3'-indolomorphinan 595, 596, 17-cyclopropylmethyl-6,7-didehydro-4,5α-epoxy-3,14β-dihydroxy-6'-methylsulfinyl-6,7-2',3'-indolomorphinan 597, 598, 17-allyl-6,7-didehydro-4,5α-epoxy-3,14β-dihydroxy-4'-methylsulfinyl-6,7-2',3'-indolomorphinan 599, 600, 17-allyl-6,7-didehydro-4,5α-epoxy-3,14β-dihydroxy-5'-methylsulfinyl-6,7-2',3'-indolomorphinan 601, 602, 17-allyl-6,7-didehydro-4,5α-epoxy-3,14β-dihydroxy-6'-methylsulfinyl-6,7-2',3'-indolomorphinan 603, 604, and 17-allyl-6,7-didehydro-4,5α-epoxy-3,14β-dihydroxy-7'-methylsulfinyl-6,7-2',3'-indolomorphinan 605, 606 are obtained, respectively.

The pharmacological effects of the compounds according to the present invention will now be described.

Example 17

δ-opioid Antagonist Activity

Using mouse was deferens (MVD), the antagonist activity against DPDPE which is a δ-opioid agonist was checked.

Experimental Method

In this experiment, ddy male mice were used. In a Magnus' tube which is filled with Krebes-Henseleit solution (NaCl 118 nM; KCl 4.7 mM; $CaCl_2$ 2.5 mM; $KH_2PO_4$ 1.1 mM; $NaHCO_3$ 25 mM; glucose 11 mM) kept at 37° C., and into which an atmosphere consisting of 5% carbon dioxide and 95% oxygen was flown, was deferens taken from the animals was suspended. Electric stimulation was applied through ring-shaped platinum electrodes mounted on the upper and lower portions of the tube at a frequency of 0.1 Hz and 5.0 mS duration. The contraction of the tissue was recorded on polygraph using isometric transducer.

First, DPDPE which is a β-agonist was cumulatively added and $IC_{50}$ value (the concentration at which the contraction by the electric stimulation is inhibited by 50%) was calculated. Then 100 nM of the test compound was added. Twenty minutes later, DPDPE was begun to be added cumulatively. The ratio of $IC_{50}$ values in the presence and absence of the test compound, Ke value (the molar concentration of the test compound necessary for translating the dose-effect curve to the curve of twice dose) and $pA_2$ value were determined. The $pA_2$ value was determined by the method of Shild et al (Shild, H. O., Br. J. Pharmac. Chamotehr., 4, 277 (1949)). That is, the logarithm of the test compound (log[test compound]) was plotted along the abscissa and the logarithm of the value obtained by subtracting 1 from the ratio of $IC_{50}$ values was plotted in the presence and absence of the test compound [log(dose ratio−1)] along the ordinate. The $pA_2$ value was determined from the value on the abscissa when the value on the ordinate of the obtained line is 0.

Results

The δ-antagonist activities of the principal compounds are shown in Tables 1 and 2. All of the compounds have high antagonist activities. In particular, compounds 77, 119 and 190 exhibited activities as high as about 1.3–1.6 times that of NTI (Ke: 0.21, $pA_2$: 9.68) which is the compound most widely used at present as a δ-antagonist.

TABLE 1

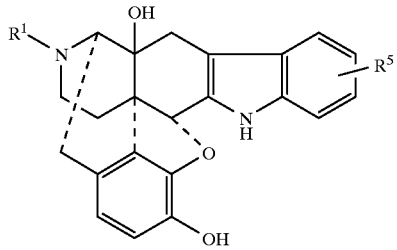

δ- opioid antagonist activities of indole compounds (1)

| Compound | $R^1$ | $R^5$ | Ratio of $IC_{50}$ Values | Ke (nM) | $pA_2$ |
|---|---|---|---|---|---|
| 1 | CPM | 5'-I | 8.88 | 12.7 | 7.90 |
| 3 | CPM | 5'-$CO_2C_2H_5$ | 5.34 | 23.0 | 7.64 |
| 4 | CPM | 5'-$OCF_3$ | 7.95 | 14.4 | 7.84 |
| 5 | CPM | 5'-$SO_2NH_2$ | 4.36 | 29.8 | 7.53 |
| 6 | CPM | 5'-$SO_2CH_3$ | 12.6 | 8.62 | 8.06 |
| 7 | CPM | 5'-CONH-CPM | 33.2 | 3.11 | 8.51 |
| 8 | CPM | 5'-CN | 3.60 | 38.5 | 7.41 |
| 9 | CPM | 5'-$C_2H_4N(CH_3)_2$ | 25.6 | 4.07 | 8.39 |
| 10 | CPM | 5'-$CH_2N(CH_3)_2$ | 11.4 | 9.62 | 8.02 |
| 40 | CPM | 4'-$C2H_4OH$ | 4.60 | 27.8 | 7.56 |
| 41 | CPM | 6'-$C_2H_4OH$ | 22.1 | 4.74 | 8.32 |
| 43 | CPM | 6'-$SCH_3$ | 168 | 0.60 | 9.22 |
| 45 | CPM | 6'-$SO_2NH$-CPM | 7.44 | 15.5 | 7.81 |
| 46 | CPM | 4'-CONH-CPM | 1.39 | 256 | 6.59 |
| 47 | CPM | 6'-CONH-CPM | 13.0 | 8.33 | 8.08 |
| 48 | CPM | 4'-$CH_2CO_2C_2H_5$ | 5.88 | 20.5 | 7.69 |
| 49 | CPM | 6'-$CH_2CO_2C_2H_5$ | 27.8 | 3.73 | 8.43 |
| 51 | CPM | 6'-$SO_2N(CH_3)_2$ | 33.2 | 3.11 | 8.57 |
| 53 | CPM | 6'-CN | 62.3 | 1.63 | 8.79 |
| 76 | CPM | 4'-$CO_2CH_3$ | 6.82 | 17.2 | 7.76 |
| 77 | CPM | 6'-$CO_2CH_3$ | 742 | 0.13 | 9.87 |
| 78 | CPM | 4'-$NO_2$ | 14.8 | 7.25 | 8.14 |
| 79 | CPM | 6'-$NO_2$ | 60.6 | 1.68 | 8.78 |
| 114 | allyl | 4'-$CO_2CH_3$ | 20.7 | 5.08 | 8.29 |
| 115 | allyl | 6'-$CO_2CH_3$ | 75.4 | 1.34 | 8.87 |
| 118 | CPM | 7'-$CF_3$ | 52.9 | 1.93 | 8.72 |
| 119 | CPM | 7'-$CO_2C_2H_5$ | 635 | 0.16 | 9.80 |
| 120 | CPM | 7'-Ph | 17.0 | 6.25 | 8.20 |
| 121 | CPM | 7'-$SCH_3$ | 33.6 | 3.07 | 8.51 |
| 136 | CPM | 7'-$NO_2$ | 192 | 0.52 | 9.28 |
| 180 | CPM | 5'-$CH_2NH$-CPM | 15.2 | 7.04 | 8.15 |
| 188 | CPM | 6'-$SO_2CH_3$ | 56.0 | 1.82 | 8.74 |
| 190 | CPM | 7'-$SO_2CH_3$ | 698 | 0.14 | 9.84 |
| 393 | CPM | 6'-$CO_2C_3H_7$ | 12.3 | 8.85 | 8.05 |

In the table, CPM means cyclopropylmethyl group.

TABLE 2

δ-antagonist Activities of Indole Compounds (2)

| Compound | Structural Formula | Ratio of IC$_{50}$ Values | Ke (nM) | pA$_2$ |
|---|---|---|---|---|
| 2 | | 22.1 | 4.74 | 8.32 |
| 156 | | 26.6 | 3.91 | 8.41 |

Example 18

Change in δ-antagonist Activity with Time

Figure 2:
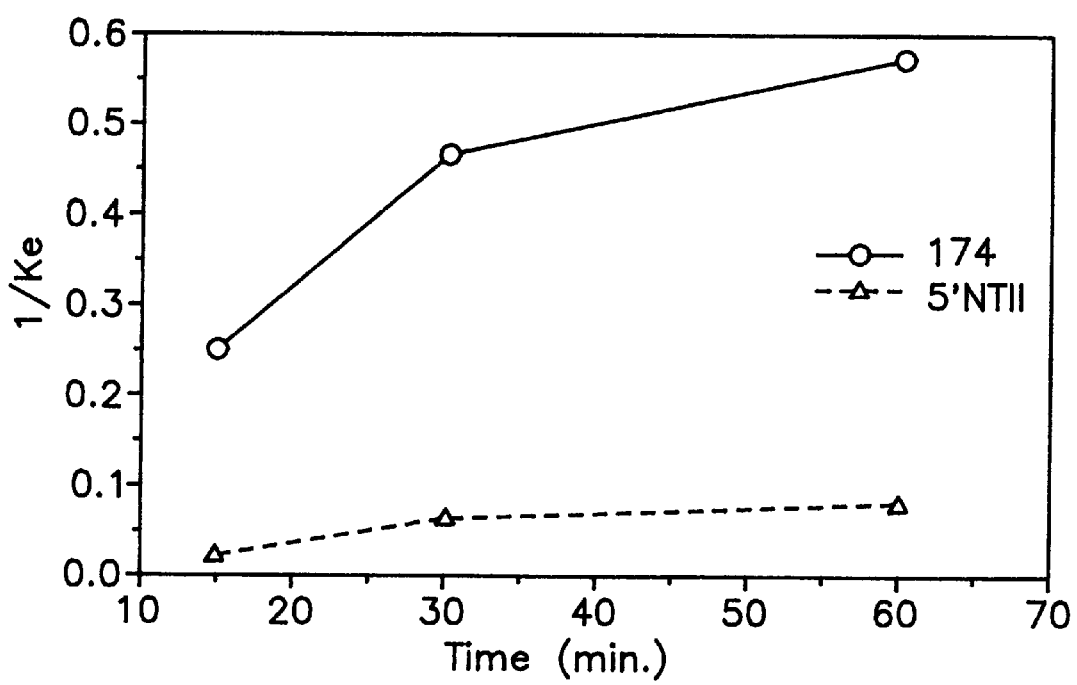
FIG. 2 shows the change in antagonist action of compound 174 according to the present invention against DPDPE in scale enlarged by changing the scale of the ordinate in FIG. 1.

Using MVD, the antagonist activities of compounds 173 and 174 against DPDPE were determined. The ratio of IC$_{50}$ values, Ke values and pA$_2$ values at 15 minutes, 30 minutes and 1 hour from the addition of the test compounds were calculated. The results are shown in Table 3 and FIGS. 1 and 2. Since the concentrations of the test compounds are different, the reciprocals of Ke values were plotted in FIGS. 1 and 2.

While the activity of NTI did not change, the antagonist activities of compounds 173 and 174 and 5'-NTII increased with time. The increase in the activity is due to irreversible binding to the receptors. Although both compounds 173 and 174 are isomers of 5'-NTII, their activities were high. That is, compound 173 exhibited an activity at 1 hour of about 3.5 times that of NTI and about 170 times that of 5'-NTII, and compound 174 exhibited an activity at 1 hour of about 7 times that of 5'-NTII. Thus, although the activity of compound 173 is inferior to that of compound 174, the activities of these compounds are drastically higher than those of the conventional antagonists.

As mentioned above, a large part of the various pharmacological actions of δ-opioid receptor has not yet been clarified. The compounds of the present invention have very high activities and selectivities, which irreversibly bind to δ-opioid receptor, so that they would be very useful in the future studies of opioids.

TABLE 3

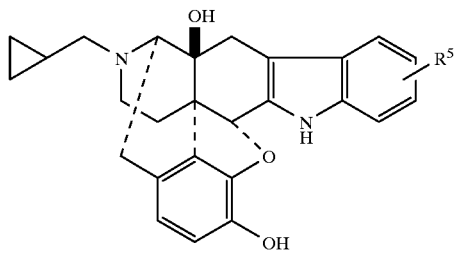

Change with Time of δ- antagonist Activities of Indole Compounds

| Compound | R$^5$ | Time (min.) | Ratio of IC$_{50}$ Values | Ke (nM) | pA$_2$ |
|---|---|---|---|---|---|
| 173 (20 nM) | 7'-NCS | 15 | 105 | 0.19 | 9.72 |
| | | 30 | 253 | 0.08 | 10.1 |
| | | 60 | 306 | 0.07 | 10.2 |
| 174 (100 nM) | 6'-NCS | 15 | 25.7 | 4.05 | 8.39 |
| | | 30 | 47.6 | 2.15 | 8.67 |
| | | 60 | 58.6 | 1.74 | 8.76 |
| 5'-NTII (100 nM) | 5'-NCS | 15 | 3.28 | 43.9 | 7.36 |
| | | 30 | 7.47 | 15.5 | 7.81 |
| | | 60 | 9.36 | 12.0 | 7.92 |
| NTI (20 nM) | H | 15 | 96.3 | 0.21 | 9.68 |
| | | 30 | 95.6 | 0.21 | 9.67 |
| | | 60 | 83.7 | 0.24 | 9.62 |

Example 19

κ-opioid Antagonist Activity

Using guinea pig ileum (GPI), antagonist activities against U-50488H which is a κ-opioid agonist was determined.

Experimental Method

Hartley male guinea pigs were used. After killing the guinea pigs by clubbing, ilea were taken. The inside of the ilea was washed with a nutrient liquid and only longitudinal muscles were peeled off. Using the thus obtained longitudinal muscles, the tests were carried out using the same apparatus as used in the experiment employing MVD.

First, U-50488H which is a κ-agonist was cumulatively added and $IC_{50}$ value was determined. Thereafter, the muscle was well washed with the nutrient liquid. After the contraction reaction became stable, 100 nM of a test compound was added. From 20 minutes after, U-50488H was cumulatively added and the ratio of $IC_{50}$ values, Ke value and $pA_2$ value were determined in the same manner as in the experiment employing MVD.

Results

Although most of the compounds did not exhibit agonist activities or antagonist activities, the five compounds shown in Table 4 exhibited strong κ-antagonist activities. These compounds also have δ-antagonist activities. A compound having both δ- and κ-antagonist activities are not known, so that it is expected that these compounds will be effective for clarifying unknown actions of opioids and relationships between δ-receptor and κ-receptor.

TABLE 4

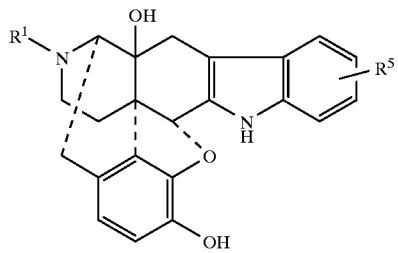

κ-antagonist Activities of Indole Compounds

| Compound | $R^1$ | $R^5$ | Ratio of $IC_{50}$ Values | Ke (nM) | $pA_2$ |
|---|---|---|---|---|---|
| 7 | CPM | 5'-CONH-CPM | 22.8 | 4.59 | 8.34 |
| 9 | CPM | 5'-$C_2H_4N(CH_3)_2$ | 99.0 | 4.07 | 8.39 |
| 10 | CPM | 5'-$CH_2N(CH_3)_2$ | 19.4 | 9.67 | 8.02 |
| 45 | CPM | 6'-$SO_2NH$-CPM | 3.22 | 45.1 | 7.35 |
| 47 | CPM | 6'-CONH-CPM | 3.11 | 47.4 | 7.32 |

In the table, CPM means cyclopropylmethyl group.

It is known that κ-opioid receptor relates to diuresis and protection of brain cells. The present inventors have already proved that nor-BNI widely known as κ-antagonist has brain cell-protecting action (Japanese Laid-open Patent Application (Kokai) No. 3-218313). Since the compounds of the invention are also κ-antagonists, it is expected that these compounds have the same actions. Thus, these compounds were tested for the brain cell-protecting actions.

Example 20

Brain Cell-protecting Action

The brain cell-protecting action was examined by MTT [3-(4,5-dimethylthiazol-2-yl)-2,5-diphenyltetrazolium bromide] method. MTT yields a dark blue formazan compound by mitochondria in living cells. This compound was dissolved in isopropanol and absorbance at 570 nm was measured, thereby measuring the number of living cells.

Experimental Method

Cerebral cortex nerve cells of fetal rats of 17 days old were placed in wells of a 96-well plate at a population density of $1 \times 10^5$ cells/cm$^2$. Then 10 μM of a test compound was added and the cells were cultured in 200 μl of mixed medium of D-MEM/F.12 (1:1) for 3 days (37° C., 5% $CO_2$). In a control group, the medium alone was added. Then 10 μl of MTT solution in PBS (6 mg/ml) was added and the mixture was allowed to react for 3 hours (37° C., 5% $CO_2$). After removing the culture medium, 100 μl of isopropanol was added and the absorbance was measured.

Results

The ratio of the absorbances of the study group and the control group was employed as an index of brain cell-protecting action. The results are shown in Table 5. Clear activities were observed with compounds 7, 9, 10 and 180. In particular, compounds 9 and 180 exhibited activities higher than that of nor-BNI. In view of the fact that while the κ-antagonist activities of the compounds of the present invention are lower than that of nor-BNI, the compounds of the present invention have superior brain cell-protecting action than nor-BNI, and that NTI which is a δ-opioid antagonist has brain cell-protecting action, it is suggested that the compounds having antagonist activities for both δ- and κ-receptors are superior as brain cell-protecting agents.

TABLE 5

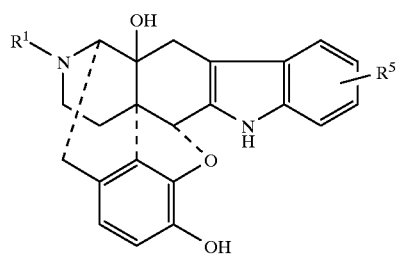

Brain Cell - Protecting Actions of Indole Compounds

| Compound | $R^1$ | $R^5$ | Ratio of Absorbances |
|---|---|---|---|
| 7 | CPM | 5'-CONH-CPM | 5.31 |
| 9 | CPM | 5'-$C_2H_4N(CH_3)_2$ | 8.27 |
| 10 | CPM | 5'-$CH_2N(CH_3)_2$ | 7.58 |
| 180 | CPM | 5'-$CH_2NH$-CPM | 8.73 |
| NTI | CPM | H | 4.21 |
| nor-BNI | | | 7.60 |

In the table, CPM means cyclopropylmethyl group.

Example 21

Immunosuppressive Activity

The immunosuppressive activities of the compounds of the present invention were examined by suppression of mouse delayed type hypersensitivity.

Mouse Delayed Type Hypersensitivity Reaction Suppression Test—1

Experimental Method

BALB/c mice (male, 7 weeks old) were used. The mice were classified into groups depending on the body weight, each group consisting of 7–8 mice. Each of the mice was sensitized by subcutaneously administering 25 μl of SRBC ($8 \times 10^8$ in saline) on the heel of the left hing leg. On day 4 from the sensitization, 25 μl of SRBC ($8 \times 10^9$ in saline) was subcutaneously administered on the right footpad so as to induce delayed type hypersensitivity. The difference in the thicknesses of the right footpad before the induction of reaction and 24 hours after the induction of the reaction was employed as an index of the degree of the reaction.

The test compound was dissolved in 10% DMSO-water and was subcutaneously administered everyday from 3 days before the sensitization to the day of induction of the reaction, totally 8 days. In the control group, 10% DMSO-water alone was administered in the same manner. The volume of administration was 5 ml/kg in both study groups and in the control group.

The % suppression of the delayed type hypersensitivity reaction was calculated according to the following equation:

$$\% \text{ Suppression} = \frac{A-B}{A} \times 100$$

wherein A means the difference in the thickness of the right hind leg before and after the reaction in control group, and B means the difference in the thickness of the right hind leg before and after the reaction in the group to which the test compound was administered.

Results

The compounds which exhibited suppressive actions and their suppression rates are shown in Table 6.

TABLE 6

Suppression of Delayed Type Hypersensitivity by Indole Compounds

| Compound | $R^1$ | $R^5$ | % Suppression |
|---|---|---|---|
| 43 | CPM | 6'-SCH$_3$ | 26 |
| 53 | CPM | 6'-CN | 18 |
| 78 | CPM | 4'-NO$_2$ | 36 |
| 119 | CPM | 7'-CO$_2$C$_2$H$_5$ | 12 |
| 121 | CPM | 7'-SCH$_3$ | 20 |
| 136 | CPM | 7'-NO$_2$ | 18 |
| NTI | CPM | H | did not suppress |
| CsA | | | 50 |

In the table, CPM means cyclopropylmethyl group.

No δ-opioid antagonists which suppress the delayed type hypersensitivity reaction are known, so that it was proved that the compounds are δ-opioid antagonists having a novel action. While the currently used immunosuppressants represented by cyclosporin A (CyA) suppresses the reaction by being administered after the sensitization, the compounds of the present invention exhibit the suppressive activity by being administered from before the sensitization. This means that the compounds of the present invention act through a mechanism which is different from that of the conventional drugs, so that it is suggested that there is a possibility that the compounds of the present invention are immunosuppressants of totally new type.

Example 22
Mouse Delayed Type Hypersensitivity Reaction Suppression Test—2

Experimental Method

BALB/c mice (male, 7 weeks old) were used, and each group consisted of 4–5 mice. Spleen cells (1×10$^7$) obtained from a donor mouse (C57BL/6) was subcutaneously administered to sensitize the mice. On Day 7 from the sensitization, the spleen cells (5×10$^6$) of the donor were subcutaneously administered on the right hing leg and spleen cells (5×10$^6$) obtained from a mouse of the same line as the recipient mice were subcutaneously administered on the left footpad. Twenty four hours later, the thicknesses of the right and left footpads were measured with a dial thickness gage, and the difference in thicknesses of the right and left footpads before the induction of the reaction and 24 hours after the induction of the reaction was employed as the index of the degree of the reaction.

The test compound was dissolved in 10% DMSO-water and was subcutaneously administered everyday from the day of sensitization to the day of induction of the reaction, totally 8 days. In the control group, 10% DMSO-water alone was administered in the same manner. The volume of administration was 10 ml/kg in both study groups and in the control group.

Delayed Type Hypersensitivity Reaction=(thickness of right foodpad after induction–thickness of right footpad before induction)–(thickness of right footpad after induction–thickness of right foodpad leg before induction)

% Suppression of Delayed Type Hypersensitivity Reaction $$= \left(1 - \frac{C}{D}\right) \times 100$$

wherein C means delayed type hypersensitivity reaction of the group to which the test compound was administered and D means the delayed type hypersensitivity reaction of the group to which vehicle was administered.

Results

The compounds which exhibited suppressive activities and their % suppression are shown in Table 7.

TABLE 7

Suppression of Delayed Type Hypersensitivity by Indole Compounds (2)

| Compound | $R^1$ | X | Y | % Suppression |
|---|---|---|---|---|
| 2 | CPM | -(CH$_2$)$_4$- | | 60 |
| 43 | CPM | SCH$_3$ | H | 27 |
| 119 | CPM | H | CO$_2$C$_2$H$_5$ | 31 |
| 120 | CPM | H | Ph | 46 |
| 393 | CPM | CO$_2$O$_3$H$_7$ | H | 33 |
| 591 | CPM | H | SOCH$_3$ | 16 |
| 592 | CPM | H | SOCH$_3$ | 20 |
| NTI | CPM | H | H | 60 |
| CsA | | | | 32 |

In the table, CPM means cyclopropylmethyl group

Example 23
Mouse Delayed Type Hypersensitivity Reaction Suppression Test—3

Experimental Method

BALB/c mice (male, 7 weeks old) were used, and each group consisted of 4–5 mice. Spleen cells (1×10$^7$) obtained from a donor mouse (C57BL/6) was subcutaneously administered to sensitize the mice. On Day 7 from the sensitization, the spleen cells ($5\times10^6$) of the donor were subcutaneously administered on the right footpad and spleen cells ($5\times10^6$) obtained from a mouse of the same strain as the recipient mice were subcutaneously administered on the left footpad. Twenty four hours later, the thicknesses of the right and left footpads were measured with a dial thickness gage, and the difference in thicknesses of the right and left footpads before the induction of the reaction and 24 hours after the induction of the reaction was employed as the index of the degree of the reaction.

The test compound was dissolved in water and $5\times10^{-8}$ mol/mouse was administered into cerebral ventricles. In the control group, water alone was administered similarly. The dose was 5 μl/mouse in both the study groups and the control group.

Results

The results are shown in Table 8.

TABLE 8

Suppression of Delayed Type Hypersensitivity by Indole Compounds (3)

| Compound | Structural Formula | % Suppression |
| --- | --- | --- |
| 2 | [structure] | 83 |
| NTI | [structure] | 40 |

By administration through cerebral ventricle, suppressive activity was observed, so that it was proved that these compounds suppress immune through the central nerve. Particularly, compound 2 according to the present invention exhibited suppressive effect far stronger than NTI, so that it was found that this is a strong immunosuppressant which acts through different mechanism from that of the conventional drugs.

Example 24

The mechanism of immunosuppression of the compound of the present invention was examined using delayed type hypersensitivity suppression test using mice from which adrenal glands have been removed.

Experimental Method

BALB/c mice (male, 7 weeks old) were used, and each group consisted of 4–5 mice. Spleen cells ($1\times10^7$) obtained from a donor mouse (C57BL/6) was subcutaneously administered to sensitize the mice. On Day 7 from the sensitization, the spleen cells ($5\times10^6$) of the donor were subcutaneously administered on the right footpad and spleen cells ($5\times10^6$) obtained from a mouse of the same strain as the recipient mice were subcutaneously administered on the left footpad. Twenty four hours later, the thicknesses of the right and left footpads were measured with a dial thickness gage, and the difference in thicknesses of the right and left footpads before the induction of the reaction and 24 hours after the induction of the reaction was employed as the index of the degree of the reaction.

The adrenectomy was performed by cutting the back of each recipient mouse under anesthesia with ether before the sensitization and removing the adrenal gland. Sham operation was performed by cutting the back of each recipient mouse but not removing the adrenal gland.

The test compound was dissolved in 10% DMSO-water and was subcutaneously administered everyday from the day of sensitization to the day of induction of the reaction, totally 8 days. In the control group, 10% DMSO-water alone was administered in the same manner. The volume of administration was 10 ml/kg in both study groups and in the control groups.

Results

The results are shown in Table 9.

TABLE 9

Suppression of Delayed Type Hypersensitivity by Indole Compounds (4)

| Compound | Structural Formula | % Suppression | |
| --- | --- | --- | --- |
| | | Sham Operation | Adrenectomy |
| 2 | (OH, cyclopropylmethyl-N, indole fused with tetrahydronaphthalene, phenol-O bridge) | 60 | 60 |
| NTI | (OH, cyclopropylmethyl-N, indole fused with isoquinoline, phenol-O bridge) | 50 | 0 |

While the suppressive effect of NTI disappeared by removing adrenal gland, the suppressive effect of compound 2 was not lost by removing adrenal gland. Thus, it was shown that the mechanisms of action of these compounds are clearly different.

Delayed type hypersensitivity reaction relates to rejection during organ transplantations and allergy. Since the compound of the present invention suppresses this reaction, it can be used for suppressing the rejection during organ transplantations. Further, the compound has wide uses such as antiallergic agent and anti-inflammatory agent.

Example 25
Mouse Contact Dermatitis Suppression Test

Experimental Method

BALB/c mice (male, 13–15 weeks old) were used, and each group consisted of 4 mice. In mixed liquid of acetone: olive oil=4:1, 2,4-difluorobenzene (DNFB) was dissolved. On Day 0 and Day 1, 0.1% DNFB (50 µl) was sensitized to the clipped skin of the abdominal wall, so as to sensitize the mouse. On day 5, 0.15% DNFB (25 µl/ear) was challenged on closal side of each ear love of each mouse, so as to induce the reaction. The compound was administered into cerebral ventricle 30 minutes before the induction.

The contact dermatitis was detected in terms of the increase in the thicknesses of the ears. The thicknesses of the ears were measured before and 24 hours after the challenge by using a dial thickness gage. One ear was taken as n=1, and the increase in the thickness of the ear was used as an index for detecting the contact dermatitis.

Contact Dermatitis=(thickness of the ear after challenge)– (thickness of the ear before challenge)

$$\% \text{ Supression} = \left(1 - \frac{E}{F}\right) \times 100$$

wherein E means the contact dermatitis of the group to which the compound was administered, and F means the contact dermatitis of the group to which the vehicle was administered.

Results

Compound 2 of the present invention exhibited suppression of 44%, so that it was shown that this compound is effective for allergic dermatitis.

What is claimed is:

1. An indole derivative represented by the formula (I):

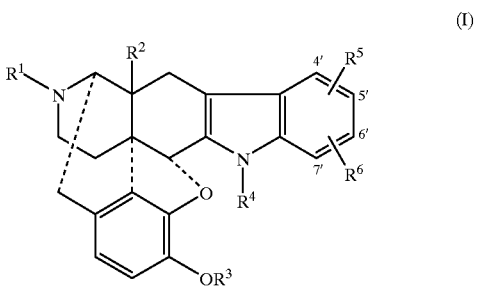

(I)

wherein $R^1$ represents $C_1$–$C_5$ alkyl, $C_4$–$C_6$ cycloalkylalkl, $C_5$–$C_7$ cycloalkenylalkyl, $C_1$–$C_3$ aralkyl, $C_4$–$C_5$ trans-alkenyl, allyl, $C_1$–$C_3$ furan-2-ylalkyl or $C_1$–$C_3$ thiophene-2-ylalkyl;

$R^2$ represents hydrogen, hydroxy, $C_1$–$C_5$ alkanoyloxy or $C_1$–$C_5$ alkoxy;

$R^3$ represents hydrogen, $C_1$–$C_5$ alkyl, $C_1$–$C_5$ alkanoyl or benzyl;

$R^4$ represents hydrogen, $C_1$–$C_5$ alkyl or benzyl;

$R^5$ and $R^6$ cooperatively represent —S=T—U=V wherein one of S, T, U and V represents a nitrogen and the remainders represent CH with the proviso that the hydrogen may be substituted with $R^{10}$ wherein $R^{10}$ represents $C_1$–$C_5$ alkyl, $C_1$–$C_5$ alkoxy, $C_1$–$C_5$ alkanoyl, $C_1$–$C_5$ hydroxyalkyl, $SR^7$, $SOR^7$, $SO_2R^7$ $(CH_2)_m CO_2R^7$, $SO_2NR^8R^9$, $CONR^8R^9$, or $(CH_2)_n NR^8R^9$ wherein m represents an integer of 0–3, n represents an integer of 1–3, $R^7$ represents $C_1$–$C_5$ alkyl, $R^8$ and $R^9$, the same or different, represent $C_1$–$C_5$ alkyl, or $C_4$–$C_6$ cycloalkylalkyl, and which $R^5$ and $R^6$ are bonded to carbon atoms adjacent to each other on the benzene ring to form a ring;

and pharmaceutically acceptable acid addition salts thereof.

2. The compound or acid addition salts according to claim 1, wherein $R^1$ is $C_4$–$C_6$ cycloalkylalkyl.

3. A pharmaceutical composition comprising an effective amount of a compound according to claim 1; and a pharmaceutically acceptable carrier.

4. A method of immunosuppressing a patient which comprises administering to a patient in need thereof an effective immunosuppressive amount of the compound according to claim 1.

5. A method of treating allergies which comprises administering to a patient in need thereof an effective antiallergic amount of the compound according to claim 1.

6. A method of treating inflammation which comprises administering to a patient in need thereof an effective anti-inflammatory amount of the compound according to claim 1.

7. A method of protecting brain cells from cytotoxic damage which comprises administering to a patient in need thereof, and effective brain cell-protecting from cytotoxic damage amount of the compound according to claim 1.

* * * * *